(12) United States Patent
Williams et al.

(10) Patent No.: US 10,676,504 B2
(45) Date of Patent: Jun. 9, 2020

(54) METHOD FOR PREPARING LARGAZOLE ANALOGS AND USES THEREOF

(71) Applicants: Colorado State University Research Foundation, Fort Collins, CO (US); Dana-Farber Cancer Institute, Inc., Boston, MA (US); University of Notre Dame du Lac, South Bend, IN (US)

(72) Inventors: Robert M. Williams, Fort Collins, CO (US); James E. Bradner, Weston, MA (US); Dane Clausen, Rahway, NJ (US); Olaf G. Wiest, South Bend, IN (US); Tenaya L. Newkirk, Denver, CO (US); Albert A. Bowers, Chapel Hill, NC (US); Jennifer Marie Guerra, Henderson, NV (US)

(73) Assignees: Colorado State University Research Foundation, Fort Collins, CO (US); Dana-Farber Cancer Institute, Inc., Boston, MA (US); University of Notre Dame du Lac, South Bend, IN (US)

( * ) Notice: Subject to any disclaimer, the term of this patent is extended or adjusted under 35 U.S.C. 154(b) by 0 days.

(21) Appl. No.: 15/555,755

(22) PCT Filed: Mar. 3, 2016

(86) PCT No.: PCT/US2016/020561
§ 371 (c)(1),
(2) Date: Sep. 5, 2017

(87) PCT Pub. No.: WO2016/144665
PCT Pub. Date: Sep. 15, 2016

(65) Prior Publication Data
US 2018/0044376 A1 Feb. 15, 2018

Related U.S. Application Data

(60) Provisional application No. 62/129,748, filed on Mar. 6, 2015.

(51) Int. Cl.
*A61K 38/00* (2006.01)
*C07K 5/062* (2006.01)
*C07D 513/18* (2006.01)
*A61K 31/429* (2006.01)
*A61K 31/437* (2006.01)
*A61K 45/06* (2006.01)
*A61K 38/05* (2006.01)
*C07B 59/00* (2006.01)

(52) U.S. Cl.
CPC ........ *C07K 5/06052* (2013.01); *A61K 31/429* (2013.01); *A61K 31/437* (2013.01); *A61K 38/05* (2013.01); *A61K 45/06* (2013.01); *C07B 59/008* (2013.01); *C07D 513/18* (2013.01); *C07B 2200/05* (2013.01)

(58) Field of Classification Search
None
See application file for complete search history.

(56) References Cited

U.S. PATENT DOCUMENTS

| 4,456,592 | A | 6/1984 | Okumura et al. |
| 5,846,933 | A | 12/1998 | Korngold et al. |
| 6,509,315 | B1 | 1/2003 | Joullie et al. |
| 8,217,076 | B2 | 7/2012 | Williams |
| 8,513,290 | B2 | 8/2013 | Williams |
| 2005/0119169 | A1 | 6/2005 | Deslongchamps et al. |
| 2007/0129289 | A1 | 6/2007 | Joullie et al. |
| 2014/0080802 | A1 | 3/2014 | Holson |
| 2014/0093449 | A1 | 4/2014 | Williams et al. |
| 2015/0010541 | A1 | 1/2015 | Liu et al. |
| 2018/0057510 | A1 | 3/2018 | Williams |

FOREIGN PATENT DOCUMENTS

| JP | 03-141296 | 6/1991 |
| WO | WO 2007/061939 | 5/2007 |
| WO | WO 2007/100385 | 9/2007 |
| WO | WO 2009/032352 | 3/2009 |
| WO | WO 2010/009334 | 1/2010 |
| WO | WO 2016/144814 | 9/2016 |

OTHER PUBLICATIONS

International Search Report and Written Opinion for PCT/US2016/020561 dated May 2, 2016.
International Preliminary Report on Patentability for PCT/US2016/020561 dated Sep. 21, 2017.
Avenoza A., et al. (2001) Tetrahedron: Asymmetry 12(6):949-957 "Enantioselective synthesis of (S)- and (R)-methylserines: application to the synthesis of (S)- and (R)-N-Boc-N,O-isopropylidene-a-methylserinals".
Berge, et al. (1977) J. Pharm. Sci. 66:1-19 "Pharmaceutical salts".
Bolden, J. E., et al. (2006) Nat. Rev. Drug Discovery 5:769-784 "Anticancer activities of histone deacetylase inhibitors".
Bowers, A.A., et al. (2008) J Am Chem Soc 130:11219-22 Total "Synthesis and Biological Mode of Action of Largazole: A Potent Class I Histone Deacetylase Inhibitor".
Bowers, A.A., et al. (2009) Org. Letters 11(6) 1301-1304 "Synthesis and Histone Deacetylase Inhibitory Activity of Largazole Analogs: Alteration of the Zinc-Binding Domain and Macrocyclic Scaffold".
Bradner (2010) Nat. Chem Biol. 6(3):238-243, "Chemical Phylogenetics of Histone Deacetylases".
Burger's Medicinal Chemistry and Drug Discovery (1995, Manfred E. Wolff ed., 5th ed. 172-178, 929-932).

(Continued)

*Primary Examiner* — Jeanette M Lieb
(74) *Attorney, Agent, or Firm* — Leydig, Voit & Mayer, Ltd.

(57) ABSTRACT

Analogs of largazole are described herein. Methods of treating cancer and blood disorders using largazole and largazole analogs and pharmaceutical compositions comprising the same are additionally described herein. Methods for preparing largazole analogs are likewise described.

12 Claims, 20 Drawing Sheets

(56) References Cited

OTHER PUBLICATIONS

Chen, Y., et al. (2003) J Org Chem 68:8902-8905 "Total Synthesis of the Depsipeptide FR-901375".
Cleve, Trip Report for 9th Tetrahedron Symposium, Berkeley, CA Klos, Jul. 22-25, 2008, "Discovery and Optimization of Diamine Analogues as Potent Inhibitors of Leukotriene A4 Hydrolase."
Freireich, et al. (1966) Cancer Chemother Rep 50:219 "Quantitative comparison to toxicity of anticancer agents in mouse, rat, hamster, dog, monkey and man".
Furumai, R., et al. (2001) PNAS USA 98:87-92 "Potent Histone Deacetylase Inhibitors Built From Trichostatin A and Cyclic Tetrapeptide Antibiotics Including Trapoxin".
Ghosh, A.K. & Kulkarni, S. (2008) Org. Lett. 10:3907-3909 "Enantioselective Total Synthesis of (+)—Largazole, a Potent Inhibitor of Histone Deacetylase".
Greshock, et al. (2008) Org Lett 10:613-616 "Improved Total Synthesis of the Potent HDAC Inhibitor FK228 (FR-901228)".
Grozinger, C.M., et al. (1999) Proc. Nat. Acad. Sci. USA 96:4868-4873 "Three proteins define a class of human histone deacetylases related to yeast Hdalp".
Handbook of Pharmaceutical Salts. Properties, Selection, and Use (P. Heinrich Stahl and C. Wermuth, Eds., Verlag Helvetica Chica Acta, Zurich, Switzerland (2002)).
International Preliminary Report on Patentability from PCT/US2016/021031 dated Sep. 21, 2017.
International Search Report and Written Opinion from PCT/US09/50878 dated Sep. 28, 2009.
International Search Report and Written Opinion from PCT/US16/21031 dated May 23, 2016.
Jeanguenat, A. & Seebach, D. (1991) J Chem Soc, Perkins Trans 1:2291-2298 "Stereoselective chain elongation at C-3 of cysteine through 2,3-dihydrothiazoles, without racemization. Preparation of 2-amino-5-hydroxy-3-mercaptoalkanoic acid derivatives".
Johnstone, R.W. (2002) Nature Rev. Drug Disc. 1:287-299 "Histone deacetylase inhibitors: novel drugs for the treatment of cancer".
Katsura, Y., et al. (1994) J Med Chem 37(1):57-66 "Studies on antiulcer drugs. 7. 2-Guanidino-4-pyridylthiazoles as histamine H2-receptor antagonists with potent gastroprotective effects against nonsteroidal antiinflammatory drug-induced injury".
Lange, U.E.W., et al. (1999) Tetrahedron Lett. 40:7067-7070 "A new mild method for the synthesis of amidines".
Li, K.W., et al. (1996) J Am Chem Soc 118:7237-7238 "Total Synthesis of the Antitumor depsipeptide FR-901, 228".
Marsault, et al. (2006) Journal of Medicinal Chemistry pp. C-D "Discovery of a New Class of Macrocyclic Antagonists to the Human Motilin Receptor."
Masuoka, Y., et al. (2001) Tetrahedron Lett. 42:41-44 "Spiruchostatins A and B, novel gene expression-enhancing substances produced by *Pseudomonas* sp.".
Miller, T. A., et al. (2003) J. Med. Chem. 46:5097-5116 "Histone deacetylase inhibitors".
Minucci, S., et al. (2006) Nature Rev. Cancer 6:38-51 "Histone deacetylase inhibitors and the promise of epigenetic (and more) treatments for cancer".
Moradei, O., et al. (2005) Curr. Med. Chem. Anti-Cancer Agents 5:529-560 "Histone deacetylase inhibitors: latest developments, trends and prospects".
Mulqueen, G.C., et al. (1993) Tetrahedron 49:5359-5364 "Synthesis of the thiazoline-based siderophore (S)-desferrithiocin".
Nasveschuk, C.G., et al. (2008) Org. Lett. 10:3595-3598 "A Concise Total Synthesis of Largazole, Solution Structure, and Some Preliminary Structure Activity Relationships".
Nishino, N., et al. (2003) Org Lett 5:5079-5082 "cyclic tetrapeptides bearing a sulfhydryl group potently inhibit histone deacetylases".
Patani and LaVoie (1996) Chem. Rev. 96:3147-3176 "Bioisosterism: A Rational Approach in Drug Design".
Phillips, A.J., et al. (2000) Org Lett 2(8):1165-1168 "Synthesis of Functionalized Oxazolines and Oxazoles with DAST and Deoxo-Fluor".
Reiner, J., et al. (2002) Bioorg Med Chem Lett 12(8):1203-1208 "Non-covalent thrombin inhibitors featuring p3-heterocycles with P1-monocyclic arginine surrogates".
Scientific Tables, Geigy Pharmaceuticals, Ardley, N.Y., (1970) 537.
Seiser, T.; et al. (2008) Angew. Chem. Int. Ed. 47:6483-6485 "Synthesis and Biological Activity of Largazole and Derivatives".
Shigematsu, N., et al. (1994) J. Antibiot. 47:311-314 "A novel antitumor bicycle depsipeptide produced by Chromobacterium violaceum No. 968".
Smith, N.D. and Goodman, M. (2003) Org. Lett. 5:1035-1037 "Enantioselective synthesis of alpha-methyl-D-cysteine and lanthionine building blocks via alpha-methyl-D-serine-beta-lactone".
Somech, R., et al. (2004) Cancer Treat. Rev. 30:461 "Histone deacetylase inhibitors—a new tool to treat cancer".
Taori, K., et al. (2008) J. Am. Chem. Soc. 130:1806-1807 and 13506 "Structure and Activity of Largazole, a Potent Antiproliferative Agent from the Floridian Marine *Cyanobacterium symploca* sp.".
Taunton, J., et al. (1996) Science 272:408-411 "A Mammalian Histone Deacetylase Related to the Yeast Transcriptional Regulator Rpd3p".
Townsend, P.A., et al. (2007) the bicyclic depsipeptide family of histone deacetylase inhibitors, in Chemical Biology; Schreiber, S.L., et al. Eds.Wiley-VCH Verlag GmbH & Co. 693-720.
Ueda, H., et al. (1994) J. Antibiot. 47:315-323 "FR901228, a novel antitumor bicyclic depsipeptide produced by Chromobacterium violaceum No. 968 III. Antitumor activities on experimental tumors in mice".
Ueda, H., et al. (1994) J. Antibiot. 47:301-310 "FR901228, a novel antitumor bicyclic depsipeptide produced by Chromobacterium violaceum No. 968. I. Taxonomy, fermentation, isolation, physicochemical and biological properties, and antitumor activity".
Vanommeslaeghe, K., et al. (2005) Bioorg. Med. Chem. 13:3987-3992 "Theoretical study revealing the functioning of a novel combination of catalytic motives in Histone Deacetylase".
Vanommeslaeghe, K., et al. (2005) Bioorg. Med. Chem. 13:6070-6082 "DFT-based Ranking of Zink-chelating Groups in Histone Deacetylase Inhibitors".
Videnov, G., et al. (1996) Angew Chem Int Ed Eng 35:1503-1506 "Synthesis of Naturally Occurring, Conformationally Restricted Oxazole and Thiazole Containing Di- and Tripeptide Mimetics".
Ying, Y., et al. (2008) J. Am. Chem. Soc. 130:8455-8459 "Total Synthesis and Molecular Target of Largazole, a Histone Deacetylase Inhibitor".
Ying, Y., et al. (2008) Organic Letters 10(18):4021-4024 "Synthesis and Activity of Largazole Analogues with Linker and Macrocycle Modification".
Yoshida, M., et al. (1990) J. Antibiot. 43:1101-1106 "Structural Specificity for Biological Activity of Trichostatin A, A Specific Inhibitor of Mammalian Cell Cycle with Potent Differentiation-Inducing Activity in Friend Leukemia Cells".
Yoshida, M., et al. (1990) J. Biol. Chem. 265:17174 "Potent and specific inhibition of mammalian histone deacetylase both in vivo and in vitro by trichostatin A".
Yurek-George, A. (2007) J. Med. Chem. 50:5720-5726 "The First Biologically Active Synthetic Analogues of FK228, the Depsipeptide Histone Deacetylase Inhibitor".
Yurek-George, A., et al. (2004) J Am Chem Soc 126:1030-1031 "Total synthesis of spiruchostatin A, a potent histone deacetylase inhibitor".
Clausen, et. Al. (2015) Bioorg. & Med. Chem. 23:5061-5074 "Modular Synthesis and Biological Activity of Pyridyl-based Analogs of the Potent Class 1 Histone Deacetylase Inhibitor Largazole".
Guerra-Bubb, J.M., Bowers, A.A., Smith, W.B., Paranal, R., Estiu, G., Wiest, O., Bradner, J.E. and Williams, R.M., (2013) Bioorganic & medicinal chemistry letters, 23(21), pp. 6025-6028. "Synthesis and HDAC inhibitory activity of isosteric thiazoline-oxazole largazole analogs."
Hong, et al. (2012) Nat. Prod. Rep. 29:449-456. "Largazole: From discovery to broad-spectrum therapy".
Liu, y. et al. (2010) J Pharm and Exp Ther 335:351-361 "Anticolon Cancer Activity of Largazole, a Marine-Derived Tunable Histone Deacetylase Inhibitor".

(56) References Cited

OTHER PUBLICATIONS

Quintas-Cardama et al. (2011) Leukemia 25:226-235 "Histone Deacetylase Inhibitors for the Treatment of Myelodysplastic Syndrome and Acute Myeloid Leukemia".
Salvador, et al. (2014) Medicinal Chem Lett 5:905-910 "Modulation of ActivityProfiles for Largazole-Based HDAC Inhibitors through Alteration of Prodrug Properties".
Souto, et al. (2010) Journ of Med Chemistry 53:4654-4667 "Synthesis and Biological Characterization of the Histone Deacetlylase Inhibitor Largazole and C7-Modified Analogues".
Zawilska, et al. (2013) Pharmacological Reports 65: 1-14 "Prodrugs: A challenge for the drug development".
Zhao, et al. (2017) Israel J. Chem. 57:319-330 "Synthesis and Biochemical Evaluation of Biotinylated Conjugates of Largazole Analogues: Selective Class I Histone Deacetlase Inhibitors".
www.cancer.org/cancer/leukemia-in-children/causes-risks-prevention/prevention.html.

Table P3 - National Cancer Institute 60 Cell Panel - Cell Site and Histology

| General | | Tissue Source | | | Histology | |
| --- | --- | --- | --- | --- | --- | --- |
| No. | Cancer Type | Cell Line | Primary Site | Site Sub type 1 | Primary | Subtype 1 | Subtype 2 |
| 1 | Leukemia | CCRF-CEM | haematopoietic & lymphoid | NS | lymphoid neoplasm | acute lymphoblastic leukemia | NS |
| 2 | Leukemia | HL-60 (TB) | haematopoietic & lymphoid | NS | haematopoietic neoplasm | acute myeloid leukemia | M3 |
| 3 | Leukemia | K-562 | H&L | NS | haematopoietic neoplasm | chronic myeloid leukemia | NS |
| 4 | Leukemia | MOLT-4 | H&L | NS | lymphoid neoplasm | acute lymphoblastic leukemia | NS |
| 5 | Leukemia | RPMI-8226 | H&L | NS | lymphoid neoplasm | plasma cell myeloma | NS |
| 6 | Leukemia | SR | H&L | NS | lymphoid neoplasm | NS | NS |
| 7 | Non-Small Cell Lung (NSCL) | A549/ATCC | lung | NS | carcinoma | NS | NS |
| 8 | NSCL | EKVX | lung | NS | carcinoma | adenocarcinoma | NS |
| 9 | NSCL | HOP-62 | lung | NS | carcinoma | adenocarcinoma | NS |
| 10 | NSCL | HOP-92 | lung | NS | carcinoma | large cell carcinoma | NS |
| 11 | NSCL | NCI-H226 | lung | NS | carcinoma | squamous cell carcinoma | NS |
| 12 | NSCL | NCI-H23 | lung | NS | carcinoma | non small cell carcinoma | NS |
| 13 | NSCL | NCI-H322M | lung | NS | carcinoma | bronchioloalveolar adenocarcinoma | NS |
| 14 | NSCL | NCI-H460 | lung | NS | carcinoma | large cell carcinoma | NS |
| 15 | NSCL | NCI-H522 | lung | NS | carcinoma | non small cell carcinoma | NS |

Fig. 6A

| 16 | Colon | COLO 205 | large intestine | colon | carcinoma | adenocarcinoma | NS |
|---|---|---|---|---|---|---|---|
| 17 | Colon | HCC-2998 | large intestine | colon | carcinoma | adenocarcinoma | NS |
| 18 | Colon | HCT-116 | large intestine | colon | carcinoma | NS | NS |
| 19 | Colon | HCT-15 | large intestine | colon | carcinoma | NS | NS |
| 20 | Colon | HT29 | large intestine | colon | carcinoma | NS | NS |
| 21 | Colon | KM12 | large intestine | colon | carcinoma | adenocarcinoma | NS |
| 22 | Colon | SW-620 | large intestine | colon | carcinoma | adenocarcinoma | NS |
| 23 | CNS | SF-268 | central nervous system | brain | glioma | NS | NS |
| 24 | CNS | SF-295 | central nervous system | brain | glioma | NS | NS |
| 25 | CNS | SF-539 | central nervous system | brain | glioma | NS | NS |
| 26 | CNS | SNB-19 | central nervous system | cerebrum | glioma | astrocytoma grade IV | glioblastoma multiforme |
| 27 | CNS | SNB-75 | central nervous system | brain | glioma | NS | NS |
| 28 | CNS | U251 | central nervous system | brain | glioma | NS | NS |
| 29 | Melanoma | LOX IMVI | skin | NS | malignant melanoma | NS | NS |
| 30 | Melanoma | MALME-3M | skin | NS | malignant melanoma | NS | NS |
| 31 | Melanoma | M14 | skin | NS | malignant melanoma | NS | NS |
| 32 | Melanoma | MDA-MB-435 | skin | NS | malignant melanoma | NS | NS |
| 33 | Melanoma | SK-MEL-2 | skin | upper leg | malignant melanoma | NS | NS |
| 34 | Melanoma | SK-MEL-28 | skin | NS | malignant melanoma | NS | NS |
| 35 | Melanoma | SK-MEL-5 | skin | axilla | malignant melanoma | NS | NS |
| 36 | Melanoma | UACC-257 | skin | NS | malignant melanoma | NS | NS |
| 37 | Melanoma | UACC-62 | skin | NS | malignant melanoma | NS | NS |
| 38 | Ovarian | IGROV1 | ovary | NS | carcinoma | NS | NS |
| 39 | Ovarian | OVCAR-3 | ovary | NS | carcinoma | adenocarcinoma | NS |
| 40 | Ovarian | OVCAR-4 | ovary | NS | carcinoma | NS | NS |
| 41 | Ovarian | OVCAR-5 | ovary | NS | carcinoma | NS | NS |
| 42 | Ovarian | OVCAR-8 | ovary | NS | carcinoma | NS | NS |

Fig. 6B

| 43 | Ovarian | NCI/ADR-RES | ovary | NS | carcinoma | NS | NS |
|---|---|---|---|---|---|---|---|
| 44 | Ovarian | SK-OV-3 | ovary | NS | carcinoma | adenocarcinoma | NS |
| 45 | Renal | 786-0 | kidney | NS | carcinoma | clear cell renal cell carcinoma | NS |
| 46 | Renal | A498 | kidney | NS | carcinoma | NS | NS |
| 47 | Renal | ACHN | kidney | NS | carcinoma | renal cell carcinoma | NS |
| 48 | Renal | CAKI-1 | kidney | NS | carcinoma | clear cell renal cell carcinoma | NS |
| 49 | Renal | RFX-393 | kidney | NS | carcinoma | renal cell carcinoma | NS |
| 50 | Renal | SN12C | kidney | NS | carcinoma | NS | NS |
| 51 | Renal | UO-31 | kidney | NS | carcinoma | renal cell carcinoma | NS |
| 52 | Renal | TK-10 | kidney | NS | carcinoma | renal cell carcinoma | NS |
| 53 | Prostate | PC-3 | prostate | NS | carcinoma | adenocarcinoma | NS |
| 54 | Prostate | DU-145 | prostate | NS | carcinoma | adenocarcinoma | NS |
| 55 | Breast | MCF7 | breast | NS | carcinoma | NS | NS |
| 56 | Breast | MDAB-231/ATCC | breast | NS | carcinoma | NS | NS |
| 57 | Breast | HS 578T | breast | NS | carcinoma | NS | NS |
| 58 | Breast | BT-549 | breast | NS | carcinoma | ductal carcinoma | papillary |
| 59 | Breast | T-47D | breast | NS | carcinoma | ductal carcinoma | NS |
| 60 | Breast | MDA-MB-468 | breast | NS | carcinoma | NS | NS |

Fig. 6C

| Table P4 | Compounds-Data expressed as growth percent (+ = cell growth, 0 = no net growth change, - =cell lethality) | | | | | | | |
|---|---|---|---|---|---|---|---|---|
| Cancer Cell Type | Largazole | aa | A | cc | bb | C | D | E |
| Colon | | | | | | | | |
| COLO 205 | -78.26 | -71.77 | -56.04 | -70.27 | -61.77 | -41.59 | -41.29 | 100.17 |
| HCC-2998 | -47.98 | -6.96 | -67.8 | -66.49 | -73.41 | 12.55 | -68.82 | 93.72 |
| HCT-116 | -34.84 | -30.3 | -17.24 | -39.23 | -27.69 | 2.91 | -63.16 | 86.77 |
| HCT-15 | 58.63 | 60.95 | 1.6 | 52.01 | 2.94 | 75.28 | 0.6 | 90.36 |
| HT29 | | -22.42 | 1.74 | 2.76 | 1 | -6.83 | 2.22 | 99.01 |
| KM12 | 1.21 | 8.82 | -3.5 | 6.09 | 3.74 | 24.89 | 1.36 | 90.05 |
| SW-620 | 1.33 | 29.61 | -1.73 | 4.68 | 3.63 | 69.3 | -29.17 | 100.92 |
| Average | -16.7 | -5 | -20.4 | -15.8 | -21.7 | 19.5 | -28.3 | 94.4 |
| CNS | | | | | | | | |
| SF-268 | 11.31 | 18.03 | 11.79 | 12.96 | 11.08 | 53.56 | 1.9 | 100.06 |
| SF-295 | 6.21 | 2.96 | -62.17 | -1.44 | -62.39 | -1.52 | -62.52 | 93.01 |
| SF-539 | 20.95 | 25.01 | 17.01 | 17.23 | 20.04 | 48.62 | 9.22 | 81.47 |
| SNB-19 | 22.25 | 20.77 | 10.19 | 23.59 | 14.32 | 38.58 | 9.15 | 90.43 |
| SNB-75 | 29.1 | 35.8 | 31.76 | 25.76 | 31.33 | 24.5 | 26.09 | 83.25 |
| U521 | -62.12 | -33.53 | -55.67 | -66.62 | -32.15 | 13.67 | -61.16 | 96.73 |
| Average | 4.6 | 11.5 | -7.8 | 1.9 | -3 | 29.6 | -12.9 | 90.8 |
| Melanoma | | | | | | | | |
| LOX IMVI | -93.09 | -91.77 | -95.06 | -94.93 | -94.35 | -1.52 | -97.17 | 99.15 |
| MALME-3M | 21.42 | 10.76 | 11.4 | 14.55 | 22.7 | 2.46 | 5.59 | 61.92 |
| M14 | 10.09 | 15.53 | 4.89 | 8.55 | 5.95 | 35.58 | -3.25 | 92.48 |
| MDA-MB-435 | 5.9 | 6.04 | -22.12 | 5.07 | -9.48 | 19.57 | -31.79 | 92.09 |
| SK-MEL-2 | -28.18 | -34.71 | -2.2 | -28.19 | -1.86 | 18.12 | -3.78 | 84.54 |
| SK-MEL-28 | 5.48 | 25.34 | -24.72 | 16.6 | 1.51 | 37.08 | -37.17 | 87.44 |
| SK-MEL-5 | -81.2 | -21.31 | -95.25 | -88.18 | -93.93 | 22.25 | -93.55 | 97.89 |
| UACC-257 | -42.55 | -19.6 | -19.66 | -25.01 | -7.88 | 6.15 | -16.08 | 87.01 |
| UAC-62 | -42.24 | -24.97 | -56.76 | -36.73 | -64.14 | 0.72 | -67.98 | 85.12 |
| Average | -27.2 | -15 | -33.3 | -25.4 | -26.8 | 15.6 | -38.4 | 87.5 |
| Renal | | | | | | | | |
| 786-0 | 10.23 | 17.19 | 11.98 | 6.38 | 10.76 | 53.97 | 10.18 | 105.24 |
| ACHN | -74.8 | -50.29 | -17.2 | -76.95 | -11.85 | 59.57 | -27.51 | 90.04 |
| CAKI-1 | 5.8 | 7.25 | -54.45 | 6.6 | -38.76 | 82.34 | -50.82 | 91.2 |
| SN12C | -57.69 | -52.83 | 21.88 | -61.67 | 22.61 | 55.67 | 12.58 | 95.99 |
| TK-10 | 31.7 | 35.5 | -16.63 | 27.78 | -16.08 | 12.01 | -18.59 | 70.26 |
| UO-31 | 10.8 | 18.88 | -10.47 | 12.02 | -8.17 | 50.78 | -13.49 | 79.25 |
| Average | -12.4 | -4.1 | -10.6 | -14.3 | -6.9 | 52.4 | -14.6 | 88.7 |
| Mean All Cells (not all data shown) | | | | | | | | |
| | -3.4 | 3.7 | -7.5 | -2.8 | -5.1 | 26.9 | -12.6 | 88.6 |
| Compound Ranking for Level of Lethality (all cell lines) | | | | | | | | |
| | 5 | 6 | 2 | 4 | 3 | 7 | 1 | 8 |

Fig. 8

| Table P5 | | Cell Lethality Against D | | | |
|---|---|---|---|---|---|
| Cancer Type | Cell Line | 0-10 % | 11-40 % | 41-70 % | 71-100 % |
| Non-Small Cell Lung | A549/ATCC | X | | | |
| Non-Small Cell Lung | HOP-62 | X | | | |
| Non-Small Cell Lung | HOP-92 | X | X | | |
| Non-Small Cell Lung | NCI-H226 | X | | | |
| Non-Small Cell Lung | NCI-H23 | X | | | |
| Non-Small Cell Lung | NCI-H322M | X | X | | |
| Non-Small Cell Lung | NCI-H522 | X | | | |
| Colon | COLO 205 | X | X | X | |
| Colon | HCC-2998 | X | X | X | |
| Colon | HCT-116 | X | X | X | |
| Colon | SW-620 | X | X | | |
| Central Nervous System | SF-295 | X | X | X | |
| Central Nervous System | U251 | X | X | X | |
| Melanoma | LOX IMVI | X | X | X | X |
| Melanoma | M14 | X | | | |
| Melanoma | MDA-MB-435 | X | X | | |
| Melanoma | SK-MEL-2 | X | | | |
| Melanoma | SK-MEL-28 | X | X | | |
| Melanoma | SK-MEL-5 | X | X | X | X |
| Melanoma | UACC-257 | X | X | | |
| Melanoma | UACC-62 | X | X | X | |
| Ovarian | IGROV1 | X | X | | |
| Ovarian | OVCAR-3 | X | X | X | |
| Ovarian | OVCAR-5 | X | | | |
| Ovarian | SK-OV-3 | X | X | | |
| Renal | ACHN | X | X | | |
| Renal | CAKI-1 | X | X | X | |
| Renal | UO-31 | X | X | | |
| Renal | TK-10 | X | X | | |
| Breast | MDAB-231/ATCC | X | | | |
| Breast | T-47D | X | | | |
| Breast | MDA-MB-468 | X | | | |

Fig. 13

| Table P6 CANCER CATEGORY | CANCER CELL LINE | | | | D | | | |
|---|---|---|---|---|---|---|---|---|
| NSC 785297, EXP 1508NS36 | | GI50 | IC50 | TGI | LC50 | Average LC50 | Total Cell Lines | Impacted Cell Lines | Percent Impacted |
| | | Conc. (M) | Conc. (M) | Conc. (M) | Conc. (M) | Conc. (M) | Number | Number | (%) |
| Leukemia | CCRF-CEM | 3.39E-08 | 1.02E-05 | | | | | | |
| Leukemia | HL-60(TB) | 2.51E-08 | 2.82E-07 | 3.55E-05 | | | | | |
| Leukemia | K-562 | 3.72E-08 | 4.90E-08 | | | | | | |
| Leukemia | MOLT-4 | 2.40E-08 | 8.13E-06 | 4.47E-05 | | | | | |
| Leukemia | RPMI-8226 | 7.59E-08 | 1.95E-07 | | | | | | |
| Leukemia | SR | 2.24E-08 | 3.31E-08 | | | 0 | 6 | 0 | 0% |
| NSCL | A549/ATCC | 1.78E-08 | 2.82E-08 | 2.04E-07 | | | | | |
| NSCL | EKVX | 3.16E-08 | 2.14E-07 | | | | | | |
| NSCL | HOP-62 | 1.82E-08 | 1.66E-07 | 2.40E-07 | | | | | |
| NSCL | HOP-92 | 9.12E-09 | | 4.90E-08 | | | | | |
| NSCL | NCI-H226 | 5.50E-08 | 3.89E-07 | 1.12E-06 | | | | | |
| NSCL | NCI-H23 | 2.45E-08 | 9.33E-08 | 4.90E-07 | | | | | |
| NSCL | NCI-H322M | 1.91E-08 | 1.23E-07 | 8.51E-07 | | | | | |
| NSCL | NCI-H460 | 1.51E-08 | 2.00E-08 | 6.76E-06 | | | | | |
| NSCL | NCI-H522 | 5.89E-09 | 2.14E-08 | 3.80E-08 | | 0 | 9 | 0 | 0% |
| Colon | COLO 205 | 3.09E-08 | 7.08E-08 | 1.51E-07 | 2.63E-06 | | | | |
| Colon | HCC-2998 | 1.51E-08 | 3.16E-08 | 7.24E-08 | 3.09E-07 | | | | |
| Colon | HCT-116 | 1.26E-08 | 1.55E-08 | 7.59E-06 | | | | | |
| Colon | HCT-15 | 1.51E-07 | 2.19E-07 | 8.32E-06 | | | | | |
| Colon | HT29 | 1.41E-08 | 1.86E-08 | 7.94E-06 | | | | | |
| Colon | KM12 | 2.40E-08 | 3.39E-08 | 5.13E-06 | | | | | |

Fig. 14A

| | | | | | | | | |
|---|---|---|---|---|---|---|---|---|
| Colon | SW-620 | 3.98E-08 | 5.89E-08 | 5.62E-06 | | 1.47E-06 | 7 | 2 | 29% |
| CNS | SF-268 | 3.39E-08 | 1.02E-07 | 5.37E-06 | | | | | |
| CNS | SF-295 | 1.10E-08 | 2.09E-08 | 5.89E-08 | | | | | |
| CNS | SF-539 | 1.51E-08 | 9.33E-08 | | | | | | |
| CNS | SNB-19 | 9.12E-08 | 3.72E-07 | | | | | | |
| CNS | SNB-75 | 5.89E-09 | | | | | | | |
| CNS | U251 | 3.89E-08 | 7.59E-08 | 3.02E-07 | 1.95E-05 | 1.95E-05 | 5 | 1 | 20% |
| Melanoma | LOX IMVI | 2.24E-08 | 3.02E-08 | 8.13E-08 | 2.24E-07 | | | | |
| Melanoma | MALME-3M | 5.01E-09 | | | | | | | |
| Melanoma | M14 | 1.74E-08 | 3.16E-08 | | | | | | |
| Melanoma | MDA-MB-435 | 1.35E-08 | 1.91E-08 | 1.48E-06 | | | | | |
| Melanoma | SK-MEL-2 | 1.20E-08 | 3.89E-08 | 1.23E-07 | | | | | |
| Melanoma | SK-MEL-28 | 1.35E-08 | 3.16E-08 | 7.24E-07 | | | | | |
| Melanoma | SK-MEL-5 | 1.55E-08 | 2.40E-08 | 6.76E-08 | 2.45E-07 | | | | |
| Melanoma | UACC-62 | 9.55E-09 | 2.04E-08 | 4.37E-08 | 6.46E-07 | 3.72E-07 | 8 | 3 | 38% |
| Ovarian | IGROV1 | 1.15E-08 | 2.69E-08 | 1.62E-07 | | | | | |
| Ovarian | OVCAR-3 | 2.24E-08 | 5.50E-08 | 1.35E-07 | 2.34E-06 | | | | |
| Ovarian | OVCAR-4 | 2.57E-08 | | | | | | | |
| Ovarian | OVCAR-5 | 7.76E-09 | 9.77E-08 | | | | | | |
| Ovarian | OVCAR-8 | 1.15E-08 | 2.57E-08 | | | | | | |
| Ovarian | NCI/ADR-RES | 4.07E-07 | 1.29E-06 | 2.00E-05 | | | | | |
| Ovarian | SK-OV-3 | 1.07E-08 | 6.31E-08 | 8.91E-08 | | 2.34E-06 | 7 | 1 | 14% |
| Renal | 786-0 | 3.72E-08 | 2.09E-07 | | | | | | |
| Renal | A498 | 1.07E-08 | 1.78E-07 | 4.17E-08 | 4.79E-07 | | | | |
| Renal | ACHN | 2.45E-08 | 4.68E-08 | 2.40E-07 | | | | | |
| Renal | CAKI-1 | 2.82E-07 | 4.27E-07 | | | | | | |
| Renal | RXF 393 | 2.75E-08 | 1.78E-07 | 1.78E-07 | 2.29E-05 | | | | |
| Renal | SN12C | 5.01E-08 | 2.95E-07 | | | | | | |
| Renal | TK-10 | 1.82E-08 | 3.80E-08 | 1.74E-07 | | | | | |

Fig. 14B

| Tissue | Cell Line | | | | | | | |
|---|---|---|---|---|---|---|---|---|
| Renal | UO-31 | 2.29E-08 | 6.61E-08 | 3.47E-07 | 1.17E-05 | 8 | 2 | 25% |
| Prostate | PC-3 | 1.32E-08 | 3.98E-08 | | | | | |
| Prostate | DU-145 | 1.23E-08 | 2.14E-08 | | 0 | 2 | 0 | 0% |
| Breast | MCF7 | 2.14E-08 | 3.98E-08 | | | | | |
| Breast | MDA-MB-231/ATCC | 4.47E-08 | 3.63E-07 | 5.13E-06 | | | | |
| Breast | HS 578T | 1.35E-08 | | | | | | |
| Breast | BT-549 | 1.20E-07 | | | | | | |
| Breast | T-47D | 3.09E-08 | 2.40E-07 | 2.00E-07 | 0 | 6 | 0 | 0% |
| Breast | MDA-MB-468 | 2.88E-08 | 9.12E-06 | 1.41E-05 | | | | |

| Concentration (M) | Number Cell Lines Inhibited | No Data Cell Lines | Total Cell Lines | Cell Lines Impacted (%) | Average Inhibition |
|---|---|---|---|---|---|
| 1.E-08 to 1.E-09 | 59 | 0 | 59 | 100% | 3.83E-08 |
| 1.00E-07 | 53 | 0 | 59 | 90% | 6.43E-07 |
| 1.00E-06 | 38 | 2 | 57 | 67% | 4.57E-06 |
| 1.00E-05 | 9 | 1 | 58 | 16% | 5.48E-06 |

Fig. 14C

METHOD FOR PREPARING LARGAZOLE ANALOGS AND USES THEREOF

RELATED APPLICATIONS

This application is a 35 U.S.C. § 371 national phase application of PCT/US16/020561 (WO 2016/144665), filed on Mar. 3, 2016, entitled "Method for Preparing Largazole Analogs and Uses Thereof", which application claims the benefit of U.S. Provisional Application Ser. No. 62/129,748, filed Mar. 6, 2015, which is incorporated herein by reference in its entirety.

STATEMENT OF RIGHTS TO INVENTIONS MADE UNDER FEDERALLY SPONSORED RESEARCH

This invention was made with government support under grant numbers CA152314, CA136283, GM049631, K08 CA128972, and N01 CO02400 awarded by The National Institutes of Health. The government has certain rights in the invention.

BACKGROUND OF THE INVENTION

Largazole (1) is a densely functionalized macrocyclic depsipeptide, recently isolated from the cyanobacterium Symploca sp. (Taori, K., et al. 2008 *J. Am. Chem. Soc.* 130:1806-1807 and 13506. Ying. Y., et al. 2008 *J. Am. Chem. Soc.* 130). This natural product exhibits exceptionally potent and selective biological activity, with two- to ten-fold differential growth inhibition in a number of transformed and non-transformed human- and murine-derived cell lines. The remarkable selectivity of this agent against cancer cells prompts particular interest in its mode of action and its value as a potential cancer chemotherapeutic.

It has previously been stated that "the 3-hydroxy-7-n-mercaptohept-4-enoic acid unit in 1 is unprecedented in natural products." (Somech, R., et al. 2004 *Cancer Treat. Rev.* 30:461-472; Miller, T. A., et al. 2003 *J. Med. Chem.* 46:5097-5116; Moradei, O., et al. 2005 *Curr. Med. Chem.; Anti-Cancer Agents* 5:529-560; Bolden. J. E., et al. 2006 *Nat. Rev. Drug Discovery* 5:769-784). In contrast to this assertion, the (S)-3-hydroxy-7-mercaptohept-4-enoic acid is, in fact, an essential motif in several cytotoxic natural products, including FK228 (FR901228) (Japanese Patent No. 03-141296, Jun. 17, 1991, Fujisawa Pharmaceutical Co., Ltd., Jpn. Kokai Tokkyo Koho J P, 1991; Ueda, H., et al. 1994; *J. Antibiot.* 47:301-310; Shigematsu. N., et al. 1994 *J. Antibiot.* 47:311-314; Ueda, H., et al. 1994 J. Antibiot. 47:315-323). FR901375 (Japanese Patent No. 03-141296, Jun. 17, 1991, Fujisawa Pharmaceutical Co., Ltd., Jpn. Kokai Tokkyo Koho JP; Ueda, H., et al. 1994; *J. Antibiot.* 47:301-310; Shigematsu, N., et al. 1994 *J. Antibiot.* 47:311-314; Ueda, H., et al. 1994 *J. Antibiot.* 47:315-323) and spiruchostatin (Masuoka, Y., et al. 2001 *Tetrahedron Lett.* 42:41-44) (structures depicted below), all of which are known histone deacetylase inhibitors (HDACi) (Townsend, Pa., et al. 2007 *The bicyclic depsipeptide family of histone deacetylase inhibitors*, in Chemical Biology; Schreiber, S. L., et al. Eds. Wiley-VCH Verlag GmbH & Co. 693-720).

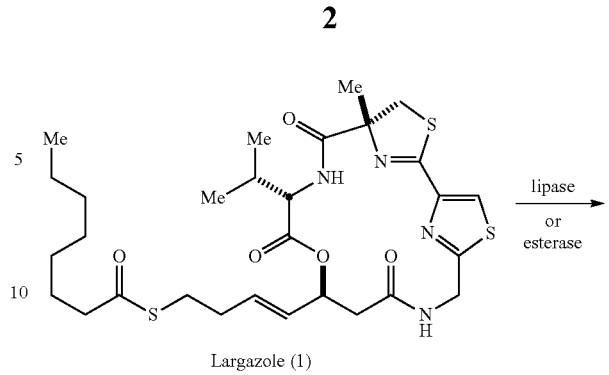

Largazole (1)

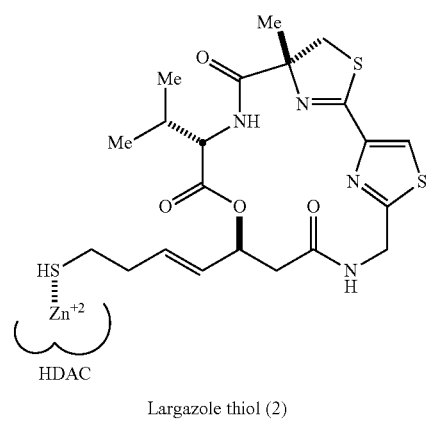

Largazole thiol (2)

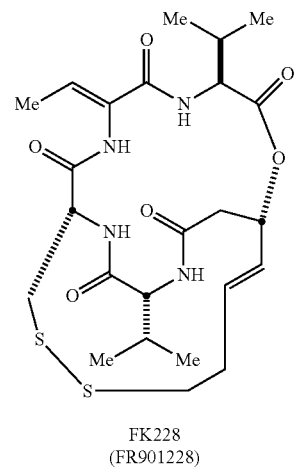

FK228
(FR901228)

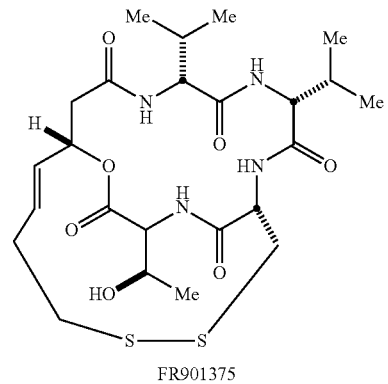

FR901375

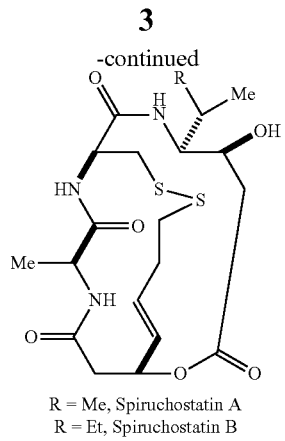

R = Me, Spiruchostatin A
R = Et, Spiruchostatin B

The histone deacetylase enzymes are zinc metalloenzymes that catalyze the hydrolysis of acetylated lysine residues in chromatin and, thereby, regulate transcription in eukaryotic cells (Somech, R., et al. 2004 *Cancer Treat. Rev.* 30:461; Miller, T. A., et al. 2003 S. *J. Med. Chem.* 46:5097-5116; Moradei, O., et al. 2005 *Curr. Med. Chem.; Anti-Cancer Agents* 5:529-560; Bolden, J. E., et al. 2006 *Nat. Rev. Drug Discovery* 5:769-784). Their selective inhibition has recently become a major area of research in cancer chemotherapy (Minucci, S., et al. 2006 *Nature Rev. Cancer* 6:38-51). To date, eighteen HDACs have been identified, which are generally divided into four classes based on sequence homology to yeast counterparts (Taunton. J., et al. 1996 *Science* 272:408-411; Grozinger, C. M., et al. 1999 *Proc. Nat. Acad. Sci. USA* 96:4868-4873; Johnstone, R. W. 2002 *Nature Rev. Drug Disc.* 1:287-299). With respect to cancer therapy, there is an emerging consensus that Class 1 HDACs are clinically relevant, and that the undesirable toxicity associated with the first generation of HDAC inhibitors may be related to class indiscriminancy. As a result, programs have been initiated that are aimed at the synthesis and modification of peptide- and depsipeptide-based HDACi with the objective of optimizing structures for class- and even isoform-specific inhibition.

BRIEF SUMMARY OF THE INVENTION

The three natural substances FK228, FR901375, and spiruchostatin, are all activated in vitro and in vivo by reductive cleavage of a disulfide bond to expose the free sulfhydryl residue of the pendant (S)-3-hydroxy-7-mercaptohept-4-enoic acid moiety that coordinates to the active-site $Zn^{+2}$ residue of the HDACs resulting in a potent inhibitory effect (Yoshida, M., et al. 1990 *J. Biol. Chem.* 265:17174-17179; Yoshida, M., et al. 1990 *J. Antibiot.* 43:1101-1106). Given that largazole contains this well-known $Zn^{+2}$-binding arm, it would appear that largazole is simply a pro-drug that is activated by hydrolytic removal of the octanoyl residue by cellular lipases and/or esterases to produce the putative cytotoxic species 2 (the "largazole thiol"). It has previously been demonstrated that thioester analogues of FK228 retain their antiproliferative activity in cell-based assays (WO 2007/061939; Yurek-George, A., et al. 2007 *J. Med. Chem.* 50:5720-5726).

Previously reported was an efficient total synthesis of largazole, and the largazole thiol (2), as well as a demonstration that 2 is an extraordinarily potent HDACi. Further reported were additional largazole analogs, as well as uses of largazole, largazole thiol, and largazole analogs for the treatment of cancer and for the treatment of blood disorders.

In one aspect, the invention provides a compound of Formula (A)

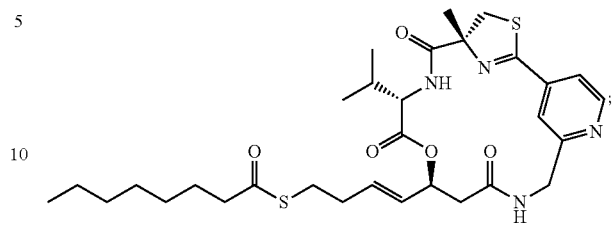

or a pharmaceutically acceptable salt, solvate, clathrate, prodrug, or stereoisomer thereof.

In another aspect, the invention provides a compound of Formula (B)

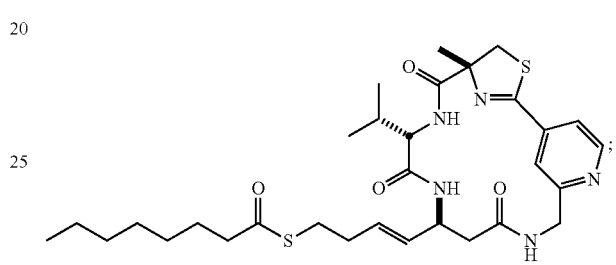

or a pharmaceutically acceptable salt, solvate, clathrate, prodrug, or stereoisomer thereof.

In another aspect, the invention provides a compound of Formula (C)

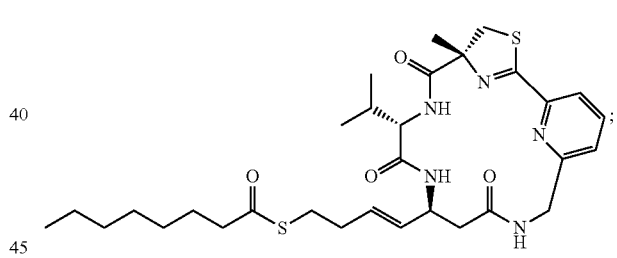

or a pharmaceutically acceptable salt, solvate, clathrate, prodrug, or stereoisomer thereof.

In another aspect, the invention provides a compound of claim Formula (D)

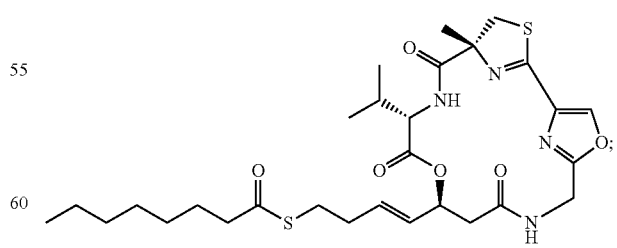

or a pharmaceutically acceptable salt, solvate, clathrate, prodrug, or stereoisomer thereof.

In another aspect, the invention provides a compound of claim Formula (E)

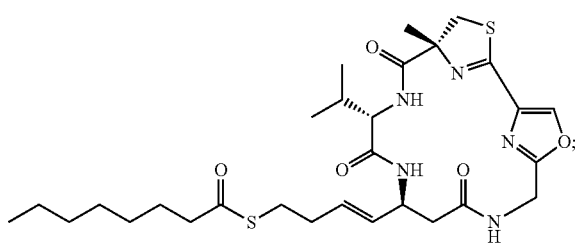 [SMILES: CCCCCCCC(=O)SCC/C=C/[C@@H]1CC(=O)NCc2nc(co2)C2=N[C@@](C)(CS2)C(=O)N[C@@H](C(C)C)C(=O)N1]

or a pharmaceutically acceptable salt, solvate, clathrate, prodrug, or stereoisomer thereof.

In one aspect, the invention provides a method for treating cancer in a subject, comprising administering to the subject a therapeutically effective amount of any one of the compounds described herein. In one embodiment, the method further comprises treating said subject with an additional form of therapy for cancer. In another embodiment, the method further comprises obtaining the compound. In yet another embodiment, the subject is human.

In another aspect, the invention provides a method for treating a blood disorder in a subject, comprising administering to the subject a therapeutically effective amount of any one of the compounds described herein. In one embodiment, the blood disorder is at least one of a hemoglobinopathy or a thalassemia. In another embodiment, the method further comprises treating said subject with an additional form of therapy for said blood disorder. In still another embodiment, the method further comprises obtaining the compound. In yet another embodiment, the subject is human.

In one aspect, the invention provides a pharmaceutical composition comprising a therapeutically effective amount of any one of the compounds described herein and at least one pharmaceutically acceptable excipient for treating cancer in a subject. In one embodiment, the subject is human.

In another aspect, the invention provides a pharmaceutical composition comprising a therapeutically effective amount of any one of the compounds described herein and at least one pharmaceutically acceptable excipient for treating a blood disorder in a subject. In another embodiment, the blood disorder is at least one of a hemoglobinopathy or a thalassemia. In still another embodiment, the subject is human.

In one aspect, the invention provides a composition comprising a radiolabelled compound of Formula (A), (B), (C), (D), or (E), or a pharmaceutically acceptable salt, solvate, clathrate, prodrug, or stereoisomer thereof.

Other aspects of the invention are described in or are obvious from the following disclosure and are within the ambit of the invention.

BRIEF DESCRIPTION OF THE FIGURES

The following Detailed Description of the Invention, given by way of Examples, but not intended to limit the invention to specific embodiments described, may be understood in conjunction with the accompanying figures, in which:

FIG. 6A-C shows Table P3, which provides tissue source and histology information for National Cancer Institute (NCI) cell lines.

FIG. 8 shows Table P4, which provides a summary of single dose studies for compounds according to the invention.

FIG. 13 shows Table P5, which provides a summary of the lethality of the compound of formula D against the impacted cell lines.

FIG. 14A-C shows Table P6, which provides the results of the five-dose studies for the compound of formula D.

DETAILED DESCRIPTION OF THE INVENTION

I. Definitions

Figure 1A:
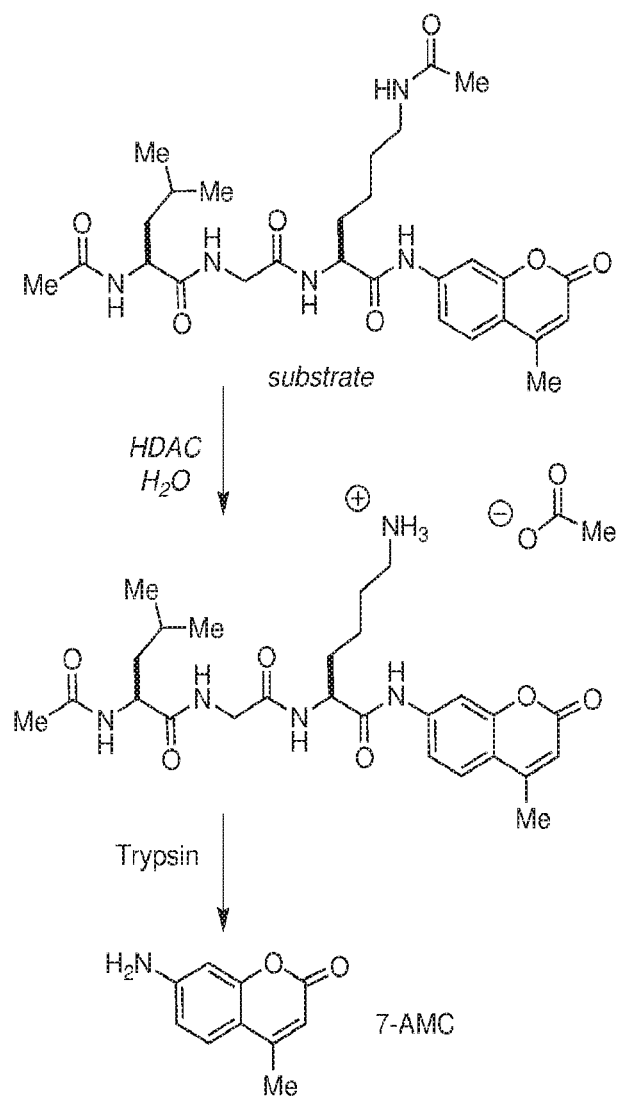
FIG. 1A schematically depicts the kinetic biochemical assay of HDAC function. The fluorophore 7-amino-4-methylcoumarin (7AMC) is linked by an amide bond to acetylated lysine in the context of a deacetylase substrate. Pictured is a derived substrate compatible with assays for HDAC1, HDAC2, HDAC3 and HDAC6. The deacetylase hydrolyzes the acetylated lysine, which is then a substrate for rapid trypsin digest releasing 7AMC (lower structure) detected in real time by a fluorescence plate-reader. Figure B graphically provides linear data captured after a pre-incubation phase (5-30 minutes) providing a kinetic assessment of deacetylase activity.

As used herein, the term "compound(s) of the invention" and similar terms refer to a compound of formula (I) or a pharmaceutically acceptable salt, solvate, clathrate, or prodrug thereof.

In the compound of Formula (I), the designation of one line parallel to a dotted line represents an optional double bond. When present, the double bond may be either is cis- or trans-configuration.

As used herein. "lower alkyl" or "lower alkyl moieties" contain from 1-12 carbon atoms, "lower aryl" or "lower aryl moieties" contain from 6-12 carbon atoms, and "lower arylalkyl" or "lower arylalkyl moieties" contain from 7-12 carbon atoms. In a preferred embodiment, lower alkyl refers to a $C_{1-7}$alkyl, lower aryl to a $C_{6-10}$aryl, and lower arylalkyl to a $C_{7-11}$aralkyl. Included are substituted derivatives of lower chain alkyl, aryl and arylalkyl moieties, wherein the substituent is selected from (but are not limited to) one or more of the following chemical moieties: —OH, —OR$_7$, —COOH, —COOR$_7$, —CONH$_2$, —NH$_2$, —NHR$_7$, —NR$_7$R$_7$, —SH, —SR$_7$, —SO$_2$R$_7$, —SO$_2$H, —SOR$_7$, —PO$_3$R$_7$, —OPO$_3$R$_7$, and halogen (including F, Cl, Br and I), wherein each occurrence of R$_7$ is independently selected from a lower chain alkyl, aryl or arylalkyl moiety. Moreover, cyclic lower chain alkyl, aryl and arylalkyl moieties of the invention include naphthalene, as well as heterocyclic compounds such as thiophene, pyrrole, furan, imidazole, oxazole, thiazole, pyrazole, 3-pyrroline, pyrrolidine, pyridine, pyrimidine, purine, quinoline, isoquinoline and carbazole.

As used herein, the term "prodrug" refers to a derivative of a compound that can hydrolyze, oxidize, or otherwise react under biological conditions (in vitro or in vivo) to provide a compound of the invention. Prodrugs may only become active upon some reaction under biological conditions, but they may have activity in their unreacted forms. Examples of prodrugs contemplated herein include, without limitation, analogs or derivatives of compounds of the invention. Examples of prodrug moieties include substituted and unsubstituted, branch or unbranched lower alkyl ester moieties. (e.g., propionoic acid esters), lower alkenyl esters, di-lower alkyl-amino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Prodrugs and their uses are well known in the art (see, e.g., Berge, et al. 1977 *J. Pharm. Sci.* 66:1-19). Prodrugs can typically be prepared using well-known methods, such as those described in Burger's Medicinal Chemistry and Drug Discovery (1995, Manfred E. Wolff ed., 5$^{th}$ ed. 172-178, 931-932).

It will be noted that the structure of some of the compounds of this invention includes asymmetric carbon atoms, and thus may exist as racemic mixtures or as isolated isomeric forms. It is to be understood accordingly that the isomers arising from such asymmetry (e.g., all enantiomers and diastereomers) are included within the scope of this invention, unless indicated otherwise. Such isomers can be obtained in substantially pure form by classical separation techniques and by stereochemically controlled synthesis. Furthermore, the structures and other compounds and moieties discussed in this application also include all tautomers thereof.

Furthermore, some of the crystalline forms of the compounds of Formula (I) may exist as polymorphs, which are included in the present invention. In addition, some of the compounds of Formula (I) may also form solvates with water or other organic solvents. Such solvates are similarly included within the scope of this invention.

The term "treating", as used herein, refers to altering the disease course of the subject being treated. Therapeutic effects of treatment include, without limitation, preventing occurrence or recurrence of disease, alleviation of symptom(s), diminishment of direct or indirect pathological consequences of the disease, decreasing the rate of disease progression, amelioration or palliation of the disease state, and remission or improved prognosis.

Cancer is a term used for diseases in which abnormal cells divide without control and are able to invade other tissues. There are more than 100 different types of cancer. Most cancers are named for the organ or type of cell in which they start—for example, cancer that begins in the colon is called colon cancer: cancer that begins in basal cells of the skin is called basal cell carcinoma. The main categories of cancer include carcinomas, sarcomas, leukemias, lymphomas and myelomas, and central nervous system cancers. Some common cancer types include, but are not limited to, bladder cancer, breast cancer, colon and rectal cancer, endometrial cancer, kidney (renal cell) cancer, leukemia, lung cancer, melanoma, non-Hodgkin's lymphoma, pancreatic cancer, prostate cancer, skin cancer (non-melanoma), and thyroid cancer. In a preferred embodiment, the cancers contemplated for treatment herein include cutaneous T-cell lymphoma, non-Hodgkin's and Hodgkin's lymphoma, pancreatic cancer, and ovarian cancer.

Hemoglobinopathies and thalassemias can both be characterized as "blood disorders". Blood disorders includes disorders that can be treated, prevented, or otherwise ameliorated by the administration of a compound of the invention. A blood disorder is any disorder of the blood and blood-forming organs. The term blood disorder includes nutritional anemias (e.g., iron deficiency anemia, sideropenic dysphasia, Plummer-Vinson syndrome, vitamin B12 deficiency anemia, vitamin B12 deficiency anemia due to intrinsic factor, pernicious anemia, folate deficiency anemia, and other nutritional anemias), myelodysplastic syndrome, bone marrow failure or anemia resulting from chemotherapy, radiation or other agents or therapies, hemolytic anemias (e.g., anemia due to enzyme disorders, anemia due to phosphate dehydrogenase (G6PD) deficiency, favism, anemia due to disorders of glutathione metabolism, anemia due to disorders of glycolytic enzymes, anemias due to disorders of nucleotide metabolism and anemias due to unspecified enzyme disorder), thalassemia, α-thalassemia, β-thalassemia, δβ-thalassemia, thalassemia trait, hereditary persistence of fetal hemoglobin (HPFP), and other thalassemias, sickle cell disorders (sickle cell anemia with crisis, sickle cell anemia without crisis, double heterozygous sickling disorders, sickle cell trait and other sickle cell disorders), hereditary hemolytic anemias (hereditary spherocytosis, hereditary elliptocytosis, other hemoglobinopathies and other specified hereditary hemolytic anemias, such as stomatocyclosis), acquired hemolytic anemia (e.g., drug-induced autoimmune hemolytic anemia, other autoimmune hemolytic anemias, such as warm autoimmune hemolytic anemia, drug-induced non-autoimmune hemolytic anemia, hemolytic-uremic syndrome, and other non-autoimmune hemolytic anemias, such as microangiopathic hemolytic anemia); aplastic anemias (e.g., acquired pure red cell aplasia (erythoblastopenia), other aplastic anemias, such as constitutional aplastic anemia and Fanconi anemia, acute posthemorrhagic anemic, and anemias in chronic diseases), coagulation defects (e.g., disseminated intravascular coagulation (difibrination syndrome)), hereditary factor VIII deficiency (hemophilia A), hereditary factor 1x deficiency (Christmas disease), and other coagulation defects such as Von Willebrand's disease, hereditary factor Xi deficiency (hemophilia C), purpura (e.g., qualitative platelet defects and Glanzmann's disease), neutropenia, agranulocytosis, functional disorders of polymorphonuclear neutrophils, other disorders of white blood cells (e.g., eosinophilia, leukocytosis, lymphocytosis, lymphopenia, monocytosis, and plasmacyclosis), diseases of the spleen, methemoglobinemia, other diseases of blood and blood forming organs (e.g., familial erythrocytosis, secondary polycythemia, essential thrombocytosis and basophilia), thrombocytopenia, infectious anemia, hypoproliferative or hypoplastic anemias, hemoglobin C, D and E disease, hemoglobin lepore disease, and HbH and HbS diseases, anemias due to blood loss, radiation therapy or chemotherapy, or thrombocytopenias and neutropenias due to radiation therapy or chemotherapy, sideroblastic anemias, myelophthisic anemias, antibody-mediated anemias, and certain diseases involving lymphoreticular tissue and reticulohistiocytic system (e.g., Langerhans' cell hystiocytosis, eosinophilic granuloma, Hand-Schuller-Christian disease, hemophagocytic lymphohistiocytosis, and infection-associated hemophagocytic syndrome).

The term "pharmaceutically acceptable excipient", as used herein, refers to carriers and vehicles that are compatible with the active ingredient (for example, a compound of the invention) of a pharmaceutical composition of the invention (and preferably capable of stabilizing it) and not deleterious to the subject to be treated. For example, solubilizing agents that form specific, more soluble complexes with the compounds of the invention can be utilized as pharmaceutical excipients for delivery of the compounds. Suitable carriers and vehicles are known to those of extraordinary skill in the art. The term "excipient" as used herein will encompass all such carriers, adjuvants, diluents, solvents, or other inactive additives. Suitable pharmaceutically acceptable excipients include, but are not limited to, water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethyl-cellulose, polyvinylpyrrolidone, etc. The pharmaceutical compositions of the invention can also be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like, which do not deleteriously react with the active compounds of the invention.

The compounds of the invention that are basic in nature are capable of forming a wide variety of salts with various inorganic and organic acids. The acids that may be used to prepare pharmaceutically acceptable acid addition salts of the compounds of the invention that are basic in nature are those that form non-toxic acid addition salts, i.e., salts containing pharmaceutically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and palmoate [i.e., 1,1'-methylene-bis-(2-hydroxy-3-naphthoate)] salts. Although such salts must be pharmaceutically acceptable for administration to a subject, e.g., a mammal, it is often desirable in practice to initially isolate a compound of the invention from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained. The preparation of other compounds of the invention not specifically described in the foregoing experimental section can be accomplished using combinations of the reactions described above that will be apparent to those skilled in the art.

Thus, as used herein, the term "pharmaceutically acceptable salt." is a salt formed from an acid and a basic group of a compound of the invention. Illustrative salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, and pamoate salts.

The term "pharmaceutically acceptable salt" also refers to a salt prepared from a compound of the invention having an acidic functional group, such as a carboxylic acid functional group, and a pharmaceutically acceptable inorganic or organic base. Suitable bases include, but are not limited to, hydroxides of alkali metals such as sodium, potassium, and lithium, hydroxides of alkaline earth metal such as calcium and magnesium: hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl. N-ethylamine; diethylamine; triethylamine; mono-, bis-, or tris-(2-hydroxy-lower alkyl amines), such as mono-, bis-, or tris-(2-hydroxyethyl)amine, 2-hydroxy-tertbutylamine, or tris-(hydroxymethyl)methylamine, N,N,-dilower alkyl-N-(hydroxy lower alkyl)-amines, such as N,N-dimethyl-N-(2-hydroxyethyl)amine, or tri-(2-hydroxyethyl)amine; N-methyl-D-glucamine; and amino acids such as arginine, lysine, and the like. Other pharmaceutically acceptable salts are described in the Handbook of Pharmaceutical Salts. Properties, Selection, and Use (P. Heinrich Stahl and C. Wermuth, Eds., Verlag Helvetica Chica Acta, Zurich, Switzerland (2002)).

The term "subject" as used herein refers to a vertebrate, preferably a mammal, more preferably a primate, still more preferably a human. Mammals include, without limitation, humans, primates, wild animals, feral animals, farm animals, sports animals, and pets.

The term "therapeutically effective amount" as used herein refers to an amount sufficient to effect a beneficial or desired clinical result upon treatment. Specifically, the term "therapeutically effective amount" means an amount of a compound of this invention sufficient to measurably (i) reduce or inhibit the growth of transformed (cancer) cells in a relevant in vitro assay or cause a measurable improvement in an animal model of cancer and/or (ii) induce expression of fetal hemoglobin in a relevant in vitro assay or cause a measurable improvement in an animal model of a hemoglobinopathy and/or thalassemia, for example, a sickle cell disease. Alternatively, a "therapeutically effective amount" is an amount of a compound of this invention sufficient to confer a therapeutic or prophylactic effect on the treated subject against (i) cancer and/or (ii) a hemoglobinopathy and/or thalassemia. Therapeutically effective amounts will vary, as recognized by those skilled in the art, depending on the specific disease treated, the route of administration, the excipient selected, and the possibility of combination therapy.

Physiological effects that can be measured to determine the therapeutically effective amount include, without limitation, substrate protein hyperacetylation (histone, tubulin, hsp90, p53. STAT, etc.), gene induction (fetal hemoglobin, spinal muscle atrophy gene), impaired protein trafficking, improved neuronal vesicle trafficking, induction of apoptosis, cell cycle arrest, and induction of p21.

Relevant assays to measure such effects include, without limitation, Western (immuno)blot. RT-PCR, expression profile by microarray or other technology, high-content immunofluorescence, cytoblot, biochemical inhibition of HDAC proteins, alterations in chromatin structure by ChIP, and alterations in histone and/or other target protein modification by mass spectrometry.

The term "obtaining" as in "obtaining the compound" is intended to include purchasing, synthesizing or otherwise acquiring the compound (or indicated substance or material).

The terms "comprises", "comprising", are intended to have the broad meaning ascribed to them in U.S. Patent Law and can mean "includes", "including" and the like.

The invention can be understood more fully by reference to the following detailed description and illustrative examples, which are intended to exemplify non-limiting embodiments of the invention.

II. Embodiments of the Invention

Compounds of the Invention

The compounds of the invention are defined herein by their chemical structures and/or chemical names. The compounds of the invention are generally named according to the IUPAC or CAS nomenclature system. Abbreviations that are well known to one of ordinary skill in the art may be used. When a compound is referred to by both a chemical structure and a chemical name, and the chemical structure and chemical name conflict, the chemical structure is determinative of the compound's identity.

A dotted line parallel to a solid line in a chemical structure indicates the optional presence of a double bond. Two dotted lines parallel to solid lines adjacent to one another indicates the optional presence of a double bond in either, but not both, of the two positions. Either an E (trans) or Z (cis) geometry is indicated. In fact, all alkenes contemplated herein can exist as either E (trans) or Z (cis) geometry.

When administered to a subject, the compounds of the invention are administered in isolated form or as the isolated form in a pharmaceutical composition. As used herein. "isolated" means that the compounds of the invention are separated from other components of either (a) a natural source, such as a plant or cell, preferably bacterial culture, or (b) a synthetic organic chemical reaction mixture. Preferably, via conventional techniques, the compounds of the invention are purified. As used herein. "purified" means that when isolated, the isolate contains at least about 80%, preferably at least about 90%, more preferably at least about 95% and even more preferably at least about 98%, of a single compound of the invention by weight of the isolate.

Radioactive compounds have a long history of use in the discovery of new drugs. The compounds of the invention all have the potential to be easily radiolabeled and can be used to discover other new agents that (i) reduce or inhibit the growth of transformed (cancer) cells and/or (ii) induce fetal hemoglobin expression. For example, radioactive compounds of the invention can be utilized to validate, optimize, and standardize bioassays used for discovery of other compounds that (i) reduce or inhibit the growth of transformed (cancer) cells and/or (ii) induce fetal hemoglobin expression. Likewise, radioactive compounds of the invention can be utilized as a benchmark to discover compounds that show improved activity in bioassays that (i) reduce or inhibit the growth of transformed (cancer) cells and/or (ii) induce fetal hemoglobin expression.

In one embodiment, the invention is directed to the largazole analogs:

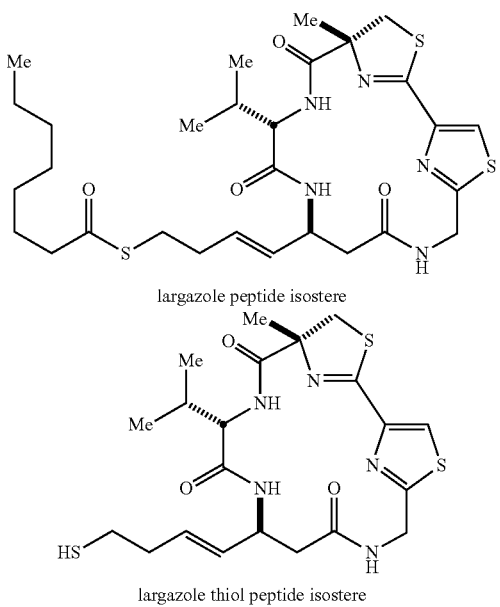

largazole peptide isostere largazole thiol peptide isostere

In another embodiment, the invention is directed to the largazole analogs:

(1) oxazole-oxazoline analog

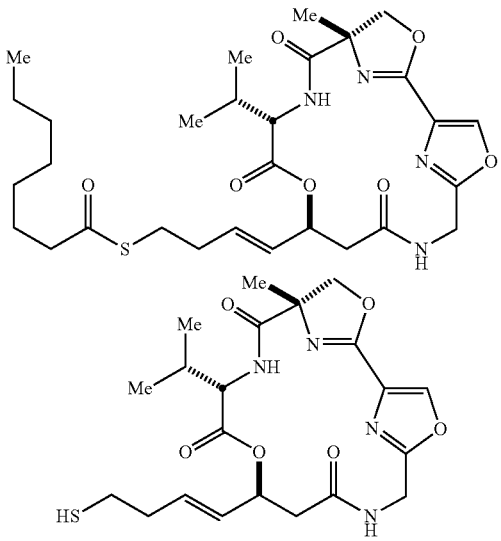

(2) Saturated largazole

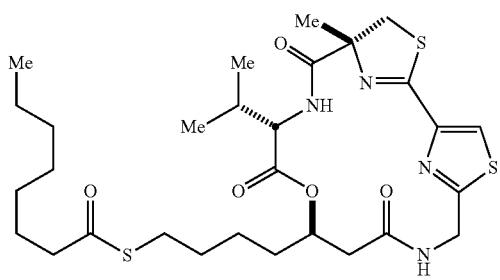

(3) Longer side-chain analogs:

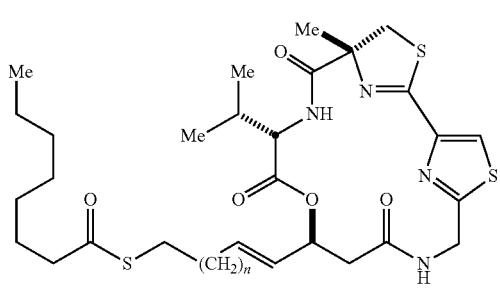

longer chain analogs,
where n = 1 = largazole
n = 2
n = 3

(4) Valine to proline replacement:

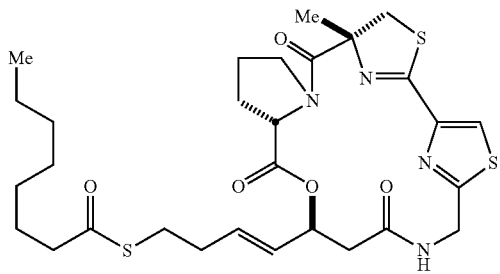

Preparation of Compounds of the Invention

The compounds of the invention can be prepared in an efficient, cost-effective manner.

Disconnection of the macrocycle to the four key subunits, that is, α-methyl cysteine (3), thiazole (4), (S)-valine (5), and (S)-3-hydroxy-7-mercaptohept-4-enoic acid (6), is illustrated below.

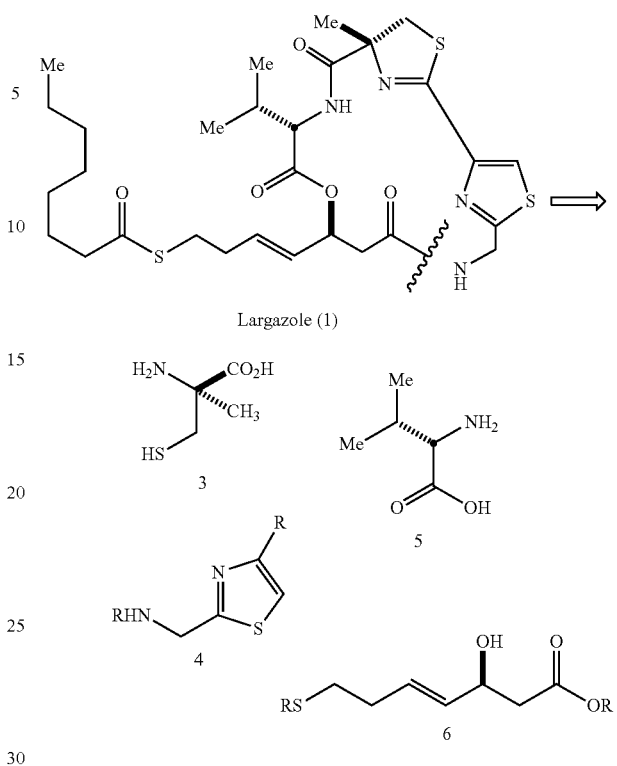

Largazole (1)

Given the ready availability of these building blocks from prior efforts (Jeanguenat. A, and Seebach 1991 *J. Chem. Soc., Perkin Trans.* 1:2291-2298; Mulqueen. G. C., et al. 1993 *Tetrahedron* 49:5359-5364; Li, K. W., et al. 1996 *J Am Chem Soc* 118:7237-7238; Chen. Y., et al. 2003 *J Org Chem* 68:8902-8905; Yurek-George, A., et al. 2004 *J Am Chem Soc* 126:1030-1031), the underlying synthetic challenge turned out to be the macrocyclization strategy. Due to the anticipated susceptibility of the β-carboxylate linkage to undergo elimination, initial efforts were focused on installing this linkage last. However, all methods, both direct (macrolactonization via Yamaguchi. Mukaiyama. Keck, and Shiina procedures) and indirect (inversion via Mitsunobu reaction) failed to provide the desired macrocycle. An additional attempt at closure of the depsipeptide ring via a late-stage thiazoline-forming reaction also failed to provide the desired macrocyclic product.

Thus, a strategy involving early installation of the ester and subsequent closure about the least-hindered amide bond was employed. The necessary α-methyl cysteine subunit with the requisite (R)-stereochemistry was obtained via the Pattenden modification of the Seebach protocol on L-cysteine methyl ester (Scheme 1, below) (Jeanguenat. A, and Seebach 1991 *J. Chem. Soc., Perkin Trans.* 1:2291-2298; Mulqueen, G. C., et al. 1993 *Tetrahedron* 49:5359-5364). Alternatively, α-methyl serine was obtained and converted into α-methyl cysteine by a published procedure (Smith, N. D. and Goodman, M. 2003 *Org. Lett.* 5:1035-1037). Gram quantities of this amino acid were obtained in high enantiomeric purity and condensed with the known nitrile (7) (Videnov. G., et al. 1996 *Angew. Chem. Int. Ed. Eng.* 35:1503-1506; Lange, U. E. W., et al. 1999 *Tetrahedron Lett.* 40:7067-7070) to provide the thiazoline-thiazole subunit (8) in high yield.

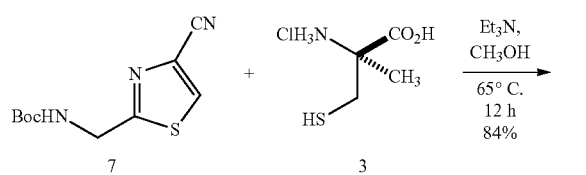

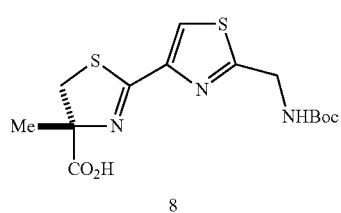

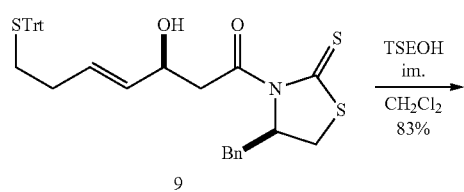

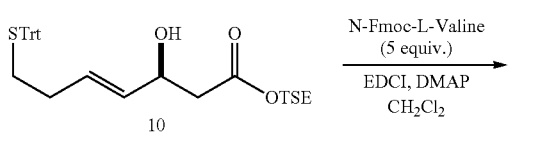

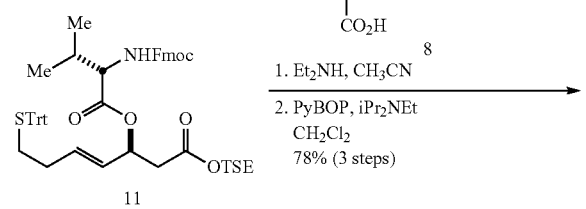

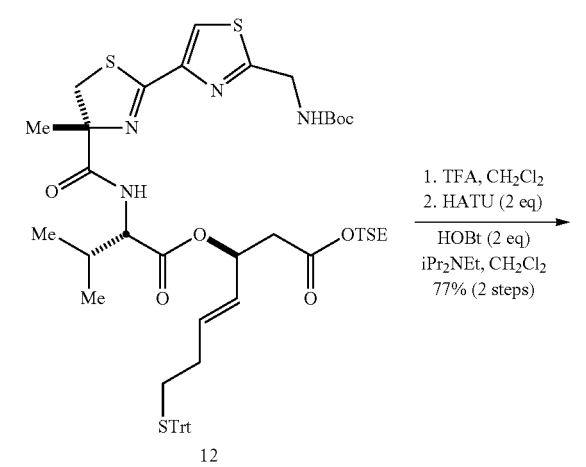

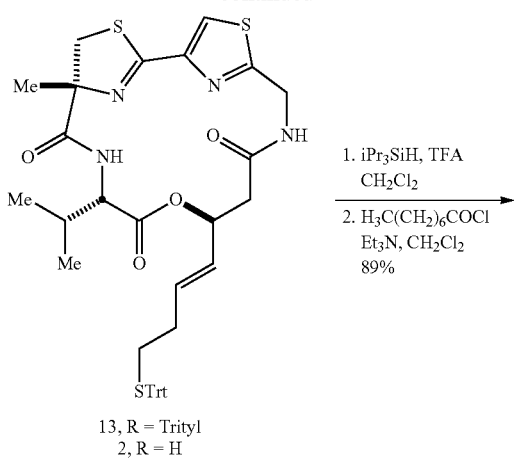

13, R = Trityl
2, R = H

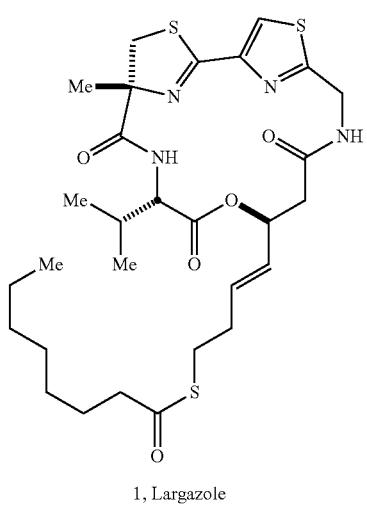

1, Largazole

A novel synthetic route to the β-hydroxy acid (10) has recently been found based on a Noyori asymmetric transfer hydrogenation (Greshock, D. M., et al. 2008 *Org Lett* 10:613-616). A recently elucidated synthesis of this subunit has also been found to be expedient and high yielding (Yurek-George. A., et al. 2004 *J. Am. Chem. Soc.* 126:1030-1031). Thiazolidinethione (9) was treated with 2-trimethylsilylethanol to provide the TSE-protected acid (10), which was subsequently coupled to N-Fmoc-L-valine to afford 11. Due to the sluggish reactivity of allylic alcohol 10, it was found necessary to use an excess (5 equivalents) of the commercially available amino acid. Removal of the Fmoc group and PyBOP-mediated coupling to the thiazoline-thiazole carboxylic acid (8) furnished the acyclic precursor (12).

Cyclization was effected under high dilution in the presence of two equivalents each of HOBt and HATU, furnishing the desired macrocycle 13 in 77% isolated yield from 12. Removal of the S-trityl protecting group was accomplished with iPr$_3$SiH and TFA to provide an authentic sample of the largazole thiol (2) in excellent yield.

Acylation of 2 with octanoyl chloride under standard conditions afforded synthetic largazole in 89% yield from 13. The spectroscopic data ($^1$H NMR, $^{13}$C NMR and HRMS) for the synthetic substance were in excellent agreement with that published for the natural product.[1]

As regards the synthesis of largazole analogs, several schemes are described as follows:
1. Synthesis of the largazole peptide isostere:
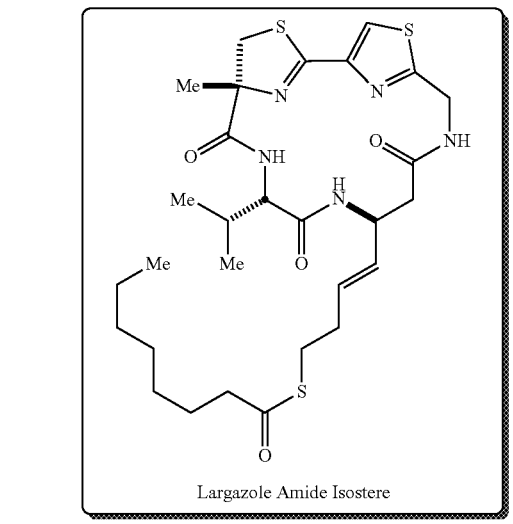
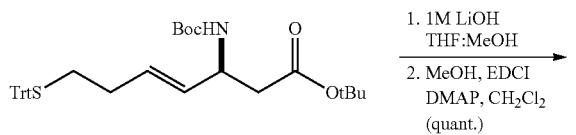
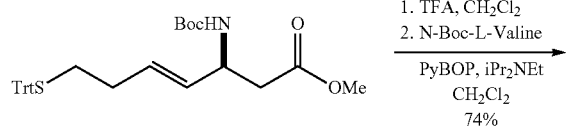
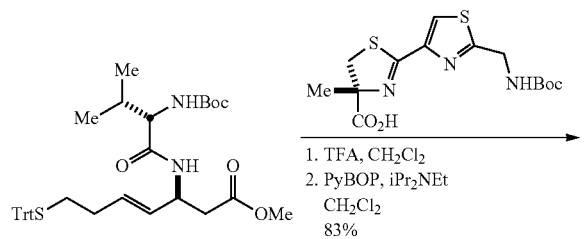
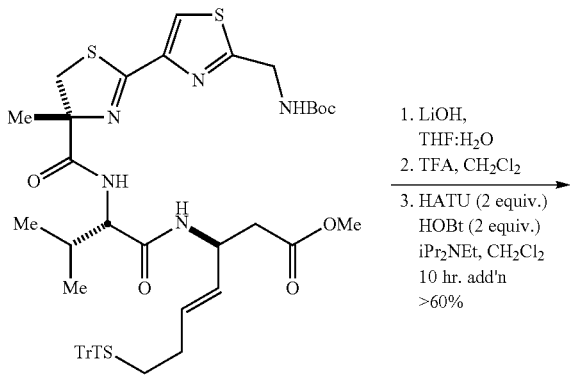
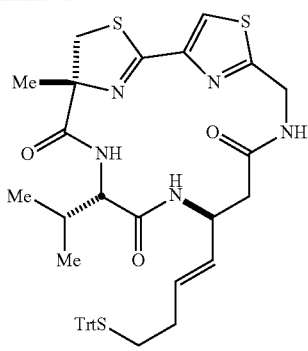
2. Synthesis of zinc-binding domain (side-chain) analogs:
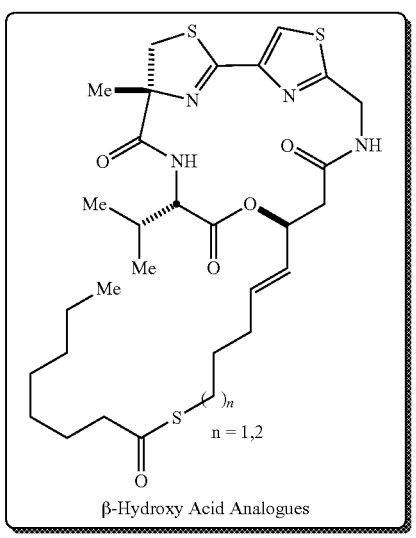
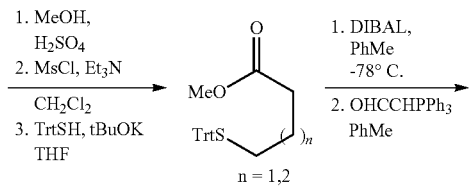
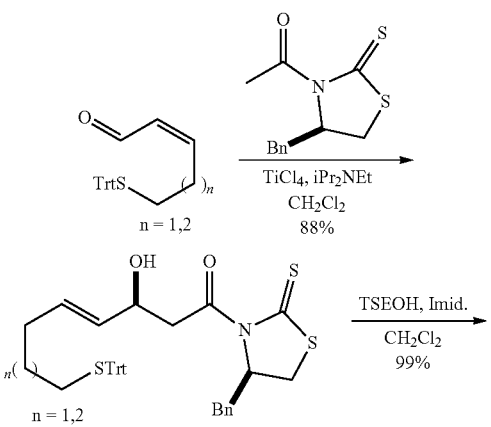

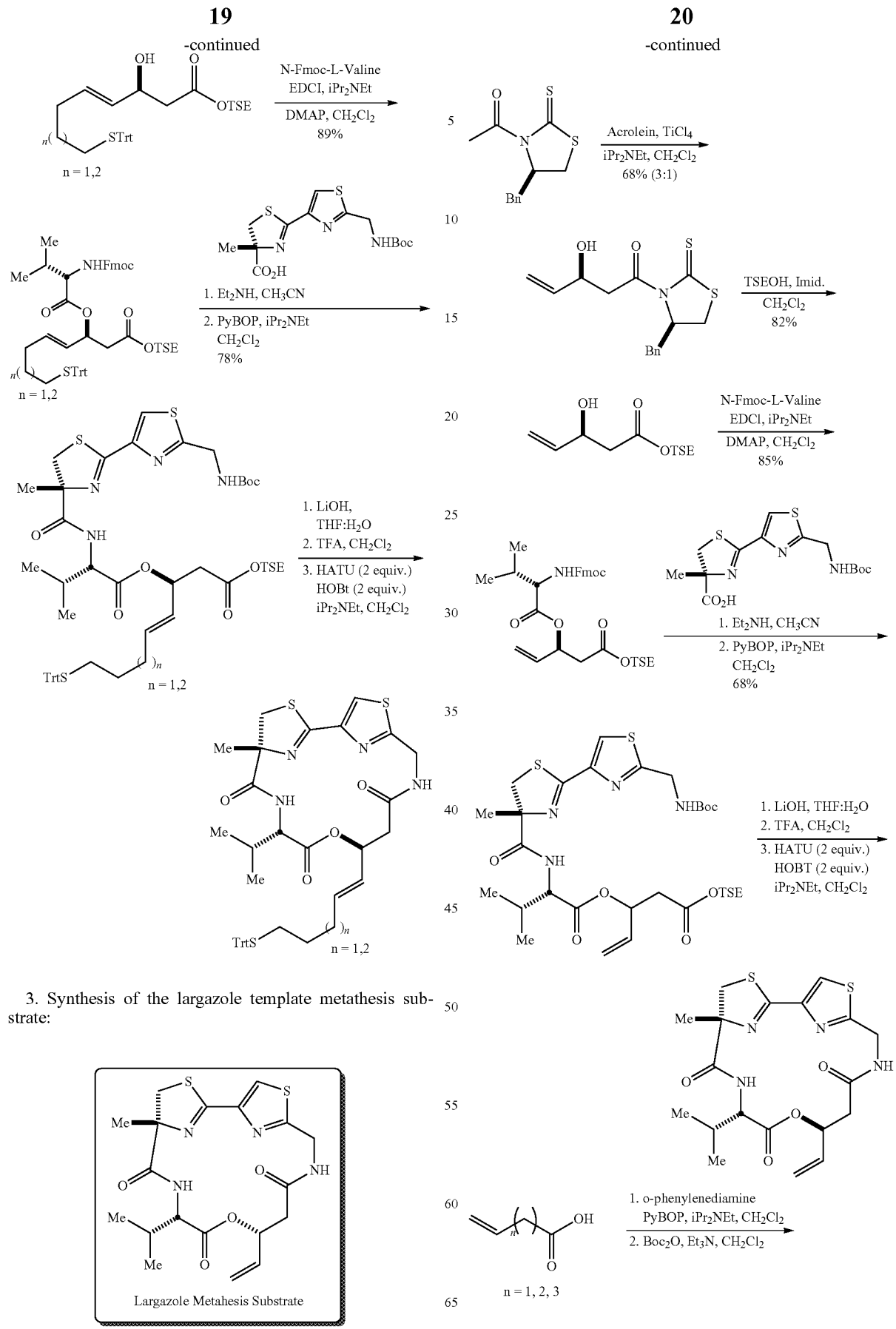
3. Synthesis of the largazole template metathesis substrate:

21
-continued
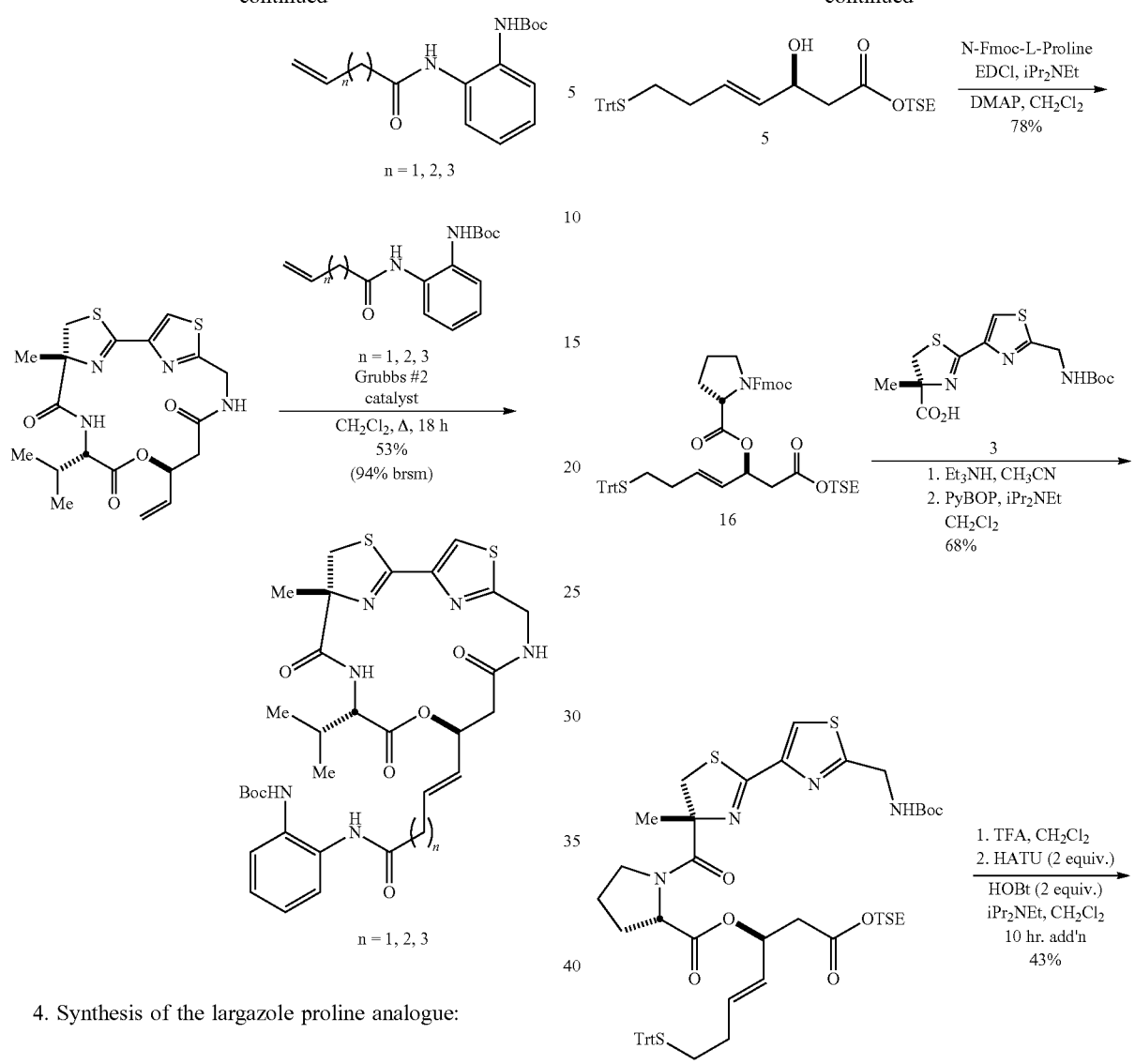
4. Synthesis of the largazole proline analogue:
22
-continued
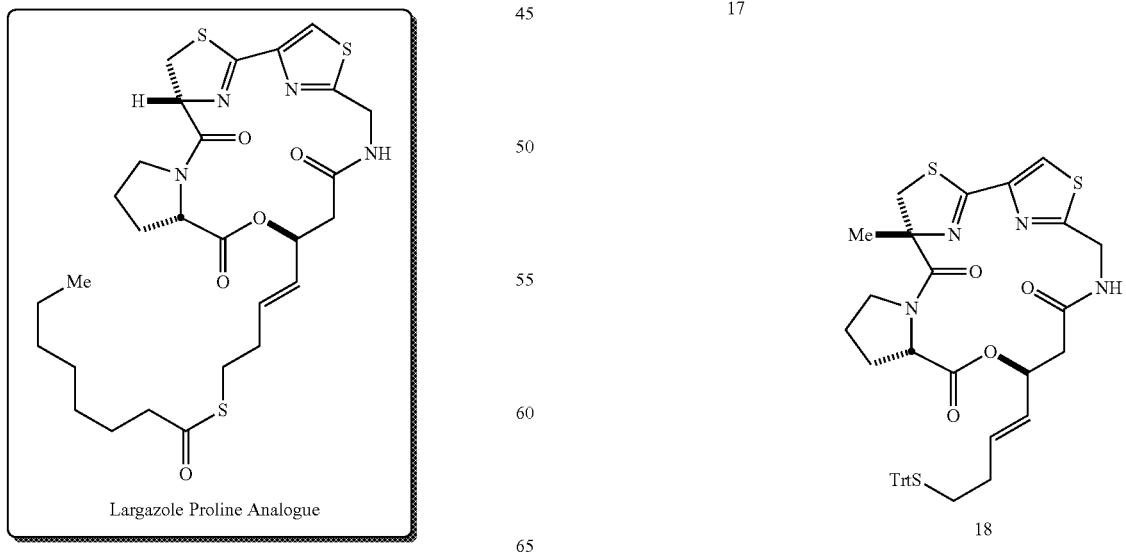

5. Synthesis of largazole oxazoline-oxazole analogue:
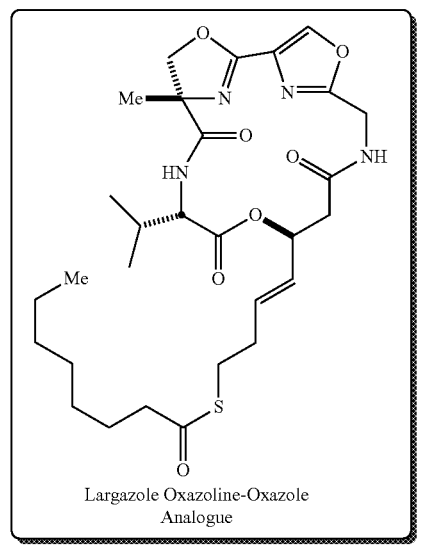
Largazole Oxazoline-Oxazole Analogue
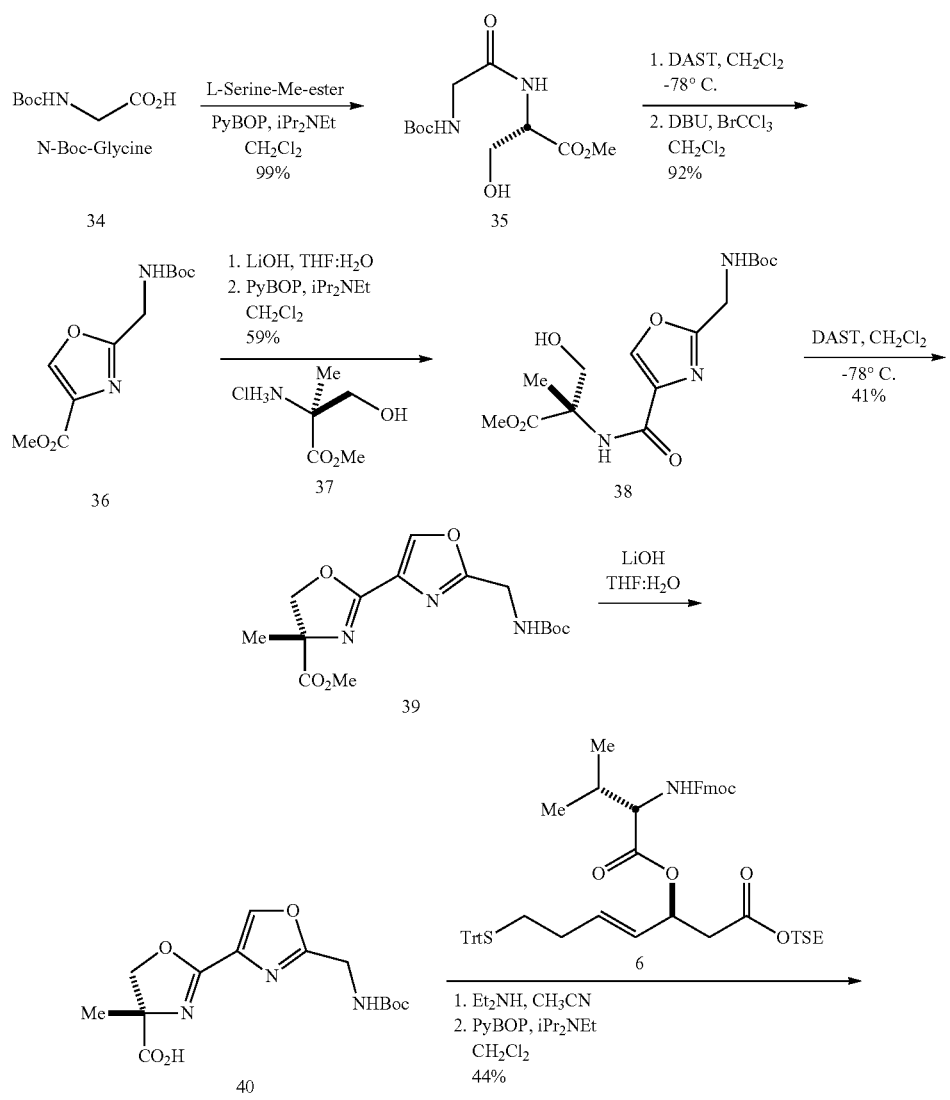

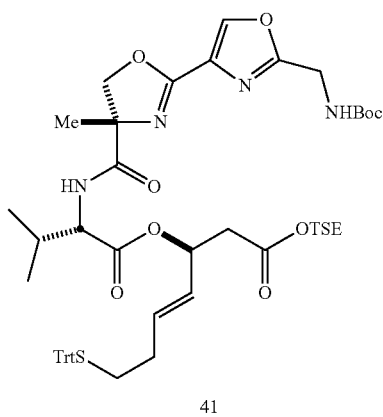

41

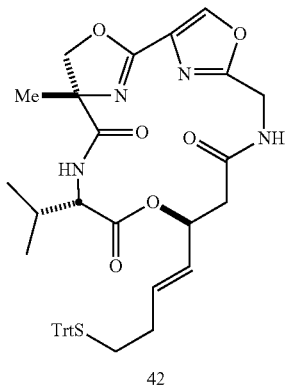

42

1. TFA, CH$_2$Cl$_2$
2. HATU (2 equiv.)

HOBt (2 equiv.)
iPr$_2$NEt, CH$_2$Cl$_2$
10 hr. add'n

Having recently disclosed a concise, modular, and scalable total synthesis of Largazole and demonstrated its picomolar activity against HDACs 1, 2, and 3, as well as low nanomolar cytotoxicity against a number of chemoresistant cancer cell lines (Vanommeslaeghe, K., et al. 2005 *Bioorg. Med. Chem.* 13:6070-6082; Vanommeslaeghe, K., et al. 2005 *Bioorg. Med. Chem.* 13:3987-3992) and having disclosed a detailed conformation-activity relationship model for Largazole, FK228, and their corresponding amide isosteres with insights into the key contacts and associated spatial determinants that provide this remarkable level of activity (Somech, R., et al. 2004 *Cancer Treat. Rev.* 30:461; Miller. T. A., et al. 2003 *J. Med. Chem.* 46:5097-5116; Moradei, O., et al. 2005 *Curr. Med. Chem.; Anti-Cancer Agents* 5:529-560; Bolden, J. E., et al. 2006 *Nat. Rev. Drug Discovery* 5:769-784), described herein are efforts to modify the structural scaffold of Largazole in an effort to further define and expand structure-activity relationships within the family of macrocyclic HDACi's.

The previously reported route to Largazole proved highly reproducible and could be adapted to simple variants of the macrocyclic core (Bowers. A. A., et al. 2008 *J Am Chem Soc* 130:11219-22). Thus, milligram quantities of the C-2 epimer (3) and the enantiomer (2) of Largazole were easily accessible. Efforts to perturb the conformation of the macrocycle by imparting greater rigidity resulted in the replacement of the valine residue with proline (4). Compound 4 could be obtained in only slightly diminished overall yield via the same synthetic route deployed in the total synthesis of Largazole.

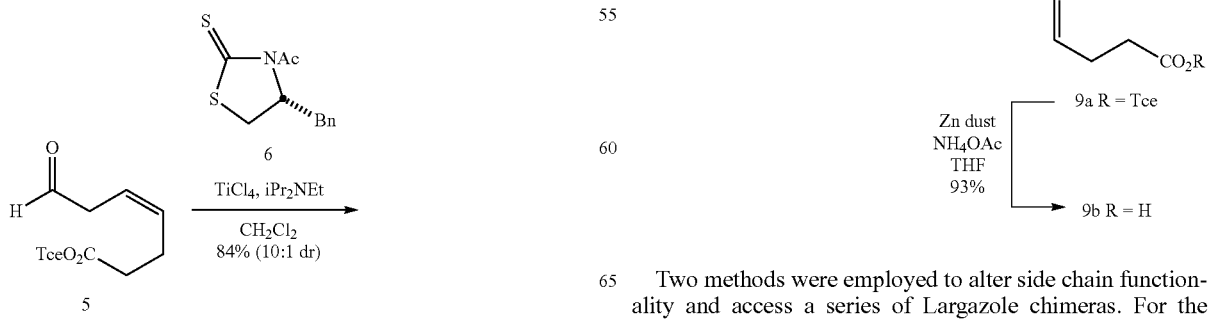

Two methods were employed to alter side chain functionality and access a series of Largazole chimeras. For the Largazole-Azumamide hybrid (9), the cis-geometry of the alkene residue necessitated its early introduction. Thus, aldol condensation of aldehyde 5 with thiazolidine-2-thione 6 provided the necessary 3-hydroxy acid building block (7, Scheme 1, above). For other variants investigated, late-stage introduction of the zinc-binding side arms via cross metathesis proved expedient. Cross metathesis to attach the natural side-chain in their syntheses of Largazole itself was investigated (Nasveschuk, C. G., et al. 2008 *Org. Lett.* 10:3595-3598; Ghosh, A. K, and Kulkarni, S. 2008 *Org. Lett.* 10:3907-3909; Ying, Y., et al. 2008 *J. Am. Chem. Soc.* 130:8455-8459; Seiser, T.: et al. 2008 *Angew. Chem. Int. Ed.* 47:6483-6485).

For Largazole, the four-atom linker length relative to the thiol has been found to be optimal for maximum HDAC inhibition. However, literature precedent has shown that a four- to five-atom chain is optimal in small molecules bearing alternative zinc-binding functionality. Therefore, in the series of analogs prepared via metathesis, both the four- and the five-atom tethers were synthesized.

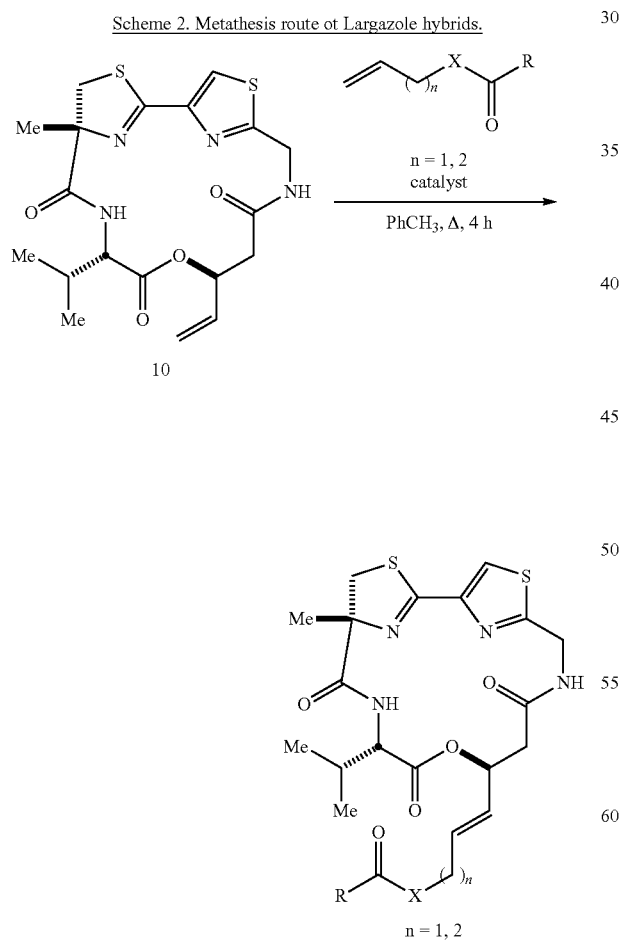

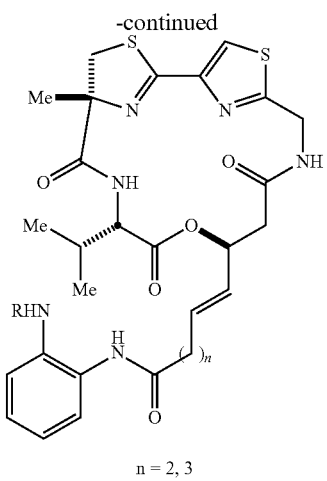

n = 2, 3

11a (n = 2, R = Boc) 30%[a]
→ 11b (n = 2, R = H)
12a (n = 3, R = Boc) 20%[a]
→ 12b (n = 3, R = H)

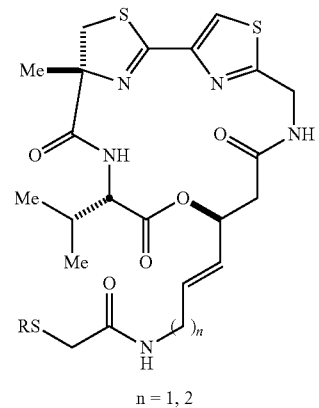

n = 1, 2

13a (n = 1, R = Trt) 42%[b]
→ 13b (n = 1, R = H)
14a (n = 2, R = Trt) 15%[a]
→ 14b (n = 2, R = H)

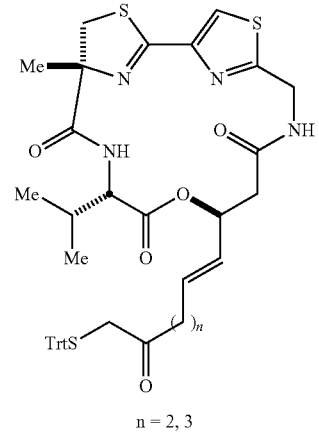

n = 2, 3

15a (n = 2) 51%[b]
16a (n = 3) 62%[b]

Conditions: (a) Grubbs's 2nd generation (b) Hoveyda-Grubb's 2nd generation

Compounds 11 and 12 bear an α-aminobenzamide group. Meanwhile, compounds 13, 14 and 15, 16 contain α-thioamides and α-thioketones, respectively. These two motifs were identified as potential candidates in a computational study and have demonstrated promise in subsequent medicinal efforts (Furumai, R., et al. 2001 *PNAS USA* 98:87-92; Nishino, N., et al. 2003 *Org Lett* 5:5079-5082). Initial yields employing Grubb's second-generation ruthenium catalyst were low with poor conversion. The Hoveyda-Grubbs second-generation catalyst proved much more efficient. All Boc- and Trityl-protecting groups were removed prior to biological assay.

The significance of the methyl substituent on the thiazoline ring was also examined. Condensation of nitrile 17 with L-cysteine proved remarkably facile, proceeding in near quantitative yield (Scheme 3, below). Initial efforts at coupling to ester 19 provided poor yields of the desired acyclic precursor 20. The major product was thiazole-thiazole 21, resulting from in situ oxidation. Optimization of conditions for this coupling eventually allowed for up to 62% yield of the desired product. Oxidation could be the cause of the somewhat diminished yields in the cyclization of 20. Compound 23 could not be detected in NMR spectra of the crude reaction mixtures from cyclization of 20. Moreover. 23 could not be prepared directly from its acyclic precursor 21. Instead, oxidation of 22 under standard conditions provided 23. This macrocycle clearly contains some added constraint, as demonstrated by the presence of rotamers in the $^1$H NMR spectrum in CDCl$_3$. Both substrate 22a and 23a could be deprotected in good yield using standard conditions previously described.

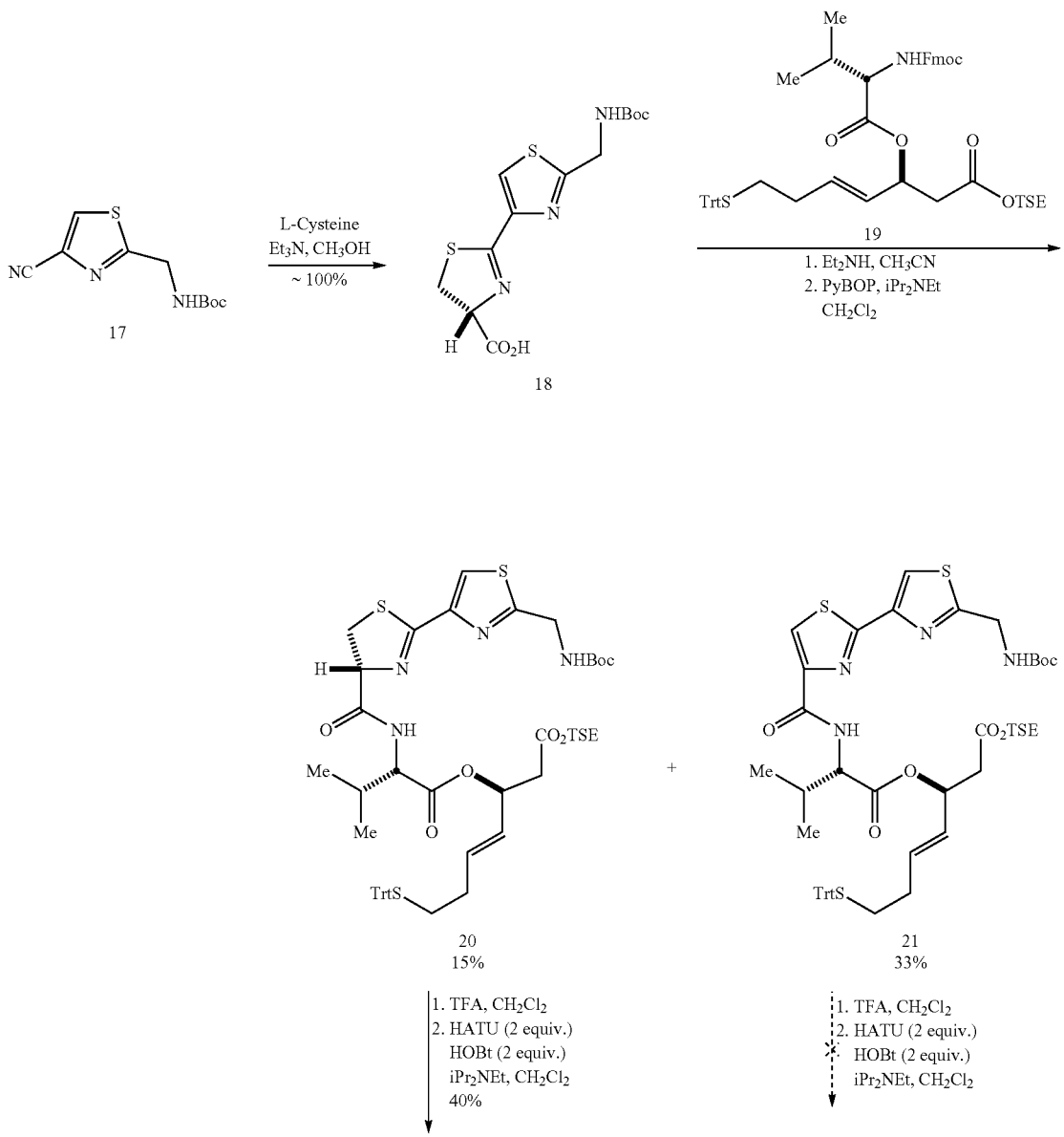

Scheme 3. Synthesis of cysteine & thiazole-thaizole analogs.

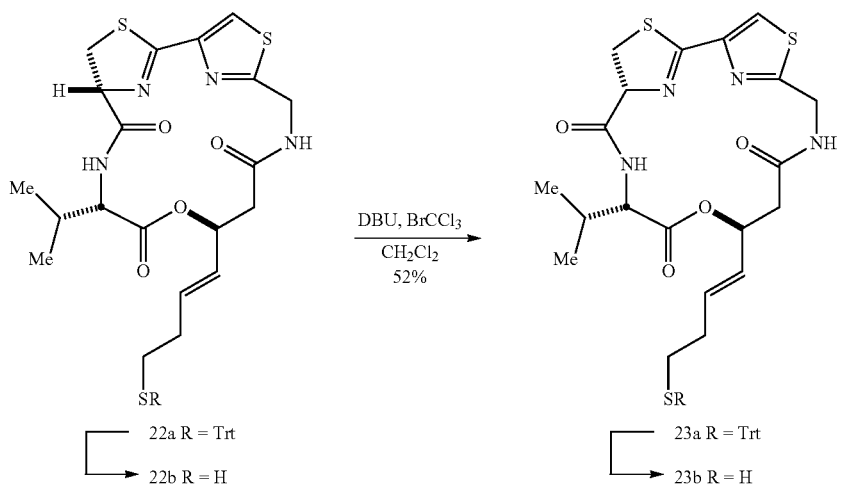

Replacement of the thiazole moiety with a pyridine residue in the heterocyclic backbone was readily amenable to the synthetic strategy described herein (Scheme 4, below). Chloro-nitrile 24 could be Boc-protected and then condensed with α-methyl cysteine to provide acid 27. Subsequent deprotection, coupling, and cyclization provided analog 29.

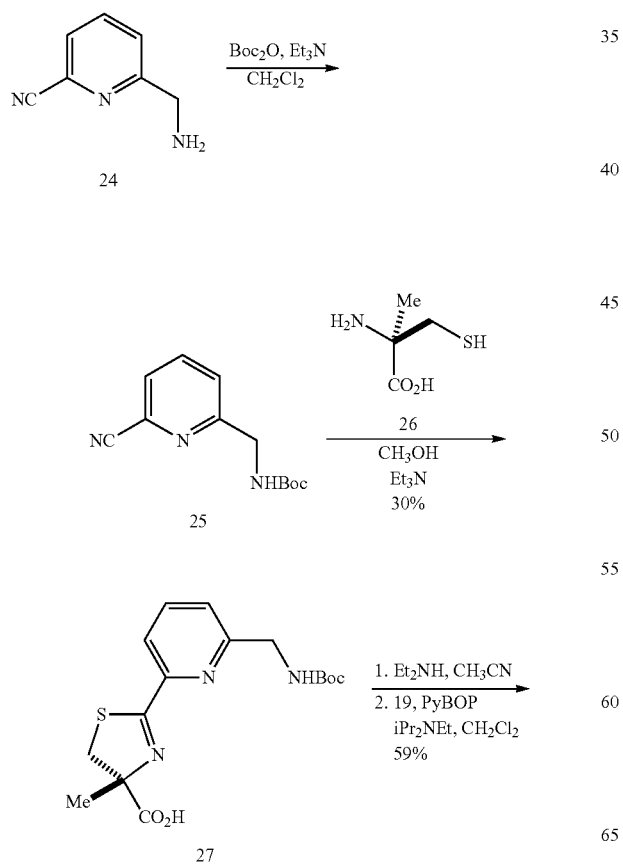

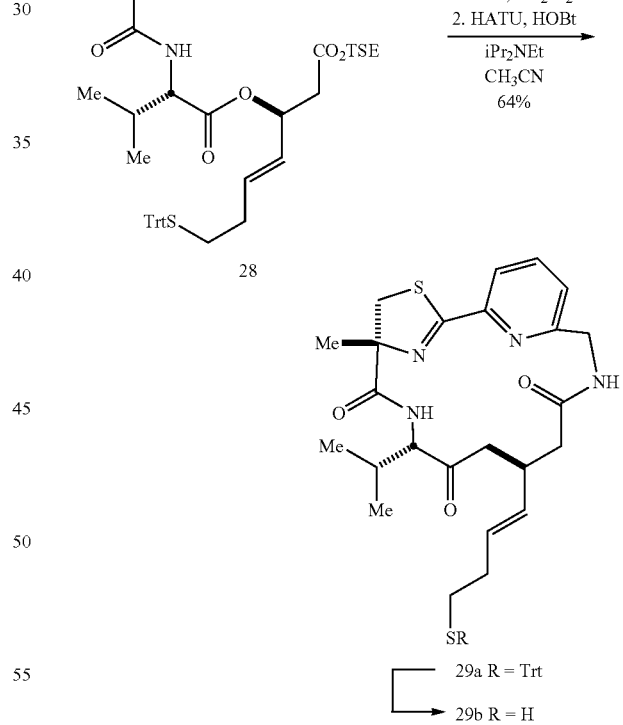

Additional single-atom replacements were performed within the largazole macrocyclic scaffold to interrogate very small structural and attendant conformational changes. Due to the inherent acid instability of oxazolines, additional protecting group manipulations were required for synthesis of oxazoline-oxazole substrate 39 (Scheme 5, below). Thus, oxazole 31 could be saponified and coupled to α-methyl serine (Taori. K., et al. 2008 *J. Am. Chem. Soc.* 130: 1806-1807 and 13506).

Switching the nitrogen protecting group then allowed for cyclization and deprotection/acylation with thiazolidine-2-thione 35 to obtain alcohol 36. Coupling to Fmoc-L-valine then provided the acyclic precursor 38.

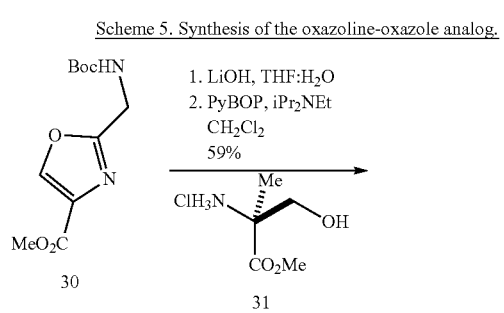

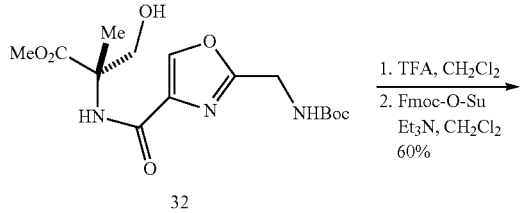

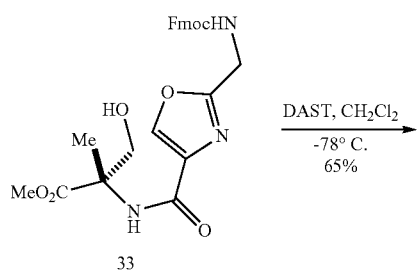

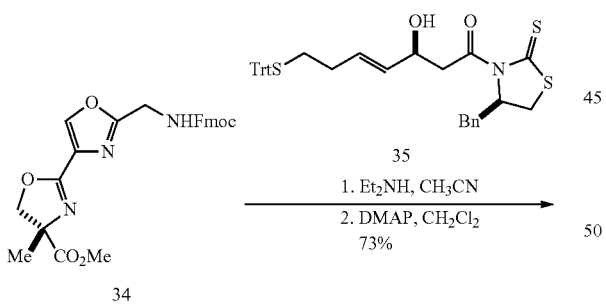

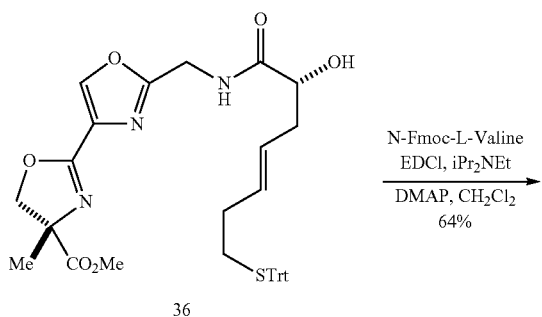

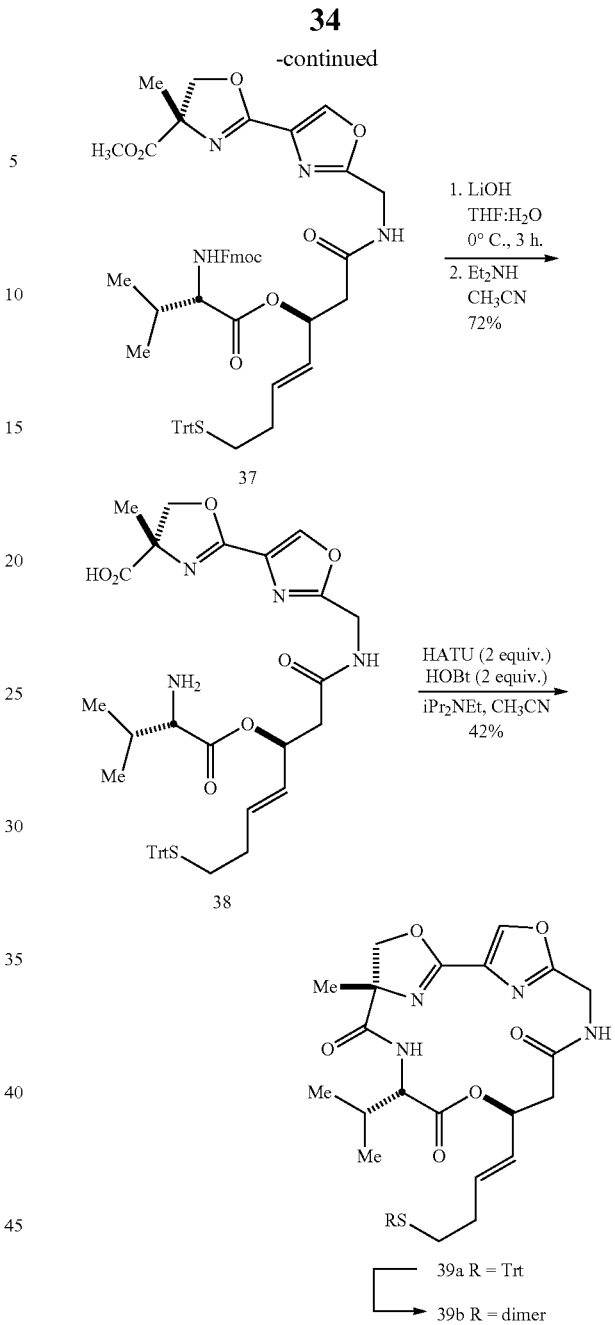

Finally, deprotection under basic conditions and cyclization gave macrocycle 39a. In this case, removal of the trityl group was performed with iodine in methanol, yielding the disulfide dimer exclusively. The dimer was reduced to the active thiol under the reducing conditions of the biochemical assay.

Methods of Treatment

In one embodiment of the invention, a therapeutically effective amount of a compound of formula (I) or a pharmaceutically acceptable salt, solvate, clathrate, and prodrug thereof, or a pharmaceutical composition comprising a compound of formula (I) or a pharmaceutically acceptable salt, solvate, clathrate, and prodrug thereof, is administered to a patient in need of treatment of cancer. In another embodiment of the invention, a therapeutically effective amount of a compound of formula (I) or a pharmaceutically acceptable salt, solvate, clathrate, and prodrug thereof, or a pharmaceutical composition comprising a compound of formula (I) or a pharmaceutically acceptable salt, solvate, clathrate, and prodrug thereof, is administered to a patient in need of treatment of a blood disorder. Other conditions, diseases and disorders that would benefit from such uses are known to those of skill in the art.

The compounds of the invention are also contemplated for the treatment of inflammatory disorders (for example, of the skin, joints, etc.), immune tolerance, transplantation rejection, graft-versus-host disease, and the like.

Responsiveness of the disease to compounds and compositions of the invention can be measured directly by comparison against conventional drugs (for example, for cancer, chemotherapeutics; for certain blood disorders, FK228 or SAHA), or can be inferred based on an understanding of disease etiology and progression. For example, there are a number of fetal hemoglobin expression assay systems that are widely accepted in the art as predictive of in vivo effects. Thus, the showing that a compound of this invention induces fetal hemoglobin expression in these assays is evidence of the clinical utility of these for treating a hemoglobinopathy and/or a thalassemia, i.e., a blood disorder.

In one embodiment of the invention. "treatment" or "treating" refers to an amelioration of cancer or at least one discernible symptom thereof. In another embodiment, "treatment" or "treating" refers to an amelioration of at least one measurable physical parameter, not necessarily discernible by the patient. In yet another embodiment, "treatment" or "treating" refers to inhibiting the progression of cancer, either physically. e.g., stabilization of a discernible symptom, physiologically, e.g., stabilization of a physical parameter, or both. In yet another embodiment. "treatment" or "treating" refers to delaying the onset of cancer or symptoms thereof.

In another embodiment of the invention, "treatment" or "treating" refers to an amelioration of a hemoglobinopathy and/or a thalassemia, i.e., a blood disorder, or at least one discernible symptom thereof. In another embodiment. "treatment" or "treating" refers to an amelioration of at least one measurable physical parameter, not necessarily discernible by the patient. In yet another embodiment, "treatment" or "treating" refers to inhibiting the progression of a hemoglobinopathy and/or a thalassemia, i.e., a blood disorder, either physically, e.g., stabilization of a discernible symptom, physiologically, e.g., stabilization of a physical parameter, or both. In yet another embodiment, "treatment" or "treating" refers to delaying the onset of a hemoglobinopathy and/or a thalassemia, i.e., a blood disorder, or symptoms thereof.

The compounds of formula (I) or pharmaceutically acceptable salts, solvates, clathrates, and prodrugs thereof can be assayed in vitro or in vivo, for the desired therapeutic or prophylactic activity, prior to use in humans. For example, animal model systems can be used to demonstrate the safety and efficacy of compounds of this invention.

Without wishing to be bound by theory, it is believed that the compounds and compositions of this invention induce gene expression, for example, BDNF (for psychiatric disease), HbF, SMA, p53, and/or p21 expression and, as a result, may be used to treat or prevent cancer. Further without wishing to be bound by theory, it is believed that the compounds and compositions of this invention induce gene expression, for example, fetal hemoglobin expression and, as a result, may be used to treat or prevent a hemoglobinopathy and/or a thalassemia, i.e., a blood disorder. It should be noted, however, that the compounds might act by a secondary or a different activity, such as, without limitation, delaying the normally fixed fetal-to-adult globin gene switch or stimulating hematopoiesis, erythropoiesis, myelopoiesis and/or neutrophil production.

Pharmaceutical Compositions

In one embodiment, pharmaceutical compositions and dosage forms of the invention comprise a compound of formula (I) or a pharmaceutically acceptable prodrug, salt, solvate, or clathrate thereof, in relative amounts and formulated in such a way that a given pharmaceutical composition or dosage form reduces or inhibits the growth of transformed (cancer) cells. In another embodiment of the invention, such pharmaceutical compositions and dosage forms comprise one or more additional active agents such as chemotherapeutic agents known in the art.

In another embodiment, pharmaceutical compositions and dosage forms of the invention comprise a compound of formula (I) or a pharmaceutically acceptable prodrug, salt, solvate, or clathrate thereof, in relative amounts and formulated in such a way that a given pharmaceutical composition or dosage form induces the expression of fetal hemoglobin. In another embodiment of the invention, such pharmaceutical compositions and dosage forms comprise one or more additional active agents.

The compounds of the invention and pharmaceutically acceptable salts thereof can be administered via, for example, the oral, parenteral, topical, rectal, subcutaneous, transdermal, and pulmonary (inhaled) routes. In general, these compounds are most desirably administered in effective dosages, depending upon the % eight and condition of the subject being treated and the particular route of administration chosen. Variations may occur depending upon the species of the subject being treated and its individual response to said medicament, as well as on the type of pharmaceutical formulation chosen and the time period and interval at which such administration is carried out.

In one embodiment, the pharmaceutical compositions of the invention may be administered alone or in combination with other known compositions for treating cancer in a subject. e.g., a mammal. Preferred mammals include cats, dogs, pigs, rats, mice, monkeys, chimpanzees, baboons and humans. In one embodiment, the subject is suffering from cancer. In another embodiment, the subject is at risk of suffering from cancer.

In another embodiment, the pharmaceutical compositions of the invention may be administered alone or in combination with other known compositions for treating blood disorders in a subject, e.g., a mammal. Preferred mammals include cats, dogs, pigs, rats, mice, monkeys, chimpanzees, baboons and humans. In one embodiment, the subject is suffering from a blood disorder. In another embodiment, the subject is at risk of suffering from a blood disorder.

The language "in combination with" a known composition is intended to include simultaneous administration of the composition of the invention and the known composition, administration of the composition of the invention first, followed by the known composition and administration of the known composition first, followed by the composition of the invention. Any of the therapeutically composition known in the art for treating cancer or blood disorders can be used in the methods of the invention.

The compounds of the invention may be administered alone or in combination with pharmaceutically acceptable carriers or diluents by any of the routes previously mentioned, and the administration may be carried out in single or multiple doses. For example, the novel therapeutic agents of this invention can be administered advantageously in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the therapeutically effective compounds of this invention are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tableting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient ma) be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration (including intraperitoneal, subcutaneous, intravenous, intradermal or intramuscular injection), solutions of a therapeutic compound of the present invention in either sesame or peanut oil or in aqueous propylene glycol may be employed. The aqueous solutions should be suitably buffered (preferably pH greater than 8) if necessary and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art. For parenteral application, examples of suitable preparations include solutions, preferably oily or aqueous solutions as well as suspensions, emulsions, or implants, including suppositories. Therapeutic compounds may be formulated in sterile form in multiple or single dose formats such as being dispersed in a fluid carrier such as sterile physiological saline or 5% saline dextrose solutions commonly used with injectables.

Additionally, it is also possible to administer the compounds of the present invention topically when treating inflammatory conditions of the skin. Examples of methods of topical administration include transdermal, buccal or sublingual application. For topical applications, therapeutic compounds can be suitably admixed in a pharmacologically inert topical carrier such as a gel, an ointment, a lotion or a cream. Such topical carriers include water, glycerol, alcohol, propylene glycol, fatty alcohols, triglycerides, fatty acid esters, or mineral oils. Other possible topical carriers are liquid petrolatum, isopropylpalmitate, polyethylene glycol, ethanol 95%, polyoxyethylene monolauriate 5% in water, sodium lauryl sulfate 5% in water, and the like. In addition, materials such as anti-oxidants, humectants, viscosity stabilizers and the like also may be added if desired.

For enteral application, particularly suitable are tablets, dragees or capsules having talc and/or carbohydrate carrier binder or the like, the carrier preferably being lactose and/or corn starch and/or potato starch. A syrup, elixir or the like can be used wherein a sweetened vehicle is employed. Sustained release compositions can be formulated including those wherein the active component is derivatized with differentially degradable coatings, e.g., by microencapsulation, multiple coatings, etc.

It will be appreciated that the actual preferred amounts of active compounds used in a given therapy will vary according to the specific compound being utilized, the particular compositions formulated, the mode of application, the particular site of administration, etc. Optimal administration rates for a given protocol of administration can be readily ascertained by those skilled in the art using conventional dosage determination tests conducted with regard to the foregoing guidelines.

It will also be understood that normal, conventionally known precautions will be taken regarding the administration of the compounds of the invention generally to ensure their efficacy under normal use circumstances. Especially when employed for therapeutic treatment of humans and animals in vivo, the practitioner should take all sensible precautions to avoid conventionally known contradictions and toxic effects.

The composition, shape, and type of dosage forms of the invention will typically vary depending on their use. For example, a dosage form suitable for mucosal administration may contain a smaller amount of active ingredient(s) than an oral dosage form used to treat the same indication. This aspect of the invention will be readily apparent to those skilled in the art, e.g., Remington's Pharmaceutical Sciences (1990) 18th ed., Mack Publishing, Eastern Pa.

The invention further encompasses pharmaceutical compositions and dosage forms that comprise one or more compounds that reduce the rate by which the compound of the invention will decompose. Such compounds, which are referred to herein as "stabilizer" include, but are not limited to, antioxidants such as ascorbic acid, pH buffers, or salt buffers.

The interrelationship of dosages for animals and humans (based on milligrams per meter squared of body surface) is described in Freireich, et al. 1966 Cancer Chemother Rep 50: 219. Body surface area may be approximately determined from height and weight of the patient. e.g., Scientific Tables. Geigy Pharmaceuticals, Ardley, N.Y., 1970, 537.

Like the amounts and types of excipients, the amount of the compound of the invention in a dosage form may differ depending on factors such as, but not limited to, the route by which it is to be administered to subjects. It is within the skill of the art to determine the appropriate dose and dosage form for a given patient.

Furthermore, the invention also pertains to the use of a compound of the invention for the preparation of a medicament. In one embodiment of the invention, the medicament may include a pharmaceutically acceptable carrier and the compound is an effective amount, e.g., an effective amount to treat cancer. In another embodiment of the invention, the medicament may include a pharmaceutically acceptable carrier and the compound is an effective amount. e.g., an effective amount to treat a blood disorder.

Kits

In one aspect, the invention provides kits comprising a unit dosage form of an effective amount of a compound of formula (I) or a pharmaceutically acceptable prodrug, salt, solvate, hydrate, or clathrate thereof, and a device that can be used to administer the compound. Examples of such devices include, but are not limited to, syringes, drip bags, patches, and inhalers.

Kits of the invention can further comprise pharmaceutically acceptable vehicles. For example, if a compound of the invention is provided in a solid form that must be reconstituted for parenteral administration, the kit can comprise a sealed container of a suitable vehicle in which the compound can be dissolved to form a particulate-free sterile solution that is suitable for parenteral administration.

Combination Therapy

The herein-described methods for treating a hemoglobinopathy and/or a thalassemia, i.e., a blood disorder, in a subject can further comprise administering to the subject being administered a compound of this invention, an effective amount of one or more other therapeutic agents. In one embodiment of the invention where another therapeutic agent is administered to a subject, the effective amount of the compound of the invention is less than its effective amount would be where the other therapeutic agent is not administered. In another embodiment, the effective amount of the other therapeutic agent is less than its effective amount would be where the compound of the invention is not administered.

In some aspects described herein, the method includes an additional therapeutic modality. For example, the additional therapeutic modality is radiation therapy or a cytotoxic chemotherapy agent, such as an anti-metabolite (e.g., 5-FU, with leucovorin), irinotecan. (or other topoisomerase inhibitor), doxorubicin, or any combination all of these agents, including administration of all of these agents.

The methods can further include the step of monitoring the subject. e.g., for a reduction in one or more of: a reduction in tumor size; reduction in cancer markers. e.g., levels of cancer specific antigen; reduction in the appearance of new lesions, e.g., in a bone scan; a reduction in the appearance of new disease-related symptoms; or decreased or stabilization of size of soft tissue mass; or any parameter related to improvement in clinical outcome. The subject can be monitored in one or more of the following periods: prior to beginning of treatment; during the treatment; or after one or more elements of the treatment have been administered. Monitoring can be used to evaluate the need for further treatment with the compound of Formula (I) or for additional treatment with additional agents. Generally, a decrease in or stabilization of one or more of the parameters described above is indicative of the improved condition of the subject. Information about the monitoring can be recorded, e.g., in electronic or digital form.

The treatment methods disclosed herein can be used in combination with one or more additional treatment modalities, including, but not limited to: surgery; radiation therapy, and chemotherapy.

With reference to the methods disclosed herein, the term "combination" refers to the use of one or more additional agents or therapies to treat the same patient, wherein the use or action of the agents or therapies overlap in time. The additional agents or therapies can be administered at the same time as the compound of Formula (I) is administered, or sequentially in any order. Sequential administrations are administrations that are given at different times. The time between administration of the one agent and another agent can be minutes, hours, days, or weeks.

The additional agent or therapy can also be another anti-cancer agent or therapy. Nonlimiting examples of anti-cancer agents include. e.g., anti-microtubule agents, topoisomerase inhibitors, antimetabolites, mitotic inhibitors, alkylating agents, intercalating agents, agents capable of interfering with a signal transduction pathway, agents that promote apoptosis, radiation, and antibodies against other tumor-associated antigens (including naked antibodies, immunotoxins and radioconjugates). Examples of the particular classes of anti-cancer agents are provided in detail as follows: antitubulin/antimicrotubule, e.g., paclitaxel, vincristine, vinblastine, vindesine, vinorelbin, taxotere; topoisomerase 1 inhibitors, e.g., irinotecan, topotecan, camptothecin, doxorubicin, etoposide, mitoxantrone, daunorubicin, idarubicin, teniposide, amsacrine, epirubicin, merbarone, piroxantrone hydrochloride; antimetabolites. e.g., 5-fluorouracil (5-FU), methotrexate. 6-mercaptopurine. 6-thioguanine, fludarabine phosphate, cytarabine/Ara-C, trimetrexate, gemcitabine, acivicin, alanosine, pyrazofurin, N-Phosphoracetyl-L-Asparate=PALA, pentostatin, 5-azacitidine, 5-Aza 2'-deoxycytidine, ara-A, cladribine. 5-fluorouridine, FUDR, tiazofurin. N-[5-[N-(3,4-dihydro-2-methyl-4-oxoquinazolin-6-ylmethyl)-N-methylamino]—2-thenoyl]-L-glutamic acid; alkylating agents. e.g., cisplatin, carboplatin, mitomycin C, BCNU=Carmustine, melphalan, thiotepa, busulfan, chlorambucil, plicamycin, dacarbazine, ifosfamide phosphate, cyclophosphamide, nitrogen mustard, uracil mustard, pipobroman, 4-ipomeanol; agents acting via other mechanisms of action, e.g., dihydrolenperone, spiromustine, and depsipeptide (also referred to as FK228 or Romidepsin); biological response modifiers, e.g., to enhance anti-tumor responses, such as interferon; apoptotic agents, such as actinomycin D; and anti-hormones, for example anti-estrogens such as tamoxifen or, for example antiandrogens such as 4'-cyano-3-(4-fluorophenylsulphonyl)-2-hydroxy-2-methyl-3'-(trifluoromethyl)propionanilide.

A combination therapy can include administering an agent that reduces the side effects of other therapies. The agent can be an agent that reduces the side effects of anti-cancer treatments. A combinational therapy can also include administering an agent that reduces the frequency of administration of other therapies. The agent can be an agent that decreases growth of tumor after the anti-cancer effects of other therapies have decreased.

Useful combination therapies will be understood and appreciated by those of skill in the art. Potential advantages of such combination therapies include the ability to use less of each of the individual active ingredients to minimize toxic side effects, synergistic improvements in efficacy, improved ease of administration or use, and/or reduced overall expense of compound preparation or formulation. For example, the compounds of the invention may be administered to the subject for treatment of a hemoglobinopathy and/or a thalassemia, i.e., a blood disorder, in combination with one or more cytokines. In one embodiment, the cytokine is selected from the group consisting of IL-3, GM-CSF. G-CSF, stem cell factor (SCF) and IL-6.

Further Contemplated Embodiments

Limiting the utility of known HDAC inhibitors more broadly in cancer and in non-malignant conditions has been (1) on-target toxicity and (2) a rather limited understanding of cancer cell sensitivity and resistance. Having established a platform capability to the chemical optimization of largazole, the mechanistic effects of natural product HDAC inhibitors on chromatin structure and function can be elucidated. The toxicity of Class 1 HDACs (1, 2, 3, and 8) represents a significant barrier to extending the therapeutic utility of such compounds beyond CTCL. Chemical approaches are directed at the targeted delivery of largazole-derived prototype therapeutics to leukemia and lymphoma cells.

It is hypothesized that largazole localizes genome-wide to sites of recruitment of HDACs1-3 containing repressive complexes, leading to enzyme inhibition and local hyperacetylation. Hyperacetylation subsequently spreads throughout bulk chromatin, causing (i) redistribution of bromodomain-containing transcriptional complexes. (ii) increased chromatin accessibility, and (iii) de-regulation of coordinated transcriptional elongation. Thus, conjugation of natural product-inspired HDAC inhibitors to cancer targeting small molecules and biomolecules is likely to enhance tumor-specific cytotoxicity, as will improving isoform-specific inhibition. Furthermore, it is likely that genetic determinants of resistance to epigenetic HDAC inhibitor therapy will map to chromatin complexes involved in transactivation and remodeling.

a) Establishment of the mechanism and site of largazole anti-cancer activity. The effect of largazole on chromatin structure and function is determined using genome-wide, integrated epigenomic analyses. A novel, retrievable derivative of Largazole allows the elucidation of engaged protein complexes by mass spectroscopy and the spatial localization of largazole within chromatin genome-wide by Chem-Seq.

b) Expansion of the cancer-specific therapeutic index of largazole through small molecule and biomolecule conjugation. To expand the therapeutic index of largazole, caged, releasable conjugates are prepared and characterized. Folate conjugation and cytokine bioconjugation (IL3 (interleukin 3)) allow selective targeting of leukemia and lymphoma, in vitro and in vivo.

c) Identification of genetic mechanisms of resistance to epigenetic HDAC inhibitor therapy. In an effort to better understand the mechanism of drug action, to anticipate clinical resistance to largazole therapy, and to explain clinical resistance to known FDA-approved HDAC inhibitors, the genetic determinants of epigenetic HDAC inhibitor resistance are elucidated using haploid genetic screens and CRISPR resistance selections.

d) Realization of next-generation macrocyclic HDAC inhibitors with improved isoform selectivity. Massively parallel synthesis and selection of RNA-encoded macrocycles are biased for HDAC activity with largazole-like pharmacophores and screened for isoform-specific inhibition. Selective compounds are resynthesized, characterized biochemically, and studied in models of cancer.

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features. From the above description and the examples that follow, one skilled in the art can easily ascertain the essential characteristics of the present invention, and without departing from the spirit and scope thereof, can make various changes and modifications of the invention to adapt it to various usages and conditions. For example, the compounds of the invention may be used as research tools (for example, to isolate new targets for performing drug discovery). The compounds may, for instance, be radiolabelled for imaging tissue or organs or be used to form bioconjugates for affinity assays. These and other uses and embodiments of the compounds and compositions of this invention will be apparent to those of ordinary skill in the art.

The disclosure also encompasses all possible permutations of the claim set, as if they were multiple dependent claims.

Various embodiments of the disclosure could also include permutations of the various elements recited in the claims as if each dependent claim was multiple dependent claim incorporating the limitations of each of the preceding dependent claims as well as the independent claims. Such permutations are expressly within the scope of this disclosure.

While the invention has been particularly shown and described with reference to a number of embodiments, it would be understood by those skilled in the art that changes in the form and details may be made to the various embodiments disclosed herein without departing from the spirit and scope of the invention and that the various embodiments disclosed herein are not intended to act as limitations on the scope of the claims. All references cited herein are incorporated in their entirety by reference.

EQUIVALENTS

Those skilled in the art will recognize, or be able to ascertain using no more than routine experimentation, numerous equivalents to the specific procedures described herein. Such equivalents are considered to be within the scope of the present invention and are covered by the following claims. The contents of all references, patents, and patent applications cited throughout this application are hereby incorporated by reference. The appropriate components, processes, and methods of those patents, applications and other documents may be selected for the present invention and embodiments thereof.

The description of the present invention has been presented for purposes of illustration and description, but is not intended to be exhaustive or limiting of the invention to the form disclosed. The scope of the present invention is limited only by the scope of the following claims. Many modifications and variations will be apparent to those of ordinary skill in the art. The embodiment described was chosen and described in order to best explain the principles of the invention, the practical application, and to enable others of ordinary skill in the art to understand the invention for various embodiments with various modifications as are suited to the particular use contemplated.

The invention is further defined by reference to the following examples describing in detail the preparation of compounds of, the invention. It will be apparent to those skilled in the art that many modifications, both to materials and methods, may be practiced without departing from the purpose and interest of this invention. The following examples are set forth to assist in understanding the invention and should not be construed as specifically limiting the invention described and claimed herein. Such variations of the invention, including the substitution of all equivalents now known or later developed, which would be within the purview of those skilled in the art, and changes in formulation or minor changes in experimental design, are to be considered to fall within the scope of the invention incorporated herein.

EXAMPLES

The following examples are provided for illustrative purposes only and are not intended to limit the scope of the invention.

General Experimental Methods

Unless otherwise noted, all reactions were run under an argon atmosphere in flame or oven dried glassware. Reactions were monitored using thin layer silica gel chromatography (TLC) using 0.25 mm silica gel 60F plates with fluorescent indicator (Merck). Plates were visualized by treatment with phosphomolybdic acid stain with gentle heating. Products were purified via column chromatography using the solvent system(s) indicated. Silica gel 60, 230-400 mesh (Sorbent Technologies). Tetrahydrofuran (THF), dichloromethane ($CH_2Cl_2$), acetonitrile ($CH_3CN$), triethylamine ($Et_3N$), toluene, diethyl ether ($Et_2O$), and N,N-dimethylformamide (DMF) were passed through an alumina drying column (Solv-Tek Inc.) using argon pressure. Melting points were determined in open-ended capillaries and are uncorrected. $^1H$ NMR and $^{13}C$ NMR spectra were recorded on Varian 300, 400, or 500 MHz NMR spectrometers. Chemical shifts are reported in ppm relative to $CHCl_3$ at $\delta=7.27$ ($^1H$ NMR) and $\delta=77.23$ ($^{13}C$ NMR) or tetramethylsilane (TMS) $\delta=0.00$, where noted. Mass spectra were obtained on Fisions VG Autospec. Optical rotations were collected at 589 nm on a Rudolph Research Automatic Polarimeter Autopol III.

Example 1. Synthesis of Largazole and Largazole Thiol

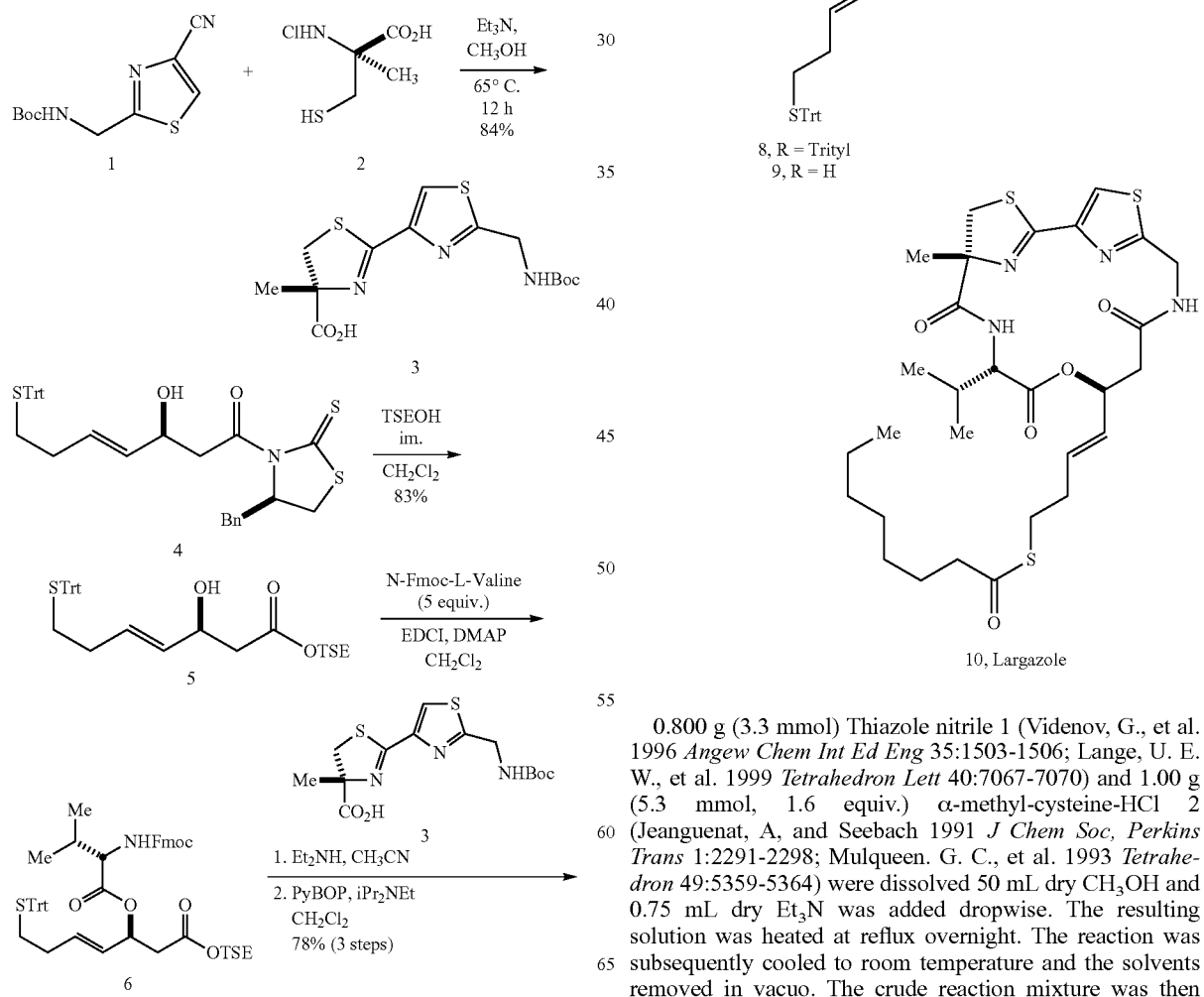

0.800 g (3.3 mmol) Thiazole nitrile 1 (Videnov, G., et al. 1996 *Angew Chem Int Ed Eng* 35:1503-1506; Lange, U. E. W., et al. 1999 *Tetrahedron Lett* 40:7067-7070) and 1.00 g (5.3 mmol, 1.6 equiv.) α-methyl-cysteine-HCl 2 (Jeanguenat, A, and Seebach 1991 *J Chem Soc, Perkins Trans* 1:2291-2298; Mulqueen. G. C., et al. 1993 *Tetrahedron* 49:5359-5364) were dissolved 50 mL dry $CH_3OH$ and 0.75 mL dry $Et_3N$ was added dropwise. The resulting solution was heated at reflux overnight. The reaction was subsequently cooled to room temperature and the solvents removed in vacuo. The crude reaction mixture was then dissolved in sat. aqu. $NaHCO_3$ and washed with diethyl ether. The aqueous layer was then acidified to pH ~3-4 by dropwise addition of 3N HCl and extracted with EtOAc (3×30 mL). The combined organics were dried over $Na_2SO_4$, filtered, and concentrated to provide 1.00 g (2.8 mmol, 84% yield) of 2-{2-[(tert-Butoxycarbonyl)methyl] thiazol-4-yl}-4-methyl-4,5-dihydrothiazole-4-carboxylic acid (3) in spectroscopically pure form. Clear oil. $[\alpha]^{24}_D$: +30.9 (c=1. $CH_3OH$). $^1H$ NMR (400 MHz, $CDCl_3$) δ 9.79 (bs, 1H), 7.98 (s, 1H), 5.59 (s, 1H), 4.59 (d J=6.3 Hz, 2H), 3.88 (d J=11.4 Hz, 1H), 3.30 (d J=11.4 Hz, 1H), 1.66 (s, 3H), $^{13}C$ NMR (100.6 MHz, $CDCl_3$): δ 175.74, 170.38, 170.16, 165.03, 155.91, 147.77, 123.3, 84.23, 80.70, 42.39, 41.31, 28.51, 27.17, 26.67, 24.30. HRMS (ESI): m/z calcd. for $C_{14}H_{19}N_3NaO_4S_2$ (M+Na) 380.07147, found 380.07165.

0.200 g (0.33 mmol) thiazoline-thione 4 (Yurek-George, A., et al. 2004 *J Am Chem Soc* 126:1030-1031) was dissolved in 5 mL $CH_2Cl_2$ and 0.470 mL (3.3 mmol, 10.0 equiv.) 2-trimethylsilyethanol was added, followed by 0.033 g (0.49 mmol, 1.5 equiv.) imidazole. The resulting solution was stirred overnight, when TLC revealed complete disappearance of starting material 4. The reaction mixture was concentrated in vacuo and submitted immediately to column chromatography (elutes 4:1 hexanes:ethyl acetate), which provided 0.142 g (83% yield) of the protected ester, (3S, 4E)-3-Hydroxy-7-[(triphenylmethyl)thio]-4-heptenoic acid (2-trimethylsilyl)ethyl ester (5), as a clear oil. $[\alpha]^{24}_D$: −1.1 (c=2, $CHCl_3$). $^1H$ NMR (400 MHz, $CDCl_3$) δ 7.40 (dd J=0.8, 8.8 Hz, 6H), 7.24-7.28 (m, 6H), 7.17-7.21 (n, 3H), 5.56 (dt J=6.4, 15.2 Hz, 1H), 5.40 (dd J=6.4, 15.2 Hz, 1H), 4.40-4.45 (m, 1H), 4.16-4.21 (m, 2H), 2.48 (dd J=4.8, 16.4 Hz, 1H), 2.43 (dd J=8.0, 16.4 Hz, 1H), 2.18-2.22 (m, 2H), 2.04-2.09 (m, 2H), 0.96-1.00 (m, 2H), 0.03 (s, 9H), $^{13}C$ NMR (100.6 MHz, $CDCl_3$): δ 172.7, 145.1, 132.2, 130.3, 129.8, 128.1, 126.8, 68.8, 66.8, 63.3, 41.7, 31.7, 31.6, 17.5, −1.3. HRMS (ESI): m/z calcd. for $C_{31}H_{38}NaO_3SSi$ (M+Na) 541.22086, found 541.22072.

0.570 g (1.1 mmol) of β-hydroxy ester 5 and 1.865 g (5.5 mmol, 5 equiv.) N-Fmoc-L-valine were dissolved in 20 mL dry $CH_2Cl_2$. The reaction was cooled to 0° C. and 1.264 g (6.6 mmol, 6 equiv.) EDCI and 0.007 g (0.11 mmol, 0.1 equiv.) DMAP were added in ~5 mL $CH_2Cl_2$, followed by 1.15 mL $iPr_2NEt$. The reaction was allowed to warm to room temperature and stirred overnight, when TLC showed complete disappearance of 5. The reaction was concentrated and passed through a short plug of silica, washing with 100% EtOAc. The product diester eluted with a by-product from the excess amino acid used, which was not separated at this time. Instead, the crude diester was taken up in 50 mL $CH_3CN$ (to ~0.02M) and treated with 5 mL diethylamine (to ~0.2M). The resulting solution was stirred for two hours and then concentrated, taken up in EtOAc, and concentrated again.

0.400 g (1.2 mmol, 1.1 equiv.) acid 3 was dissolved in 20 mL dry $CH_2Cl_2$ and treated with 1.020 g (2 mmol, 2.0 equiv) PyBOP and 0.510 mL (2.9 mmol, 3.0 equiv.) $iPr_2NEt$. After stirring for ~5 min., the crude amine in 10 mL $CH_3CN$ was added to the mixture dropwise. After 2 hrs, the reaction was concentrated and submitted immediately to column chromatography. 0.820 g (0.86 mmol, 78% from 5) of (3S,4E)-2-(Trimethylsilyl)ethyl-3-[(S)-2-((R)-2-{2-[(tert-butoxyearbonyl)methyl]thiazol-4-yl}-4-methyl-4,5-dihydrothiazole-4-carboxamido)-3-methylbutanoyloxy]-7-(tritylthio)hept-4-enoate (7) eluting cleanly in (1:1 hexanes:EtOAc). Clear oil. $^1H$ NMR (300 MHz, $CDCl_3$) δ 7.91 (s, 1H), 7.36-7.41 (m, 6H), 7.16-7.29 (m, 9H), 5.59-5.71 (m, 2H), 5.36 (dd J=7.5, 15.3 Hz, 1H), 5.30 (s, 1H), 4.62 (d J=6.0 Hz, 2H), 4.48 (dd J=4.8, 9.3 Hz, 1H), 4.12-2.18 (m, 2H), 3.77 (d J=11.4 Hz, 1H), 3.32 (d J=11.4 Hz, 1H), 2.69 (dd J=8.1, 15.9 Hz, 1H), 2.54 (dd J=5.1, 15.9 Hz, 1H), 2.03-2.18 (m, 5H), 1.57 (s, 3H), 1.47 (s, 9H), 0.93-0.99 (m, 2H), 0.81 (d J=6.9 Hz, 3H), 0.74 (d J=6.9 Hz, 3H), 0.02 (s, 9H), $^{13}C$ NMR (75.5 MHz, $CDCl_3$): δ 174.6, 170.6, 169.9, 155.8, 148.8, 145.0, 134.2, 129.7, 128.1, 128.0, 126.8, 121.7, 85.3, 80.7, 77.5, 72.0, 66.8, 63.4, 57.0, 42.5, 41.7, 39.9, 31.5, 31.4, 31.3, 28.5, 25.0, 19.3, 17.7, 17.5, −1.3. HRMS (ESI): m/z calcd. for $C_{50}H_{64}N_4NaO_7S_3Si$ (M+Na)$^+$ 979.36041, found 979.36045.

0.100 g (0.1 mmol) Acyclic precursor 7 was dissolved in 5 mL $CH_2Cl_2$ (to ~0.03M), cooled to 0° C. and treated with 1 mL TFA (to ~0.6M). The reaction was allowed to warm to room temperature and stirred overnight (shorter reaction times resulted in only partial deprotection of the TSE group). Solvents were evaporated and the crude amino acid redissolved in toluene and concentrated a second time to remove residual TFA. The crude amino acid was then taken up in ~5 mL $CH_2Cl_2$ and added dropwise to a stirred solution of 0.115 mL (6.0 equiv.) $iPr_2Net$ in 100 mL dry $CH_3CN$ (to ~0.001M). The resulting moderately opaque solution was allowed to stir ~10 min., before 0.085 g (0.2 mmol, 2 equiv.) HATU and 0.030 g (0.2 mmol, 2 equiv.) HOBt were added dropwise in ~5 mL $CH_3CN$. The reaction was allowed to stir for 16 hr., then concentrated and submitted immediately to column chromatography. S-Trityl macrocycle (8) (0.060 g, 77% yield) eluted quickly in EtOAc, after a general wash with 10:1 hexanes:EtOAc. Clear oil. $[\alpha]^{24}_D$: +16.1 (c=1, $CH_3OH$). $^1H$ NMR (400 MHz, $CDCl_3$) δ 7.72 (s, 1H), 7.30-7.33 (m, 6H), 7.19-7.24 (m, 6H), 7.11-7.15 (m, 3H), 7.08 (d J=9.6 Hz, 1H), 6.47 (d J=6.8 Hz, 1H), 5.65 (dt J=7.2, 15.6 Hz, 1H), 5.59 (t J=6.0 Hz, 1H), 5.32 (dd J=6.0, 15.6 Hz, 1H), 5.13 (dd J=8.4, 17.6 Hz, 1H), 4.49 (dd J=3.2, 9.6 Hz, 1H), 4.03 (d J=17.6 Hz, 1H), 3.98 (d J=11.6 Hz, 1H), 3.22 (d J=11.6 Hz, 1H), 2.73 (dd J=9.6, 15.6 Hz, 1H), 2.57 (dd J=2.4, 15.6 Hz, 1H), 2.09-2.16 (m, 2H), 1.92-2.04 (m, 3H), 1.77 (s, 3H), 0.60 (d J=6.8 Hz, 3H), 0.43 (d J=6.8 Hz, 3H), $^{13}C$ NMR (100.6 MHz, $CDCl_3$): δ 173.3, 169.6, 168.9, 168.4, 147.1, 145.0, 133.4, 129.8, 128.1, 127.5, 126.9, 77.5, 72.1, 66.8, 58.1, 43.5, 41.2, 40.8, 34.3, 31.6, 31.5, 19.1, 17.0. HRMS (ESI): m/z calcd. for $C_{40}H_{42}N_4NaO_4S_3$ (M+Na)$^-$ 761.22659, found 761.22598.

0.030 g (0.04 mmol) S-Trityl macrocycle 8 was dissolved in 5 mL dry $CH_2Cl_2$ and cooled to 0° C. The mixture was successively treated with 0.017 mL (0.08 mmol. 2 equiv.) $iPr_3SiH$ and 0.200 mL TFA (to ~0.2M in 8). The reaction mixture was allowed to warm to room temperature and stirred for 2 hrs before being concentrated and chromatographed (EtOAc) to provide 0.019 g (0.038 mmol, 95%) thiol 9. Clear oil. $[\alpha]^{24}_D$: +11.0 (c=1, $CHCl_3$), $^1H$ NMR (400 MHz, $CDCl_3$) δ 7.70 (s, 1H), 7.10 (d J=9.2 Hz, 1H), 6.43 (d J=6.8 Hz, 1H), 5.75 (dt J=8.4, 15.2 Hz, 1H), 5.58-5.63 (m, 1H), 5.45 (dd J=6.8, 15.2 Hz, 1H), 5.20 (dd J=9.2, 17.4 Hz, 1H), 4.53 (dd J=3.6, 9.6 Hz, 1H), 4.20 (dd J=2.4, 17.4 Hz, 1H), 3.96 (d J=11.2 Hz, 1H), 3.20 (d J=11.2 Hz, 1H), 2.79 (dd J=10.0, 16.8 Hz, 1H), 2.62 (dd J=2.8, 16.8 Hz, 1H), 2.48 (q J=7.2 Hz, 2H), 2.27-2.30 (m, 2H), 1.99-2.04 (m, 2H), 1.79

(s, 3H), 0.60 (d J=6.8 Hz, 3H), 0.43 (d J=6.8 Hz, 3H). $^{13}$C NMR (100.6 MHz, CDCl$_3$): δ 173.7, 169.6, 169.1, 168.2, 147.5, 132.8, 129.0, 124.6, 84.5, 77.5, 72.4, 58.0, 43.6, 41.3, 40.8, 36.6, 34.4, 24.4, 24.1, 19.1, 16.9. HRMS (ESI): m/z calcd. for C$_{21}$H$_{29}$N$_4$O$_4$S$_3$ (M+H)$^+$ 497.13509, found 497.13462.

0.010 g (0.020 mmol) thiol 9 was dissolved in 2 mL dry CH$_2$Cl$_2$ and cooled to 0° C. The mixture was successively treated with 0.010 mL (0.040 mmol, 2 equiv.) Et$_3$N and 0.021 mL (0.10 mmol, 5 equiv.) octanoyl chloride. The reaction was allowed to warm to room temperature and stirred for 2 hrs. when TLC showed complete disappearance of starting material in favor of a less polar compound. The reaction was cooled to 0° C. and quenched with 5 mL CH$_3$OH, before being concentrated and chromatographed (EtOAc) to provide 0.012 g (0.019 mmol, 94% yield) largazole 10. Clear oil. [α]$^{24}_D$: +25.9 (c=1, CH$_3$OH); lit.: [α]$^{20}_D$: +22 (c=0.1, CH$_3$OH). $^1$H NMR (400 MHz, CDCl$_3$) δ 7.77 (s, 1H), 7.15 (d J=9.6 Hz, 1H), 6.49 (bs, 1H), 5.82 (dt J=6.9, 15.6 Hz, 1H), 5.66 (t J=6.3 Hz, 1H), 5.50 (dd J=6.6, 15.6 Hz, 1H), 5.29 (dd J=7.8, 17.7 Hz, 1H), 4.60 (dd J=2.7, 8.7 Hz, 1H), 4.26 (d J=17.1 Hz, 1H), 4.05 (d J=11.4 Hz, 1H), 3.27 (d J=11.4 Hz, 1H), 2.89 (t J=6.9 Hz, 2H0, 2.84 (d J=14.7 Hz, 1H), 2.68 (d J=14.7 Hz, 1H), 2.53 (t J=7.2 Hz, 2H), 2.27-2.36 (m, 2H), 2.08-2.13 (m, 1H), 1.87 (s, 3H0, 1.61-1.66 (m, 2H), 1.25-1.29 (m, 8H), 0.87 (t J=7.2 Hz, 3H), 0.68 (d J=6.6 Hz, 3H), 0.50 (d J=6.6 Hz, 3H), $^{13}$C NMR (100.6 MHz, CDCl$_3$): δ 199.6, 173.7, 169.7, 169.1, 168.2, 147.5, 133.0, 128.6, 124.6 84.5, 72.3, 58.0, 44.4, 43.6, 41.4, 40.7, 34.5, 32.5, 31.9, 29.3, 29.2, 28.2, 25.9, 24.4, 22.9, 19.1, 16.9, 14.3. HRMS (ESI): m/z calcd. for C$_{29}$H$_{42}$N$_4$NaO$_5$S$_3$ (M+Na) 645.22150, found 645.22103.

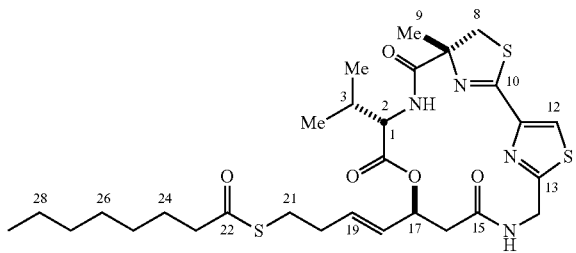

TABLE 1

Comparison of $^1$H and $^{13}$C NMR Spectra of Natural (Isolated)$^4$ and Synthetic Largazole (1).

| C/H no. | Natural | Synthetic | Natural | Synthetic |
|---|---|---|---|---|
| 1 | | | 168.9, qC | 169.1, qC |
| 2 | 4.61 (dd J = 9.2, 3.3) | 4.60 (dd J = 9.0, 3.3) | 57.7, CH | 58.0, CH |
| 3 | 2.10 (m) | 2.11 (m) | 34.2, CH | 34.5, CH |
| 4 | 0.68 (d J = 7.2) | 0.68 (d J = 6.9) | 18.9, CH$_3$ | 19.1, CH$_3$ |
| 5 | 0.50 (d J = 7.2) | 0.50 (d J = 6.9) | 16.6, CH$_3$ | 16.9, CH$_3$ |
| 2-NH | 7.15 (d J = 9.2) | 7.15 (d J = 9.3) | | |
| 6 | | | 173.5, qC | 173.7, qC |
| 7 | | | 84.4, qC | 84.5, qC |
| 8a | 4.04 (d J = 11.4) | 4.05 (d J = 11.4) | 43.3, CH$_2$ | 43.6, CH$_2$ |
| 8b | 3.27 (d J = 11.4) | 3.27 (d J = 11.4) | | |
| 9 | 1.87 (br s) | 1.87 (br s) | 24.2, CH$_3$ | 24.4, CH$_3$ |
| 10 | | | 164.6, qC | 165, qC |
| 11 | | | 147.4, qC | 147.5, qC |
| 12 | 7.76 (s) | 7.77 (s) | 124.4, CH | 124.6, CH |
| 13 | | | 167.9, qC | 168.2, qC |
| 14a | 5.29 (dd J = 17.4, 9.6) | 5.29 (dd J = 17.4, 9.6) | 41.1, CH | 41.4, CH |
| 14b | 4.27 (dd J = 17.4, 2.5) | 4.26 (dd J = 17.7, 3.3) | | |
| 14-NH | 6.45 (dd J = 9.6, 2.5) | 6.49 (dd J = 9.6, 3.0) | | |
| 15 | | | 169.4, qC | 169.7, qC |
| 16a | 2.86 (dd J = 16.5, 10.5) | 2.84 (dd J = 16.8, 10.5) | 40.5, CH$_2$ | 40.7, CH$_2$ |
| 16b | 2.68 (dd J = 16.5, 1.8) | 2.68 (dd J = 16.2, 2.7) | | |
| 17 | 5.66 (ddd J = 10.5, 7.2, 1.8) | 5.66 (ddd J = 9.9, 6.9, 2.7) | 72.0, CH | 72.3, CH |
| 18 | 5.51 (dd J = 15.6, 7.2) | 5.50 (dd J = 15.6, 6.6) | 128.4, CH | 128.6, CH |
| 19 | 5.82 (dt J = 15.6, 7.2) | 5.82 (dt J = 15.6, 6.9) | 132.7, CH | 133.0, CH |
| 20 | 2.31 (br q J = 7.2 2H) | 2.30 (br q J = 7.2 2H) | 32.3, CH$_2$ | 32.5, CH$_2$ |
| 21 | 2.90 (t J = 7.2 2H) | 2.89 (t J = 6.9 2H) | 27.9, CH$_2$ | 28.2, CH$_2$ |
| 22 | | | 199.4, qC | 199.6, qC |
| 23 | 2.52 (t J = 7.5 2H) | 2.53 (t J = 7.2 2H) | 44.1, CH$_2$ | 44.4, CH$_2$ |
| 24 | 1.64 (m 2H) | 1.64 (m 2H) | 25.6, CH$_2$ | 25.9, CH$_2$ |
| 25 | 1.29 (m 2H) | 1.25-1.29 (m 8H) | 28.9, CH$_2$ | 29.2, CH$_2$ |
| 26 | 1.25 (m 2H) | | 28.9, CH$_2$ | 29.3, CH$_2$ |
| 27 | 1.26 (m 2H) | | 31.6, CH$_2$ | 31.9, CH$_2$ |
| 28 | 1.28 (m 2H) | | 22.6, CH$_2$ | 22.9, CH$_2$ |
| 29 | 0.87 (br t J = 6.9) | 0.87 (br t J = 7.2) | 14.0, CH$_3$ | 14.3, CH$_3$ |

Example 2. Synthesis of Largazole Amide Isostere

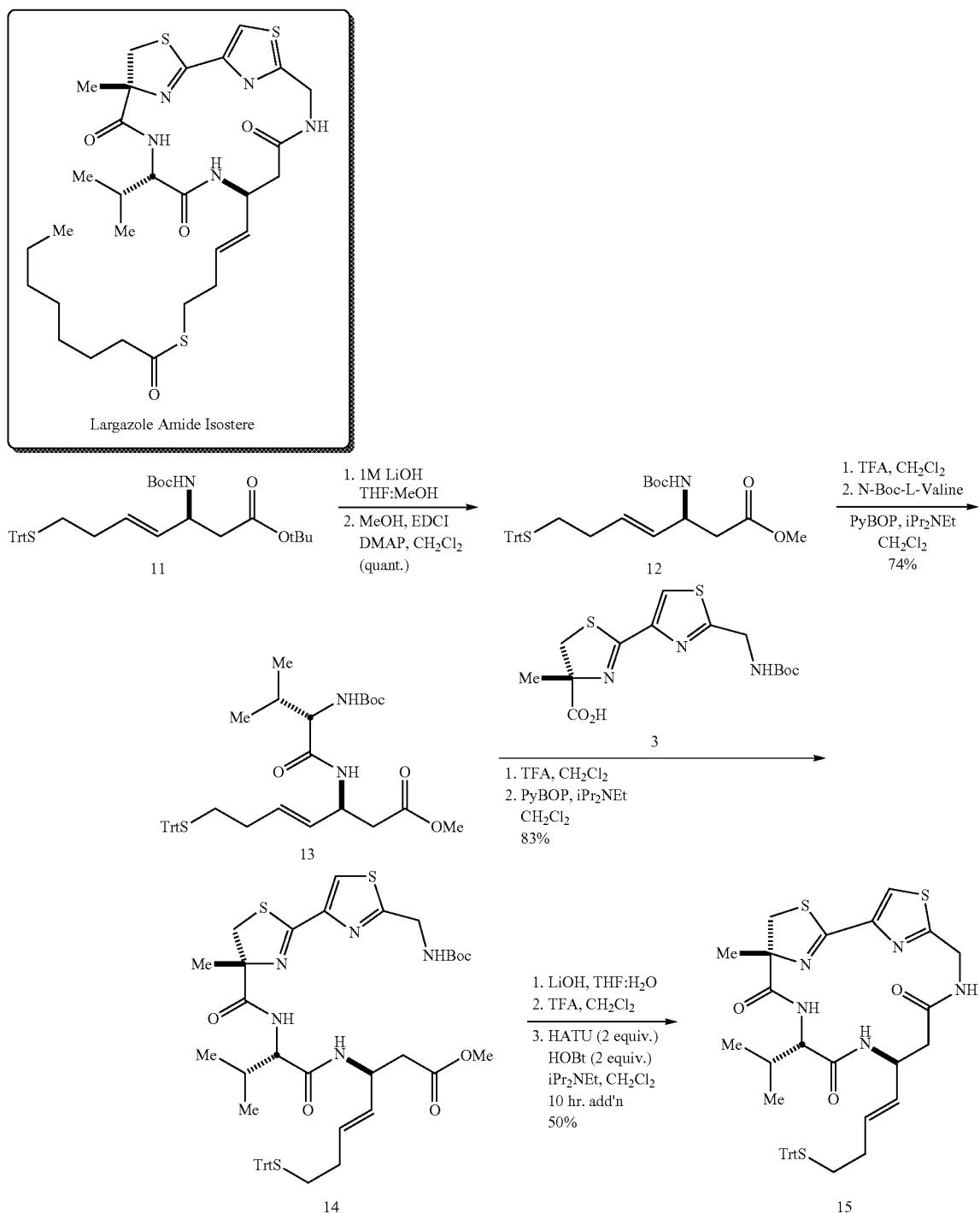

Largazole Amide Isostere 0.400 g (0.77 mmol, 1 equiv.) of β-amino acid 11 was dissolved in 8 mL dry $CH_2Cl_2$ and 0.890 g (4.63 mmol, 6 equiv.) EDCI and 0.019 g (0.15 mmol, 0.2 equiv.) DMAP were added, followed by 0.3 mL (7.7 mmol, 10 equiv.) $CH_3OH$. The resulting solution was stirred under argon for ~12 hrs, when TLC showed complete consumption of the starting material. The solvent was evaporated and the crude reaction mixture submitted immediately to column chromatography. 0.410 g (0.77 mmol, 100% yield) of the product ester eluted cleanly in 1:1 hexanes:EtOAc.

0.164 g (0.31 mmol, 1 equiv.) of β-amino ester 12 was dissolved in 10 mL dry $CH_2Cl_2$ at 0° C. and treated with ~1 mL TFA. The resulting solution was warmed to room temperature and stirred for 2 hrs. The solvents were removed in vacuo. The crude salt was then dissolved in toluene, concentrated, and dried on mechanical pump to remove residual TFA. Meanwhile. 0.134 g (0.62 mmol, 2 equiv.) N-Boc-L-valine was dissolved in ~10 mL dry CH$_2$Cl$_2$ and treated with 0.321 g (0.62 mmol, 2 equiv.) PyBOP and 0.160 mL (0.92 mmol, 3 equiv.) iPr$_2$NEt. The resulting solution was stirred under argon for ~5 min, and then cooled to 0° C. The crude TFA-salt was taken up in 5 mL dry CH$_2$Cl$_2$ and added dropwise to the activated acid. The mixture was warmed to room temperature and stirred for 2 hrs, when the reaction was assumed complete. The solvents were removed in vacuo and the crude reaction mixture submitted immediately to column chromatography. 0.163 g (0.23 mmol. 74% yield) of peptide 13 eluted in 1:1 hexanes:EtOAc.

0.346 g (0.40 mmol, 83% yield) of amino ester 14 was synthesized from 0.343 g (0.48 mmol) 13, according to the same procedure employed for compound 13 itself. The product ester was purified by column chromatograph, eluting in 1:2 hexanes:EtOAc.

0.094 g (0.11 mmol, 1.0 equiv.) methyl ester 14 was dissolved in 2 mL THF and 1 mL water and treated with 0.005 g (0.21 mmol, ~2.0 equiv.) LiOH. The reaction was stirred for ~0.5 hr., when TLC showed complete consumption of the starting material. The reaction mixture was cooled to 0° C. and acidified to pH ~3-4 by dropwise addition of 1N HCl. The solution was diluted up with water and extracted with CH$_2$Cl$_2$. The organic layer was dried with Na$_2$SO$_4$, filtered, and concentrated to provide the free acid, which was used without further purification. The acid was dissolved in 5 mL (to ~0.03M in substrate) dry CH$_2$Cl$_2$ at 0° C. and treated with 1 mL (to ~0.3M in substrate) TFA. The mixture was then warmed to room temperature and stirred for 2 hrs. The solvents were removed in vacuo. The crude salt was then dissolved in toluene, concentrated, and dried on mechanical pump to remove residual TFA. It was then dissolved in 5 mL dry CH$_2$Cl$_2$ and added dropwise to a solution of 0.122 mL (0.70 mmol, 6.0 equiv.) iPr$_2$NEt in 10 mL CH$_3$CN at 0° C. The solution was stirred ~0.5 hr., then taken up in syringe and added via syringe pump over 10 hr. to a solution of 0.088 g (0.23 mmol, 2.0 equiv.) HATU, 0.032 g (0.23 mmol, 2.0 equiv.), and 0.122 mL (0.7 mmol, 6.0 equiv.) iPr$_2$NEt in 100 mL (to ~0.001M) CH$_3$CN. Upon completion of the addition, the solution was stirred a further 6 hrs, then concentrated and redissolved in ~2 mL CH$_2$Cl$_2$. Solids were removed by filtration through a cotton plug and the product macrocycle was purified via chromatotron. 0.040 g (0.054 mmol, 50% yield) macrocycle 15 eluted in 10:1 CH$_2$Cl$_2$:CH$_3$OH. HRMS (ESI): m/z calcd. for C$_{40}$H$_{43}$N$_5$NaO$_3$S$_3$ (M+Na)$^+$ 760.24257, found 760.24209.

Example 3. Synthesis of Largazole Proline Analogue

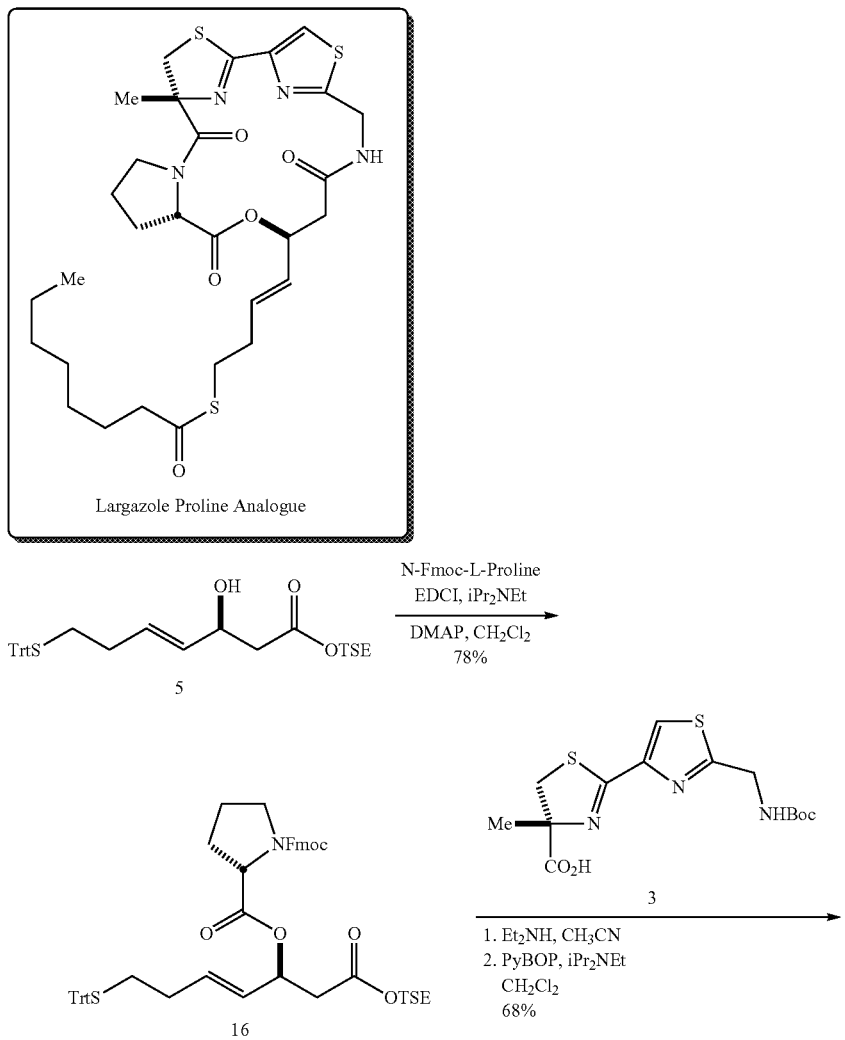

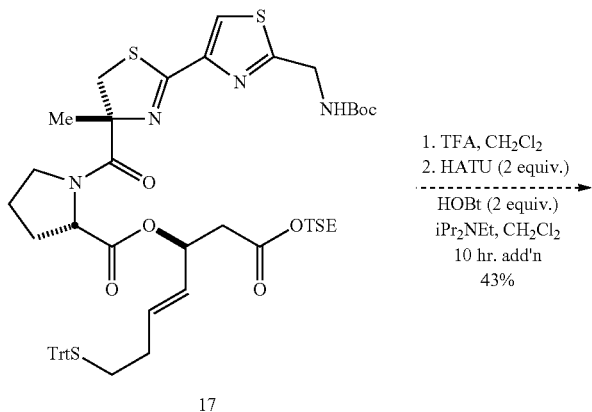

17

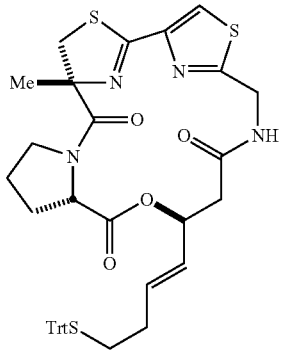

18

1. TFA, CH$_2$Cl$_2$
2. HATU (2 equiv.)
   HOBt (2 equiv.)
   iPr$_2$NEt, CH$_2$Cl$_2$
   10 hr. add'n
   43%

0.185 g (0.36 mmol, 1.0 equiv.) of β-hydroxy ester 5 and 0.601 g (1.8 mmol. 5 equiv.) N-Fmoc-L-proline were dissolved in 10 mL dry CH$_2$Cl$_2$. The reaction was cooled to 0° C. and 0.341 g (1.8 mmol, 5 equiv.) EDCI and 0.004 g (0.036 mmol, 0.1 equiv.) DMAP were added in ~5 mL CH$_2$Cl$_2$, followed by 0.370 mL (2.1 mmol, 6 equiv.) iPr$_2$NEt. The reaction was allowed to warm to room temperature and stirred over night, when TLC showed complete disappearance of β-hydroxy ester 5. The reaction was concentrated and submitted immediately to column chromatography. 0.234 g (0.28 mmol, 78% yield) Fmoc-protected diester 16 eluted in 4:1 hexanes:EtOAc.

0.100 g (0.12 mmol, 1.0 equiv.) Fmoc-protected diester 16 was taken up in 12 mL CH$_3$CN (to ~0.01M) and treated with 0.600 mL diethylamine (to ~0.2M). The resulting solution was stirred for 2 hr, and then concentrated, taken up in EtOAc, reconcentrated, and dried on a mechanical pump to remove residual diethylamine. Meanwhile, 0.046 g (0.13 mmol, 1.1 equiv.) acid 3 was dissolved in 5 mL dry CH$_2$Cl$_2$ and treated with 0.124 g (0.24 mmol, 2.0 equiv) PyBOP and 0.0.62 mL (0.36 mmol, 3.0 equiv.) iPr$_2$NEt. After stirring for ~5 min., the crude amine in 10 mL CH$_3$CN was added to the mixture dropwise. After 2 hrs, the reaction was assumed complete, concentrated, and submitted immediately to column chromatography. 0.078 g (0.081 mmol, 68% yield) of acyclic precursor 17 eluted cleanly in 2:1 hexanes:EtOAc. Clear oil. HRMS (ESI): m/z calcd. for C$_{50}$H$_{62}$N$_4$NaO$_7$S$_3$Si (M+Na)$^+$ 977.34476, found 977.34522.

0.091 g (0.095 mmol, 1.0 equiv.) acyclic precursor 17 was dissolved in 5 mL (to ~0.03M in substrate) dry CH$_2$Cl$_2$ at 0° C. and treated with 1 mL (to ~0.3M in substrate) TFA. The mixture was then warmed to room temperature and stirred overnight. The solvents were removed in vacuo. The crude salt was dissolved in toluene, concentrated, and dried on mechanical pump to remove residual TFA. It was then dissolved in 5 mL dry CH$_2$Cl$_2$ and added dropwise to a solution of 0.100 mL (0.57 mmol, 6.0 equiv.) iPr$_2$NEt in 10 mL CH$_3$CN at 0° C. The solution was stirred ~0.5 hr., then taken up in syringe and added via syringe pump over 10 hr, to a solution of 0.072 g (0.19 mmol, 2.0 equiv.) HATU, 0.026 g (0.19 mmol, 2.0 equiv.), and 0.100 mL (0.57 mmol, 6.0 equiv.) iPr$_2$NEt in 100 mL (to ~0.001M) CH$_3$CN. Upon completion of the addition, the solution was stirred a further 6 hrs. then concentrated and redissolved in ~2 mL CH$_2$Cl$_2$. Solids were removed by filtration through a cotton plug and the product macrocycle was purified via chromatotron. 0.030 g (0.041 mmol, 43% yield) macrocycle 18 eluted in 30:1 CH$_2$Cl$_2$:CH$_3$OH.

Example 4. Synthesis of Largazole Metathesis Substrate

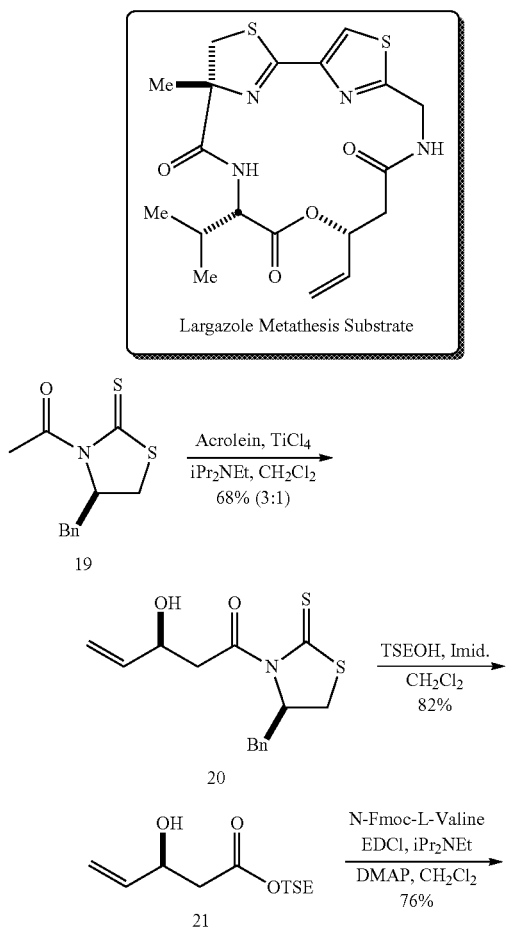

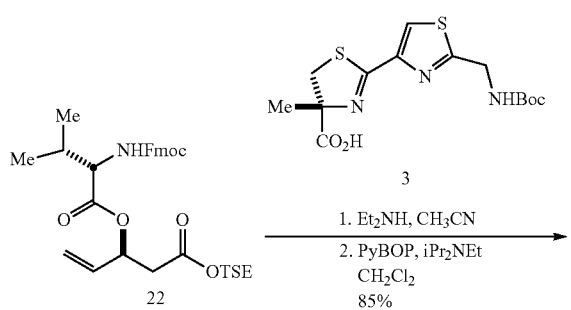

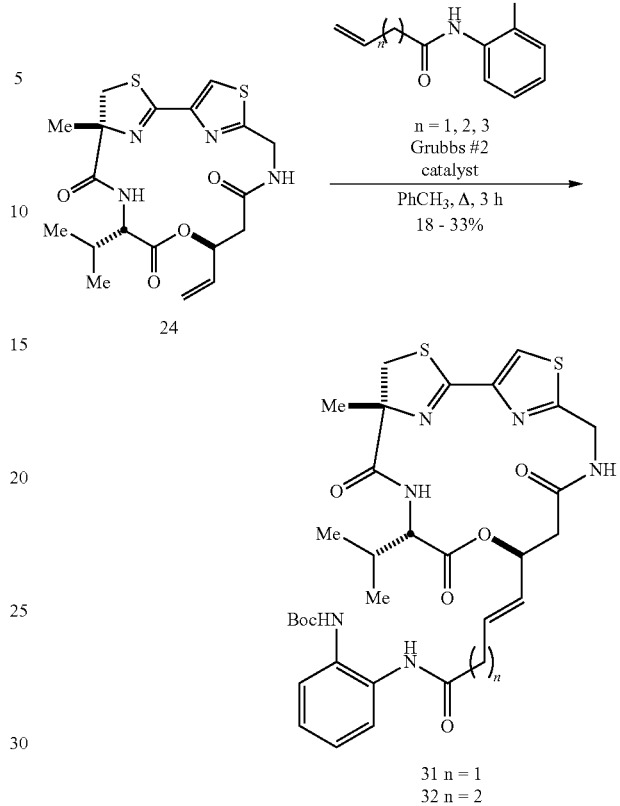

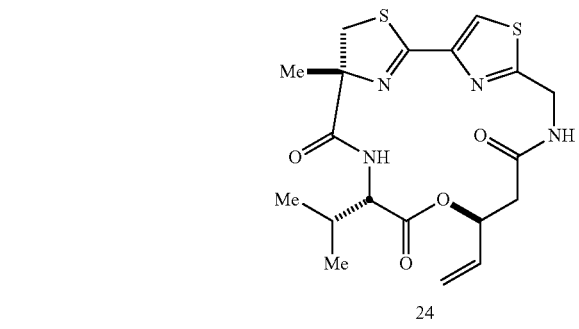

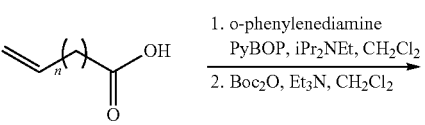

25 n = 1
26 n = 2
27 n = 3

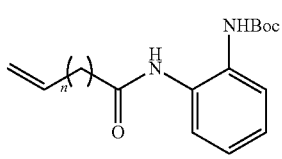

28 n = 1
29 n = 2
30 n = 3

0.520 g (1.7 mmol) thiazoline-thione 20 (Yurek-George. A., et al. 2004 *J Am Chem Soc* 126:1030-1031) was dissolved in 5 mL $CH_2Cl_2$ and 2.42 mL (16.9 mmol, 10.0 equiv.) 2-trimethylsilyethanol was added, followed by 0.173 g (2.5 mmol, 1.5 equiv.) imidazole. The resulting solution was stirred overnight, when TLC revealed complete disappearance of the starting material. The reaction mixture was concentrated in vacuo and submitted immediately to column chromatography (elutes 4:1 hexanes:ethyl acetate), which provided 0.300 g (1.4 mmol, 82% yield) of the protected ester, (3S)-3-Hydroxy-4-pentenoic acid (2-trimethylsilyl) ethyl ester (21), as a clear oil.

0.570 g (1.06 mmol, 76% yield) of diester 22 was synthesized from 0.300 g (1.39 mmol) 21, according to the same procedure employed for compound 6 above. The product diester was purified by column chromatography, eluting in 4:1 hexanes:EtOAc.

0.600 g (0.92 mmol, 85% yield) of acyclic precursor 23 was synthesized from 0.580 g (1.08 mmol) diester 22, according to the same procedure employed for compound 17 above. The product diester was purified by column chromatography, eluting in 2:1 hexanes:EtOAc.

0.308 g (0.47 mmol, 1.0 equiv.) Acyclic precursor 23 was dissolved in 15 mL $CH_2Cl_2$ (to ~0.03M), cooled to 0° C. and treated with 5 mL TFA (to ~0.6M). The reaction was allowed to warm to room temperature and stirred overnight. Solvents were evaporated and the crude amino acid redissolved in toluene and concentrated a second time to remove residual TFA. The crude amino acid was then taken up in ~5 mL $CH_2Cl_2$ and added dropwise to a stirred solution of 0.491 mL (2.8 mmol, 6.0 equiv.) $iPr_2NEt$ in 500 mL dry $CH_3CN$ (to ~0.001M). The resulting moderately opaque solution was allowed to stir ~10 min, before 0.358 g (0.94 mmol, 2 equiv.) HATU and 0.127 g (0.94 mmol, 2 equiv.) HOBt were added dropwise in ~5 mL CH$_3$CN. The reaction was allowed to stir for 16 hrs, then concentrated and submitted immediately to column chromatography. Macrocycle 24 (0.131 g. 0.30 mmol, 64% yield) eluted in 10:10:1 hexanes:EtOAc:CH$_3$OH. Clear oil.

For the cross-metathesis reaction, macrocycle 24 was dissolved in dry toluene (to ~0.026M) and heated to reflux under argon. Solutions of sacrificial olefin (2.0 equiv., ~0.26M in toluene) and catalyst (0.2 equiv., ~0.052M in toluene) were then added to the reaction. The resulting mixture was stirred at 110° C. for a further 3 hrs, with equivalent portions of olefin (2.0 equiv., ~0.26M in toluene) and catalyst (0.2 equiv., ~0.052M in toluene) being added each hour. After 3 hrs, the reaction mixture was cooled to room temperature and several drops of DMSO were added and the mixture was stirred overnight. Concentration in vacuo, followed by column chromatography provided the substituted olefins as products.

According to this general procedure. 0.025 g (0.057 mmol) macrocycle 24 was combined with olefin 29 to yield 0.006 g (0.0087 mmol, 15% yield) compound 32, which eluted slowly in 100% EtOAc. Clear oil. HRMS (ESI): m/z calcd. for $C_{33}H_{42}N_6NaO_7S_2$ (M+Na)$_+$ 721.24541, found 721.24526.

According to this general procedure, 0.039 g (0.089 mmol) macrocycle 24 was combined with olefin 30 to yield 0.012 g (0.017 mmol, 20% yield) compound 33, which eluted slowly in 100% EtOAc. Clear oil. HRMS (ESI): m/z calcd. for $C_{34}H_{44}N_6NaO_7S_2$ (M+Na)$^+$ 735.26106, found 735.2609.

Example 5. Synthesis of Largazole Oxazoline-Oxazole Analogue

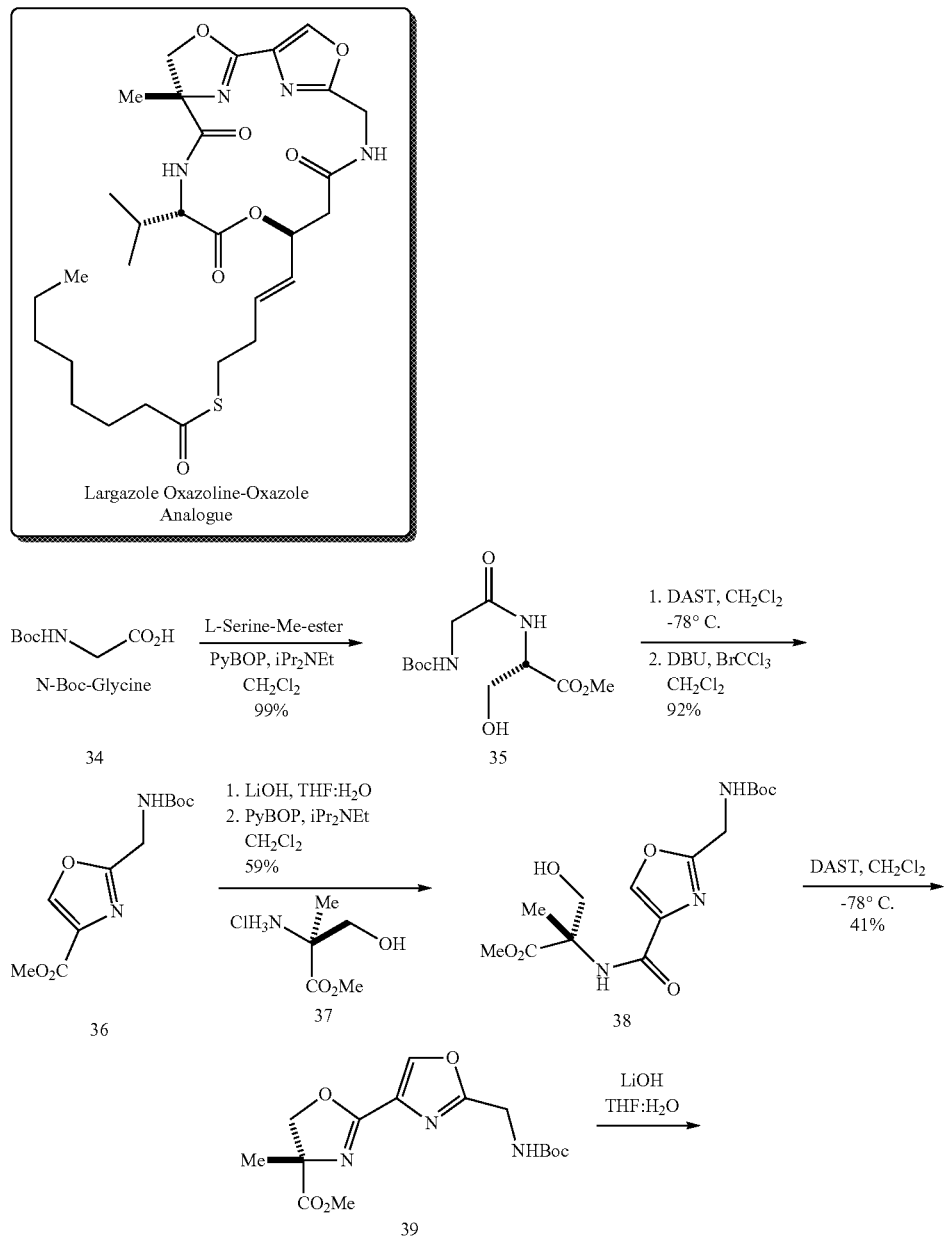

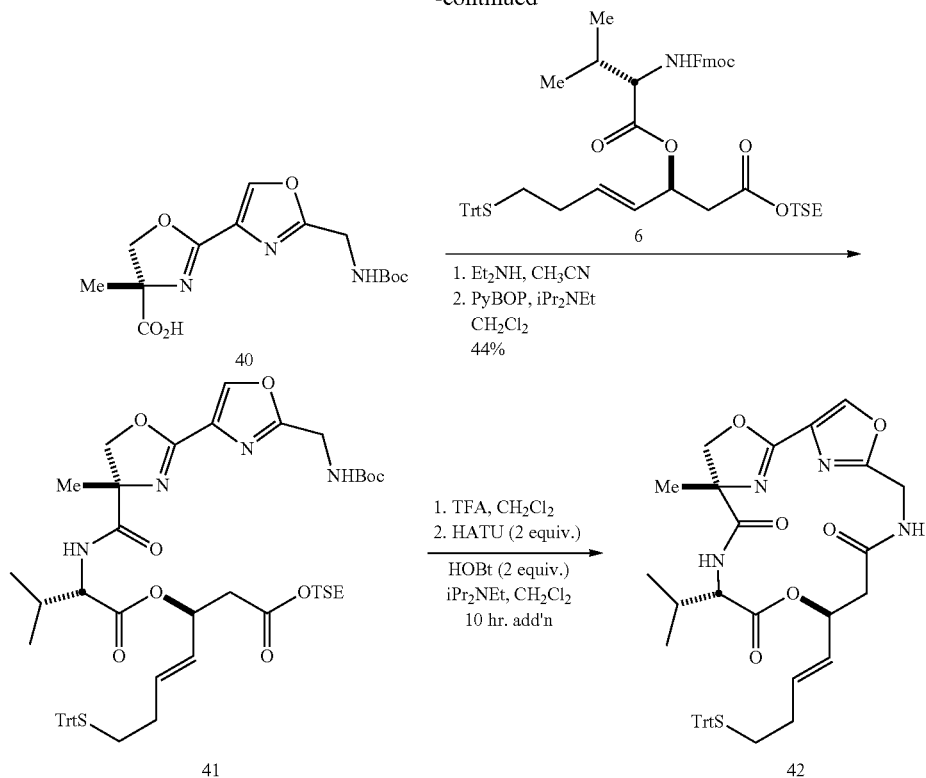

Under argon 1.126 g (6.43 mmol, 1.0 equiv.) N-Boc-glycine was dissolved in ~60 mL dry CH$_2$Cl$_2$ (to ~0.1M) and 4.01 g (7.7 mmol, 1.2 equiv.) PyBOP was added. The reaction and cooled to 0° C. and 3.36 mL (19.3 mmol, 3 equiv.) iPr$_2$NEt was added dropwise. The mixture was allowed to stir for 10 min further at 0° C. when 1.00 g (6.43 mmol, 1.0 equiv.) L-serine methyl ester hydrochloride salt was added. The reaction was allowed to warm to room temperature and stirred ~2 hrs, when it was assumed complete. Removal of the solvent by rotary evaporator, followed by column chromatography provided 1.77 g (6.41 mmol, 99% yield) alcohol 35 (elutes 100% EtOAc).

0.476 g (1.7 mmol, 1.0 equiv.) Alcohol 35 was dissolved in 5 mL dry CH$_2$Cl$_2$ (to ~0.3M) under argon and cooled to −78° C. 0.273 mL (2.07 mmol, 1.2 equiv.) DAST in 5 mL CH$_2$Cl$_2$ was added dropwise to the reaction mixture, and it was allowed to stir at −78° C. for ~1.5 hrs, when TLC showed complete disappearance of the starting alcohol. The reaction mixture was poured onto saturated aqueous NaHCO$_3$ at 0° C. stirred and extracted with CH$_2$Cl$_2$. The organic layer was dried over Na$_2$SO$_4$, filtered and concentrated to give the crude oxazoline. This was then dissolved in 10 mL CH$_2$Cl$_2$ (to ~0.25M) and 0.850 mL (8.6 mmol, 5.0 equiv.) BrCCl$_3$ and 1.29 mL (8.6 mmol, 5.0 equiv.) DBU were added. The resulting reaction mixture was stirred for 3 hrs, when TLC showed disappearance of the oxazoline in favor of a slightly less polar UV-active compound. The solvents were removed in vacuo and the product purified by column chromatography. 0.406 g (1.6 mmol, 92% yield) oxazole eluted in 1:1 hexanes:EtOAc.

0.170 g (0.66 mmol, 1.0 equiv.) Oxazole 36 was dissolved in 16 mL THF and 8 mL water and treated with 0.032 g (1.3 mmol, ~2.0 equiv.) LiOH. The reaction was stirred for ~0.5 hrs, when TLC showed complete consumption of the starting material. The reaction mixture was cooled to 0° C. and acidified to pH ~3-4 by dropwise addition of 1N HCl. The solution was diluted up with water and extracted with CH$_2$Cl$_2$. The organic layer was dried with Na$_2$SO$_4$, filtered, and concentrated to provide the free acid, which was used without further purification. The acid was dissolved in ~10 mL dry CH$_2$Cl$_2$ (to ~0.1M) and 0.690 g (1.3 mmol, 2.0 equiv.) PyBOP was added. The reaction and cooled to 0° C. and 0.347 mL (2.0 mmol, 3.0 equiv.) iPr$_2$NEt was added dropwise. The mixture was allowed to stir for 10 min further at 0° C., when 0.112 g (0.66 mmol, 1.0 equiv.) α-methyl-serine methyl ester hydrochloride salt was added. The reaction was allowed to warm to room temperature and stirred ~2 hrs, when it was assumed complete. Removal of the solvent by rotary evaporator, followed by column chromatography provided 0.140 g (0.39 mmol, 59% yield) alcohol 38 (elutes 100% EtOAc).

0.080 g (0.22 mmol, 1.0 equiv.) Alcohol 38 was dissolved in 5 mL dry CH$_2$Cl$_2$ (to ~0.3M) under argon and cooled to −78° C. 0.035 mL (0.27 mmol, 1.2 equiv.) DAST in 5 mL CH$_2$Cl$_2$ was added dropwise to the reaction mixture and it was allowed to stir at −78° C. for ~1.5 hrs. when TLC showed complete disappearance of the starting alcohol. The reaction mixture was poured onto saturated aqueous NaHCO$_3$ at 0° C., stirred and extracted with CH$_2$Cl$_2$. The organic layer was dried over Na$_2$SO$_4$, filtered and concentrated. Purification by column chromatography (eluant 100% EtOAc) provided 0.031 g (0.091 mmol. 41% yield) oxazoline-oxazole 39. Clear oil. HRMS (ESI): m/z calcd. for C$_{15}$H$_{22}$N$_3$O$_6$ (M+H)$^+$ 340.15031, found 340.15034.

0.025 g (0.074 mmol, 1.0 equiv.) Oxazole-oxazoline 39 was dissolved in 2 mL THF and 1 mL water and treated with 0.004 g (0.15 mmol, ~2.0 equiv.) LiOH. The reaction was stirred for ~0.5 hr., when TLC showed complete consumption of the starting material. The reaction mixture was cooled to 0° C. and acidified to pH ~3-4 by dropwise addition of 1N HCl. The solution was diluted up with water and extracted with $CH_2Cl_2$. The organic layer was dried with $Na_2SO_4$, filtered, and concentrated to provide the free acid, which was used without further purification. This acid was coupled to 0.068 g (0.081 mmol, 1.0 equiv.) diester 6 according to the same procedure used in preparation of acyclic precursor 41. The product oxazole-oxazoline acyclic precursor was purified by column chromatography. 0.030 g (0.032 mmol, 44% yield) eluted in 1:1 hexanes:EtOAc. White solid. $[\alpha]^{24}_D$: −14.5 (c=1, $CHCl_3$), $^1$H NMR (300 MHz, $CDCl_3$) 9.79 (bs, 1H), 7.98 (s, 1H), 5.59 (s, 1H), 4.59 (d J=6.3 Hz, 2H), 3.88 (d J=11.4 Hz, 1H), 3.30 (d J=11.4 Hz, 1H), 1.66 (s, 3H), $^{13}$C NMR (75.3 MHz, $CDCl_3$): δ 174.4, 170.3, 169.9, 162.7, 158.0, 145.0, 142.0, 133.9, 130.6, 129.8, 128.1, 128.0, 126.8, 80.6, 75.2, 71.8, 66.8, 63.3, 57.2, 39.9, 38.2, 31.6, 31.3, 31.1, 29.9, 28.5, 26.6, 19.3, 18.1, 17.5, −1.3. HRMS (ESI): m/z calcd. for $C_{50}H_{64}N_4NaO_9SSi$ $(M+Na)^+$ 947.40610, found 947.40756.

Example 6. Synthesis of β-Hydroxy Acid Analogues

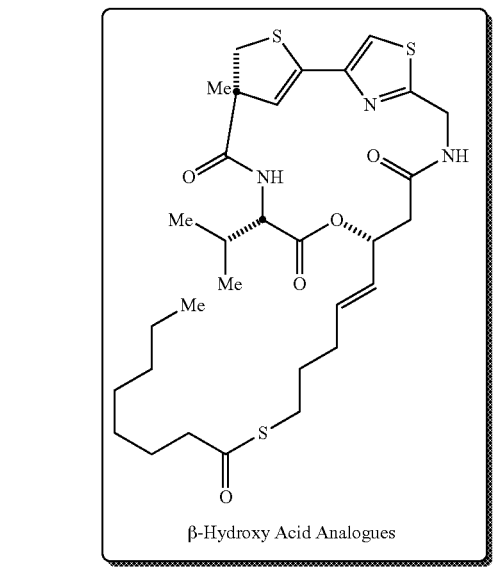

β-Hydroxy Acid Analogues

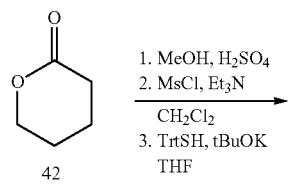

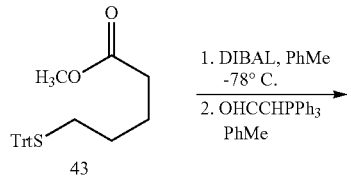

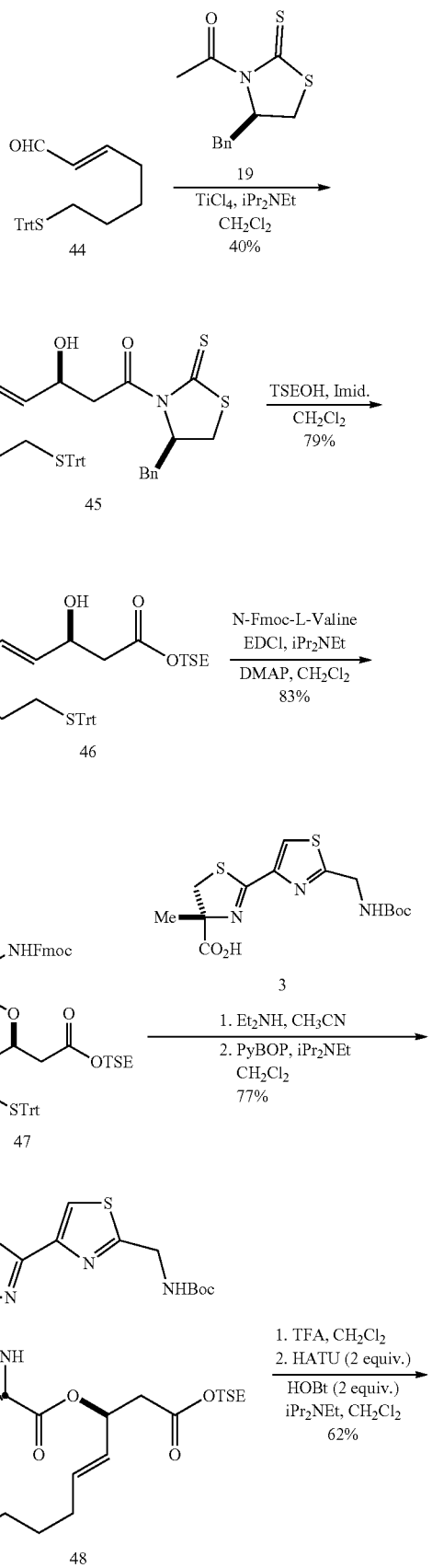

-continued

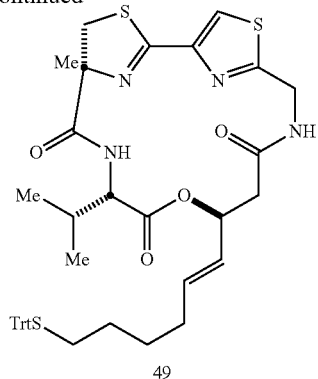

49

6.4 mL (69.3 mmol, 1.0 equiv.) δ-Valerolactone was added to ~150 mL CH$_3$OH (to ~0.5M) together with 12 drops of H$_2$SO$_4$ and the mixture was heated at reflux for 5 hr. The reaction mixture was then cooled to 0° C. and 1.00 g NaHCO$_3$ was added with stirring. The result suspension was placed in the −40° C. freezer for ~2 hrs to precipitate the unconsumed base, which was then filtered off. The solvent was evaporated under water aspirator (bath temp. <35° C.) and dried on a mechanical pump. The crude alcohol, so prepared was dissolved in ~250 mL CH$_2$Cl$_2$ (to ~0.3M) and 15 mL (104 mmol, 1.5 equiv.) Et$_3$N and cooled to 0° C. 6.5 mL (83.2 mmol, 1.2 equiv.) Methanesulfonyl chloride was added dropwise. The reaction was then allowed to warm to room temperature and stirred ~2 hrs. when TLC showed complete consumption of the alcohol. The reaction was cooled back to 0° C. and ~50 mL 1N HCl was added. The organic layer was separated, dried over Na$_2$SO$_4$, filtered, and concentrated to provide the crude mesylate, which was used without further purification.

15.00 g (52 mmol, 1.5 equiv.) Triphenylmethanethiol was dissolved in 100 mL dry THF (to ~0.2M) under argon and 11.66 g (52 mmol, 1.5 equiv.) potassium tert-butoxide was added. The resulting suspension was stirred for ~0.5 hrs and then cooled to 0° C. Approximately half of the crude mesylate was taken up in 10 mL dry THF and added to the thiolate anion dropwise. The reaction mixture was allowed to warm to room temperature and stirred overnight. It was then cooled back to 0° C., and ~15 mL 1N HCl was added. The organic layer was separated and the aqueous layer further extracted with EtOAc. The combined organics were then washed with brine, dried over Na$_2$SO$_4$, filtered, concentrated, and chromatographed to provide ester 43 (eluent 9:1 hexanes:EtOAc).

1.760 g (4.5 mmol, 1.0 equiv.) Ester 43 was dissolved in 25 mL dry toluene and cooled to −78° C. 6.75 mL (6.8 mmol, 1.0M in toluene, 1.5 equiv.) DIBAL was added via syringe pump over ~0.5 hrs and the reaction was allowed to stir ~1.5 hrs at ~78° C. The reaction was then quenched by slow addition of ~5 mL CH$_3$OH and warmed to room temperature. 25 mL Saturated aqueous sodium potassium tartrate was added and stirred ~5 min. The reaction was diluted with CH$_2$Cl$_2$ and the organics separated, dried over Na$_2$SO$_4$, filtered, and concentrated to provide the crude aldehyde, which was carried on without further purification.

The crude aldehyde was dissolved in 25 mL toluene (to ~0.2M), 1.66 g (5.45 mmol, 1.1 equiv.) (triphenylphosphoranylidene)acetaldehyde was added, and the reaction mixture was heated to reflux for 7 hrs. It was then cooled to room temperature, concentrated, chromatographed to provide aldehyde 44 (elutes 4:1 hexanes:EtOAc).

To a stirred solution of 0.243 g (0.97 mmol, 1.2 equiv.) Nagao auxiliary in 10 mL CH$_2$Cl$_2$ at 0° C. was added 0.115 mL (1.05 mmol, 1.3 equiv.) TiCl$_4$. The reaction mixture was stirred for 5 minutes, cooled to −78° C. before the addition of 0.182 mL (1.05 mmol, 1.3 equiv.) iPr$_2$NEt and stirred for 2 hours. 0.311 g (0.96 mmol, 1.0 equiv.) Aldehyde 44 in 5 ml. CH$_2$Cl$_2$ was added dropwise and the reaction mixture stirred for 1.5 hrs. 25 mL Saturated NH$_4$Cl$_2$ was then added and the reaction mixture diluted with CH$_2$Cl$_2$ (20 mL), allowed to attain room temperature, extracted with CH$_2$Cl$_2$ (3×50 mL), washed with brine, and dried over Na$_2$SO$_4$. The solvent was then removed and the residue purified by flash chromatography (eluant 4:1 hexanes:EtOAc) to give 0.201 g (0.32 mmol, 40% yield) of the major isomer 45 as a yellow oil.

0.200 g (0.31 mmol) thiazoline-thione 45 was dissolved in 5 mL CH$_2$Cl$_2$ and 0.450 mL (3.1 mmol, 10.0 equiv.) 2-trimethylsilyethanol was added, followed by 0.032 g (0.47 mmol, 1.5 equiv.) imidazole. The resulting solution was stirred overnight, when TLC revealed complete disappearance of the starting material. The reaction mixture was concentrated in vacuo and submitted immediately to column chromatography (elutes 4:1 hexanes:ethyl acetate), which provided 0.135 g (0.25 mmol, 79% yield) of the protected ester, (3S,4E)-3-Hydroxy-7-[(triphenylmethyl)thio]-4-heptenoic acid (2-trimethylsilyl)ethyl ester (46), as a clear oil.

0.177 g (0.204 mmol, 83% yield) of diester 47 was synthesized from 0.0.135 g (0.247 mmol) 46, according to the same procedure employed for compound 16 above. The product diester was purified by column chromatography, eluting in 4:1 hexanes:EtOAc.

0.155 g (0.157 mmol, 77% yield) of acyclic precursor 48 was synthesized from 0.177 g (0.204 mmol) diester 47, according to the same procedure employed for compound 17 above. The product diester was purified by column chromatography, eluting in 2:1 hexanes:EtOAc.

0.010 g (0.013 mmol, 62% yield) of macrocycle 49 was synthesized from 0.021 g (0.021 mmol) acyclic precursor 48, according to the same cyclization procedure employed for compound 10 above. The product macrocycle was purified by column chromatography, eluting in 100% EtOAc.

Example 7. Biochemical Activity of Synthetic Largazole and Largazole Thiol

The biochemical activity of synthetic largazole (1) and the largazole thiol (2) against HDACs 1, 2, 3 and 6 was investigated employing robust, kinetic biochemical assays. To measure the inhibitory effect on deacetylase function in vitro, a continuous kinetic biochemical assay miniaturized to 384-well plate format was optimized. In this assay, purified, full-length HDAC protein (HDAC1 1.67 ng/µL, HDAC2 0.067 ng/µL, HDAC3/NCor2 0.033 ng/µL, HDAC6 0.67 ng/µL; BPS Biosciences) was incubated with a commercially available fluorophore-conjugated substrate at a concentration equivalent to the substrate K$_m$ (Upstate 17-372; 6 µM for HDAC1, 3 µM for HDAC2, 6 µM for HDAC3/NCoR2 and 20 µM for HDAC6).

Figure 1B:
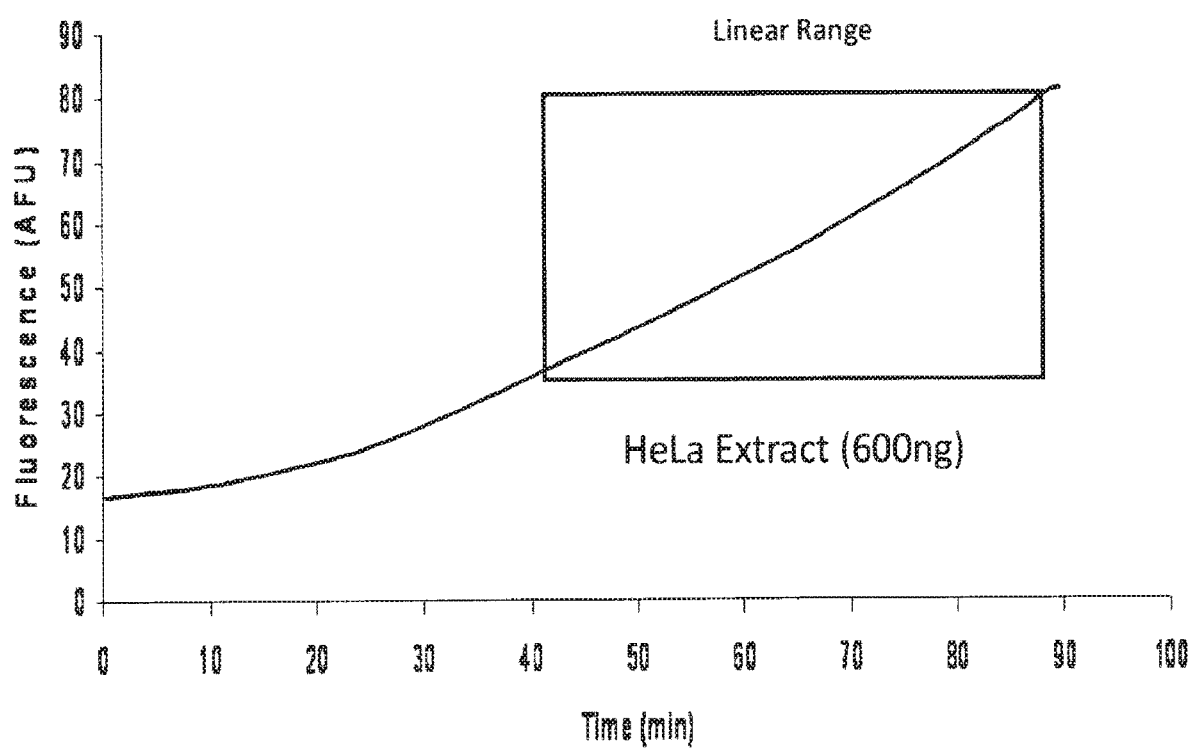

Reactions were performed in assay buffer (mM HEPES, 100 mM KCl, 0.001% Tween-20, 0.05% BSA, 200 µM Tris(2-Carboxyethyl)-Phosphine Hydrochloride, pH 7.4) and followed for fluorogenic release of 7-amino-4-methylcoumarin from substrate upon deacetylase and trypsin enzymatic activity (FIG. 1). Fluorescence measurements were obtained in real-time on a Varioskan microtiter plate reader (Thermo). Triplicate experimental data from incubations with inhibitor were normalized to solvent-only wells and analyzed by logistic regression (Spotfire DecisionSite). Calculation of $K_i$ was determined using a derivation of the standard formula $K_i=[\text{inhibitor}]/(1+S/K_m))-[\text{substrate}]/K_m)^{-1}$.

Figure 2:
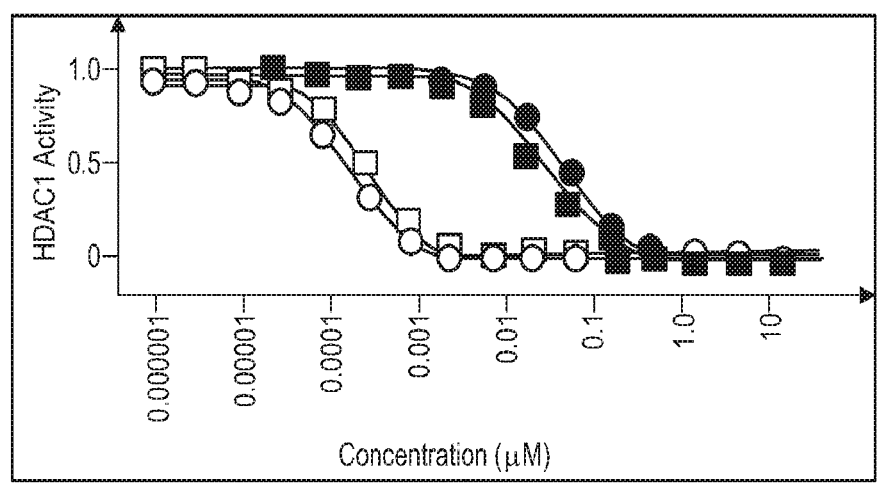
FIG. 2 graphically depicts the inhibition of HDAC1 by largazole (filled circles), largazole thiol (open circles), SAHA (filled squares), and FK228 (open squares).

As presented in FIGS. 2, 3, and Table 2, below, largazole thiol is an extraordinarily potent inhibitor of HDAC1 and HDAC2 ($K_i$=70 pM). The table indicates the HDAC inhibitory activity (Ki; nM) of largazole (1) and largazole thiol (2), as compared to pharmaceutical HDAC inhibitors.

TABLE 2

| Compound | HDAC1 | HDAC2 | HDAC3 | HDAC6 |
| --- | --- | --- | --- | --- |
| largazole (1) | 20 | 21 | 48 | >1000 |
| largazole thiol (2) | 0.07 | 0.07 | 0.17 | 25 |
| FK228[a] | 0.12 | 0.14 | 0.28 | 35 |
| SAHA | 10 | 10 | 15 | 9 |

[a]The FK228 sample used in this study was synthesized12a and then purified by PTLC to homogeneity.

The parent natural product largazole itself, on the other hand, is a comparatively weak HDAC inhibitor, with potency approximating the non-selective pharmaceutical product SAHA (Vorinostat; Merck Research Laboratories). In fact, the measurement of potency obtained in these studies of largazole define the maximal possible HDAC inhibitory effect. That is, even a trace contamination of largazole thiol or free thiol liberated under aqueous assay conditions or by trypsin (present in this enzyme-coupled reaction) could account for the substantial decrease in enzyme potency observed.

Detailed studies of FK228 isoform selectivity previously identified a strong bias favoring the Class I enzymes, HDAC1, HDAC2 and HDAC3, over the Class IIb enzyme, HDAC6.[12b] Similarly, the active depsipeptide largazole thiol (2) exhibits substantial potency against HDAC1, HDAC2 and HDAC3 in the picomolar range (Table 2, above). Indeed, this degree of inhibitory potency against HDAC1, HDAC2 and HDAC3 is unprecedented. Only FK228 itself has HDACi potency approaching that of 2.

The biochemical data provided herein reflect activity in highly robust, miniaturized homogeneous assays with Z' calculations compatible with high-throughput screening. In this assay, high concordance with published, kinetic measurements of enzyme inhibition (Ki) was observed. Thus, the accuracy of the instant HDAC inhibitory data would be expected to be markedly improved. This is important due to the recorded observation of the unusual, likely unprecedented potency of largazole thiol for HDAC1 and the direct comparison provided to FK228. Of note, the present synthesis is significantly higher yielding than that previously reported[i(b)].

Example 8. Biochemical Activity of Largazole Thiol Compared to FK228

Figure 3:
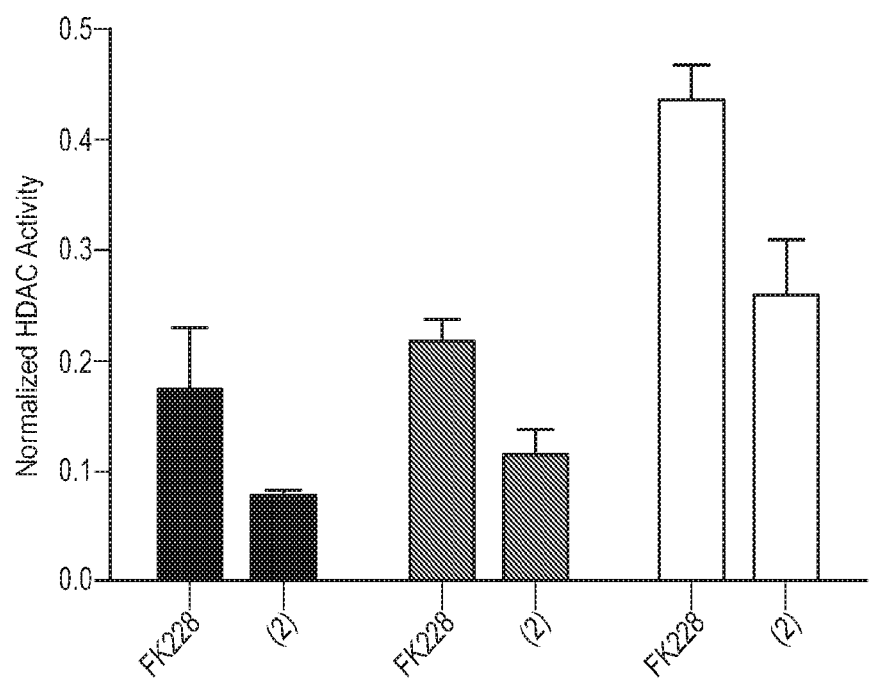
FIG. 3 depicts, in bar graph form, the results of dose-ranging studies of FK228, largazole, and largazole thiol performed against Class 1 HDAC proteins. As a comparative measure of potency, compounds were studied in triplicate at a standard concentration (0.6 nM). Average data are presented for inhibition of HDAC1 (black). HDAC2 (gray), and HDAC3/NCoR2 (white). Error bars reflect one standard deviation from the mean.

Comparative profiling of FK228 and the largazole thiol (2) demonstrated superior inhibitory potency of the thiol derivative against HDAC1, HDAC2 and HDAC3 (FIG. 3). The comparatively diminished potency of largazole itself in these homogeneous assays indicated pro-drug activation of largazole.

Example 9. Investigation of Antiproliferative Effects of Largazole and Largazole Thiol Studies aimed at determining the potential utility of largazole as an HDAC inhibitor-based therapeutic agent have been initiated, including studies to determine the antineoplastic effects of largazole (1) and the largazole thiol (2) on cultured human cancer cells. Predicting a potent anti-proliferative effect of largazole based on the biochemical potency for Class I HDACs as described above, a panel of malignant melanoma cell lines was selected for study, due to the typically extreme chemoresistance of this tumor. Effects on cell viability were evaluated using a panel of human malignant melanoma cell lines, using the standard, surrogate measurement of ATP content (Cell TiterGlo; Promega) in 384-well plate format. Replicate measurements were normalized to vehicle-only controls and $IC_{50}$ calculations were performed by logistic regression (Spotfire DecisionSite).

Figure 4:
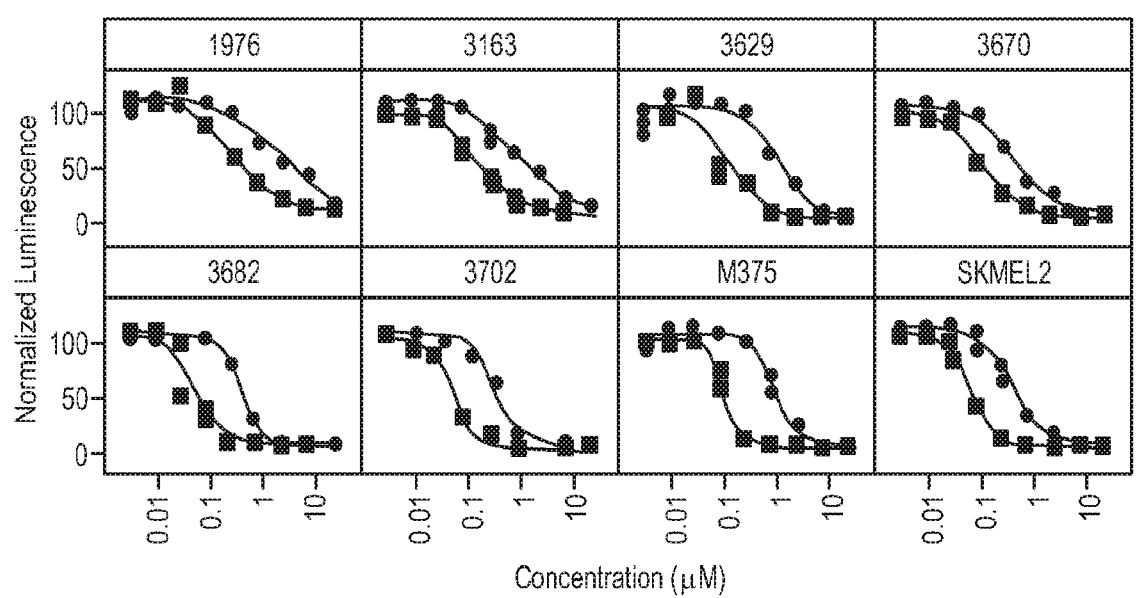
FIG. 4 graphically depicts the effects on cell viability evaluated using a panel of human malignant melanoma cell lines, using the standard, surrogate measurement of ATP content (Cell TiterGlo: Promega) in 384-well plate format. Replicate measurements were normalized to vehicle-only controls, and $IC_{50}$ calculations were performed by logistic regression (Spotfire DecisionSite). Shaded circles depict the antiproliferative effects of largazole thiol, and shaded squares depict the antiproliferative effects of largazole.

As demonstrated in FIG. 4, largazole exhibited sub-micromolar inhibitory effect on melanoma cell proliferation. Of note, largazole has a consistent, superior potency ($IC_{50}$ 45 nM-315 nM) compared to largazole thiol ($IC_{50}$ 360 nM-2600 nM).

Example 10. HDAC Inhibition of Largazole Analogs

A biochemical study of HDAC2 inhibition was carried out using the trypsin-coupled, kinetic fluorescence homogeneous assay described above. Compounds of the invention were assayed in comparison with known standards such as SAHA and a trypsin inhibitor.

TABLE 3

Results from scatter plots depicting activity versus concentration of various compounds.
Conc (uM)

| CompoundName-Leupeptin | CompoundName-ab6_113b Largazole | CompoundName-ab6_125 Pyrloyl Disulfide of depsipeptide | CompoundName-ab6_162alr1 n + 2 thiol |
| --- | --- | --- | --- |
| R2 = 0.9912 | R2 = 0.9617 | R2 = 0.9905 | R2 = 0.9884 |
| min = −25 | min = −2.21E4 | min = 108.2 | min = −240.1 |
| max = 9169 | max = 9652 | max = 9761 | max = 9258 |
| Hill = −1.205 | Hill = −1.165 | Hill = −1.887 | Hill = −1.035 |
| X50 = 0.3077 | X50 = 7.136 | X50 = 0.3265 | X50 = 0.07852 |
| CompoundName-SAHA | CompoundName-ab6_1236 acyl amide | CompoundName-ab6_161alr1 Proline thiol | CompoundName-ab6_162b |
| R2 = 0.9926 | Reached max iterations | R2 = 0.9761 | R2 = 0.9404 |
| min = 102.4 | R2 = 0.009834 | min = 340.3 | min = −1720 |
| max = 9012 | min = 9527 | max = 9470 | max = 8721 |
| Hill = −1.115 | max = 4.862E4 | Hill = −1.823 | Hill = −1.241 |
| X50 = 0.02683 | Hill = 0.2128 | X50 = 0.7733 | X50 = 2.689 |
| CompoundName-ab6_113a thiol | X50 = 1.677E12 | | CompoundName-none |

TABLE 3-continued

Results from scatter plots depicting activity versus
concentration of various compounds.
Conc (uM)

| depsipeptide | CompoundName-ab6_123a amide thiol | CompoundName-ab6_161b Proline acyl | Not solved. All data points have the same x-value. |
|---|---|---|---|
| $R^2$ = 0.994 | $R^2$ = 0.995 | Reached max iterations | |
| min = −84.01 | min = −40.61 | $R^2$ = 0.04023 | |
| max = 9677 | max = 9382 | min = 7262 | |
| Hill = −1.55 | Hill = −1.09 | max = 9299 | |
| X50 = 0.003574 | X50 = 0.01112 | Hill = −0.3774 | |
| | | X50 = 707.6 | |

Figure 5:
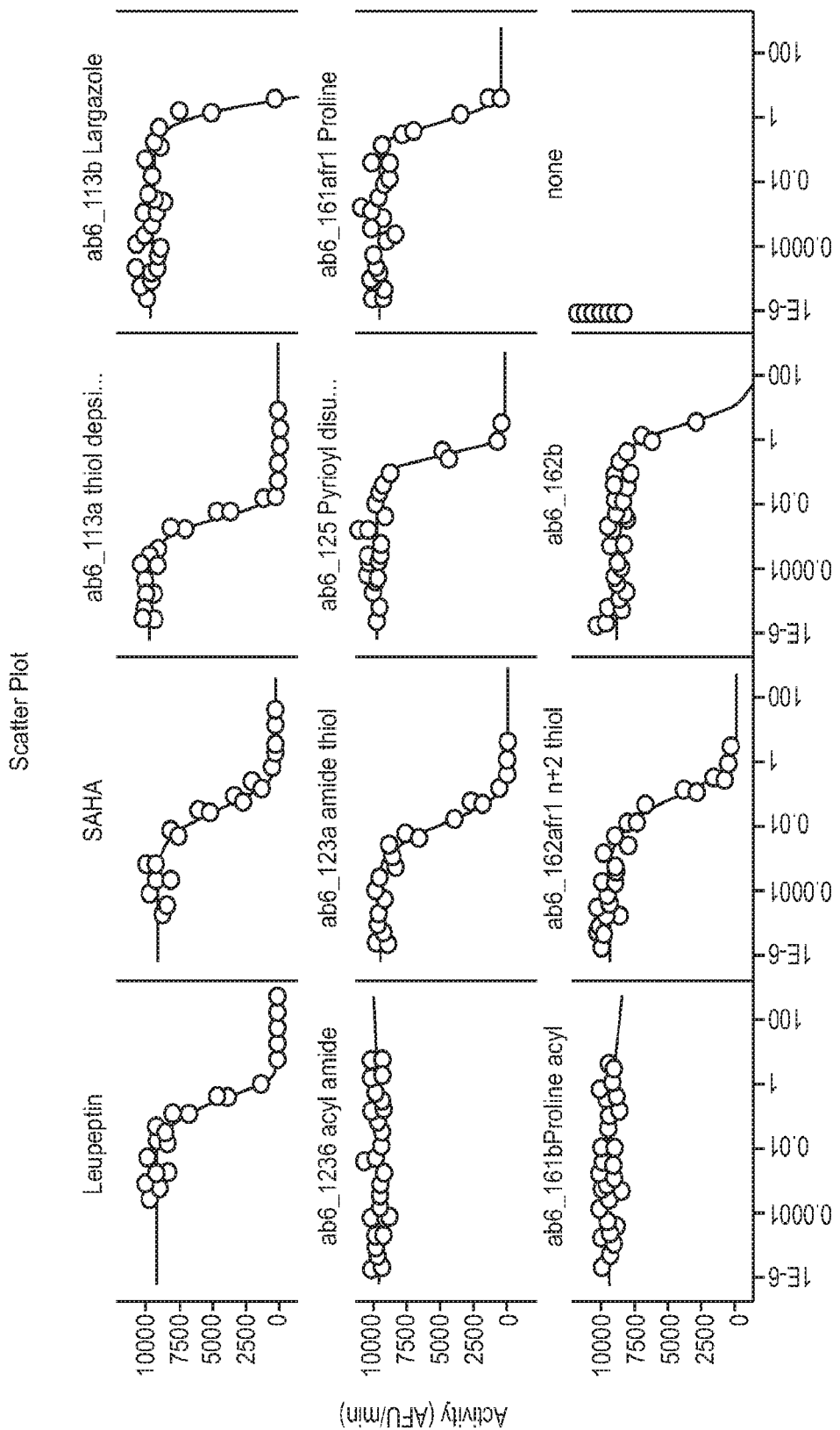
FIG. 5 shows scatter plots depicting HDAC inhibition by various largazole analogs. The curves represent IC50 curves comparing compounds of the invention to standards (SAHA and a trypsin inhibitor).

The chemical structures of the compounds designated numerically in FIG. 5, above, are shown below.

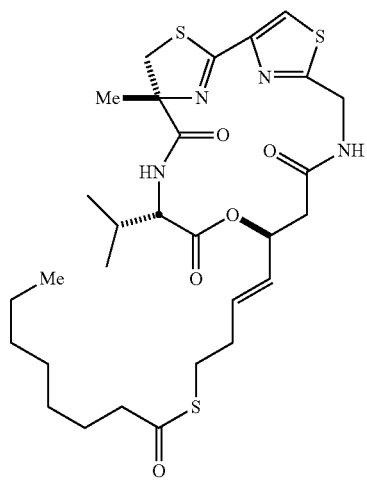

ab6_113b Largazole

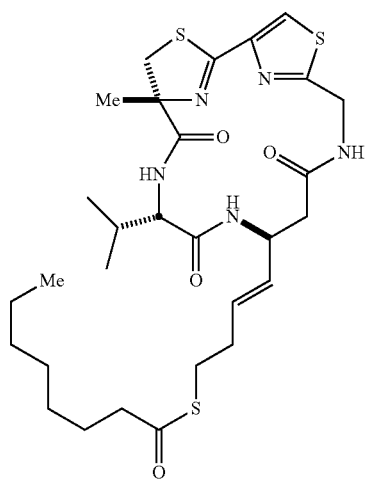

ab6_1236 acyl amide

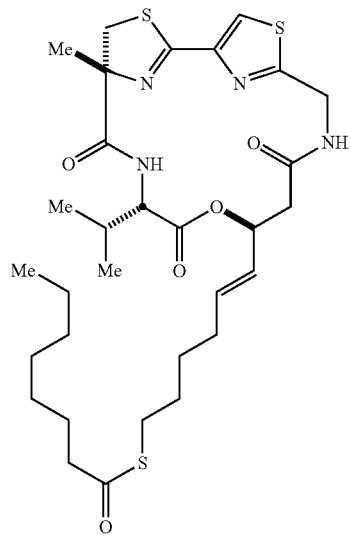

ab6_162b

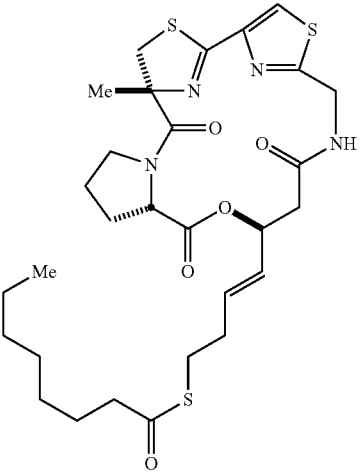

ab6_161b Proline acyl

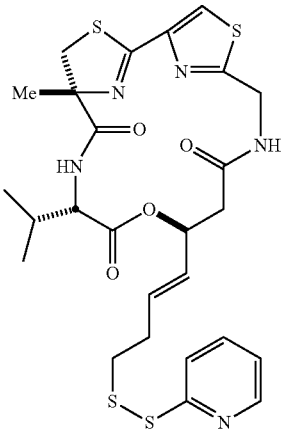

ab6_125 Pyridyl Disulfide

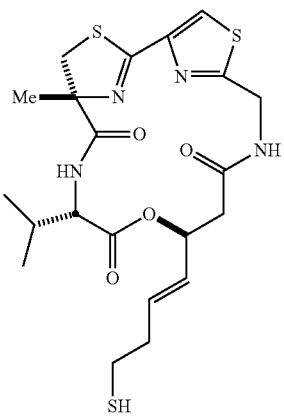

ab6_113a thiol depsipeptide

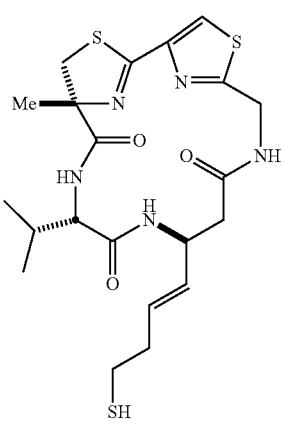

ab6_123a amide thiol

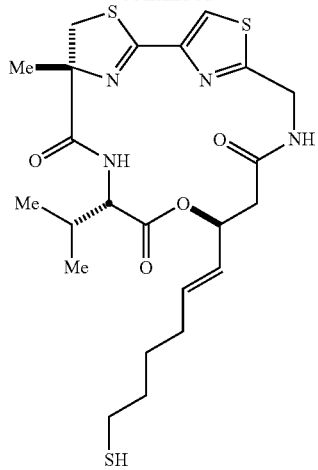

ab6_162afr1 n + 2 thiol

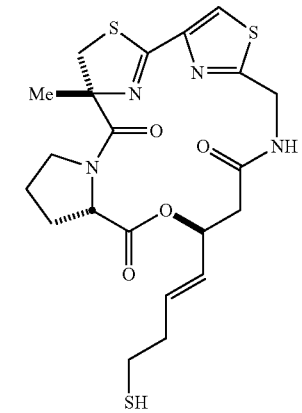

ab6_161afr1 Proline thiol

Thus, described herein thus far is an efficient total synthesis of largazole (1) in eight linear steps and 37% overall yield, and its active metabolite, the largazole thiol (2) in seven linear steps. The synthesis recorded herein provided 12 milligrams of synthetic largazole and 19 milligrams of largazole thiol on the first pass (and should be readily scaleable to gram-quantities), allowing for further investigation of the biological activity of this potential cancer chemotherapeutic.

Further described herein is that largazole is, in fact, a pro-drug, which must be converted to its active form, free-thiol 2. The combination of cap group and zinc-binding motif present in this thiol provide the most potent and selective HDACi reported to date. The octanoyl residue in largazole likely serves a dual role, imparting better cell-permeability and allowing facile presentation of the free thiol within the cell. The observed inverse difference in cytotoxicity can be attributed to the superior cell-permeability of the thioester (1) as compared to the thiol (2). The data presented herein can be used to design and develop potent and therapeutically active agents that target inhibition of HDAC's.

Since FK228. FR901375 and spiruchostatin mask the common and key 3-hydroxy-7-mercaptohept-4-enoic acid unit as a reductively labile disulfide, other protect-and-release strategies for exploiting this potent zinc-binding arm in the context of new molecular scaffolds are contemplated. In addition, the molecular scaffold of largazole provides yet another macrocyclic template from which a myriad of potentially active and isoform-selective HDAC inhibitors can be designed and synthesized.

Example 11. Synthesis of Largazole-Azumamide Hybrid

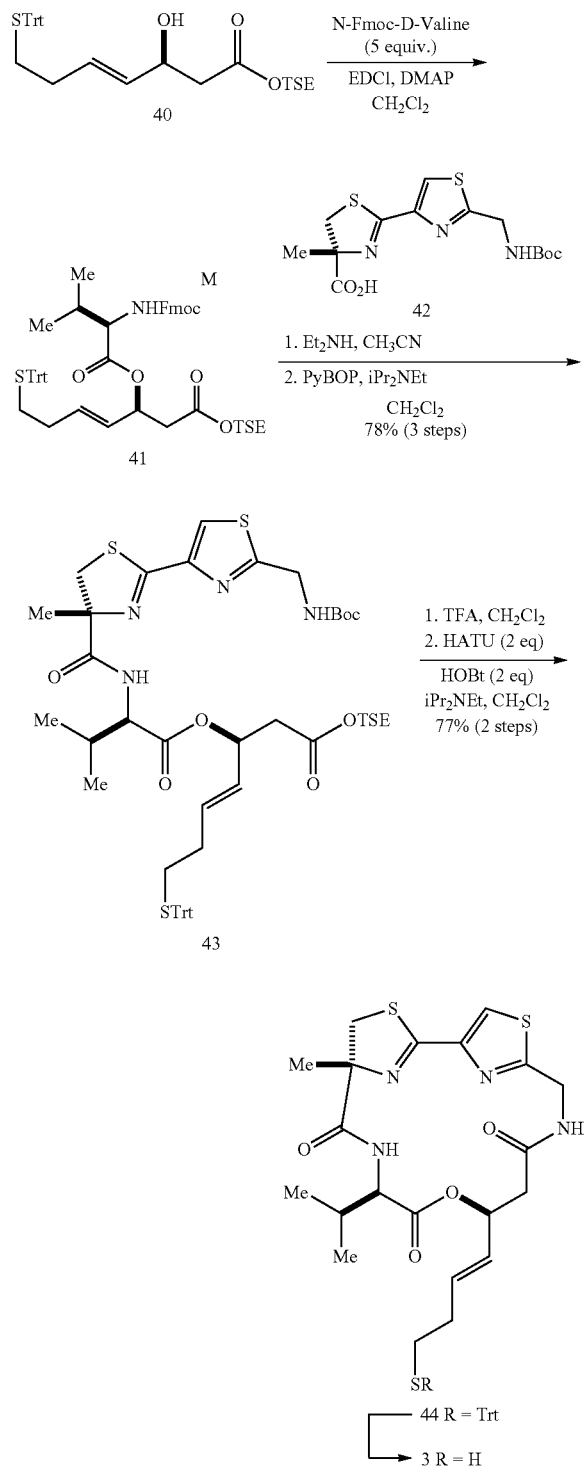

(3S,4E)-2-(Trimethylsilyl)ethyl-3-[(R)-2-((R)-2-{2-[(tert-butoxycarbonyl)methyl]thiazol-4-yl}-4-methyl-4, 5-dihydrothiazole-4-carboxamido)-3-methylbutanoyloxy]-7-(tritylthio)hept-4-enoate (43)

0.104 g (0.2 mmol) of β-hydroxy ester 40 and 0.340 g (1.0 mmol, 5 equiv.) N-Fmoc-D-valine were dissolved in 5 mL dry $CH_2Cl_2$. The reaction was cooled to 0° C. and 0.192 g (1.0 mmol, 5 equiv.) EDCI and 0.003 g (0.02 mmol, cat.) DMAP were added in ~5 mL $CH_2Cl_2$, followed by 0.2 mL $iPr_2NEt$. The reaction was allowed to warm to room temperature and stirred over night, when TLC showed complete disappearance of 40. The reaction was concentrated and passed through a short plug of silica, washing with 100% EtOAc. The product diester eluted with a by-product from the excess amino acid used, which was not separated at this time. Instead, the crude diester was taken up in 15 mL $CH_3CN$ (to ~0.01M) and treated with 1 mL diethylamine (to ~0.2M). The resulting solution was stirred for two hours and then concentrated, taken up in EtOAc, and concentrated again.

0.061 g (0.22 mmol, 1.1 equiv.) acid 42 was dissolved in 5 mL dry $CH_2Cl_2$ and treated with 0.151 g (0.44 mmol, 2.0 equiv) PyBOP and 0.076 mL (0.66 mmol, 3.0 equiv.) $iPr_2NEt$. After stirring for ~5 min., the crude amine in 5 mL $CH_2Cl_2$ was added to the mixture dropwise. After 2 hrs, the reaction was concentrated and submitted immediately to column chromatography. 0.056 g (0.058 mmol, 30% from 40) of peptide 43 eluting cleanly in (2:1 hexanes:EtOAc). Clear oil. $[\alpha]^{24}_D$: -6.0 (c=1, $CHCl_3$). $^1H$ NMR (300 MHz, $CDCl_3$) δ 0.02 (s, 9H), 0.88 (d J=6.9 Hz, 3H), 0.95 (d J=6.9 Hz, 3H), 1.32-1.38 (m, 2H), 1.47 (s, 9H), 1.59 (s, 3H), 1.96-2.05 (m, 2H), 2.12-2.21 (m, 3H), 2.45 (dd J=5.1, 15.9 Hz, 1H), 2.59 (dd J=8.4, 15.9 Hz, 1H), 3.29 (d J=11.4 Hz, 1H), 3.73 (d J=11.4 Hz, 1H), 4.05-4.17 (m, 2H), 4.52 (dd J=4.5, 9.0 Hz, 1H), 4.63 (d J=6.3 Hz, 1H), 5.26-5.35 (m, 2H), 5.54-5.61 (m, 2H), 7.18-7.39 (m, 16H), 7.93 s. 1H), $^{13}C$ NMR (75.5 MHz, $CDCl_3$): δ -1.3, 11.3, 12.0, 17.5, 17.6, 18.8, 19.2, 19.3, 25.4, 28.5, 29.9, 31.2, 31.5, 31.7, 39.8, 41.2, 42.1, 42.5, 53.7, 57.0, 63.3, 66.8, 71.8, 80.6, 85.3, 121.9, 126.8, 127.8, 128.0, 129.7, 133.4, 145.0, 148.8, 155.8, 163.5, 169.9, 170.5, 174.7. HRMS (ESI): m/z calcd. for $C_{50}H_{64}N_4NaO_7S_3Si$ (M+Na)$^+$ 979.35986, found 979.35980.

General Procedure for Macrocyclization 0.056 g (0.058 mmol) Acyclic precursor 43 was dissolved in 5 mL $CH_2Cl_2$ (to ~0.03M), cooled to 0° C. and treated with 1 mL TFA (to ~0.6M). The reaction was allowed to warm to room temperature and stirred overnight. Solvents were evaporated and the crude amino acid redissolved in toluene and concentrated a second time to remove residual TFA. The crude amino acid was then taken up in ~5 mL $CH_2Cl_2$ and added dropwise to a stirred solution of 0.061 mL (6.0 equiv.) $iPr_2Net$ in 60 mL dry $CH_3CN$ (to ~0.001M). The resulting moderately opaque solution was allowed to stir ~10 min., before 0.044 g (0.12 mmol, 2 equiv.) HATU and 0.016 g (0.12 mmol, 2 equiv.) HOBt were added dropwise in ~5 mL $CH_3CN$. The reaction was allowed to stir for 16 hr., then concentrated and submitted immediately to column chromatography. Macrocycle 44 (0.020 g, 57% yield) eluted quickly in EtOAc, after a general wash with 10:1 hexanes:EtOAc. Clear oil. $[\alpha]^{24}_D$: +16.1 (c=1, $CH_3OH$). $^1H$ NMR (300 MHz, 5:1 $CDCl_3$:$CD_3OD$) δ 0.70 (d J=6.6 Hz, 3H), 0.80 (d J=6.6 Hz, 3H), 1.71 (s, 3H), 1.90-2.03 (m, 3H), 2.05-2.12 (m, 2H), 2.41 (d J=16.8 Hz, 1H), 2.80 (dd J=10.5, 16.8 Hz, 1H), 3.14 (d J=11.4 Hz, 1H), 4.08-4.19 (m, 3H), 4.90 (d J=17.1 Hz, 1H), 5.21 (dd J=8.4, 15.3 Hz, 1H), 5.57-5.71 (m, 2H), 7.09-7.22 (m, 10H), 7.28-7.32 (m, 6H), 7.67 (s, 1H), $^{13}$C NMR (100.6 MHz, 5:1 CDCl$_3$:CD$_3$OD): δ 18.0, 18.8, 26.4, 31.0, 31.4, 32.2, 38.7, 39.9, 40.7, 41.5, 59.8, 59.9, 66.8, 73.0, 77.5, 84.6, 125.0, 126.8, 127.9, 128.0, 129.7, 135.3, 144.9, 147.1, 163.8, 167.9, 168.5, 170.4, 174.0. HRMS (ESI): m/z calcd. for C$_{40}$H$_{42}$N$_4$NaO$_4$S$_3$ (M+Na)$^+$ 761.22604, found 761.22478.

General Procedure for Trityl Deprotection 0.010 g (0.04 mmol) S-Trityl macrocycle 44 was dissolved in 5 mL dry CH$_2$Cl$_2$ and cooled to 0° C. The mixture was successively treated with 0.017 mL (0.08 mmol. 2 equiv.) iPr$_3$SiH and 0.200 mL TFA (to ~0.2M in 44). The reaction mixture was allowed to warm to room temperature and stirred for 2 hrs, before being concentrated and chromatographed (EtOAc) to provide 0.019 g (0.038 mmol, 95%) thiol 9. Clear oil. [α]$^{24}_D$: +11.0 (c=1, CHCl$_3$). $^1$H NMR (300 MHz, CDCl$_3$) δ 0.89 (d J=6.9 Hz, 3H), 0.97 (d J=6.9 Hz, 3H), 1.42 (t J=7.8 Hz, 1H), 2.10-2.18 (m, 1H), 2.29-2.40 (m, 2H), 2.53-2.63 (m, 3H), 2.82-2.94 (m, 1H), 3.22 (d J=11.4 Hz, 1H), 4.23-4.35 (m, 3H), 5.10 (dd J=7.8, 16.5 Hz. 1H), 5.45 (dd J=8.7, 15.9 Hz, 1H), 5.82 (t J=9.9 Hz, 1H). 5.90 (dt J=7.8, 15.3 Hz, 1H), 6.43 (s, 1H), 7.25 (s, 1H), 7.72 (s, 1H), $^{13}$C NMR (100.6 MHz, CDCl$_3$): δ 18.3, 19.1, 23.9, 26.7, 32.5, 36.6, 38.8, 40.6, 41.0, 41.9, 59.9, 72.9, 85.0, 124.8, 124.9, 129.1, 134.8, 167.9, 168.1, 169.8, 173.4. HRMS (ESI): m/z calcd. for C$_{21}$H$_{28}$N$_4$NaO$_4$S$_3$ (M+Na)$^+$ 519.11649. found 519.11777.

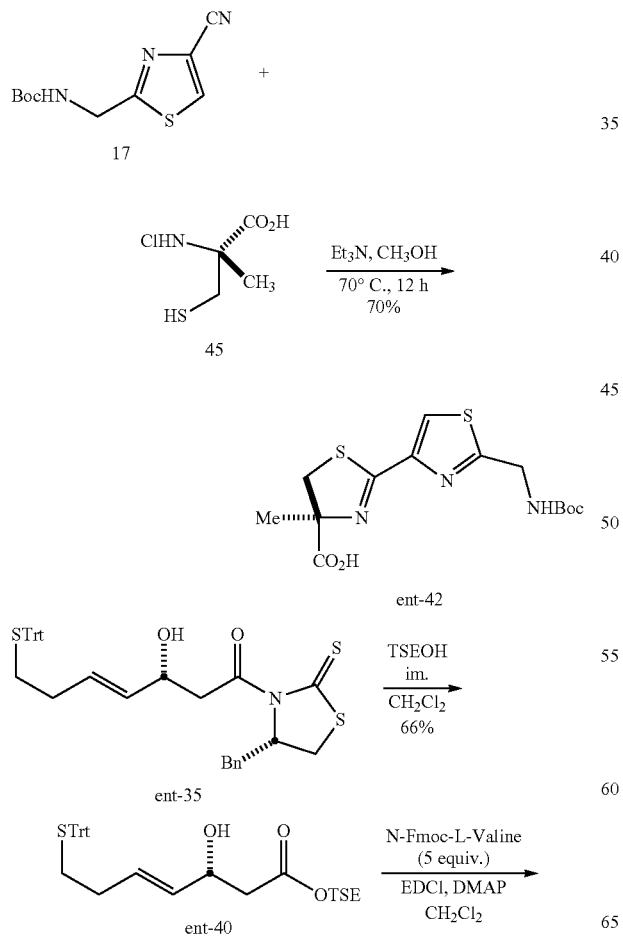

(S)-2-(2-((tert-Butoxycarbonylamino)methyl)thiazol-4-yl)-4-methyl-4,5-dihydrothiazole-4-carboxylic Acid (ent-42)

To a solution of sodium bicarbonate (0.65 g. 7.68 mmol) in CH$_3$OH (22 ml) and pH 7 phosphate buffer (14.4 ml) was added 17 and 45. The mixture was stirred overnight at 70° C. and then cooled to room temperature. The solvent was evaporated, and the residue dissolved in ether and water. Following extraction into ether, the organic layers were discarded and the aqueous layer was acidified to pH 2 with 3 N HCl. This was then extracted into EtOAC (3×20 mil), washed with brine, and dried over sodium sulfate to give ent-42 as a light brown foam (0.96 g. 70% yield). [α]$^{24}_D$: +22.0 (c=1, CH$_3$OH). Both $^1$H and $^{13}$C NMR spectra of ent-42 matched previously published spectra of 42 itself.

(R,E)-2-(Trimethylsilyl)ethyl 3-hydroxy-7-(tritylthio)hept-4-enoate (ent-40)

To a stirred solution of ent-35 (0.88 g, 1.44 mmol) in CH$_2$Cl$_2$ (14 ml) was added 2-(trimethylsilyl)ethanol (2 mil. 14.4 mmol) and imidazole (0.15 g. 2.16 mmol). The mixture was stirred overnight, after which the solvent was evaporated and the residue purified by column chromatography (10:1 to 4:1 hexanes/ethyl acetate) to give ent-40 as a clear oil (0.49 g, 66%). [α]$^{24}_D$: +5.0 (c=2, CHCl$_3$). Both $^1$H and $^{13}$C NMR spectra of ent-40 matched previously published spectra of 40 itself.

(3R,4E)-2-(Trimethylsilyl)ethyl-3-[(S)-2-((S)-2-{2-[(tert-butoxycarbonyl)methyl]thiazol-4-yl}-4-methyl-4,5-dihydrothiazole-4-carboxamido)-3-methylbutanoyloxy]-7-(tritylthio)hept-4-enoate (46)

46 was prepared from ent-40 (0.14 g, 0.28 mmol) in the same fashion as 43, to give 46 in 50% yield (0.12 g, 0.14 mmol). [α]$^{24}_D$: +20.0, (c=0.2, CHCl$_3$. Both $^1$H and $^{13}$C NMR spectra of 43 matched previously published spectra of ent-43.

(−)-Largazole Thiol (2)

The general procedure for both cyclization and deprotection described above was followed to give trityl protected macrocycle 47 in 87% yield (0.07 g, 0.14 mmol). [α]n=−6, c=0.0.1 in methanol. Ent-Largazole (2) was completed in 90% yield (0.03 g, 0.05 mmol). [α]$_D$=−21.0 (c=0.1, CHCl$_3$). $^1$H and $^{13}$C NMR of both 47 and 2 match those of (+)-Largazole.

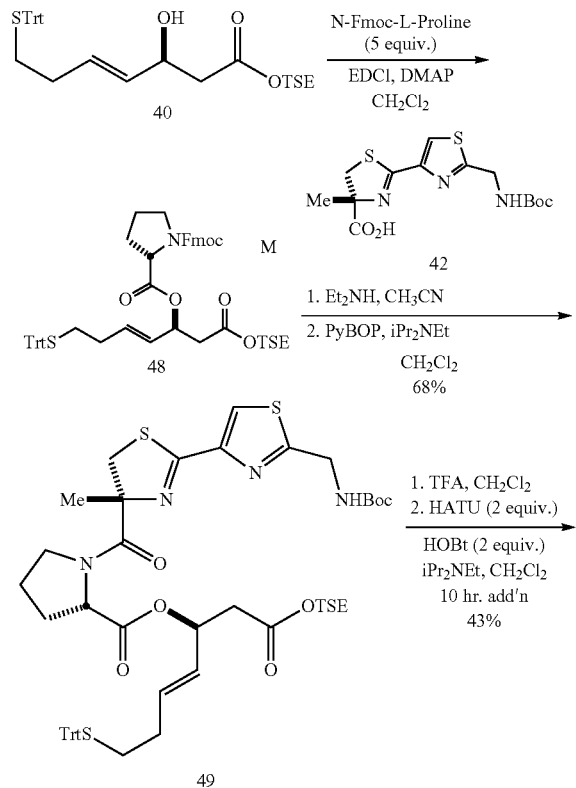

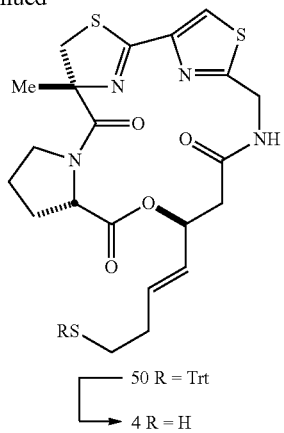

50 R = Trt
4 R = H

Acyclic Precursor 49.

0.185 g (0.36 mmol, 1.0 equiv.) of β-hydroxy ester 40 and 0.601 g (1.8 mmol, 5 equiv.) N-Fmoc-L-proline were dissolved in 10 mL dry CH$_2$Cl$_2$. The reaction was cooled to 0° C. and 0.341 g (1.8 mmol, 5 equiv.) EDCI, and 0.004 g (0.036 mmol, 0.1 equiv.) DMAP were added in ~5 mL CH$_2$Cl$_2$, followed by 0.370 mL (2.1 mmol, 6 equiv.) iPr$_2$NEt. The reaction was allowed to warm to room temperature and stirred overnight, when TLC showed complete disappearance of β-hydroxy ester 40. The reaction was concentrated and submitted immediately to column chromatography. 0.234 g (0.28 mmol, 78% yield) Fmoc-protected diester 48 eluted in 4:1 hexanes:EtOAc.

0.100 g (0.12 mmol, 1.0 equiv.) Fmoc-protected diester 48 was taken up in 12 mL, CH$_3$CN (to ~0.01M) and treated with 0.600 mL diethylamine (to ~0.2M). The resulting solution was stirred for 2 hrs and then concentrated, taken up in EtOAc, reconcentrated, and dried on a mechanical pump to remove residual diethylamine. Meanwhile, 0.046 g (0.13 mmol, 1.1 equiv.) acid 42 was dissolved in 5 mL dry CH$_2$Cl$_2$ and treated with 0.124 g (0.24 mmol, 2.0 equiv) PyBOP and 0.0.62 mL (0.36 mmol, 3.0 equiv.) iPr$_2$NEt. After stirring for ~5 min., the crude amine in 10 mL CH$_3$CN was added to the mixture dropwise. After 2 hrs, the reaction was assumed complete, concentrated, and submitted immediately to column chromatography. 0.078 g (0.081 mmol, 68% yield) of acyclic precursor 49 eluted cleanly in 2:1 hexanes:EtOAc. (49): Clear oil. Compound NMRs display highly complex mixtures of conformational isomers; the room temperature $^1$H NMR spectrum (300 MHz, CDCl$_3$) and $^{13}$C NMR spectrum (100.6 MHz, CDCl$_3$), as well as elevated temperature $^1$H NMR spectra (300 MHz. DMSO-d$_6$) not shown. HRMS (ESI): m/z calcd. for C$_{50}$H$_{62}$N$_4$NaO$_7$S$_3$Si (M+Na)$^+$ 977.34476, found 977.34522.

S-Trityl Macrocycle 50 and Thiol 4

0.091 g (0.095 mmol, 1.0 equiv.) acyclic precursor 49 was dissolved in 5 ml. (to ~0.03M in substrate) dry CH$_2$Cl$_2$ at 0° C. and treated with 1 mL (to ~0.3M in substrate) TFA. The mixture was then warmed to room temperature and stirred overnight. The solvents were removed in vacuo. The crude salt was dissolved in toluene, concentrated, and dried on mechanical pump to remove residual TFA. It was then dissolved in 5 mL dry CH$_2$Cl$_2$ and added dropwise to a solution of 0.100 mL (0.57 mmol, 6.0 equiv.) iPr$_2$NEt in 10 mL CH$_3$CN at 0° C. The solution was stirred ~0.5 hrs, then taken up in syringe and added via syringe pump over 10 hrs to a solution of 0.072 g (0.19 mmol, 2.0 equiv.) HATU. 0.026 g (0.19 mmol, 2.0 equiv.), and 0.100 mL (0.57 mmol, 6.0 equiv.) iPr$_2$NEt in 100 mL (to ~0.001M) CH$_3$CN. Upon completion of the addition, the solution was stirred a further 6 hrs, then concentrated and redissolved in ~2 mL CH$_2$Cl$_2$. Solids were removed by filtration through a cotton plug, and the product macrocycle was purified via chromatotron. 0.030 g (0.041 mmol, 43% yield) macrocycle 50 eluted in 30:1 CH$_2$Cl$_2$:CH$_3$OH. (50): [α]$^{24}_D$: +29.1 (c=1, CHCl$_3$). $^1$H NMR (400 MHz, CDCl$_3$) δ 1.43 (s, 3H), 1.56-1.60 (m, 2H), 1.70-1.79 m, 2H), 1.89-1.95 (m, 1H), 2.03-2.19 (m, 4H), 2.26 (d J=17.6 Hz, 1H), 2.56 (dd J=2.8, 14.0 Hz, 1H), 2.81 (dd J=5.2, 14.0 Hz, 1H), 3.51 (dd J=11.6, 16.4 HZ, 1H), 3.52 (d J=11.6 Hz. 1H), 3.76-3.80 (m, 1H), 3.86 (d J=11.6 Hz, 1H), 3.88 (dd J=4.8, 17.7 Hz, 1H), 4.72 (dd J=6.4, 17.6 Hz, 1H), 5.12 (dd J=2.8, 8.4 Hz, 1H), 5.21-5.25 (m, 1H), 5.70 (dt J=6.4, 16.0 Hz, 1H), 5.91 (dd J=5.6, 16.0 Hz, 1H), 7.15-7.23 (m, 10H), 7.59 (s, 1H), $^{13}$C NMR (100.6 MHz, CDCl$_3$): δ 25.7, 31.5, 31.8, 32.5, 41.1, 42.8, 44.9, 49.6, 60.8, 67.0, 73.0, 77.4, 86.9, 124.0, 127.0, 128.1, 128.5, 129.8, 130.6, 130.8, 144.7, 147.9, 158.4, 167.2, 170.1, 172.3, 173.8. HRMS (ESI): m/z calcd. for C$_{40}$H$_{40}$N$_4$NaO$_4$S$_3$ (M+Na)$^+$ 759.21039, found 759.21059. 0.009 g 50 was deprotected according to the general procedure to provide 4, which was purified by preparative thin layer chromatography.

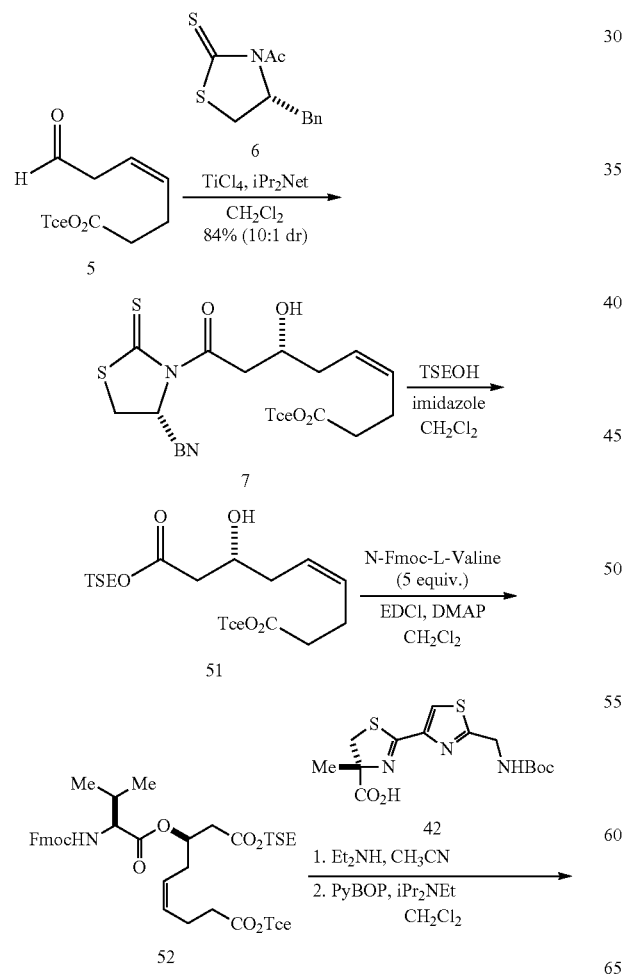

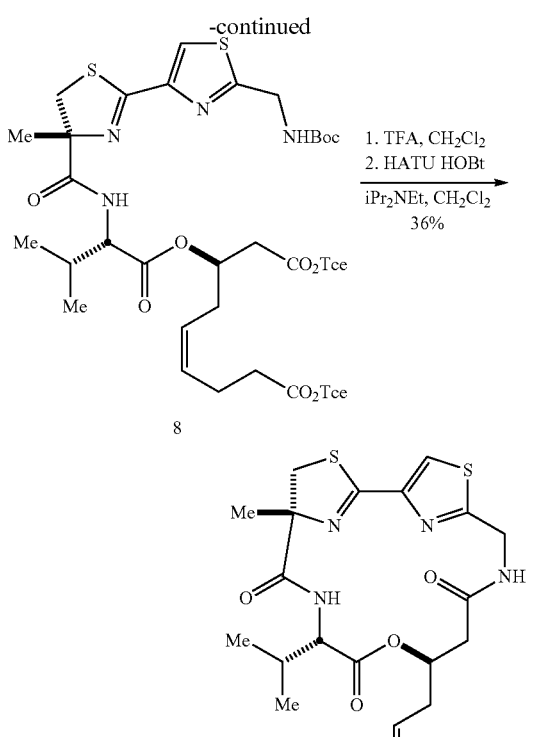

(R,Z)-2,2,2-trichloroethyl 9-((R)-4-benzyl-2-thioxothiazolidin-3-yl)-7-hydroxy-9-oxonon-4-enoate 7

A solution of the chiral auxiliary (887 mg, 3.53 mmol) in CH$_2$Cl$_2$ (28.5 mL) was cooled to 0° C., followed by addition of TiCl$_4$ (0.47 mL, 4.39 mmol). The reaction was allowed to stir for 5 minutes, then cooled to −78° C., before iPr$_2$NEt (0.76 mL, 4.37 mmol) were slowly added and stirred for 2 hours. The aldehyde was dissolved in CH$_2$Cl$_2$ (2.2 mL) and added dropwise to the auxiliary solution, then stirred for 1.5 hours. The reaction was quenched with saturated aq NH$_4$Cl and diluted with CH$_2$Cl$_2$ and warmed to room temperature. The reaction w as extracted with CH$_2$Cl$_2$, then washed with brine and dried over Na$_2$SO$_4$, filtered and condensed. Purification was accomplished with silica gel chromatography (30% EtOAc/Hex) to afford yellow oil. $^1$H NMR (400 MHz, CDCl$_3$) d83m. 1H), 1.23 (s, 1H), 2.35 (m, 2H), 2.45 (m, 2H), 2.53 (m, 2H), 2.88 (dd, 3.2, 11.6 Hz, 1H), 3.02 (dd, 10.4, 13.2 Hz, 1H), 3.17 (m, 2H), 3.42 (m, 2H), 3.62 (dd, 2.8, 17.6 Hz, 1H) 4.15 (m, 2H), 4.73 (s, 2H), 5.37 (m, 1H), 5.52 (m, 2H), 7.30 (m, 5H), $^{13}$C NMR (75 MHz, CDCl$_3$) δ 22.8, 29.8, 32.2, 33.8, 34.3, 34.5, 36.9, 45.1, 45.5, 67.7, 68.2, 68.4, 68.5, 95.1, 126.8, 127.4, 129.1, 129.6, 130.5, 136.5, 169.1, 171.6, 173.1, 173.7. HRMS (ESI): m/z calcd. for C$_{21}$H$_{25}$Cl$_3$NO$_4$S$_2$ (M+H)$^+$ 524.02742, found 524.02851 [a]$_D$=−74.2 (c 2, CHCl$_3$).

(R,Z)-1-(2,2,2-trichloroethyl) 9-(2-(trimethylsilyl)ethyl) 7-hydroxynon-4-enedioate 51

The alcohol (764 mg, 1.45 mmol) dissolved in CH$_2$Cl$_2$ (2.9 mL) was treated with imidazole (148 mg, 2.175 mmol)

followed by the addition of 2-(trimethylsilyl)ethanol (2.08 mL, 14.5 mmol). The reaction was stirred overnight, then condensed and purified by silica gel chromatography (30% EtOAc/Hex) to give the protected β-hydroxy acid as yellow oil. $^1$H NMR (300 MHz CDCl$_3$) d0.04 (s, 9H), 0.99 (m, 2H), 2.30 (m, 2H), 2.45 (m, 4H), 2.54 (m, 2H), 4.06 (m, 1H), 4.20 (m, 2H), 4.73 (s, 2H), 5.52 (m, 2H), $^{13}$C NMR (75 MHz, CDCl$_3$) d −0.127, 17.5, 22.8, 33.8, 34.5, 41.0, 63.3, 67.9, 74.1, 95.1, 126.8, 130.3 171.7, 173.2. [α]$_D$=−1.7 (c 2, CHCl$_3$)

(R,Z)-1-(2,2,2-trichloroethyl) 9-(2-(trimethylsilyl) ethyl) 7-((S)-2-(((9H-fluoren-9-yl)methoxy)carbonylamino)-3-methylbutanoyloxy)non-4-enedioate 52

The protected acid (97 mg, 0.224 mmol) and N-Fmoc-L-Val (380 mg, 1.123 mmol) were dissolved in CH$_2$Cl$_2$ (4.08 mL) and cooled to 0° C. EDCI (258 mg, 1.347 mmol) and DMAP (2.7 mg, 0.0225 mmol) were dissolved in CH$_2$Cl$_2$ (1.02 mL) and added to the cooled reaction followed by the slow addition of iPr$_2$NEt (0.23 mL, 1.347 mmol). The reaction was allowed to warm to room temperature and stirred overnight, then condensed and purified with column chromatography (30% EtOAc/Hex) $^1$H NMR (300 MHz CDCl$_3$) d3s, 9 H), 0.88 (d, 3H), 0.97 (m, 5H) 2.15 (m, 1H), 2.43 (m, 3H), 2.50 (d, 2H), 2.59 (m, 3H), 4.25 (m, 3H), 4.38 (m, 2H), 4.73 (s, 2H), 5.32 (m, 2H) 5.43. (m, 1H), 5.53 (m, 1H), 7.35 (m, 4H), 7.60 (d, 2H), 7.76 (d, 2H), $^{13}$C NMR (75 MHz, CDCl$_3$) d −1.27, 17.5, 19.2, 28.1, 31.4, 31.7, 33.7, 38.7, 47.4, 59.1, 63.3, 67.2, 71.5, 71.6, 74.1, 95.1, 120.2, 125.1, 125.3, 127.2, 127.9, 131.1, 131.2, 141.5, 143.9, 144.1, 156.3, 156.4, (M+Na$^−$) calcd for C$_{36}$H$_{46}$Cl$_3$NO$_8$Si 753.20627, found 776.19549. [a]$_D$=0.0 (c 2, CHCl$_3$)

(R,Z)-1-(2,2,2-trichloroethyl) 9-(2-(trimethylsilyl) ethyl) 7-((S)-2-((R)-2-(2-((tert-butoxycarbonylamino)methyl)thiazol-4-yl)-4-methyl-4,5S-dihydrothiazole-4-carboxamido)-3-methylbutanoyloxy) non-4-enedioate 8

The protected amine (118 mg, 0.157 mmol) was dissolved in CH$_2$Cl$_2$ (7.85 mL) and treated with Et$_2$NH, then allowed to stir for 2 hrs. The reaction was concentrated, then taken up in EtOAc and re-concentrated again to remove any left-over Et$_2$NH. The thiazolinethiazole (61.7 mg, 0.172 mmol) and PyBOP (164 mg, 0.471 mmol) were dissolved in CH$_2$Cl$_2$ (2.87 mL) and treated with iPr$_2$NEt and allowed to stir for 5 minutes. Then the crude amine in CH$_3$CN (1.42 mL) was slowly added to the PyBOP solution and allowed to stir overnight. The reaction was then condensed and purified with column chromatography (30-50% EtOAc/Hex). $^1$H NMR (300 MHz CDCl$_3$) d3s, 9H), 0.82 (d, J=3H), 0.88 (m, 3H), 0.97 (m, 2H), 1.47 (s, 9H), 1.62 (s, 3H), 2.15 (m, 1H), 2.45 (m, 3H), 2.57 (m, 5H), 3.34 (d, J=11.4 1H), 3.81 (d, J=11.4, 1H), 4.15 (m, 2H), 4.48 (m, 1H), 4.63 (d, J 6.3 Hz, 2 H), 4.74 (s, 2H), 5.31 (m, 2H), 5.43 (m, 1H), 5.54 (m, 1H), 8.06 (s, 1H), $^{13}$C NMR (75 MHz, CDCl$_3$) d −1.3, 17.5, 17.7, 19.3, 22.8, 24.9, 28.5, 31.2, 33.7, 38.7, 38.8, 41.6, 42.6, 51.4, 57.3, 63.3, 71.5, 74.1, 80.7, 85.0, 95.1, 125.1, 125.3, 131.0, 131.1, 148.5, 155.9, 170.3, 170.4, 170.8, 170.9, 171.4, 171.5, 174.4, (M+H$^−$) calcd for C$_{35}$H$_{53}$Cl$_3$N$_4$O$_8$S$_2$Si 870.21108. found 871.21836. [a]$_D$= −19.86 (c 2, CHCl$_3$)

Formation of the Trichloroethyl Ester Protected Largazole Azumamide Hybrid 9a

The acyclic precursor (77 mg, 0.088 mmol) was dissolved in CH$_2$Cl$_2$ (2.95 mL) and cooled to 0° C. TFA (0.15 mL) was slowly added to the cooled solution. The reaction was allowed to warm to room temperature and stirred overnight. The reaction was then condensed, and re-dissolved in toluene and condensed again to remove any excess TFA. The crude amino acid was dissolved in CH$_2$Cl$_2$ (4.4 mL), then cooled to 0° C. and treated with iPr$_2$NEt (0.093 mL, 0.53 mmol) and stirred for 30 min. In a separate flask, HOBt (23 mg, 0.177 mmol). HATU (67 mg, 0.177 mmol) were dissolved in CH$_3$CN (88.7 mL) and treated with iPr$_2$NEt (0.093 mL. 0.53 mmol). The crude amino acid solution was then added via syringe pump addition to the HATU solution in a 10-hour addition. The reaction was allowed to stir for an additional 6 hours before solvents were removed and purified with silica gel chromatography (30%-50% EtOAc/Hex). $^1$H NMR (300 MHz CDCl$_3$) d0.47, d, J=6.9 Hz, 3H), 0.69 (d, J=8.7 Hz, 3H), 1.24 (s, 1H), 1.87 (s, 3H), 2.13 (m, 1H), 2.43 (m, 3H), 2.52 (d, J=6.6 Hz, 2H), 2.72 (m, 4H), 3.29 (d, J=12.3 Hz, 1H), 4.05 (d, J=11.4 Hz, 1H), 4.27 (dd, J=3, 17.7 Hz, 1H), 4.64 (dd, J=3, 9.3 Hz, 1H), 4.75 (s, 2H), 5.25 (m, 2H), 5.40 (m, 1H), 5.53 (m, 1H), 6.33 (m, 1H), 7.10 (d, J=9.3 Hz, 1H), 7.78 (s, 1H) $^{13}$C NMR (75 MHz, CDCl$_3$) d 14.4, 16.5, 18.5, 18.7, 19.3, 22.8, 24.1, 24.9, 29.4, 31.2, 32.7, 33.7, 33.9, 34.3, 35.5, 39.2, 41.2, 43.4, 43.7, 57.8, 59.7, 60.6, 72.5, 74.1, 83.8, 95.1, 110.5, 118.4, 124.9, 125.1, 127.3, 131.2, 146.8, 167.0, 168.7, 169.5, 170.6, 171.5, 173.2, (M+H$^−$) calcd for C$_{25}$H$_{31}$Cl$_3$O$_6$S$_2$ 675.0637, found 675.06428 [a]$_D$=−0.94 (c 2, CHCl$_3$)

Largazole Auzumamide E Hybrid 9b

The macrocycle (40) (9.8 mg, 0.015 mmol) was dissolved in dry THF (0.5 mL. 0.03M) and vigorously stirred. Then Zn dust (35 mg, 36 mmol) was added to the solution followed by 1M NH$_4$OAc (0.083 mL. 18M) and allowed to stir for 24 hours under argon. The reaction was then filtered and taken up in EtOAc and washed with 5% aq KHSO$_4$ (2×2 mL) and Brine (2×2 mL) then dried over Na$_2$SO$_4$, filtered and solvents removed. Purification by PTLC (MeOH/CH$_2$Cl$_2$ 10%). $^1$H NMR (300 MHz CDCl$_3$) d0.47 (d, J=6.9 Hz, 3H), 0.69 (d, J=6.9 Hz, 3H), 0.85 (m, 2H), 1.88 (s, 3H), 2.14 (m, 1H), 2.41 (m, 5H), 2.71 (m, 4H), 3.29 (d, J=11.4 Hz, 1H), 4.06 (d, J=1.4 Hz, 1H), 4.27 (dd, J=3.3, 17.4 Hz. 1H), 4.45 (d, J=6.0 Hz, 2H), 4.64 (dd, J=3.0, 9.3 Hz, 1H), 5.29 (m, 2H), 5.42 (m, 1H), 5.51 (m, 1H), 5.85 (t, J=6.0 Hz, 1H), 6.40 (m, 1H), 7.11 (d, J=9.3 Hz, 1H), 7.79 (s, 1H), $^{13}$C NMR (75 MHz, CDCl$_3$) d 14.4, 16.6, 19.2, 21.8, 24.2, 29.9, 31.1, 33.7, 39.3, 41.3, 43.5, 57.8, 60.6, 68.4, 68.6, 72.4, 124.8, 131.4, 168.2, 169.6, 170.2, 172.1, 173.6, (M−H$^−$) calcd for C$_{23}$H$_{30}$N$_4$O$_6$S$_2$ 521.1534, found 521.15292. [a]$_D$=+10.107 (c 2, CHCl$_3$)

Example 12. Metathesis Route to Largazole Hybrids

General Procedure for the Cross-Metathesis Reactions

Adapting the procedure described by Luesch and co-workers, macrocycle 10 was dissolved in the indicated solvent (to ~0.026M) and heated to reflux under argon. Solutions of sacrificial olefin (2.0 equiv., ~0.26M) and catalyst (0.2 equiv., ~0.052M) were then added to the reaction. The resulting mixture was stirred at reflux for a further 3 hrs, with equivalent portions of olefin (2.0 equiv., ~0.26M in toluene) and catalyst (0.2 equiv., ~0.052M in toluene) being added each hour. After the last addition of olefin and catalyst, the reaction was refluxed for 1 hr, and then cooled to room temperature. Several drops of DMSO were added and the mixture was stirred overnight. Concentration in vacuo, followed by column chromatography, provided the substituted olefins as products. Alternatively, dichloroethane can be used as the solvent and Grubbs-Hoveyda second generation as the catalyst in the cross-metathesis reaction.

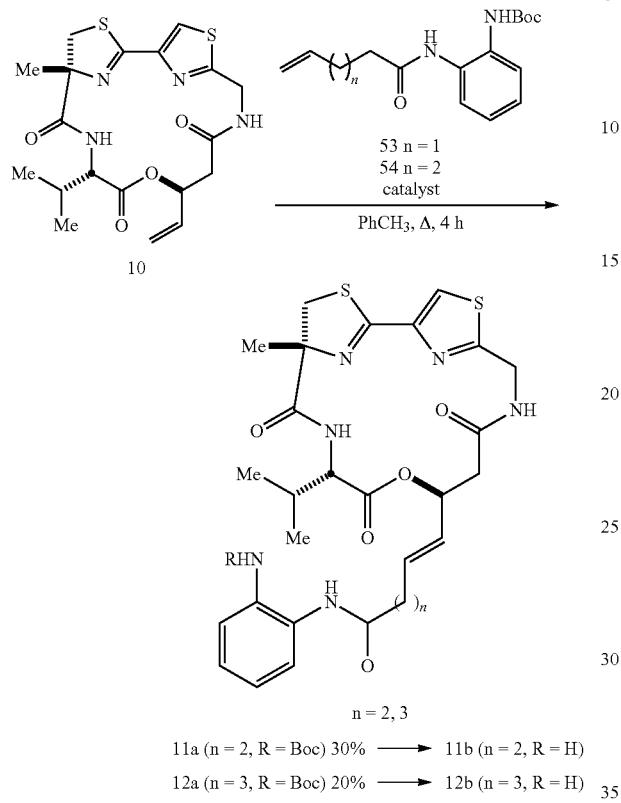

Boc-Protected Benzamide 11a and Amine 11b

According to the general procedure, 0.025 g (0.057 mmol) macrocycle 10 was combined with olefin 53 to yield 0.012 g (0.017 mmol, 30% yield) compound 11a, which eluted slowly in 100% EtOAc. Clear oil. $^1$H NMR (300 MHz, CDCl$_3$) δ 0.62 (d J=6.9 Hz, 3H), 0.73 (d J=6.9 Hz, 3H), 1.53 (s, 9H), 1.87 (s, 3H), 1.98-2.00 (m, 1H), 2.42-2.65 (m, 5H), 2.77 (dd J=6.0, 15.6 Hz, 1H), 3.31 (d J=11.4 Hz, 1H), 3.91 (dd J=4.2, 16.8 Hz, 1H), 4.00 (d J=11.4 Hz, 1H), 4.54 (dd J=4.8, 9.3 Hz, 1H), 4.86 (d J=8.1, 16.8 Hz, 1H), 5.69-5.79 (m, 2H), 5.86-5.97 (m, 1H), 6.61-6.67 (m, 1H), 6.90 (t J=7.8 Hz, 1H), 6.98 (d J=7.2 Hz, 1H), 7.08 (td J=1.2, 8.1 Hz, 1H), 7.19 (d J=9.0 Hz, 1H), 7.48 (d J=7.8 HZ, 1H), 7.67 (s, 1H), 7.98 (bs. 1H), 8.40 (bs. 1H). HRMS (ESI): m/z calcd. for C$_{33}$H$_{42}$N$_6$NaO$_7$S$_2$ (M+Na)$^+$ 721.24541, found 721.24526. 0.010 g Benzamide 11a was deprotected in 1 mL CH$_2$Cl$_2$ and 0.2 mL TFA. After 2 hrs, the solvents were removed and the product amine 1b purified by preparative thin layer chromatography.

Boc-Protected Benzamide 12a and Amine 12b

According to the general procedure, 0.039 g (0.089 mmol) macrocycle 10 was combined with olefin 54 to yield 0.012 g (0.017 mmol, 20% yield) compound 12a, which eluted slowly in 100% EtOAc. Clear oil. $^1$H NMR (300 MHz, CDCl$_3$) δ 0.59 (d J=6.9 Hz. 3H), 0.73 (d J=6.9 Hz, 3H), 1.50 (s, 9H), 1.86 (s, 3H), 1.99-2.00 (m, 1H), 2.15-2.32 (m. 3H), 2.32-2.41 (m, 3H), 2.66-2.73 (m, 2H), 3.30 (d J=11.4 Hz, 1H), 4.02 (d J=11.4 Hz, 1H), 4.28 (dd J=3.6, 17.7 Hz, 1H), 4.57 (dd J=4.5, 9.6 Hz, 1H), 4.99 (dd J=6.9, 17.7 Hz. 1H), 5.61-5.72 (m, 2H), 5.86 (dt J=7.2, 14.4 Hz, 1H), 6.59-6.66 (m, 1H), 7.01 (t J=8.4 Hz. 1H), 7.11-7.16 (m, 3H), 7.26 (d J=9.0 Hz, 1H), 7.49 (d J=8.1 Hz, 1H), 7.67 (s, 1H), 8.48 (s, 1H). HRMS (ESI): m/z calcd. for C$_{34}$H$_{44}$N$_6$NaO$_7$S$_2$ (M+Na)$^+$ 735.26106, found 735.2609. 0.004 g Benzamide 12a was deprotected in 1 mL CH$_2$Cl$_2$ and 0.2 mL TFA. After 2 hrs, the solvents were removed and the product amine 12b purified by preparative thin layer chromatography.

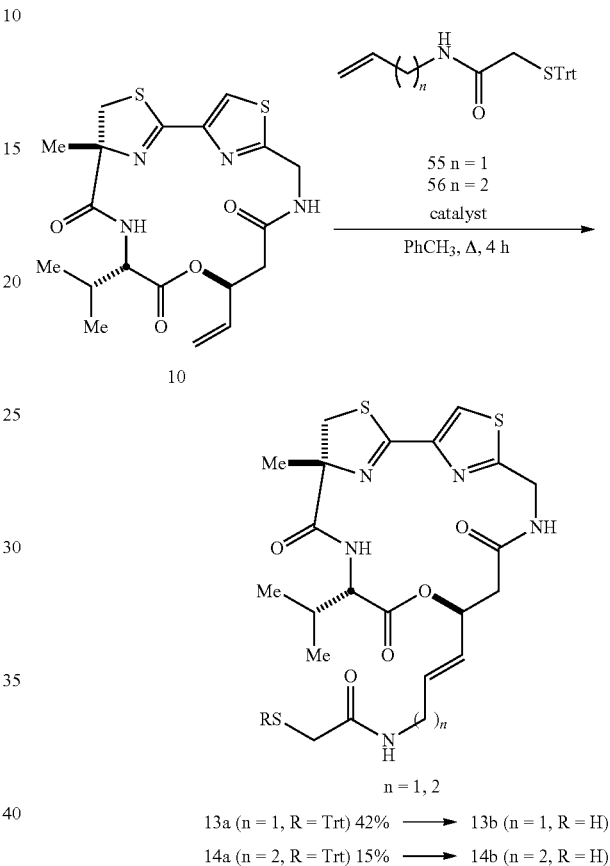

S-Trityl-α-thioamide 13a

According to the general procedure, 0.060 g (0.14 mmol) macrocycle 10 was combined with olefin 55 in presence of the Hoveyda-Grubbs second generation catalyst in toluene to yield 0.046 g (0.058 mmol, 42% yield) compound 13a, which eluted in 10:1 CH$_2$Cl$_2$:CH$_3$OH. Clear oil. (13a): [α]$^{24}$$_D$: +12.4 (c=1, CHCl$_3$), $^1$H NMR (400 MHz, CDCl$_3$) δ 0.53 (d J=6.8 Hz, 3H), 0.69 (d J=6.8 Hz, 3H), 1.81 (s, 3H), 1.96-2.10 (m, 3H), 2.64 (dd J=3.6, 15.6 Hz, 1H), 2.76 (dd J=8.8, 15.6 Hz, 1H), 3.03 (s, 2H), 3.25 (d J=11.2 Hz, 1H), 3.52 (t J=5.6 Hz, 1H), 4.00 (d J=11.2 Hz, 1H), 4.25 (dd J=3.2, 17.2 Hz, 1H), 4.55 (dd J=4.0, 9.6 Hz, 1H), 5.20 (dd J=8.8, 17.2 Hz, 1H), 5.49 (dd J=6.4, 15.6 Hz, 1H), 5.63-5.96 (m, 1H), 5.71 (dt J=4.2, 15.6 Hz, 1H), 6.00 (t J=4.2 Hz, 1H), 6.50-6.52 (m, 1H), 7.15-7.29 (m, 9H), 7.37-7.39 (m, 6H), 7.70 (s, 1H), $^{13}$C NMR (100.6 MHz, CDCl$_3$): δ 14.3, 17.1, 19.1, 24.4, 29.9, 34.1, 35.9, 40.8, 41.2, 41.4, 43.5, 58.2, 68.0, 71.5, 127.3, 128.1, 128.4, 129.6, 130.0, 144.1, 168.4, 168.9, 169.3. HRMS (ESI): m/z calcd. for C$_{41}$H$_{43}$N$_5$NaO$_5$S$_3$ (M+Na)$^+$ 804.23185, found 804.23259.

Thiol 13b

According to the general procedure. 0.035 g 13a was deprotected to give 0.022 g 13b after preparative thin layer chromatography. (13b): [α]$^{24}_D$: +6.1 (c=0.5, CHCl$_3$). $^1$H NMR (300 MHz, CDCl$_3$) δ 0.56 (d J=6.9 Hz, 3H), 0.71 (d J=6.9 Hz, 3H), 1.88 (s, 3H), 1.95 (t J=9.0 Hz, 1H), 2.04-2.16 (m, 1H), 2.26-2.33 (m, 2H), 2.70 (dd J=3.0, 16.2 Hz, 1H), 2.88 (dd J=9.9, 16.2 Hz, 1H), 3.24-3.32 (m, 2H), 3.19 (d J=8.7 Hz, 1H), 3.30 (d J=11.4 Hz, 1H), 3.42-3.50 (m, 1H), 4.06 (d J=11.4 Hz, 1H), 4.35 (dd J=3.6, 17.7 Hz, 1H), 4.61 (dd J=3.3, 9.3 Hz, 1H), 5.25 (dd J=9.3, 17.7 Hz, 1H), 5.56 (dd J=7.2, 15.3 Hz, 1H), 5.64-5.70 (m, 1H), 5.83 (dt J=7.2, 15.3 Hz, 1H), 6.44 (d J=6.0 Hz, 1H), 6.74 (s, 1H), 7.19 (d J=9.6 Hz, 1H), 7.80 (s, 1H). $^{13}$C NMR (100.6 MHz, CDCl$_3$): δ 17.0, 19.1, 24.5, 28.5, 32.3, 34.4, 38.8, 40.8, 41.3, 43.6, 58.1, 72.6, 77.4, 84.6, 124.6, 129.8, 131.8, 147.7, 168.2, 169.4, 169.5, 169.6, 173.7. HRMS (ESI): m/z calcd. for C$_{23}$H$_{31}$N$_5$NaO$_5$S$_3$ (M+Na)$^+$ 576.13795, found 576.13795.

S-Trityl-α-thioamide 14a

According to the general procedure. 0.052 g (0.12 mmol) macrocycle 10 was combined with olefin 56 in presence of the Grubbs second generation catalyst in toluene to yield 0.014 g (0.018 mmol, 15% yield) compound 14a, which eluted in 10:1 CH$_2$Cl$_2$:CH$_3$OH. Clear oil. (14a): [α]$^{24}_D$: + 8.1 (c=1, CHCl$_3$). $^1$H NMR (300 MHz, CDCl$_3$) δ 0.50 (d J=6.9 Hz, 3H), 0.67 (d J=6.9 Hz, 3H), 1.89 (s, 3H), 2.00-2.11 (m, 3H), 2.61 (dd J=2.7, 16.5 Hz, 1H), 2.78 (dd J=10.2, 16.5 Hz, 1H), 2.94-3.05 (m, 2H), 3.10 (s, 2H), 3.27 (d J=11.4 Hz, 1H), 4.04 (d J=11.4 Hz, 1H), 4.25 (dd J=3.0, 17.7 Hz, 1H), 4.58 (dd J=3.6, 9.6 Hz, 1H), 5.25 (dd J=9.3, 17.4 Hz, 1H), 5.43 (dd J=6.9, 15.6 Hz, 1H), 5.57-5.63 (m, 1H), 5.69 (dt J=6.9, 11.1 Hz, 1H), 6.06 (t J=5.4 Hz, 1H), 6.33 (dd J=3.0, 9.3 Hz, 1H), 7.14 (d J=9.6 Hz, 1H), 7.20-7.37 (m, 9H), 7.38-7.42 (m, 6H), 7.75 (s, 1H). $^{13}$C NMR (100.6 MHz, CDCl$_3$): δ 16.9, 19.1, 24.4, 32.2, 34.4, 36.1, 38.9, 40.7, 41.3, 43.6, 58.0, 68.0, 72.4, 77.5, 84.5, 124.7, 127.3, 128.4, 129.2, 129.7, 131.8, 144.2, 147.6, 168.1, 169.1, 169.5, 173.7. HRMS (ESI): m/z calcd. for C$_{42}$H$_{45}$N$_5$NaO$_5$S$_3$ (M+Na)$^+$ 818.2475, found 818.2469.

Thiol 14b

According to the general procedure, 0.035 g 14a was deprotected to give 0.022 g 14b after preparative thin layer chromatography. (14b): [α]$^{24}_D$: +15.6 (c=0.5, CHCl$_3$), $^1$H NMR (300 MHz, CDCl$_3$) δ 0.56 (d J=6.9 Hz, 3H), 0.71 (d J=6.9 Hz, 3H), 1.88 (s, 3H), 1.95 (t J=9.0 Hz, 1H), 2.04-2.16 (m, 1H), 2.26-2.33 (m, 2H), 2.70 (dd J=3.0, 16.2 Hz, 1H), 2.88 (dd J=9.9, 16.2 Hz, 1H), 3.24-3.32 (m, 2H), 3.19 (d J=8.7 Hz, 1H), 3.30 (d J=11.4 Hz, 1H), 3.42-3.50 (m, 1H), 4.06 (d J=11.4 Hz, 1H), 4.35 (dd J=3.6, 17.7 Hz, 1H), 4.61 (dd J=3.3, 9.3 Hz, 1H), 5.25 (dd J=9.3, 17.7 Hz, 1H), 5.56 (dd J=7.2, 15.3 Hz, 1H), 5.64-5.70 (m, 1H), 5.83 (dt J=7.2, 15.3 Hz, 1H), 6.44 (d J=6.0 Hz, 1H), 6.74 (s, 1H), 7.19 (d J=9.6 Hz, 1H), 7.80 (s, 1H). $^{13}$C NMR (100.6 MHz, CDCl$_3$): δ 17.0, 19.1, 24.5, 28.5, 32.3, 34.4, 38.8, 40.8, 41.3, 43.6, 58.1, 72.6, 77.4, 84.6, 124.6, 129.8, 131.8, 147.7, 168.2, 169.4, 169.5, 169.6, 173.7. HRMS (ESI): m/z calcd. for C$_{23}$H$_{31}$N$_5$NaO$_5$S$_3$ (M+Na)$^+$ 576.13795, found 576.13795.

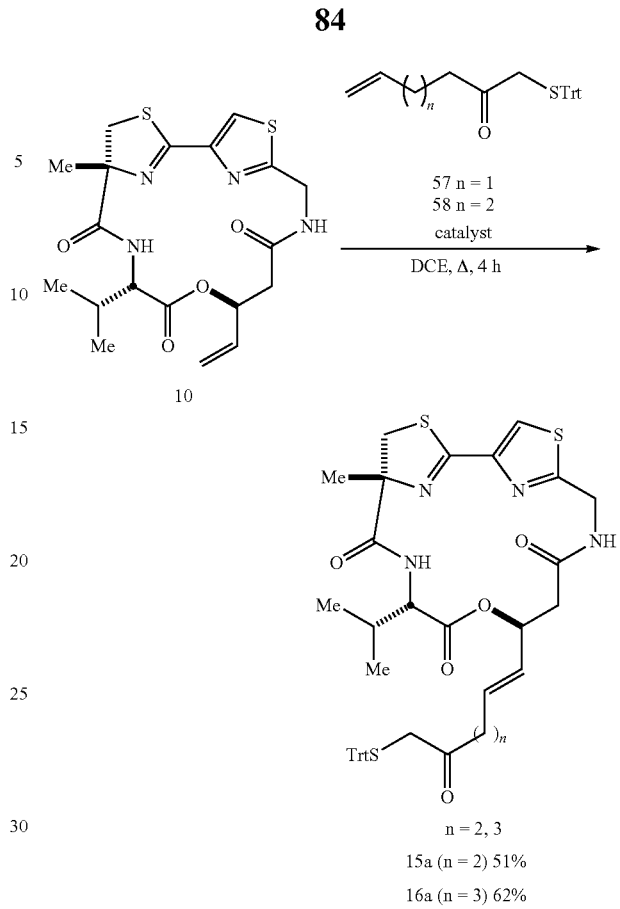

15a (n = 2) 51%
16a (n = 3) 62%

S-Trityl-α-thioketone 15a

According to the general procedure. 0.044 g (0.10 mmol) macrocycle 10 was combined with olefin 57 in presence of the Hoveyda-Grubbs second generation catalyst in 1,2-dichloroethane to yield 0.040 g (0.051 mmol, 51% yield) compound 15a, which eluted in EtOAc. Clear oil. (15a): [α]$^{24}_D$: +11.0 (c=1, CHCl$_3$). $^1$H NMR (300 MHz, CDCl$_3$) δ 0.55 (d J=6.9 Hz, 3H), 0.71 (d J=6.9 Hz, 3H), 1.85 (s, 3H), 2.04-2.41 (m, 7H), 2.66 (dd J 3.6, 15.9 Hz, 1H), 2.79 (dd J=8.4, 15.9 Hz, 1H), 2.93 (d J=14.7 Hz, 1H), 3.00 (d J=14.7 Hz, 1H), 3.28 (d J=11.4 Hz, 1H), 4.03 (d J=11.4 Hz, 1H), 4.29 (dd J=6.3, 17.7 Hz, 1H), 4.57 (dd J=3.9, 9.6 Hz, 1H), 5.25 (dd J=9.3, 17.7 Hz, 1H), 5.45 (dd J=6.3, 15.3 Hz, 1H), 5.62-5.68 (m, 1H), 5.79 (dt J=6.3, 15.3 Hz, 1H), 6.54 (dd J=2.4, 9.0 Hz, 1H), 7.18-7.33 (m, 10H), 7.36-7.41 (m, 6H), 7.72 (s, 1H). $^{13}$C NMR (100.6 MHz, CDCl$_3$): δ 17.1, 19.1, 24.5, 26.3, 34.2, 40.4, 40.8, 41.4, 42.8, 43.5, 58.2, 67.3, 71.8, 84.7, 124.4, 127.2, 127.4, 128.3, 129.8, 133.7, 144.3, 147.7, 164.8, 168.3, 168.9, 169.5, 173.7, 205.5. HRMS (ESI): m/z calcd. for C$_{42}$H$_{44}$N$_4$NaO$_5$S$_3$ (M+Na)$^+$ 803.2366, found 803.23654.

S-Trityl-α-thioketone 16a

According to the general procedure. 0.048 g (0.11 mmol) macrocycle 10 was combined with olefin 58 in presence of the Hoveyda-Grubbs second generation catalyst in 1,2-dichloroethane to yield 0.054 g (0.067 mmol, 62% yield) compound 16a, which eluted in EtOAc. Clear oil. (16a): [α]$^{24}_D$: +5.1 (c=2, CHCl$_3$). $^1$H NMR (300 MHz, CDCl$_3$) δ 0.52 (d J=6.9 Hz, 3H), 0.70 (d J=6.9 Hz, 3H), 1.43-1.53 (m, 2H), 1.87 (s, 3H), 1.89-1.97 (m. 2H), 2.06-2.23 (m, 3H), 2.65 (dd J=2.7, 16.5 Hz, 1H), 2.82 (dd J=10.5, 16.5 Hz, 1H), 3.06 (s, 2H), 3.28 (d J=11.4 Hz, 1H), 4.05 (d J=11.4 Hz, 1H), 4.26 (dd J=2.4, 17.7 Hz, 1H), 4.60 (dd J=3.3, 9.3 Hz, 1H), 5.27 (dd J=9.0, 17.7 Hz, 1H), 5.38 (dd J=6.9, 17.7 Hz, 1H), 5.60-5.66 (m, 1H), 5.74 (dt J=6.6, 15.3 Hz, 1H), 6.43 (d J=7.8 Hz, 1H), 7.15-7.33 (m, 10H), 7.37-7.44 (m, 6H), 7.77 (s, 1H), $^{13}$C NMR (100.6 MHz, CDCl$_3$): δ 16.9, 19.2, 22.9, 24.4, 31.5, 34.5, 40.8, 41.0, 41.3, 42.9, 43.6, 57.9, 67.3, 72.6, 84.6, 124.5, 127.2, 127.3, 128.3, 129.8, 134.8, 144.4, 147.7, 164.8, 168.2, 169.2, 169.7, 173.8, 205.8. HRMS (ESI): m/z calcd. for $C_{43}H_{46}N_4NaO_5S_3$ (M+Na)$^+$ 817.25225, found 817.25292.
Example 13. Synthesis of Cysteine & Thiazole-Thiazole Analogs
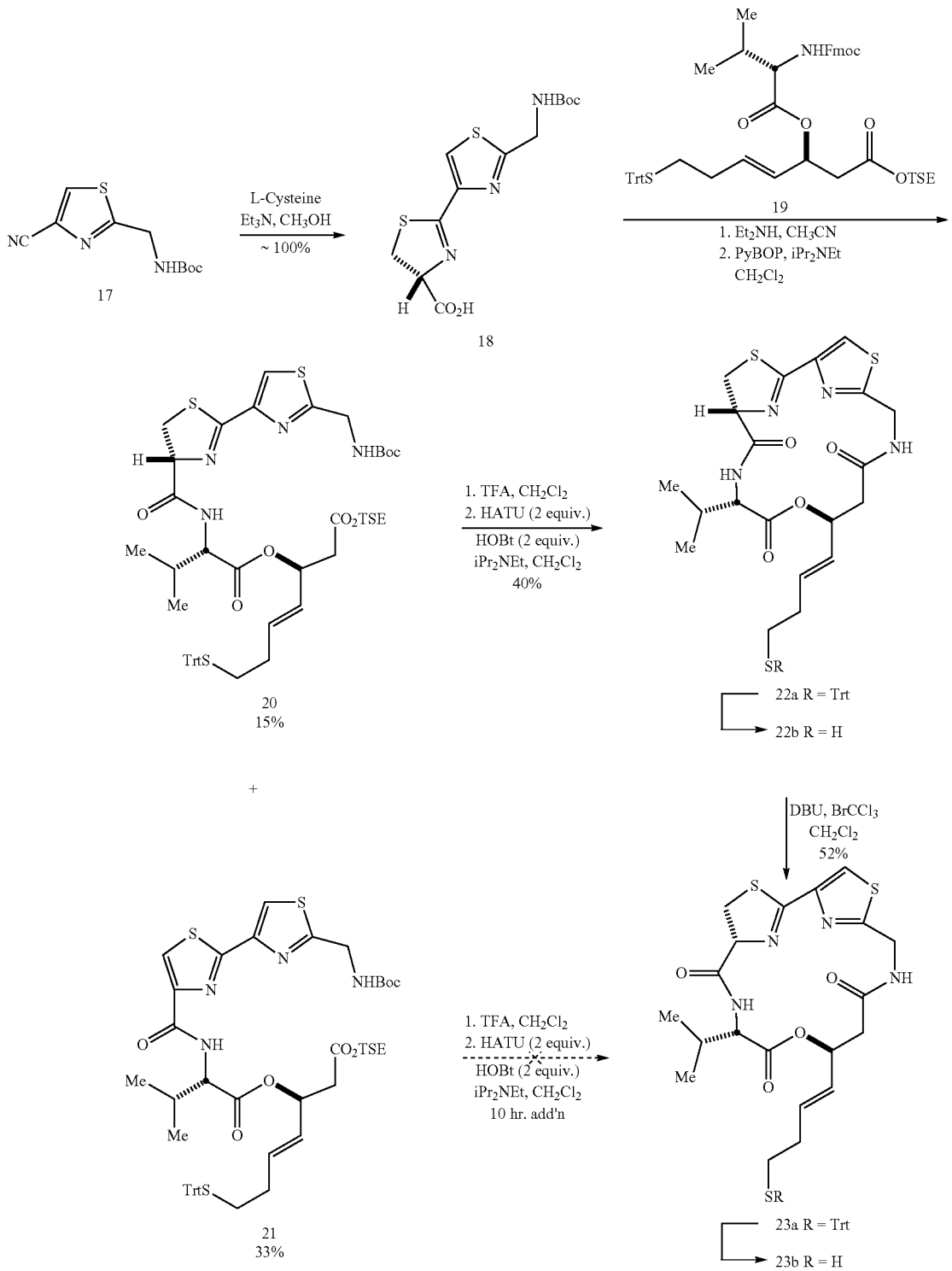

2-{2-[(tert-Butoxycarbonyl)methyl]thiazol-4-yl}-4,5-dihydrothiazole-4-carboxylic Acid (18)

0.800 g (3.3 mmol) Thiazole nitrile 17 (Reiner, J., et al. 2002 *Bioorg Med Chem Lett* 12(8): 1203-1208) and 0.446 g (3.6 mmol, 1.1 equiv.) cysteine were dissolved 33 mL dry $CH_3OH$ and 0.5 mL dry $Et_3N$ was added dropwise. The resulting solution was heated at reflux overnight. The reaction was subsequently cooled to room temperature and the solvents removed in vacuo. The crude reaction mixture was then dissolved in sat. aqu. $NaHCO_3$ and washed with diethyl ether. The aqueous layer was then acidified to pH ~3-4 by dropwise addition of 3N HCl and extracted with EtOAc (3×30 mL). The combined organics were dried over $Na_2SO_4$, filtered, and concentrated to provide 1.15 g (3.3 mmol, ~ 100% yield from 17) of acid 18 in spectroscopically pure form. Pale orange foam. $[\alpha]^{24}_D$: +30.9 (c=1. $CH_3OH$). $^1H$ NMR (400 MHz, $CDCl_3$) δ 9.79 (bs, 1H), 7.98 (s, 1H), 5.59 (s, 1H), 4.59 (d J=6.3 Hz, 2H), 3.88 (d J=11.4 Hz, 1H), 3.30 (d J=11.4 Hz, 1H), 1.66 (s, 3H), $^{13}C$ NMR (100.6 MHz, $CDCl_3$): δ 175.74, 170.38, 170.16, 165.03, 155.91, 147.77, 123.3, 84.23, 80.70, 42.39, 41.31, 28.51, 27.17, 26.67, 24.30. HRMS (ESI): m/z calcd. for $C_{14}H_{19}N_3NaO_4S_2$ (M+Na)+ 380.07147, found 380.07165.

Thiazoline-Thiazole Acyclic Precursor 20 and Thiazole-Thiazole Acyclic Precursor 21

0.300 g (0.36 mmol, 1.0 equiv.) diester 19 and 0.147 g (0.42 mmol, 1.2 equiv.) acid 18 were coupled according to the same procedure described above for synthesis of 43. The two resulting products could be separated via column chromatography, washing first with 4:1, then with 2:1 hexanes: EtOAc. 0.110 g (33% yield) 21 eluted first, followed quickly by 0.052 g (15% yield) 20. (20): $^1H$ NMR (300 MHz, $CDCl_3$) δ 0.03 (s, 9H), 0.75 (d J=6.9 Hz, 3H), 0.82 (d J=6.9 Hz, 3H), 0.93-0.99 (m, 2H), 1.49 (s, 9H), 1.99-2.21 (m, 5H), 2.55 (dd J=5.4, 15.6 Hz, 1H), 2.69 (dd J=7.8, 15.6 Hz, 1H), 3.61-3.74 (m, 2H), 4.12-4.18 (m, 2H), 4.53 (dd J=4.8, 9.0 Hz, 1H), 4.62 (d J=6.0 Hz, 1H), 5.19 (t J=9.0 Hz, 1H), 5.25-5.32 (m, 1H), 5.37 (dd J=7.5, 15.3 Hz, 1H), 5.59-5.74 (m, 2H), 7.16-7.29 (m, 9H), 7.37-7.40 (m, 6H), 7.92 (s, 1H). $^{13}C$ NMR (100.6 MHz, $CDCl_3$): δ −1.2, 17.5, 17.7, 19.2, 28.6, 31.3, 31.5, 31.7, 35.8, 39.9, 42.6, 57.0, 63.4, 66.8, 72.1, 79.4, 80.7, 121.7, 126.8, 128.0, 128.1, 129.8, 134.3, 145.0, 148.7, 155.9, 165.7, 169.9, 170.6, 171.2 HRMS (ESI): m/z calcd. for $C_{49}H_{63}N_4O_7S_3Si$ (M+H)+ 943.35463, found 943.3619. (21): $[\alpha]^{24}_D$: −1.1 (c=2, $CHCl_3$). $^1H$ NMR (300 MHz, $CDCl_3$) δ −0.01 (s, 9H), 0.90-0.98 (m, 81H), 1.49 (s, 9H), 2.01-2.08 (m, 2H), 2.14-2.21 (m, 2H), 2.23-2.30 (m, 1H), 2.56 (dd J=5.4, 15.6 Hz, 1H), 2.70 (dd J=8.1, 15.6 Hz, 1H), 4.11-4.16 (m, 2H), 4.66 (d J=5.7, 2H), 4.72 (dd J=4.8, 9.3 Hz, 1H), 5.32-5.43 (m, 1H), 5.39 (dd J=8.7, 15.6 Hz, 1H), 5.63-5.76 (m, 2H), 7.19-7.30 (m, 8H), 7.37-7.44 (m, 7H), 7.88 (d J=9.0 Hz, 2H), 7.92 (s, 1H), 8.11 (s, 1H). $^{13}C$ NMR (100.6 MHz, $CDCl_3$): δ −1.3, 17.5, 18.0, 19.4, 28.6, 31.3, 31.6, 32.0, 40.0, 42.6, 57.2, 63.5, 66.9, 72.3, 77.5, 80.8, 117.6, 124.4, 126.9, 127.9, 128.1, 129.8, 134.5, 145.1, 148.4, 150.4, 156.0, 161.2, 162.7, 170.5, 171.0. HRMS (ESI): m/z calcd. for $C_{45}H_{60}N_4NaO_7S_3Si$ (M+Na)+ 963.32911, found 963.32983.

S-Trityl Macrocycle 22a

According to the general procedure, 0.054 g acyclic precursor 20 was deprotected and cyclized to provide 0.030 g (72% yield) macrocycle 22a after purification by column chromatography. Eluent: EtOAc. (22a) Light yellow foam. $[\alpha]^{24}_D$: +30.0 (c=1, $CHCl_3$). $^1H$ NMR (300 MHz, 1:1 $CDCl_3$:$CD_3OD$) δ 0.39 (d J=6.9 Hz, 3H), 0.63 (d J=6.9 Hz, 3H), 1.97-2.18 (m, 5H), 2.54 (dd J=2.4, 16.5 Hz, 1H), 3.66 (dd J=9.0, 14.7 Hz, 1H), 3.95 (dd J=1.2, 11.4 Hz, 1H), 4.12 (d J=17.4 Hz, 1H), 4.54 (dd J=3.6, 9.6 Hz, 1H), 5.15 (d J=17.4 Hz, 1H), 5.29-5.34 (m, 1H), 5.35 (dd J=6.9, 15.6 Hz, 1H), 5.50-5.57 (m, 1H), 5.65 (dt J=6.9, 15.3 Hz, 1H), 6.98 (d J=9.6 Hz, 1H), 7.14-7.26 (m, 10H), 7.32-7.36 (m, 6H), 7.77 (s, 1H), $^{13}C$ NMR (100.6 MHz, $CDCl_3$): δ 16.6, 19.4, 31.6, 31.8, 34.4, 37.8, 38.9, 40.1, 41.2, 58.0, 73.2, 78.2, 125.7, 127.1, 127.3, 128.3, 130.0, 133.8, 145.2, 147.0, 166.4, 169.0, 169.5, 171.0, 171.5. HRMS (ESI): m/z calcd. for $C_{39}H_{40}N_4NaO_4S_3$ (M+Na)+ 747.21039, found 747.21042.

Thiol 22b

According to the general procedure. 0.035 g 22a was deprotected to give 0.022 g 22b after preparative thin layer chromatography. Clear oil. (22b) $[\alpha]^{24}_D$: −1.1 (c=0.2, $CHCl_3$). $^1H$ NMR (300 MHz, 1:1 $CDCl_3$:$CD_3OD$) δ 0.52 (d J=6.9 Hz, 3H), 0.70 (d J=6.9 Hz, 3H), 1.42 (t J=4.8 Hz, 1H), 2.08-2.14 (m, 1H), 2.32-2.40 (m, 2H), 2.53-2.61 (m, 2H), 2.89 (dd J=10.2, 16.8 Hz, 1H), 3.68 (dd J=8.7, 14.1 Hz, 1H), 4.02 (d J=11.4 Hz, 1H), 4.30 (dd J=3.3, 17.7 Hz, 1H), 4.63 (dd J=3.6, 9.6 Hz, 1H), 5.28 (dd J=9.3, 17.7 Hz, 1H), 5.40 (d J=6.0 Hz, 1H), 5.55 (dd J=1.5, 6.6, 15.3 Hz, 1H), 6.45-6.50 (m, 1H), 7.13 (d J=9.0 Hz, 1H), 7.79 (s, 1H), $^{13}C$ NMR (100.6 MHz, $CDCl_3$): δ 16.8, 19.2, 24.1, 34.3, 36.6, 37.8, 38.9, 40.8, 41.4, 57.9, 72.3, 124.7, 129.0, 132.9, 147.5, 168.0, 169.1, 169.6, 170.8. HRMS (ESI): m/z calcd. for $C_{20}H_{26}N_4NaO_4S_3$ (M+Na)+ 505.10139, found 505.10156.

S-Trityl-thiazole-thiazole Macrocycle 23a 0.020 g (0.028 mmol, 1.0 equiv.) 22a was dissolved in 1 mL dry $CH_2Cl_2$ and cooled to 0° C. 0.021 mL (0.14 mmol, 5.0 equiv.) DBU was added dropwise, followed by 0.014 mL (0.14 mmol, 5 equiv.) $BrCCl_3$ in 1 mL $CH_2Cl_2$. The reaction was allowed to warm to room temperature and stirred overnight. The resulting solution as then poured over cold (0° C.) saturated aqueous $NaHCO_3$, extracted, concentrated, and dried. The product was then purified by column chromatography, eluting in 1:2 hexanes:EtOAc (0.010 g, 52% yield), (23a) $[\alpha]^{24}_D$: −7.0 (c=1, $CHCl_3$). $^1H$ NMR (300 MHz, DMSO-d6) δ 0.70 (d J=6.9 Hz, 3H), 0.79 (d J=6.9 Hz, 3H), 1.91-1.99 (m, 2H), 2.07-2.12 (m, 2H), 2.16-2.24 (m, 1H), 2.33 (d J=14.1 Hz, 1H), 2.61 (dd J=10.8, 15.0 Hz, 1H), 4.39 (dd J=5.1, 17.4 Hz, 1H), 4.77 (dd J=7.2, 17.4 Hz, 1H), 5.17 (dd J=3.9, 9.9 Hz, 1H), 5.35 (dd J=7.5, 15.0 Hz, 1H), 5.50-5.65 (m. 2H), 7.19-7.28 (m, 3H), 7.28-7.35 (m, 12H), 7.62 (d J=9.6 Hz, 1H), 8.30 (s, 1H), 8.32 (s, 1H), 8.72 (t J=6.3 Hz, 1H), $^{13}C$ NMR (100.6 MHz, DMSO-d6): δ 16.6, 19.4, 31.6, 31.8, 34.4, 37.8, 38.9, 40.1, 41.2, 58.0, 73.2, 78.2, 125.7, 127.1, 127.3, 128.3, 130.0, 133.8, 145.2, 147.0, 166.4, 169.0, 169.5, 171.0, 171.5. HRMS (ESI): m/z calcd. for $C_{39}H_{38}N_4NaO_4S_3$ (M+Na)+ 745.19474, found 745.19430.

Thiol 23b

According to the general procedure. 0.010 g 23a was deprotected to give 0.005 g 23b after preparative thin layer chromatography. (23b): Clear oil. $[\alpha]^{24}_D$: −1.1 (c=0.2. $CHCl_3$). $^1H$ NMR (300 MHz. DMSO-d6) δ 0.82-0.85 (m, 6H), 2.21-2.29 (m, 4H), 2.39 (d J=14.1 Hz, 1H), 2.65 (dd J=10.5, 14.7 Hz, 1H), 4.40 (dd J=4.8, 17.1 Hz, 1H), 4.77 (dd J=7.2, 18.3 Hz, 1H), 5.21 (dd J=3.9, 9.9 Hz, 1H), 5.47-5.61 (m, 2H), 5.75 (dt J=6.9, 14.7 Hz, 1H), 7.68 (d J=9.9 Hz, 1H), 8.31 (s, 1H), 8.33 (s, 1H), 8.74 (t J=5.4 Hz, 1H), $^{13}$C NMR (100.6 MHz. DMSO-d6): δ 16.8, 19.2, 24.1, 34.3, 36.6, 37.8, 38.9, 40.8, 41.4, 57.9, 72.3, 124.7, 129.0, 132.9, 147.5, 168.0, 169.1, 169.6, 170.8. HRMS (ESI): m/z calcd. for $C_{20}H_{24}N_4NaO_4S_3$ (M+Na)$^+$ 503.08519, found 503.08369.

Example 14. Synthesis of Thiazole to Pyridine Substitution

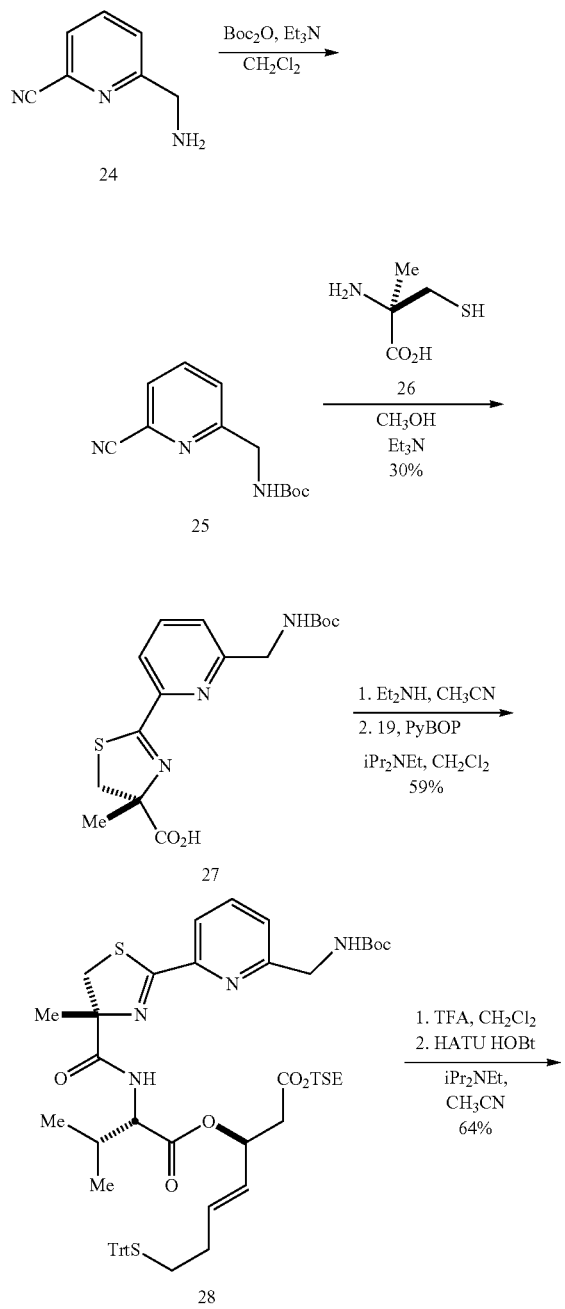

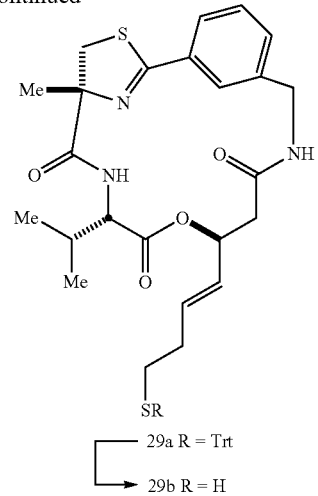

Acid 27

Amine 24 (Katsura. Y., et al. 1994 *J Med Chem* 37(1): 57-66) was dissolved in $CH_2Cl_2$ and treated with 1.83 ml, (1.31 mmol, 1.5 equiv.) $Et_3N$, followed by dropwise addition of a solution of 2.29 g (10.5 mmol, 1.2 equiv.) Boc anhydride in $CH_2Cl_2$. The resulting reaction was stirred overnight, then quenched with saturated aqueous $NaHCO_3$. The organic layer was separated, dried over $Na_2SO_3$, filtered, and concentrated to give the Boc protected amine as a white solid. This solid was then dissolved in 90 mL $CH_3OH$ together with 1.62 g (8.7 mmol, 1.0 equiv.) α-methyl cysteine and 2.44 mL (17.5 mmol, 2.0 equiv.) $Et_3N$. The resulting solution was heated at reflux overnight. The reaction was subsequently cooled to room temperature and the solvents removed in vacuo. The crude reaction mixture was then dissolved in saturated aqueous $NaHCO_3$ and washed with diethyl ether. The aqueous layer was then acidified to pit ~3-4 by dropwise addition of 3N HCl and extracted with EtOAc (3×30 mL). The combined organics were dried over $Na_2SO_4$, filtered, and concentrated to provide 0.500 g (1.4 mmol, 30% yield) of acid 27 in spectroscopically pure form. (27) [α]$^{24}$$_D$: +55.2 (c=2, $CHCl_3$). $^1$H NMR (300 MHz, $CDCl_3$) δ 1.46 (s, 9H), 1.67 (s, 3H), 3.28 (d J=11.7 Hz, 1H), 3.81 (d J=11.7 Hz, 1H), 4.47 (d J=5.4 Hz, 2H), 5.53 (s, 1H), 7.37 (d J=7.8 Hz, 1H), 7.74 (t J=7.8 Hz, 1H), 8.00 (d J=7.8 Hz, 1H), $^{13}$C NMR (100.6 MHz, $CDCl_3$): δ 21.9, 24.2, 28.6, 36.1, 40.5, 45.5, 47.9, 79.8, 85.1, 120.6, 123.9, 137.4, 149.9, 156.4, 157.4, 157.6, 171.3, 175.8. HRMS (ESI): m/z calcd. for $C_{16}H_{20}N_3Na_2O_4S$ (M−H+2Na)$^+$ 396.09699, found 396.09616.

Thiazoline-Pyridine Acyclic Precursor 28

1.100 g (1.3 mmol, 1.0 equiv.) diester 19 and 0.500 g (1.4 mmol, 1.1 equiv.) acid 27 were coupled according to the same procedure described above for synthesis of 43. 0.800 g (0.90 mmol, 59% yield) 28 was obtained after column chromatography. (28): Clear oil. [α]$^{24}$$_D$: −22.1 (c=2, $CHCl_3$). $^1$H NMR (300 MHz, $CDCl_3$) δ 0.73 (d J=6.9 Hz, 3H), 0.81 (d J=6.9 Hz, 3H), 0.94-0.99 (m, 2H), 1.47 (s, 9H), 1.58 (s, 3H), 2.03-2.19 (m, 5H), 2.55 (dd J=5.7, 15.9 Hz, 1H), 2.69 (dd J=8.1, 15.9 Hz, 1H), 3.31 (d J=11.7 Hz, 1H), 3.69 (d J=11.7 Hz, 1H), 4.13-4.18 (m, 2H), 4.48-4.53 (m, 3 Hz, 5.37 (dd J=7.5, 15.3 Hz, 1H), 5.48-5.52 (m, 1H), 5.61-5.74 (m, 2H), 7.18-7.29 (m, 10H), 7.35-7.40 (m, 7H), 7.68 (t J=7.8 Hz, 1H), 7.98 (d J=7.8 Hz, 1H). $^{13}$C NMR (100.6 MHz, CDCl$_3$): δ −1.2, 17.5, 17.6, 19.3, 25.0, 28.7, 31.3, 31.5, 39.9, 40.8, 45.7, 56.9, 63.3, 66.8, 72.0, 79.8, 85.9, 120.2, 124.0, 126.8, 128.0, 128.1, 129.7, 134.2, 137.6, 145.0, 150.1, 156.3, 157.9, 169.9, 170.7, 171.2, 174.7. HRMS (ESI): m/z calcd. for C$_{52}$H$_{66}$N$_4$NaO$_7$S$_2$Si (M+Na)$^+$ 973.40344, found 973.40443.

S-Trityl Macrocycle 29a

According to the general procedure. 0.400 g (0.42 mmol) 28 was deprotected and cyclized to provide 0.200 g (0.27 mmol, 64% yield) macrocycle 29a after column chromatography. Eluent: EtOAc. (29a): Clear oil. [α]$^{24}$$_D$: +16.7 (c=1, CHCl$_3$). $^1$H NMR (300 MHz, 10:1 CDCl$_3$:CD$_3$OD) δ 0.52 (d J=6.9 Hz, 3H), 0.74 (d J=6.9 Hz, 3H), 1.84 (s, 3H), 2.03-2.17 (m, 5H), 2.64-2.79 (m, 2H), 3.38 (d J=11.4 Hz, 1H), 4.09 (d J=11.4 Hz, 1H), 4.30 (d J=17.7 Hz, 1H), 4.68 (dd J=3.9, 9.9 Hz, 1H), 5.00 (dd J=6.6, 17.7 Hz. 1H), 5.40 (dd J=6.6, 15.6 Hz, 1H), 5.60-5.66 (m, 1H), 5.75 (dt J=7.8, 15.6 Hz, 1H), 7.10-7.37 (m. 18H), 7.64 (d J=7.5 Hz, 1H), 7.80 (t J=7.5 Hz, 1H). $^{13}$C NMR (100.6 MHz, 10:1 CDCl$_3$:CD$_3$OD): δ 16.2, 19.0, 24.5, 31.3, 31.5, 33.5, 38.7, 41.2, 43.4, 43.6, 51.4, 57.4, 66.7, 73.3, 84.3, 123.2, 124.7, 126.7, 128.0, 128.2, 129.7, 133.3, 138.2, 144.9, 148.7, 157.4, 166.0, 169.2, 170.0, 173.3, 173.6. HRMS (ESI): m/z calcd. for C$_{42}$H$_{44}$N$_4$NaO$_4$S$_2$ (M+Na)$^+$ 755.26962, found 755.26961.

Thiol 23b

According to the general procedure, 0.033 g 23a was deprotected to give 0.019 g 23b after preparative thin layer chromatography. (29b): Clear oil. [α]$^{24}$$_D$: +3.4 (c=0.2, CHCl$_3$). $^1$H NMR (300 MHz, 10:1 CDCl$_3$:CD$_3$OD) δ 0.54 (d J=6.9 Hz, 3H), 0.75 (d J=6.9 Hz, 3H), 1.43 (t J=7.8 Hz, 1H), 1.89 (s, 3H), 2.04-2.17 (m, 1H), 2.32-2.39 (m, 2H), 2.49-2.57 (m, 2H), 2.69-2.86 (m, 2H), 3.39 (d J=11.4 Hz, 1H), 4.10 (d J=11.4 Hz, 1H), 4.37 (dd J=2.4, 17.7 Hz, 1H), 4.72 (dd J=3.9, 9.9 Hz, 1H), 5.04 (dd J=6.9, 17.7 Hz, 1H), 5.57 (dd J=6.6, 15.6 Hz, 1H), 5.67-5.73 (m, 1H), 5.87 (dt J=7.2, 15.6 Hz, 1H), 7.38 (d J=7.8 Hz, 1H), 7.66 (d J=7.8 Hz, 1H), 7.84 (t J=7.8 Hz, 1H). $^{13}$C NMR (100.6 MHz, 10:1 CDCl$_3$:CD$_3$OD): δ 16.9, 19.2, 24.1, 24.8, 33.8, 36.7, 41.8, 43.8, 44.1, 51.4, 57.7, 72.5, 85.0, 123.5, 124.6, 128.6, 132.7, 138.1, 156.9, 169.0, 169.3, 173.6. HRMS (ESI): m/z calcd. for C$_{23}$H$_{30}$N$_4$NaO$_4$S$_2$ (M+Na)$^+$ 513.16007, found 513.16058.

Example 15. Synthesis of the Oxazoline-Oxazole Analog

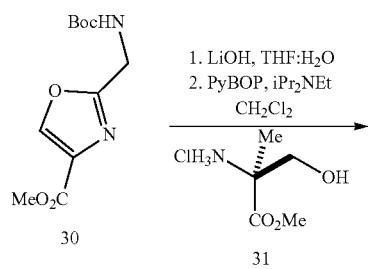

30

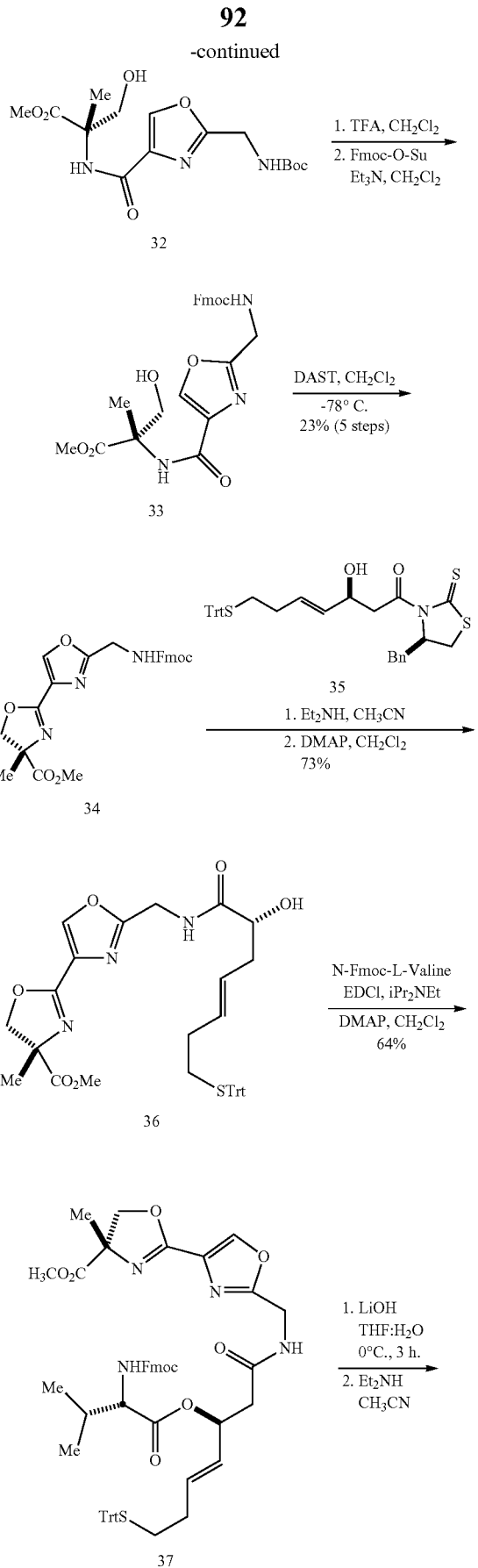

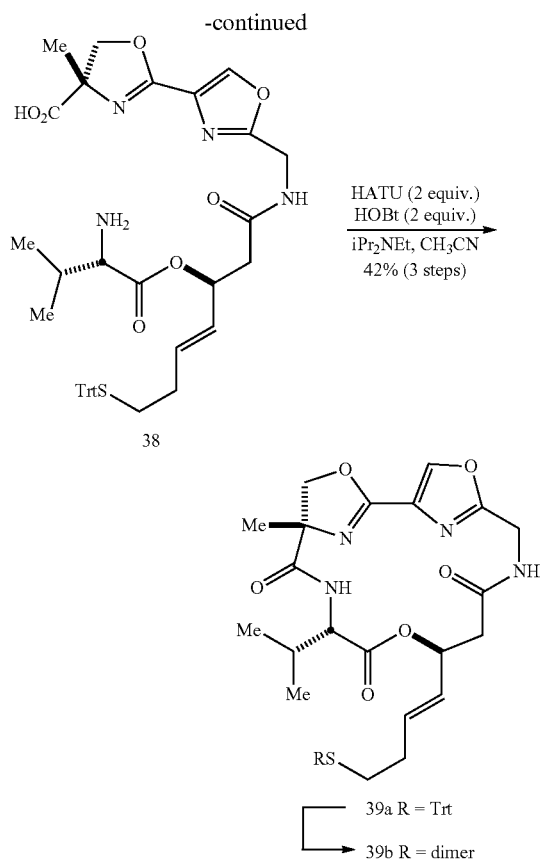

38

39a R = Trt
39b R = dimer

Oxazoline-Oxazole 34

1.1 g (4.3 mmol, 1.0 equiv.) Oxazole 30 (Phillips. A. J., et al. 2000 Org Left 2(8):1165-1168) was dissolved in 200 mL 2:1 THF:H$_2$O and treated with 0.205 g (8.6 mmol, 2.0 equiv.) LiOH. The resulting solution was stirred for ~1 hr., when TLC showed complete disappearance of starting material. The reaction was acidified with 1N HCl and extracted with CH$_2$Cl$_2$. The organic layer was dried over Na$_2$SO$_3$, filtered, and concentrated to give the crude acid, which was taken on without further purification. The acid was taken up in dry CH$_2$Cl$_2$. 4.47 g (8.6 mmol, 2.0 equiv.) PyBOP was added, followed by 0.874 g (5.2 mmol, 1.2 equiv.) α-methyl-serine-methylester-HCL salt (Avenoza, A., et al. 2001 Tet Assym 12(6):949-957) and 2.24 mL (12.9 mmol, 3.0 equiv.) iPr$_2$NEt. The resulting reaction was stirred for ~2 hrs, then concentrated and passed through a short plug of silica, washing with EtOAc, to give alcohol 32.

Crude alcohol 32 was dissolved in 100 mL. CH$_2$Cl$_2$ (to ~0.003M), cooled to 0° C., and treated with 14 mL TFA (to ~0.3M). The reaction was stirred for ~2 hrs, when TLC showed complete disappearance of starting material. The reaction mixture was concentrated, the residue dissolved in toluene, and concentrated again. The crude amine salt was dried on an oil pump for ~2 hrs, then dissolved in 50 mL dry CH$_2$Cl$_2$, cooled to 0° C., and treated successively with 0.720 mL (8.6 mmol, 2.0 equiv.) Et$_3$N and 1.72 g (5.2 mmol, 1.2 equiv.) Fmoc-O-succinimide in 10 mL CH$_2$Cl$_2$. The resulting reaction was allowed to warm to room temperature and stirred overnight. The reaction was then quenched with saturated aqueous NaHCO$_3$ dried over Na$_2$SO$_3$, filtered, and concentrated. The residue was passed through a short plug of silica, washing with EtOAc to give alcohol 33.

Crude alcohol 33 was dissolved in 20 mL dry CH$_2$Cl$_2$ and cooled to –78° C. 0.690 mL (5.6 mmol, 1.2 equiv.) DAST was added dropwise and the reaction was allowed to stir at –78° C. for an additional 2 hrs. The mixture was then poured onto a saturated aqueous solution of NaHCO$_3$ at 0° C. The organic layer was separated, dried over Na$_2$SO$_3$, filtered, and concentrated. The residue was purified by column chromatography. An unidentified by-product elutes first in 1:1 hexanes:EtOAc, followed by the desired oxazoline 34 in 1:2 hexanes:EtOAc (0.455 g, 0.99 mmol, 23% yield from 30). (34): $[\alpha]^{24}_D$: +72.7 (c=1, CHCl$_3$). $^1$H NMR (300 MHz, CDCl$_3$) δ 1.62 (s, 3H), 3.78 (s, 3H), 4.17 (d J=8.7 Hz, 1H), 4.23 (t J=6.9 Hz, 1H), 4.42-4.58 (m, 4H), 4.82 (d J=8.7 Hz, 1H), 5.54-5.57 (m, 1H), 7.31 (t J=7.5 Hz, 2H), 7.40 (t J=7.5 Hz, 2H), 7.59 (d J=7.5 Hz, 21H), 7.76 (d J=7.5 Hz, 2H), 8.12 (s, 1H), $^{13}$C NMR (100.6 MHz, CDCl$_3$): δ 25.1, 38.5, 47.3, 53.1, 67.4, 74.5, 77.6, 120.2, 125.3, 127.3, 127.9, 130.4, 141.5, 142.0, 143.9, 156.5, 158.5, 162.3, 173.4. HRMS (ESI): m/z calcd. for C$_{25}$H$_{23}$N$_3$NaO$_6$ (M+Na)$^+$ 484.14791, found 484.14790.

Alcohol 36

0.250 g (0.54 mmol, 1.0 equiv.) 34 was dissolved in 30 mL CH$_3$CN and treated with 3 mL Et$_2$NH. The reaction was allowed to stir for 2 hrs and then concentrated, redissolved in EtOAc, and concentrated again. The crude amine thus obtained was taken up in 5 mL dry CH$_2$Cl$_2$ together with 0.010 g (0.08 mmol, 0.15 equiv.) DMAP and added dropwise to a solution of 0.495 g (0.81 mmol, 1.5 equiv.) 35 in 20 mL CH$_2$Cl$_2$. The resulting reaction mixture was allowed to stir overnight, then concentrated and submitted immediately to column chromatography. 0.253 g (0.39 mmol, 73% yield) alcohol 36 eluted in 1:2 hexanes:EtOAc. (36): $[\alpha]^{24}_D$: –18.1 (c=1, CHCl$_3$). $^1$H NMR (300 MHz, CDCl$_3$) 1.61 (s, 3H), 2.03-2.10 (m, 2H), 2.16-2.22 (m, 2H), 2.38 (dd J=8.4, 15.3 Hz, 1H), 2.46 (dd J=3.9, 15.3 Hz, 1H), 3.77 (s, 3H), 4.17 (d J=9.0 Hz. II), 4.41-4.47 (m, 1H), 4.58 (d J=5.4 Hz. 2H), 4.81 (d J=9.0 Hz, 1H), 5.41 (dd J=6.3, 15.6 Hz, 1H), 5.56 (dt J=6.9, 15.6 Hz, 1H), 6.63-6.66 (m, 1H), 7.17-7.30 (m, 9H), 7.37-7.41 (m. 6H), 8.11 (s, 1H), $^{13}$C NMR (100.6 MHz, CDCl$_3$): δ 25.2, 31.6, 31.7, 36.7, 43.0, 53.1, 66.8, 69.1, 74.4, 76.4, 126.8, 128.1, 129.8, 129.9, 130.2, 132.7, 142.1, 145.1, 158.6, 162.3, 172.4, 173.4. HRMS (ESI): m/z calcd. for C$_{36}$H$_{37}$N$_3$NaO$_6$S (M+Na)$^+$ 662.22953, found 662.22913.

Oxazoline-Oxazole Acyclic Precursor 37

0.250 g (0.39 mmol) of alcohol 36 and 0.663 g (2.0 mmol, 5 equiv.) N-Fmoc-L-valine were dissolved in 20 mL dry CH$_2$Cl$_2$. The reaction was cooled to 0° C., and 0.449 g (2.4 mmol, 6 equiv.) EDCI and 0.003 g (0.02 mmol, cat.) DMAP were added in ~5 mL CH$_2$Cl$_2$, followed by 0.4 mL iPr$_2$NEt. The reaction was allowed to warm to room temperature and stirred overnight, when TLC showed complete disappearance of 36. The reaction was concentrated and the product (0.240 g, 64% yield) purified by silica gel chromatography. Eluent: 1:2 hexanes:EtOAc. (37): $[\alpha]^{24}_D$: –2.0 (c=1, CHCl$_3$). $^1$H NMR (300 MHz, CDCl$_3$) δ 0.83 (d J=6.9 Hz, 3H), 0.90 (d J=6.9 Hz, 3H), 1.58 (s, 3H), 1.64-1.73 (m, 1H), 2.00-2.18 (in. 5H), 2.49-2.62 (m, 2H), 3.76 (s, 3H), 4.12 (d J=8.7 Hz, 1H), 4.10-4.21 (m, 2H), 4.36 (d J=6.9 Hz, 2H), 4.45-4.60 (m, 2H), 4.77 (d J=8.7 Hz, 1H), 5.34-5.42 (m, 2H), 5.58-5.71 (m, 2H), 6.50 (t J=5.1 Hz, 1H), 7.17-7.32 (m, 12H), 7.36-7.41 (m, 8H), 7.57 (d J=7.5 Hz, 2H), 7.75 (d J=7.5 Hz, 2H), 8.06 (s, 1H). $^{13}$C NMR (100.6 MHz, CDCl$_3$):

δ 17.6, 17.9, 18.8, 19.3, 25.1, 31.2, 31.3, 31.5, 37.0, 41.5, 47.4, 53.1, 53.8, 59.4, 66.8, 67.1, 72.4, 74.5, 76.3, 120.2, 125.3, 126.8, 127.3, 127.9, 128.1, 129.8, 130.3, 134.1, 141.5, 142.0, 144.0, 144.1, 145.0, 156.6, 158.5, 162.0, 169.3, 171.3, 173.4. HRMS (ESI): m/z calcd. for $C_{56}H_{56}N_4NaO_9S$ (M+Na)$^+$ 983.36602, found 983.36673.

S-Trityl Macrocycle 39a 0.240 g (0.25 mmol, 1.0 equiv.) acyclic precursor 37 was dissolved in 7.5 mL 4:1 THF:H$_2$O and cooled to 0° C. 0.5 mL of a 0.5M aqueous solution of LiOH was added dropwise, and the resulting reaction mixture was allowed to stir for ~3 hrs at 0° C., when TLC demonstrated disappearance of the starting material. The reaction was neutralized by dropwise addition of 1N HCl and extracted with CH$_2$Cl$_2$. The combined organics were dried and filtered and solvents evaporated to provide the crude acid. This was immediately dissolved in 25 mL CH$_3$CN (to ~0.01M) and treated with 1.25 mL Et$_2$NH (to ~0.2M). The reaction was stirred for ~2 hrs. when the reaction was assumed to be complete. The resulting solution was concentrated, taken up in EtOAc, and concentrated again. The crude amino acid was dried on the mechanical pump overnight and then submitted to cyclization conditions as described above. Column chromatography provided 0.074 g (0.10 mmol, 74% yield) macrocycle 39a as a clear oil. (39a): [α]$^{24}_D$: +42.2 (c=1, CHCl$_3$). $^1$H NMR (300 MHz. CDCl$_3$) δ 0.53 (d J=6.9 Hz, 3H), 0.56 (d J=6.9 Hz, 3H), 1.58 (s, 3H), 1.89-2.16 (m, 5H), 2.51 (dd J=1.8, 17.1 Hz, 1H), 2.87 (dd J=9.9, 17.1 Hz, 1H), 3.82 (dd J=3.6, 17.7 Hz, 1H), 3.99 (d J=9.0 Hz, 1H), 4.32-3.36 (m, 1H), 4.62 (d J=9.0 Hz, 1H), 4.60-4.69 (m, 1H), 5.34-5.49 (m, 2H), 5.58 (dt J=6.9, 14.7 Hz, 1H), 7.08-7.21 (in. 9H), 7.26-7.31 (m, 7H), 7.62-7.67 (m, 1H), 7.97 (s, 1H), $^{13}$C NMR (100.6 MHz, 10:1 CDCl$_3$:CD$_3$OD): δ 17.1, 18.7, 21.1, 31.4, 34.0, 37.4, 39.9, 58.0, 66.8, 72.7, 73.6, 77.5, 78.8, 126.8, 128.0, 128.4, 129.2, 129.7, 133.2, 141.7, 144.9, 162.2, 164.1, 168.7, 171.9, 174.3, FIRMS (ESI): m/z calcd. for $C_{40}H_{42}N_4NaO_6S$ (M+Na)$^+$ 729.27173, found 729.27147.

Disulfide Dimer 39b

To a vigorously stirring solution of 0.319 g (1.3 mmol, 12 equiv.) 12 in 300 mL 10% MeOH/CH$_2$Cl$_2$ was added 0.074 g (0.10 mmol, 1.0 equiv.) protected thiol 39a in 60 mL 10% MeOH/CH$_2$Cl$_2$ dropwise over 10 minutes. The resulting mixture was stirred for a further 10 minutes. 250 mL 0.01 N Na$_2$S$_2$O$_3$ was added and the organic phase extracted with CH$_2$Cl$_2$ the combined organic extract washed with brine, dried over Na$_2$SO$_3$, filtered, and the solvent removed. The residue was purified by flash chromatography, washing first with EtOAC, then 10:1 CH$_2$Cl$_2$:CH$_3$Cl$_3$. (39b): Clear oil. [α]$^{24}_D$: +19.0 (c=0.5, CHCl$_3$). $^1$H NMR (300 MHz, CDCl$_3$) d 0.67-0.70 (m, 6H), 1.66 (s, 3H), 2.12-2.18 (m, 1H), 2.40-2.47 (m, 2H), 2.71-2.80 (m, 3H), 3.02 (dd J=9.6, 16.5 Hz, 1H), 3.96 (dd J=4.5, 17.4 Hz, 1H), 4.05 (d J=9.0 Hz, 1H), 4.51 (dd J=3.6, 8.7 Hz, 1H), 4.73 (d J=9.0 Hz, 1H), 4.85 (dd J=9.0, 17.4 Hz, 1H), 5.54-5.69 (m, 2H), 5.90 (dt J=6.9, 15.6 Hz, 1H), 6.89-6.94 (m, 1H), 8.01 (s, 1H), $^{13}$C NMR (100.6 MHz, 10:1 CDCl$_3$:CD$_3$OD): δ 17.4, 18.7, 21.4, 29.8, 31.9, 34.1. 37.6, 38.0, 40.3, 51.4, 58.1, 72.4, 74.0, 78.9, 128.5, 129.8, 133.7, 141.2, 161.0, 164.2, 168.7, 170.8, 174.1. HRMS (ESI): m/z calcd. for $C_{42}H_{54}N_8NaO_{12}S_2$ (M+Na)$^+$ 949.31948, found 949.32045.

Scheme O1.

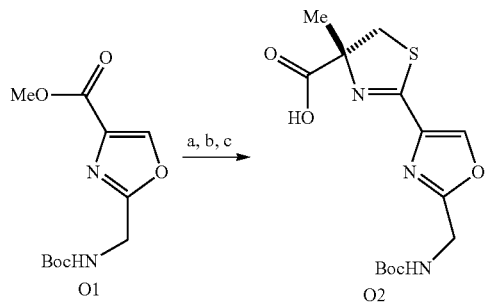

(a) NH$_4$OH, MeOH; (b) POCl$_3$, Et$_3$N, CH$_2$Cl$_2$; (c) a-Me-Ser-OH·HCl, Et$_3$N, MeOH.

Scheme O2.

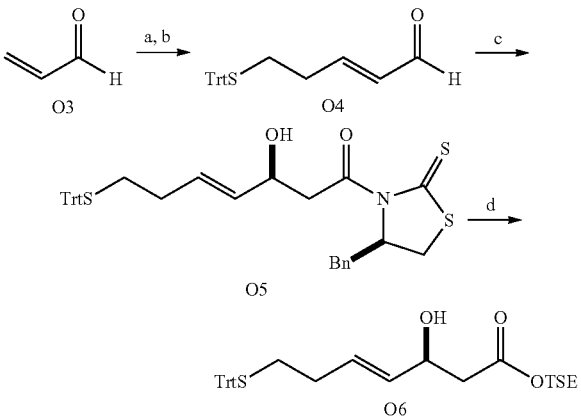

(a) TrtSH, Et$_3$N, CH$_2$Cl$_2$; (b) (formylmethylene)triphenylphosphorane, PhH, 80° C., 62%; (c) (R)-1-(4-benzyl-2-thioxothiazolidin-3-yl)ethanone, TiCl$_4$, DIPEA, CH$_2$Cl$_2$, 56%; (d) 2-(trimethylsilyl)ethanol, imidazole, CH$_2$Cl$_2$.

Scheme O3.

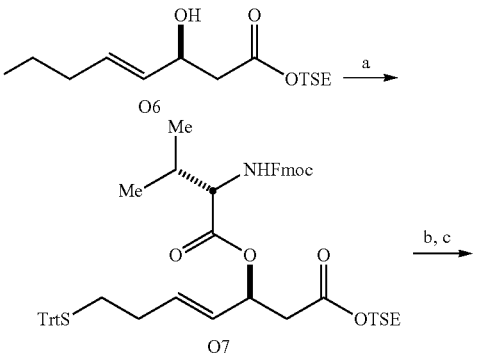

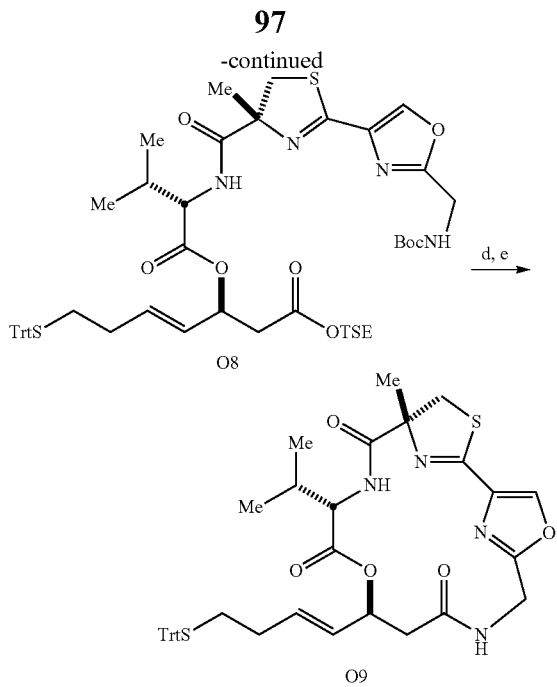

(a) N-Fmoc-Val-OH, EDCI, DIPEA, CH$_2$Cl$_2$, 65%; (b) Et$_2$NH, CH$_3$CN; (c) PyBOP, DIPEA, O2, CH$_2$Cl$_2$, 91%; (d) CF$_3$CO$_2$H, CH$_2$Cl$_2$; (e) T3P, DIPEA, CH$_2$Cl$_2$, 30%.

HDAC Biochemical Assay

Compounds O10-O12 were tested against HDACs 1-3, 6-8 and the activity was determined with an optimized homogenous assay performed in a 384-well plate (Table O1). Reactions were performed in assay buffer (50 mM HEPES. 100 mM KCl, 0.001% Tween-20, 0.05% BSA and pH 7.4. Additional 200 μM TCEP was added for HDAC6) and followed by fluorogenic release of 7-amino-4-methyl-coumarin from substrate upon deacetylase and trypsin enzymatic activity. Fluorescence measurements were obtained every five minutes using a multilabel plate reader and plate-stacker (Envision; Perkin-Elmer). Each plate was analyzed by plate repeat, and the first derivative within the linear range was imported into analytical software (Spotfire DecisionSite). Replicate experimental data from incubations with inhibitor were normalized to DMSO controls ([DMSO] <0.5%). IC50 is determined by logistic regression with unconstrained maximum and minimum values. The recombinant, full-length HDAC protein (BPS Biosciences) was incubated with fluorophore conjugates substrate, MAZ1600 and MAZ1675 at Km=[substrate].

Scheme O4.

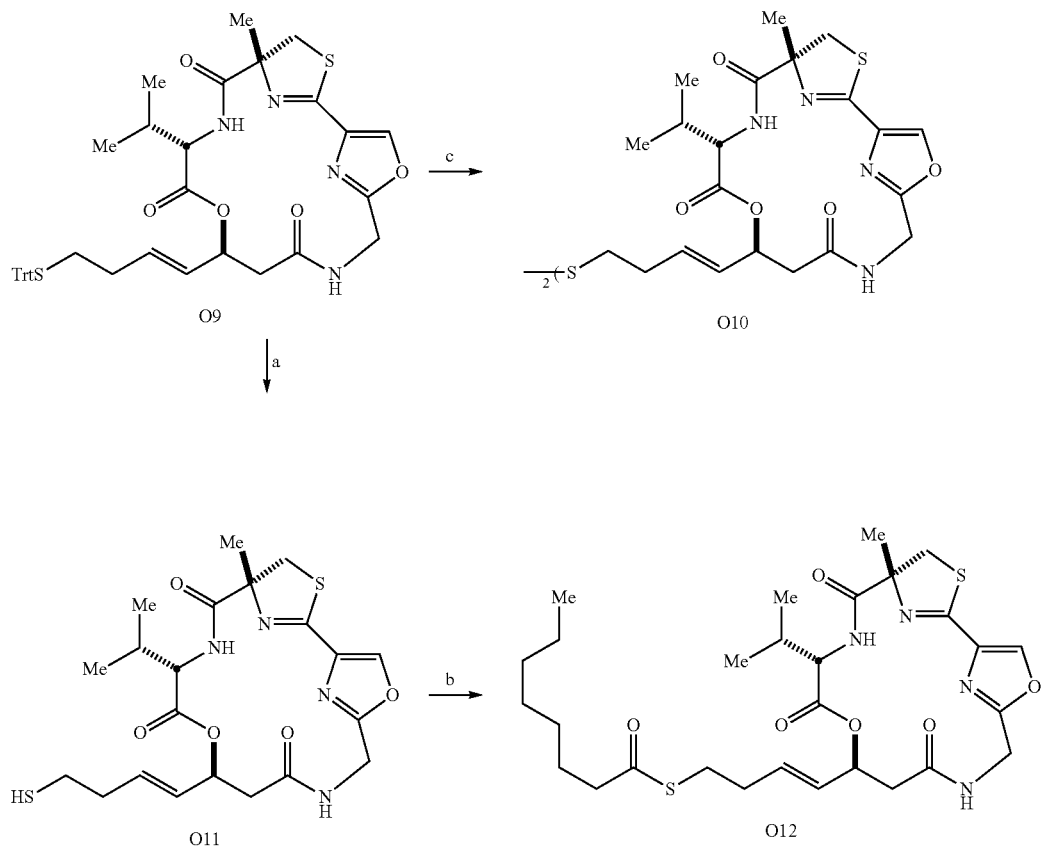

(a) CF$_3$CO$_2$H, Et$_3$SiH, CH$_2$Cl$_2$, 83%; (b) octanoylchloride, Et$_3$N, CH$_2$Cl$_2$, 36%; (c) CF$_3$CO$_2$H, iPr$_3$SiH, CH$_2$Cl$_2$, 35%.

TABLE O1

HDAC Activity of largazole analogs(IC$_{50}$ µM).

| Cmpd | HDAC1 | HDAC2 | HDAC3 | HDAC6 | HDAC7 | HDAC8 |
|---|---|---|---|---|---|---|
| O10 | 0.15 | 1.3 | 0.55 | 0.05 | — | — |
| O11 | 0.0044 | 0.020 | 0.0072 | 0.098 | 0.96 | 1.2 |
| O12 | 0.95 | 2.1 | 1.9 | 1.1 | — | — |
| largazole | 0.23 | 0.90 | 0.67 | 0.34 | — | — |

MM1S Cell Viability (Figure O1):

For dose-response cellular viability assays, MM1S cells were seeded onto 384-well tissue culture-treated plates at a density of 2.0×104 cells/well in a volume of 50 µL/well. Addition of compound was performed with a JANUS Workstation (PerkinElmer Life and Analytical Sciences) using a 384-well pinhead tool that is calibrated to deliver 100 nL drug/well. After 48 hours of incubation with compound, cells were analyzed for cell viability using the ATPLite (Perkin Elmer) luminescent assay kit per the manufacturer's instructions. Luminescence was read on an EnVision 2104 Multilabel Plate Reader (PerkinElmer Life and Analytical Sciences). Replicate measurements were analyzed with respect to dose and estimates of IC50 were calculated by logistic regression (GraphPad Prism).

Figure O1. Activity of largazole analogs in MM1S cell line.

Thiazoline-Oxazole Acid (O2)

To oxazole O1 (*Org. Lett.* 2009, 11, 1301) (880 mg, 3.436 mmol) under argon at room temperature was added MeOH (90 mL) then NH$_4$OH (20 mL). The reaction was allowed to stir overnight. The reaction mixture was then concentrated and put under vacuum for several hours. The crude amide was then dissolved in DCM (120 mL) and Et$_3$N (7.5 mL, 53.068 mmol) was added and the reaction was cooled to 0° C. POCl$_3$ (824 µL, 8.845 mmol) was then added dropwise and the reaction was allowed to warm to room temperature and stir for 16 hours. The reaction was then concentrated down and taken on immediately. To the crude material was added MeOH (60 mL) then α-Me-Cys-OH.HCl (610 mg, 3.554 mmol) was added and the reaction was stirred at room temperature. Et$_3$N (2 mL, 14.120 mmol) was then added and the reaction was stirred overnight. The reaction was subsequently concentrated and purified through a silica plug providing O2 (72%).

HRMS (ESI): m/z calcd. for C$_{14}$H$_{19}$N$_3$O$_5$S (M+H)+: 342.1124, found 342.1112. [α]D=−3.46, c=0.005 in DCM. 1H NMR (400 MHz, CDCl$_3$) d TMS: 1.47 (9H, s); 1.69 (3H, s); 3.34 (1H, d, J=11.1); 3.88 (1H, d, J=11.7); 4.50-4.51 (2H, m, J=2.7); 5.29 (1H, bs); 8.20 (1H, s). 13C NMR (100.8 MHz, CDCl$_3$) δ TMS: 24.02, 26.27, 37.83, 40.74, 80.44, 83.98, 134.65, 140.49, 155.49, 162.36, 162.50, 174.80. IR (λmax) 3321.20, 2978.02, 1711.95, 1625.16, 1165.44, 947.31 cm$^{-1}$ Thiazoline-Oxazole Acycle Analog (O8)

O7 (*J. Am. Chem. Soc.* 2008, 130, 11219) (880 mg, 1.047 mmol) was dissolved in CH3CN (5.5 mL) and Et2NH (5.3 mL) was added. The reaction was allowed to stir at room temperature for 3 hours and was then concentrated, dissolved in EtOAc and concentrated down two more times and then put under high vacuum overnight. The crude amine was then dissolved in DCM (15 mL) and PyBOP (1.1 g, 2.094 mmol) was added and the solution was cooled to 0° C. Hünig's base (911 µl, 5.235 mmol) was then added and the reaction was stirred for 10 minutes. Thiazoline-oxazole fragment (2) (360 mg, 0.869 mmol) was then added in DCM (10 mL). The reaction was allowed to stir at room temperature for 5 hours and was then concentrated down onto silica gel and purified via column chromatography, hexanes:EtOAc, 93:7 to 70:30 to afford the desired acycle (O8) in 91% yield.

HRMS (ESI): m/z calcd. for C$_{50}$H$_{64}$N$_4$O$_8$S$_2$Si (M+Na)+ 963.3833, found 963.3827. [α]D=+30, c=6 in CH$_2$Cl$_2$. 1H-NMR (300 MHz; CDCl$_3$): δ 0.04 (s, 9H), 0.76 (d, J=6.9 Hz, 3H), 0.83 (d, J=6.8 Hz, 3H), 1.00-0.94 (m, 4H), 1.47 (s, 9H), 1.57 (s, 3H), 2.09-2.02 (m, 3H), 2.22-2.12 (m, 2H), 2.55 (dd, J=15.8, 5.8 Hz, 1H), 2.69 (dd, J=15.6, 7.8 Hz, 1H), 3.31 (d, J=11.6 Hz, 1H), 3.78 (d, J=11.5 Hz, 1H), 4.15 (ddd, J=10.0, 7.1, 3.3 Hz. 3H), 4.50-4.44 (m, 2H), 5.15 (bs, 1H), 5.37 (dd, J=15.6, 7.4 Hz, 1H), 5.66 (tt, J=14.8, 7.3 Hz, 2H), 7.12 (d, J=8.9 Hz, 1H), 7.41-7.20 (m, 5H), 8.10 (s, 1H), 13-C NMR (75 MHz; CDCl$_3$): δ −1.27, 17.51, 17.74, 19.27, 24.91, 28.54, 31.31, 31.55, 39.93, 41.42, 57.12, 63.33, 66.83, 71.97, 77.43, 85.49, 126.82, 128.07, 129.78, 134.07, 145.04, 162.12, 169.85, 170.50, 174.41. IR (λmax) 3388.61, 2960.13, 1736.44, 1681.31, 1510.68, 1250.17, 1171.92 cm$^{-1}$ Thiazoline-Oxazole Macrocycle Analog (O9)

O8 (433 mg, 0.460 mmol) was dissolved in DCM (I 5 mL) and cooled to 0° C. TFA (1.5 mL) was then added and the reaction was stirred at room temperature overnight. The reaction was then pulled down and pulled down again from DCM and placed under vacuum for several hours. The reaction was then dissolved in DCM (460 mL) and cooled to 0° C. and Hünig's base (640 µl, 3.680 mmol) was then added dropwise. T3P (400 mg, 0.552 mmol) was then taken up into a syringe with DMF (2 mL) and added to the starting material via a syringe pump over 1 hour. The reaction was then allowed to stir at room temperature for 48 hours and was then concentrated down and diluted with EtOAc and washed with brine (3×30 mL). Purification via column chromatography, hexanes:EtOAc, 50:50 gave the desired product (O9) in 30-40% yield.

HRMS (ESI): m/z calcd for C$_{40}$H$_{42}$N$_4$NaO$_5$S$_2$ (M+Na)+ 745.2494, found 745.2486. [α]D=+23, c=0.04 in CH$_2$Cl$_2$. 1H (300 MHz, CDCl$_3$): 0.68 (6H, t, J=6.8), 1.83 (3H, s), 1.94 (4H, m), 2.20 (2H), 2.64 (1H, dd, J=3.8, 16.0), 2.75 (1H, dd, J=7.7, 15.9). 3.24 (1H, d, J=11.3); 3.79 (1H, dd, J=4.1, 17.5), 4.00 (1H, d, J=11.3), 4.46 (1H, dd, J=4.0, 8.6). 4.76 (1H, dd, J=9.0, 17.3), 5.53 (3H, m,), 6.40 (1H, dd, J=4.2, 9.4), 7.15 (1H, d, J=8.8), 7.22 (10H, m), 7.37 (5H, m), 7.97 (1H, s). $^{13}$C (75.5 MHz, CDCl$_3$): 17.72, 18.86, 24.20, 31.11, 31.59, 34.03, 37.25, 37.28, 41.31, 43.48, 58.68, 66.93, 71.78, 77.44, 84.10, 126.96, 128.18, 128.91, 129.80, 133.00, 135.30, 141.16, 144.88, 162.08, 163.34, 168.67, 170.32, 173.59. IR (ηmax) 3376.15, 2959.87, 1735.69, 1674.72, 1541.38, 1245.67 cm$^{-1}$ Thiazoline-Oxazole Dimer (O10)

O9 (128 mg, 0.177 mmol) in DCM (25 mL) was cooled to 0° C. i-Pr$_3$SiH (75 µl, 0.354 mmol) was added and then TFA (885 µl) was then added to the reaction at room temperature.

The reaction was allowed to stir at room temperature for 2 hours and then was concentrated and purified via column chromatography, hexanes:EtOAc, 50:50 then 100% EtOAc to give the desired dimer (O10) in 35% yield.

HRMS (ESI): m/z calcd. for $C_{42}H_{54}N_8O_{10}S_4Na$ (M+Na)+: 981.2743, found: 981.2715. HRMS calcd. for $C_{42}H_{55}N_8O_{10}S_4$ (M+11)+: 959.2924, found: 959.2906. [α]D=+4, c=0.005 in $CH_2Cl_2$ 1H NMR (400 MHz, $CDCl_3$); 0.61 (3H, d, J=6.9); 0.65 (3H, d, J=6.9); 1.79 (3H, s); 2.02 (2H, m), 2.38 (2H, m); 2.67 (2H, t, J=7.4); 2.85 (2H, dd, J=9.7, 16.6); 3.20 (1H, d, J=11.4); 3.93 (3H, m); 4.49 (1H, dd, J=3.6, 9.0); 4.86 (1H, dd, J=9.4, 17.6); 5.51 (1H, dd, J=7.1, 15.4); 5.61 (1H, m); 5.82 (1H, m); 6.45 (1H, dd, J=3.8, 9.1); 7.04 (11H, d, J=9.1); 7.95 (1H, s). $^{13}C$ NMR (100.8 MHz, $CDCl_3$): 17.48, 18.97, 24.15, 29.93, 31.93, 34.46, 37.54, 37.97, 38.84, 40.56, 43.56, 58.44, 72.18, 77.46, 84.05, 128.74, 133.18, 135.28, 141.39, 162.21, 163.65, 165.99, 168.99, 170.57, 173.72. IR (ηmax) 3336.37, 2925.71, 1736.10, 1676.07, 1620.05, 1501.02, 1244.86 cm$^{-1}$ Thiazoline-Oxazole Thiol Analog (O11)

Macrocycle (O9) (40 mg, 0.055 mmol) was dissolve in degassed DCM (7 mL) and $Et_3SiH$ (20 μl, 0.111 mmol) was added, followed by TFA (275 μl). The reaction as stirred at room temperature for 1 hour and then pulled down and immediately purified via column chromatography, hexanes: EtOAc, 20:80 to 0:100, provided the desired thiol (O11) in 83% yield.

HRMS (ESI): m/z calcd for $C_{21}H_{29}N_4O_5S_2$ (M+H)+: 481.1579, found 481.1574. HRMS calcd for $C_{21}H_{28}N_4NaO_5S_2$ (M+Na)+: 503.1399, found 503.1389. [α]D=+24, c=0.8 in $CH_2Cl_2$ 1H NMR (400 MHz, $CDCl_3$): 0.65 (d, 3H, J=6.9), 0.69 (d, 3H, J=6.9), 1.84 (s, 3H), 2.08 (m, 1H), 2.34 (m, 2H), 2.56 (q, 2H, J=7.3), 2.69 (dd, 1H, J=3.1, 16.4), 2.87 (dd, 1H, J=11.4), 3.24 (d, 1H, J=11.6), 4.01 (d, 1H, J=11.2), 4.02 (dd, 1H, J=3.6, 17.6), 4.53 (dd, 1H, J=3.7, 8.9), 4.94 (dd, 1H, J=9.6, 17.6), 5.55 (ddt, 1H, J=1.3, 6.8, 15.4), 5.66 (ddd, 1H, J=2.8, 6.7, 9.4), 5.81 (dt, 1H, J=7.3, 14.9), 6.21 (dd, 1H, J=3.5, 9.4), 7.11 (d, 1H, J=8.8), 7.99 (s, 1H), $^{13}C$ NMR (100.8 MHz, $CDCl_3$): 17.71, 19.18, 24.36, 30.17, 34.66, 36.75, 37.78, 40.99, 43.80, 58.68, 72.34, 77.63, 84.28, 99.17, 129.41, 132.99, 135.52, 141.62, 162.38, 163.68, 169.18, 170.86, 173.92. IR (ηmax) 3374.08, 2960.18, 2530.09, 1734.46, 1671.79, 1505.02, 1247.74, 1038.66, 753.00 cm$^{-1}$ Thiazoline-Oxazole Thioester Analog (O12)

Macrocycle O11 (40 mg, 0.055 mmol) was dissolved in degassed DCM (7 mL) and $Et_3SiH$ (20 μl, 0.111 mmol) was added, followed by TFA (275 μl). The reaction as stirred at room temperature for 1 hour and then pulled down and immediately dissolved in 7 mL of degassed DCM. Octanoyl chloride (600 μl, 3.300 mmol) was added, followed by $Et_3N$ (900 μl, 4.950 mmol). The reaction was stirred at room temperature overnight and then filtered over Celite and concentrated down and put onto a column and purified with 75% EtOAc to 100%. Then p-TLC was performed with 100% EtOAc, giving 9 mg of product (O12, 36%).

HRMS (ESI): m/z calcd for $C_{29}H_{43}N_4O_6S_2$ (M+H)+: 607.2624, found: 607.2628. HRMS calcd for $C_{29}H_{42}N_4NaO_6S_2$ 629.2443, found: 629.2444. [α]D=+18, c=0.7 in $CH_2Cl_2$ 1H NMR (400 MHz; $CDCl_3$): 0.65 (d, 3H, J=6.9), 0.69 (d, 3H, J=6.9), 0.88 (m, 3H), 1.28 (m, 9H), 1.65 (m, 2H), 1.85 (s, 3H), 2.1 (td, 1H, J=3.5, 6.9), 2.33 (dt, 2H, J=7.6, 15.4), 2.54 (t, 2H, J=7.6), 2.69 (dd, 1H, J=2.9, 16.51), 2.91 (t, 2H, J=7.4), 3.25 (d, 1H, J=11.4), 4.05 (m, 2H), 4.12 (q, 1H, J=7.1), 4.55 (dd, 1H, J=3.6, 8.9), 4.99 (dd, 1H, J=9.7, 17.7), 5.55 (ddt, 1H, J=1.3, 6.9, 15.5), 5.65 (m, 1H), 5.84 (m, 1H), 6.14 (dd, 1H, J=4.3, 8.6), 7.09 (d, 1H, J=9.1), 7.99 (s, 1H). $^{13}C$ NMR (100.8 MHz, $CDCl_3$): 14.02, 17.16, 18.66, 22.55, 24.70, 27.91, 28.88, 29.93, 34.02, 37.28, 40.31, 43.31, 44.13, 58.10, 71.91, 77.17, 128.42, 132.72, 141.18, 163.22, 168.64, 170.50, 173.39, 199.35. IR (ηmax) 3302.06, 2918.74, 1735.94, 1677.30, 1541.73, 1242.57 cm$^{-1}$ Example 16. HDAC Biochemical Assay The inhibitory effect of compounds on deacetylase isoenzyme function was determined in vitro using an optimized homogenous assay performed in 384-well plate format. In this assay, recombinant, full-length HDAC protein (HDAC1 3.33 ng/μL, HDAC2 1 ng/μL, HDAC3/NCor2 0.17 ng/μL, HDAC6 1.3 ng/μL; BPS Biosciences) is incubated with a commercially-available fluorophore conjugated substrate at a concentration equivalent to the substrate $K_m$ (Upstate 17-372; 6 μM for HDAC1, 3 μM for HDAC2, 6 μM for HDAC3 and 16 μM for HDAC6). Reactions are performed in assay buffer (50 mM HEPES. 100 mM KCl, 0.001% Tween-20, 0.05% BSA, 200 μM TCEP, pH 7.4) and followed for fluorogenic release of 7-amino-4-methylcoumarin from substrate upon deacetylase and trypsin enzymatic activity. Fluorescence measurements are obtained approximately every five minutes using a multilabel plate reader and plate-stacker (Envision; Perkin-Elmer). Data are analyzed on a plate-by-plate basis for the linear range of fluorescence over time. Data from the plate capture corresponding to the mid-linear range is imported into analytical software and annotated with well identity and compound concentration (Spotfire DecisionSite). Replicate experimental data from incubations with inhibitor are normalized to control, solvent-only wells and IC-50 is determined by logistic regression.

Thus, small-molecule inhibitors were arrayed at twelve-point dose-response (3-fold increments) in 384-well library plates and transferred by robotic pin device to replicate assay plates containing assay buffer under reducing conditions (TCEP 200 μM). A liquid handling device then transferred a tripeptide substrate terminating in acetyl-lysine and amide conjugated to 4-methyl-7-aminocoumarin (AMC), recombinant human histone deacetylase (BPS Bioscience, San Diego, Calif.), and recombinant human trypsin (Sigma-Aldrich, St. Louis, Mo.). Following deacetylase hydrolysis of acetyl-lysine, trypsin cleavage liberated the AMC fluorophore. Kinetic (fluorescence per unit time) and end-point (total fluorescence) data were captured by a multilabel plate reader. Replicate data were analyzed by curve-fit using logistic regression (Spotfire Decision-Site). A summary of assay data are in Table 4, below.

TABLE 4

| Biochemical inhibition of human HDACs (IC$_{50}$, μM). | | | | |
|---|---|---|---|---|
| Compound | HDAC1 | HDAC2 | HDAC3 | HDAC6 |
| Largazole thiol (1b) | 0.0012 | 0.0035 | 0.0034 | 0.049 |
| Enantiomer (2) | 1.2 | 3.1 | 1.9 | 2.2 |
| C-2 epimer (3) | 0.030 | 0.082 | 0.084 | 0.68 |
| Proline substitution (4) | 0.11 | 0.80 | 0.58 | 13 |
| Largazole-Azumamide hybrid (9b) | >30 | >30 | >30 | >30 |
| Benzamide (11b) | 0.27 | 4.1 | 4.1 | >30 |
| Benzamide (12b) | 23 | 29 | 14 | >30 |
| Thioamide (13b) | 0.67 | 1.6 | 0.96 | 0.7 |
| Thioamide (14b) | 1 | 1.9 | 1.5 | 0.24 |

TABLE 4-continued

Biochemical inhibition of human HDACs (IC$_{50}$, μM).

| Compound | HDAC1 | HDAC2 | HDAC3 | HDAC6 |
|---|---|---|---|---|
| Cysteine substitution 22b | 0.0019 | 0.0048 | 0.0038 | 0.13 |
| Thiazole-thiazole (23b) | 0.077 | 0.12 | 0.085 | >30 |
| Thiazole-pyridine substitution (29b) | 0.00032 | 0.00086 | 0.0011 | 0.029 |
| Oxazoline-oxazole (39b) | 0.00069 | 0.0017 | 0.0015 | 0.045 |
| MS-275 | 0.045 | 0.13 | 0.17 | >30 |

Several striking observations emerge from this dataset. The Largazole enantiomer (2) exhibits a decrease in potency by almost exactly three orders of magnitude for all isoforms tested, underscoring the obligate, stereochemical and conformation-activity relationship between the natural product and its protein targets. This is further substantiated by the intermediate potency of the C-2 epimer (3), the valine-to-proline substitution (4) and the oxidized and strained thiazole-thiazole derivative (23b). Of note, the single-atom substitutions of the sulfur atoms for oxygen atoms in the oxazoline-oxazole derivative (29b) provided a compound equipotent to Largazole itself.

The synthetic approach described herein allowed rapid diversification of the zinc-binding arm, modulating both potency and specificity (as for 11b, 12b, 13b and 14b). A significant increase in potency was observed with pyridine substitution of the thiazole; this compound (29b) possesses sub-nanomolar activity against Class I HDACs. Compound 29b constitutes a highly biochemically potent Class I HDAC inhibitor—between three and four times more potent than Largazole itself against HDACs 1, 2 and 3. Notably, the methyl substituent of the thiazoline ring has been demonstrated to be non-essential for the dramatic potency of the natural product (cf. 22b).

The commercial availability of relatively inexpensive cysteine, compared with that of the α-methylcysteine residue of natural Largazole, permitted for a reduction in the overall synthetic approach to 22b by four steps, establishing a high-yielding, scalable, five-step synthesis of this agent. This highly efficient synthesis is compatible with further derivitization and potential for practical scale-up endeavors. Additionally provided herein is additional insight into the structural, functional, stereochemical, and conformational aspects of the Largazole molecular scaffold that constitutes the basis for the further design and synthesis of extraordinarily potent HDAC inhibitors with potential therapeutic significance.

Example 17. Preparation of Pyridyl Analog Series

The synthesis of fragment P23 for the depsipeptide version of the macrocycle is displayed in Scheme P1. The formation of aldehyde P21 was achieved through a hetero-Michael addition of trityl mercaptan into acrolein followed by a Wittig olefination. The stereocenter present in alcohol P22 was set using a Crimmins's type chiral auxiliary, (Crimmins, et al. (2000) Org. Lett. 2:775-777. "Titanium Enolates of Thiazolidinethione Chiral Auxiliaries: Versatile Tools for Asymmetric Aldol Additions.") This asymmetric aldol transformation occurred to produce alcohol P22 in very high diastereomeric purity. This material was submitted to cleavage of the chiral auxiliary using 2-(trimethylsilyl) ethanol. Installation of the $_L$-valine derived amino acid was mediated by EDCI to access depsipeptide bottom fragment P23.

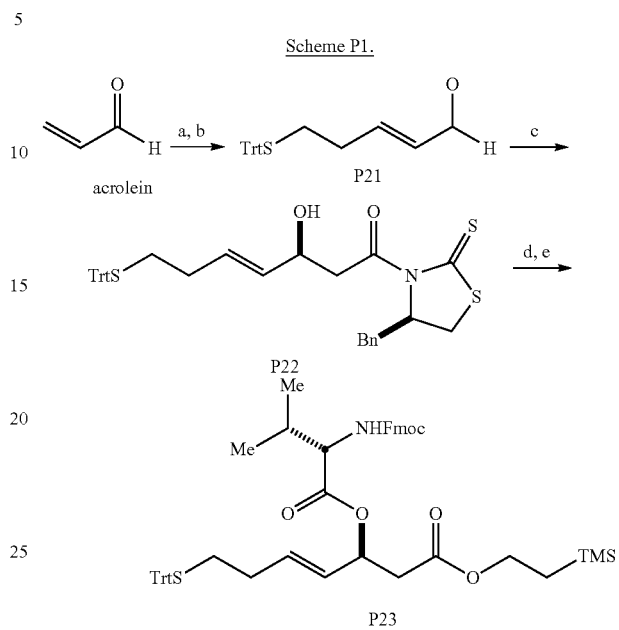

Synthesis of fragment P23 for depsipeptide macrocycle. Reagents and conditions: (a) TrtSH, Et$_3$N, CH$_2$Cl$_2$; (b)

Reagents and conditions: (a) TrtSH, Et$_3$N, CH$_2$Cl$_2$; (b) (formylmethylene)triphenylphosphorane. PhH. 80° C. 77% over 2 steps: (c) (R)-1-(4-benzyl-2-thioxothiazolidin-3-yl) ethanone, TiCl$_4$, DIPEA, CH$_2$Cl$_2$, −78° C. 76%: (d) 2-(trimethylsilyl)ethanol, imidazole, CH$_2$Cl$_2$, 83%: N-Fmoc-Val-OH, EDCI, DIPEA, DMAP, CH$_2$Cl$_2$. 77%.

Peptide precursor P28 was furnished using the previously established protocol (Scheme P2). (Bowers, et al. (2009) J. Am. Chem. Soc. 131:2900-2905, "Synthesis and Conformation-Activity Relationships of the Peptide Isosteres of FK228 and Largazole.") Commercially available amino acid derivative P24 was converted to the primary alcohol through reduction of a mixed anhydride. Swern oxidation followed by Wittig olefination achieved formation of terminal alkene P25. Scrambling of the stereogenic center was not apparent through an aqueous KHSO$_4$ workup of the oxidation step and submission of the aldehyde directly to the olefination reaction. The cross metathesis to construct alkene P26 proved to be troublesome in producing high yielding and reproducible results. (Fürstner, et al. (2000) Angew. Chem. Int. Ed. 39:3012-3043.) The primary alcohol was converted to the protected thiol through activation with TsCl and displacement with trityl thiol anion. After methyl ester formation, the amine present on substrate P27 was unmasked using TFA and coupled with an $_L$-valine derived amino acid to yield peptide precursor P28.

-continued

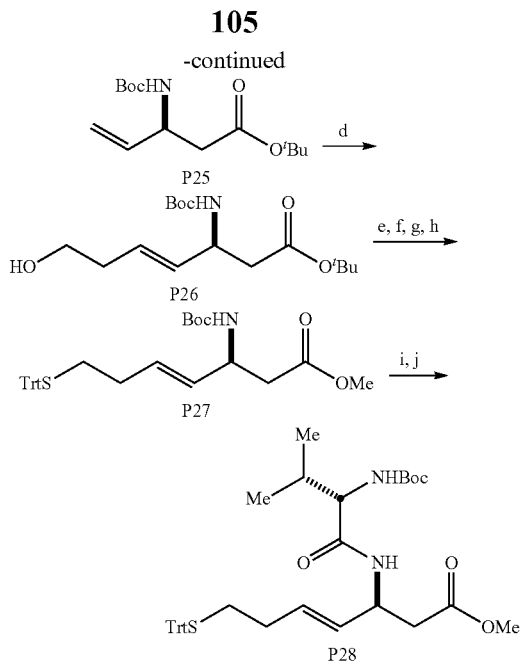

Reagents and conditions: (a) 4-methylmorpholine, isobutyl chloroformate, THF, -40° C.; NaBH₄, MeOH, -20° C., 66%; (b) oxalyl chloride, DMSO, DIPEA, CH₂Cl₂, -65° C.; (c) methyltriphenylphosphonium bromide, KHMDS, THF, -78° C., 80% over 2 steps; (d) 3-buten-1-ol, Grubbs catalyst, 2ⁿᵈ generation, CH₂Cl₂, 50° C., 25%; (e) TsCl, Et₃N, DMAP, CH₂Cl₂, 82%; (f) TrtSH, KOᵗBu, THF, 87%; (g) LiOH, THF, MeOH, 50° C., 96%; (h) MeOH, EDCl, DIPEA, DMAP, CH₂Cl₂, 77%; (i) TFA, CH₂Cl₂; (j) N-Boc-Val-OH, PyBOP, DIPEA, CH₂Cl₂, 88% over 2 steps.

Aryl fragment P32 was constructed starting with dicarboxylic acid P29 (Scheme P3). Fischer esterification and reduction of one of the ethyl esters provided the requisite primary alcohol functionality. After using NH₄OH to generate an amide from the corresponding carboxylic acid. POCl₃ successfully dehydrated the amide to generate the requisite nitrile and chloride present in compound P30. Gabriel's protocol was utilized to convert the chloride into an amine, which was readily protected to provide cyclization partner P31. Cyclocondensation with α-methyl-ₗ-cysteine (Mulqueen, et al. (1993) Tetrahedron 49:5359-5364. "Synthesis of the Thiazoline-Based Siderophore (S)-Desferrithiocin") proceeded in high yields to generate the pyridyl fragment P32.

Scheme P3.

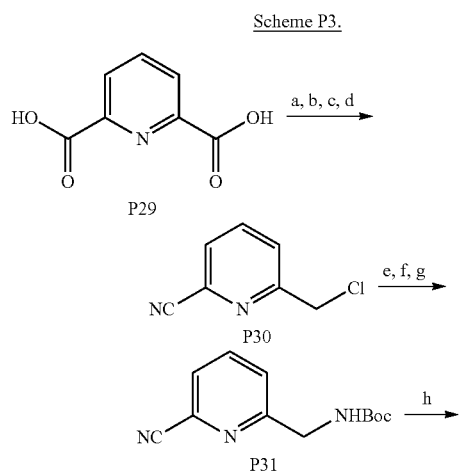

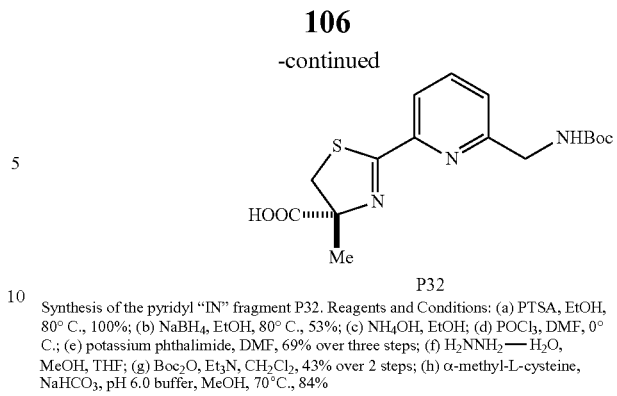

P32

Synthesis of the pyridyl "IN" fragment P32. Reagents and Conditions: (a) PTSA, EtOH, 80° C., 100%; (b) NaBH₄, EtOH, 80° C., 53%; (c) NH₄OH, EtOH; (d) POCl₃, DMF, 0° C.; (e) potassium phthalimide, DMF, 69% over three steps; (f) H₂NNH₂→H₂O, MeOH, THF; (g) Boc₂O, Et₃N, CH₂Cl₂, 43% over 2 steps; (h) α-methyl-L-cysteine, NaHCO₃, pH 6.0 buffer, MeOH, 70°C., 84%

The route for the pyridyl "OUT" aryl fragment P36 is displayed in Scheme P4. The synthetic strategy follows the same method mentioned previously for the pyridine "IN" variant except dicarboxylic acid P33 was used instead.

Scheme P4. Synthesis of pyridine "OUT" fragment.

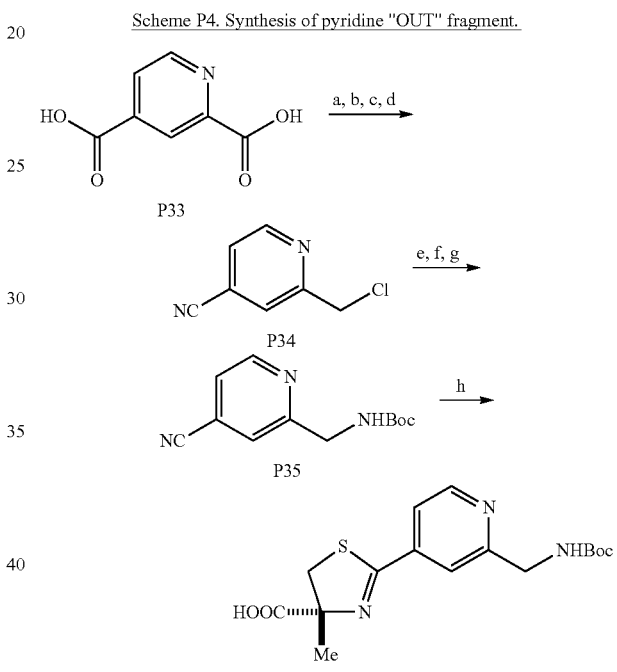

Reagents and conditions: (a) PTSA, EtOH, 90°C., 100%; (b) NaBH₄, CsCl₂, EtOH, 80° C., 61%; (c) NH₄OH, EtOH; (d) POCl₃, DMF, 0° C.; (e) potassium phthalimide, DMF, 50% over three steps; (f) H₂NNH₂→H₂O, MeOH, THF; (g) Boc₂O, Et₃N, CH₂Cl₂, 84% over 2 steps; (h) α-metyl-L-cysteine, NaHCO, pH 6.0 buffer, MeOH, 70° C., 85%.

The final steps to access the desired inhibitors were performed upon the successful assembly of the four key fragments. The depsipeptide class construction is shown in Scheme P5. The protected amine present in substrate P23 was unmasked using diethylamine. The successful union between the nascent amine and acid P32 or P36 was accomplished cleanly using PyBOP. The macrolactamization was performed using HATU and HOBt after exposing the requisite functionality through acid-mediated deprotection. Accessing pure material from the ring closure transformation required rigorous column chromatography. Trityl cleavage granted the formation of inhibitors P6 and P8. Unfortunately, adding the octanoyl residue was only viable using standard acid chloride procedure on pyridine "OUT" depsipeptide thiol P8. Pyridine "IN" thiol P6 gave rise to dioctanoylation when exposed to the same conditions. The N-octanoyl-imidazole reagent was prepared and then was exposed to thiol P6. The change in the reactivity of the carbonyl gave rise to only the thioester being formed.

Scheme P5.

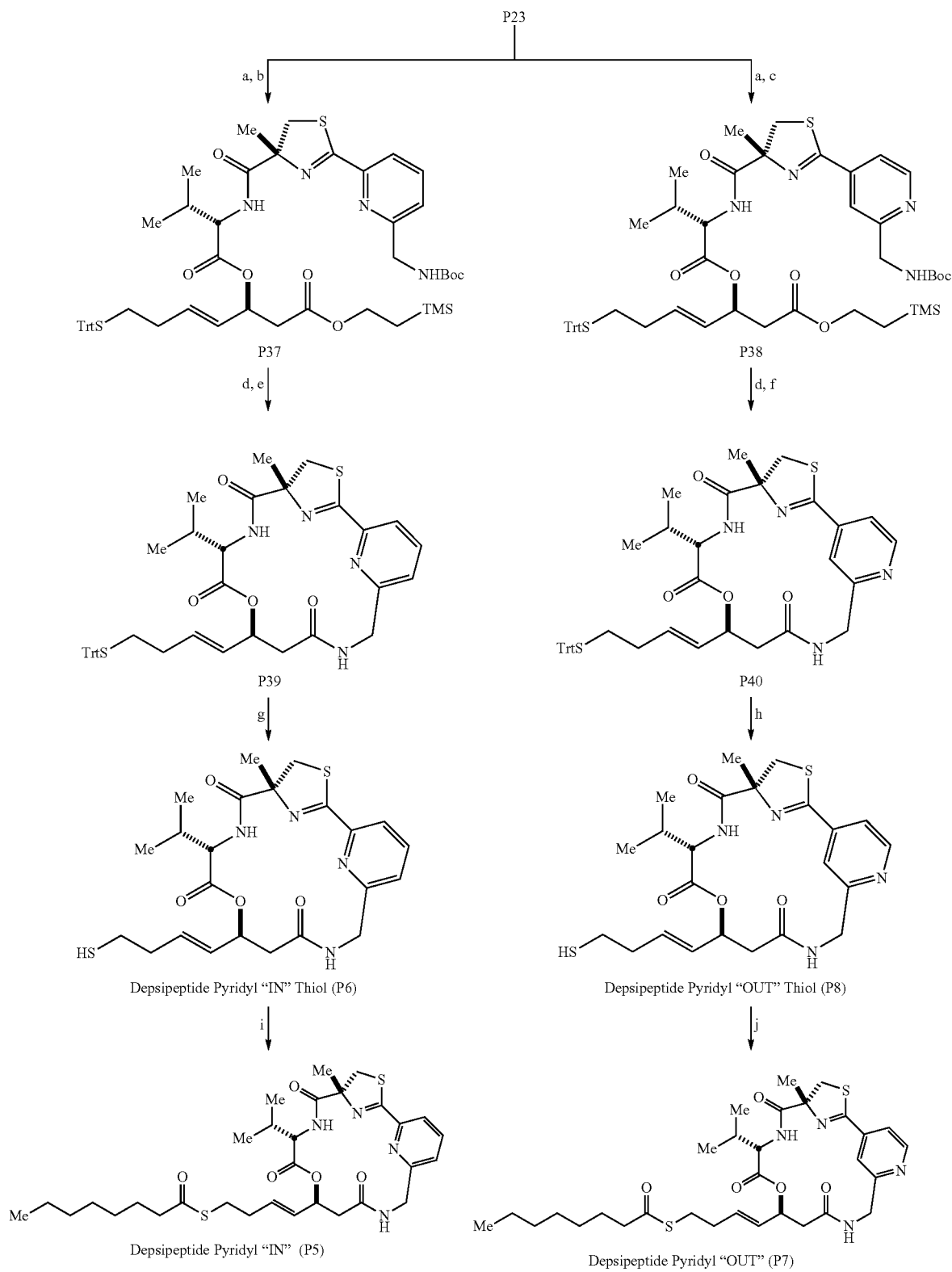

Synthesis of depsipeptide containing analogs. Reagents and conditions: (a) Et$_2$NH, CH$_3$CN; (b) P32, PyBOP, DIPEA, 79% over 2 steps; (c) P36, PyBOP, DIPEA, 81% over 2 steps; (d) TFA, CH$_2$Cl$_2$; (e) HATU, HOBt, DIPEA, CH$_3$CN, 20% over 2 steps; (f) HATU, HOBt, DIPEA, CH$_3$CN, 23% over 2 steps; (g) TFA, $^i$Pr$_3$SiH, CH$_2$Cl$_2$, 82%; (h) TFA, $^i$Pr$_3$SiH, CH$_2$Cl$_2$ 89%; (i) N-octanoyl-imidazole, imidazole, DMAP, THF, 50° C., 69%; (j) octanoyl chloride, Et$_3$N, 49%.

The creation of the peptide class of pyridine-thiazoline inhibitors P10 and P12 followed the same method discussed for their depsipeptide counterparts. The only difference in their route arose during the deprotection steps. The same strategy was employed as previously discussed to add the octanoyl fragment to arrive at inhibitors P9 and P11.

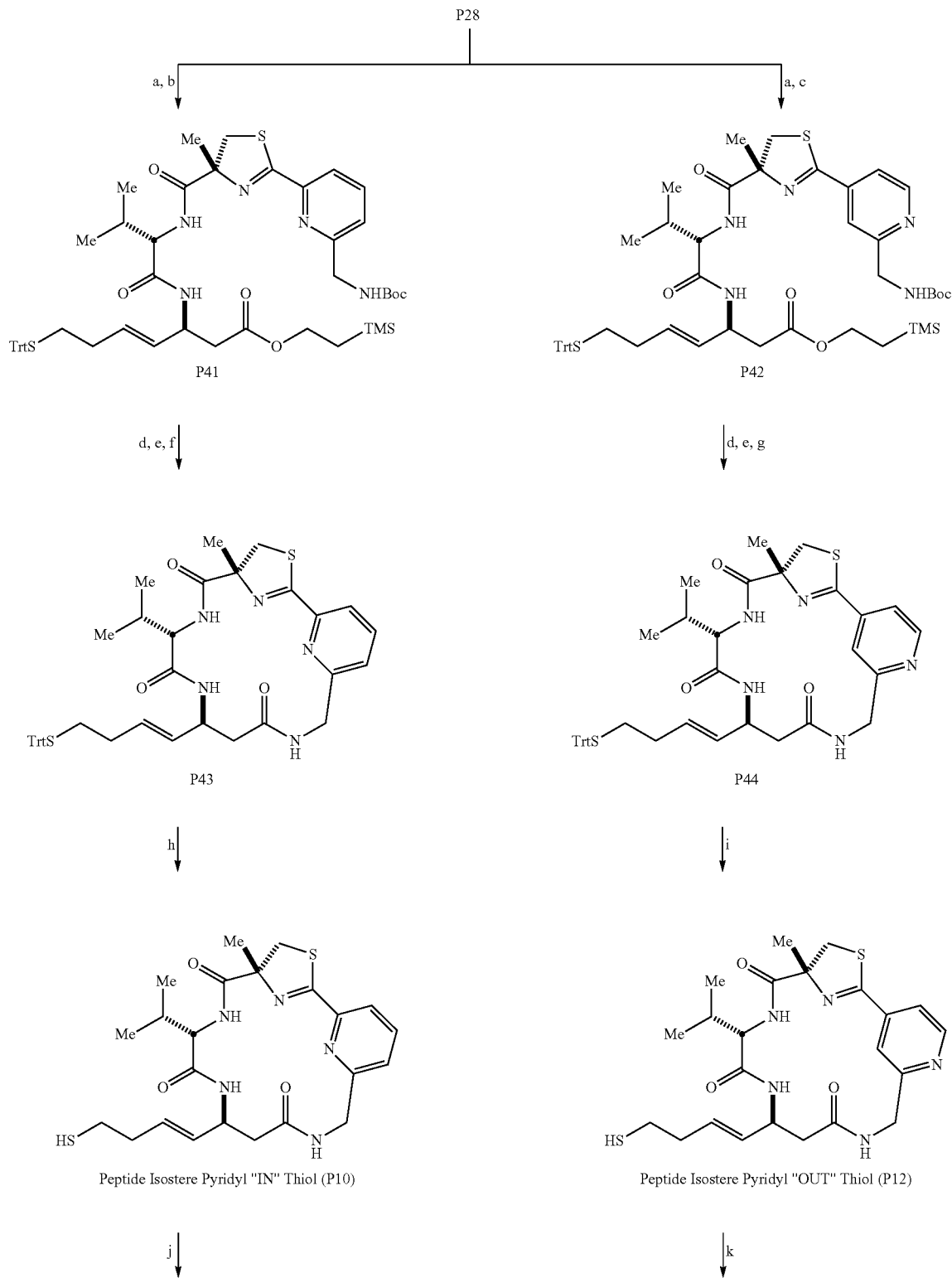

Scheme P6. Synthesis of peptide containing inhibitors.

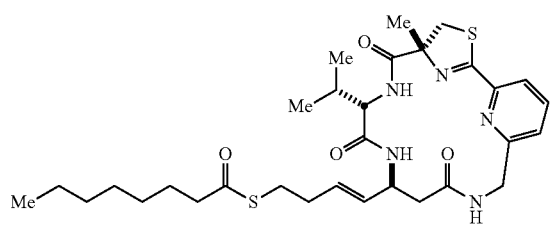

Peptide Isostere Pyridyl "IN" (P9)

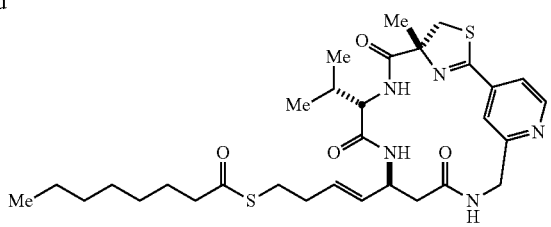

Peptide Isostere Pyridyl "OUT" (P11)

Reagents and conditions: (a) TFA, CH$_2$Cl$_2$; (b) P32, PyBOP, DIPEA, 84% over 2 steps; (c) P36, PyBOP, DIPEA, 92% over 2 steps; (d) LiOH, THF, H$_2$O; (e) TFA, CH$_2$Cl$_2$; (f) HATU, HOBt, DIPEA, CH$_3$CN, 33% over 3 steps; (g) HATU, HOBt, DIPEA, CH$_3$CN, 32% over 3 steps; (h) TFA, iPr$_3$SiH, CH$_2$Cl$_2$, 94%, (i) TFA, iPr$_3$SiH, CH$_2$Cl$_2$, 89%; (j) N-octanoyl-imidazole, imadazole, DMAP, THF, 50° C., 66%, (k) octanoyl choloride, Et$_3$N, 55%.

Biochemical & Biological Evaluation.

Compounds P5-P12 were tested for inhibitory activity against HDACs 1-9, using an optimized homogenous assay performed in a 384-well plate, as described previously. (Bowers, et al. (2008) J. Am. Chem. Soc. 130:11219-11222, "Total Synthesis and Biological Mode of Action of Largazole: A Potent Class I Histone Deacetylase Inhibitor.") The results of these studies, summarized in Table P1 and Figure PS1, identify that the thiol derivatives of Largazole including compounds 2, 4, 6, 8, 10, and 12, are among the most potent with IC$_{50}$ values below 25 nM for HDACs 1-3. Of these thiols, the depsipeptide pyridine thiols 6, 8 show similar potency to Largazole thiol (2) and Largazole peptide isostere thiol (4) with IC$_{50}$ values in the single digit nM range for HDACs 1-3. Conversely, the peptide pyridine thiols 10, 12 show a decrease in potency with IC$_{50S}$ in the double-digit nM range for HDACS 1-3. Largazole (1) and derivatives 3, 5, 7, 9, 11 display IC$_{50}$ values in the 200 nM-1 μM range. Of these compounds, Largazole (1) and peptide pyridine "OUT" derivative 11 were similar in potency for HDACs 1-3 with IC$_{50S}$ in the high nM-μM range while the depsipeptide pyridines and peptide pyridine "IN" derivative 5, 7, 11 exhibited an increased potency with IC$_{50S}$ in the 200 nM-350 nM range for HDAC 1. These studies demonstrate that the free thiol is important for increased inhibition, as previously reported, with the depsipeptide pyridine derivatives displaying increased inhibition over the peptide isostere derivatives.

TABLE P1

HDAC inhibitory activity of Largazole analogs (IC$_{50}$ nM).

| Compound | HDAC1 | HDAC2 | HDAC3 | HDAC6 | HDAC8 |
|---|---|---|---|---|---|
| Largazole | 10.09 | 18.65 | 9.09 | 165.6 | 1068 |
| Largazole thiol | 2.51 | 4.19 | 2.78 | 28.11 | 228.4 |
| Largazole peptide isostere | 544.1 | 825.2 | 1151 | — | — |
| Largazole peptide isostere thiol | 1.95 | 3.38 | 2.59 | 102 | 255.3 |
| P5 | 203.6 | 349.5 | 332.1 | — | — |
| P6 | 2.68 | 4.39 | 3.07 | 48.55 | 341.3 |
| P7 | 340 | 655.4 | 319.5 | — | — |
| P8 | 2.20 | 4.42 | 2.31 | 35.16 | 101.8 |
| P9 | 340.3 | 471.8 | 332.4 | — | — |
| P10 | 42 | 69.8 | 42.5 | — | — |
| P11 | 816.9 | 1240 | 846.5 | — | — |
| P12 | 13.2 | 20.77 | 14.59 | 2849 | 1491 |

Next, we tested the activity of the novel analogs in the 797 and 10326 NUT midline carcinoma cell line. As can be seen in Table P2 and Figure PS2, depsipeptide pyridine "OUT" P7 showed the greatest potency against both cell lines with an IC$_{50}$ of 10 nM. This was comparable to both Largazole and depsipeptide pyridine "IN" 1, 5 with IC$_{50S}$ of 20 nM against both 797 and 30 nM and 40 nM against 10326 respectively.

TABLE P2

Activity of Largazole analogs in 797 and 10326 cell lines (IC$_{50}$s μM)

| Compound | 797 | 10326 |
|---|---|---|
| Largazole | 0.024 | 0.025 |
| Largazole thiol | 0.1 | 0.08 |
| Largazole peptide isostere | 0.11 | 0.17 |
| Largazole peptide isostere thiol | 1.74 | 11.94 |
| P5 | 0.03 | 0.038 |
| P6 | 0.22 | 0.29 |
| P7 | 0.01 | 0.01 |
| P8 | 0.09 | 0.12 |
| P9 | 0.31 | 0.55 |
| P10 | — | — |
| P11 | 0.07 | 0.13 |
| P12 | 4.25 | 8.64 |

Conversely, the peptide isosteres P9, P11 exhibited ~10-fold decreased inhibition in comparison to the depsipeptide pyridine derivatives, demonstrating that the depsipeptide mimetic may be important for increased inhibition.

(S,E)-2-(Trimethylsilyl)ethyl 3-(((S)-2-((((9H-fluoren-9-yl)methoxy)carbonyl)amino)-3-methylbutanoyl)oxy)-7-(tritylthio)hept-4-enoate (P23): To a solution of 2-(trimethylsilyl)ethyl (S,E)-3-hydroxy-7-(tritylthio)hept-4-enoate[6] (300 mg, 0.578 mmol) in CH$_2$Cl$_2$ (15.0 mL) at ambient temperature was added N-Fmoc-L-valine (981 mg, 2.89 mmol), EDCI HCl (665 mg, 3.47 mmol), DMAP (7.1 mg, 0.058 mmol), and DIPEA (0.60 mL, 3.47 mmol). After stirring for 18 h, the reaction mixture was concentrated. The crude residue was purified using flash chromatography (1% to 20% ethyl acetate in hexanes) to provide ester (375 mg, 77%): $^1$H-NMR (CDCl$_3$, 400 MHz) δ 7.71-7.75 (m, 2H), 7.56-7.58 (m, 2H), 7.18-7.38 (m, 19H), 5.58-5.69 (m, 2H), 5.34 (dd, J=15.6, 7.6 Hz, 1H), 5.25 (d, J=9.2 Hz, 1H), 4.30-4.40 (m, 2H), 4.25 (dd, J=8.8, 4.4 Hz, 1H), 4.20 (t, J=6.8 Hz, 1H), 4.12 (t, J=8.8 Hz, 2H), 2.65 (dd, J=16.0, 8.0 Hz, 1H), 2.52 (dd, J=15.6, 5.2 Hz. 1H), 2.10-2.17 (m, 3H), 2.02 (q, J=6.8 Hz, 2H), 0.91-0.99 (m, 2H), 0.89 (d, J=6.8 Hz, 3H), 0.77 (d, J=6.8 Hz, 3H), −0.01 (s, 9H); $^{13}$C-NMR (CDCl$_3$, 100 MHz) δ 170.9, 169.6, 156.1, 144.8, 143.9, 143.8, 141.3, 134.0, 129.6, 127.9, 127.7, 127.0, 126.6, 125.1, 120.0, 71.8, 67.0, 66.6, 63.1, 58.7, 47.2, 39.7, 31.4, 31.3, 31.1, 19.0, 17.3, −1.5; IR (neat) 3059, 2979, 1731, 1509, 1447, 1249, 1182, 1033, 858, 741; HRMS (ESI) m/z calcd for C$_{51}$H$_{57}$NNaO$_6$SSi [M+Na]$^+$ 862.3574, found 862.3583: [α]$_D$=−15.0 (c 1.18, CHCl$_3$).

(S,E)-Methyl 3-((S)-2-((tert-butoxycarbonyl)amino)-3-methylbutanamido)-7-(tritylthio)hept-4-enoate (P28)

To a solution of Boc protected amine P27[10] (0.650 g, 1.22 mmol) in $CH_2Cl_2$ (37 mL) at 0° C. was treated with TFA (0.37 mL). After 2 h, the reaction mixture was concentrated under vacuum, taken back up in toluene (15 mL), and concentrated again. In another flask. Boc-L-valine (0.531 g, 2.44 mmol), PyBOP (1.27 g, 2.44 mmol), and DIPEA (0.65 mL, 3.66 mmol) were combined in $CH_2Cl_2$ (60 mL). The freshly deprotected amine was added via $CH_2Cl_2$ (10 mL) to the flask containing the activated acid at ambient temperature. After 3 h, the resulting mixture was concentrated under reduced pressure. The crude residue was purified using flash chromatography (5% to 50% ethyl acetate in hexanes) to obtain the desired amide (0.680 g, 88%): $^1$H-NMR ($CDCl_3$, 400 MHz) δ 7.15-7.37 (m, 15H), 6.49 (d, J=8.0 Hz, 1H), 5.45 (dtd, J=15.2, 6.4, 0.8 Hz, 1H), 5.34 (dd, J=15.6, 6.0 Hz, 1H), 4.97-5.02 (m, 1H), 4.67-4.74 (m, 1H), 3.82-3.86 (m, 1H), 3.59 (s, 3H), 2.53 (d, J=5.2 Hz, 2H), 2.05-2.16 (m, 3H), 2.01 (q, J=6.8 Hz, 2H), 1.40 (s, 9H), 0.89 (d, J=6.8 Hz, 3H), 0.83 (d, J=6.8 Hz, 3H); $^{13}$C-NMR ($CDCl_3$, 100 MHz) δ 171.6, 170.5, 155.8, 144.8, 130.5, 129.5, 127.8, 126.5, 79.7, 66.5, 59.9, 51.7, 47.2, 38.7, 31.3, 31.0, 28.3, 19.3, 17.6; IR (neat) 3304, 2965, 1738, 1685, 1650, 1522, 1492, 1365, 1172, 751; HRMS (ESI) m/z calcd for $C_{37}H_{46}N_2NaO_5S$ $[M+Na]^+$ 653.3025, found 653.3032; $[α]_D$=−14.0 (c 1.21, $CHCl_3$).

6-((((tert-Butoxy)carbonyl)amino)methyl)picolinonitrile (P31)

To a solution of commercially available chloride P30 (9.66 g. 63.3 mmol) in DMF (400 mL) at ambient temperature was treated with potassium phthalimide (11.7 g. 63.3 mmol). After stirring for 5 h, the mixture was concentrated under vacuum. The remaining mixture was taken up in $H_2O$ (200 mL) and was filtered to collect the solid. The solid was washed with $H_2O$ (100 mL) and THF (100 mL) to obtain the desired phthalimide derivative (11.5 g. 69%) and was moved forward without further purification. To a solution of the crude phthalimide derivative (5.84 g, 22.2 mmol) in THF/MeOH (200 mL, 1:1, v/v) at ambient temperature was treated with hydrazine monohydrate (1.18 mL, 24.4 mmol). After 2 h, 1.0 M HCl (24.5 mL) was added to the mixture and was stirred for another 3 h before concentrating the reaction mixture under vacuum. The remaining residue was taken up in $H_2O$ (200 mL) and the unwanted solid was removed through filtration. The filtrate was concentrated and placed under vacuum to remove the remaining $H_2O$. The crude solid was taken up in $CH_2Cl_2$ (175 mL) and triethylamine (9.28 mL. 66.6 mmol) and $Boc_2O$ (4.86 g, 24.4 mmol) was added. After stirring for 12 h at room temperature, the reaction was quenched with a saturated solution of $NaHCO_3$ (200 mL), extracted with $CH_2Cl_2$ (3×150 mL), dried over $MgSO_4$, and concentrated under reduced pressure. The residue was purified using flash chromatography (10% to 45% ethyl acetate in hexanes) to provide the aryl pyridine "IN" fragment (2.24 g. 43%): $^1$H-NMR ($CDCl_3$, 400 MHz) δ 7.78 (t, J=7.6 Hz, 1H), 7.56 (d, J=7.6 Hz, 1H), 7.49 (d, J=8.0 Hz, 1H), 5.51 (s, 1H), 4.44 (d, J=5.6 Hz, 2H), 1.43 (s, 9H); $^{13}$C-NMR ($CDCl_3$, 100 MHz) 160.1, 155.9, 137.6, 133.0, 127.0, 125.1, 117.1, 79.9, 45.5, 28.3; IR (neat) 3347, 2979, 2934, 2239, 1699, 1518, 1453, 1250, 1170, 862; HRMS (ESI) m/z calcd for $C_{12}H_{15}N_3NaO_3$ $[M+Na]^+$ 256.1062, found 256.1062.

(R)-2-(6-(((tert-Butoxycarbonyl)amino)methyl)pyridin-2-yl)-4-methyl-4,5-dihydrothiazole-4-carboxylic Acid (P32)

To a solution of nitrile 31 (1.50 g, 6.43 mmol) in MeOH/pH 6.0 butter (105 mL. 3:2, v/v) was added α-methyl-L-cysteine (1.32 g, 7.72 mmol) and $NaHCO_3$ (1.08 g. 12.9 mmol). The reaction mixture was heated to 70° C. for 48 h. The mixture was cooled to ambient temperature and the MeOH was removed under reduced pressure. The aqueous layer was extracted with diethyl ether (3×30 mL) before being acidified to a pH of ~2 using 1.0 M HCl. The aqueous layer was then extracted with ethyl acetate (3×30 mL) and the ethyl acetate layer was dried over $MgSO_4$. The solution was concentrated to give the desired acid (1.89 g. 84%): $^1$H-NMR ($CDCl_3$, 400 MHz) δ 7.97 (d, J=7.6 Hz, 1H), 7.74 (t, J=8.0 Hz, 1H), 7.37 (d, J=7.6 Hz, 1H), 5.45 (bs, 1H), 4.46 (d, J=5.2 Hz, 2H), 3.77 (d, J=11.6 Hz, 1H), 3.29 (d, J=11.6 Hz, 1H), 1.65 (s, 3H), 1.45 (s, 9H); $^{13}$C-NMR ($CDCl_3$, 100 MHz) δ 176.3, 171.5, 157.5, 156.1, 149.6, 137.3, 123.9, 120.5, 84.9, 79.7, 45.3, 40.3, 28.4, 24.1; IR (neat) 3415, 2977, 1688, 1515, 1455, 1366, 1278, 1160, 754; HRMS (ESI) m/z calcd for $C_{16}H_{22}N_3O_4S$ $[M+H]^+$ 352.1331, found 352.1329; $[α]_D$=−36.6 (c 0.98, $CHCl_3$).

2-(((((tert-Butoxy)carbonyl)amino)methyl)isonicotinonitrile (P35)

To a solution of commercially available chloride P34 (5.84 g, 38.3 mmol) in DMF (250 mL) at ambient temperature was treated with potassium phthalimide (7.09 g, 38.3 mmol). After stirring for 5 h, the mixture was concentrated under vacuum. The remaining mixture was taken up in $H_2O$ (100 mL) and was filtered to collect the solid. The solid was washed with $H_2O$ (50 mL) and THF (50 mL) to obtain the desired phthalimide derivative (5.04 g, 50%) and was moved forward without further purification. To a solution of the crude phthalimide derivative (5.04 g, 19.1 mmol) in THF/MeOH (170 mL, 1:1, v/v) at ambient temperature was treated with hydrazine monohydrate (1.02 mL, 21.1 mmol). After 2 h. 1.0 M HCl (21.4 mL) was added to the mixture and was stirred for another 3 h before concentrating the reaction mixture under vacuum. The remaining residue was taken up in $H_2O$ (200 mL) and the unwanted solid was removed through filtration. The filtrate was concentrated and placed under vacuum to remove the remaining $H_2O$. The crude solid was taken up in $CH_2Cl_2$ (150 mL) and triethylamine (8.00 mL, 57.4 mmol) and $Boc_2O$ (4.59 g, 21.1 mmol) was added. After stirring for 12 h at room temperature, the reaction was quenched with a saturated solution of $NaHCO_3$ (200 mL), extracted with $CH_2Cl_2$ (3×150 mL), dried over $MgSO_4$, and concentrated under reduced pressure. The residue was purified using flash chromatography (15% to 50% ethyl acetate in hexanes) to provide the aryl pyridine "IN" fragment (3.74 g. 84%): $^1$H-NMR ($CDCl_3$, 400 MHz) δ 8.69 (d, J=5.2 Hz, 1H), 7.51 (s, 1H), 7.39 (dd, J=5.2, 0.8 Hz, 1H), 5.45 (s, 1H), 4.47 (d, J=5.6 Hz, 2H), 1.44 (s, 9H): $^{13}$C-NMR ($CDCl_3$, 100 MHz) 159.9, 155.9, 150.0, 123.6, 123.1, 121.1, 116.4, 80.1, 45.6, 28.3; IR (neat) 3337, 2978, 2934, 2245, 1709, 1514, 1246, 1168, 949; HRMS (ESI) m/z calcd for $C_{12}H_{16}N_3O_3$ $[M+H]^+$ 234.1243, found 234.1237.

(R)-2-(2-(((tert-Butoxycarbonyl)amino)methyl)pyridin-4-yl)-4-methyl-4,5-dihydrothiazole-4-carboxylic Acid (P36)

To a solution of nitrile P35 (1.50 g. 6.43 mmol) in MeOH/pH 6.0 buffer (105 mL, 3:2, v/v) was added α-methyl-L-cysteine (1.32 g, 7.72 mmol) and NaHCO$_3$ (1.08 g, 12.9 mmol). The reaction mixture was heated to 70° C. for 48 h. The mixture was cooled to ambient temperature and the MeOH was removed under reduced pressure. The aqueous layer was extracted with diethyl ether (3×30 mL) before being acidified to a pH of ~2 using 1.0 M HCl. The aqueous layer was then extracted with ethyl acetate (3×30 mL) and the ethyl acetate layer was dried over MgSO$_4$. The solution was concentrated to give the desired acid (1.89 g, 85%): $^1$H-NMR (CDCl$_3$, 400 MHz) δ 8.61 (d, J=4.8 Hz, 1H), 7.68 (s, 1H), 7.58 (dd, J=5.2, 1.6 Hz, 1H), 5.64 (bs, 1H), 4.48 (d, J=4.8 Hz. 2H) 3.94 (d, J=11.6 Hz, 1H), 3.38 (d, J=11.6 Hz, 1H), 1.66 (s, 31H), 1.43 (s, 9H): $^{13}$C-NMR (CDCl$_3$, 100 MHz) δ 175.5, 166.5, 158.5, 156.1, 148.7, 141.4, 121.2, 120.9, 85.0, 79.8, 45.1, 41.8, 28.3, 23.8; IR (neat) 3355, 2979, 2359, 1707, 1517, 1284, 1167.754; HRMS (ESI) m/z calcd for C$_{16}$H$_{22}$N$_3$O$_4$S [M+H]$^+$ 352.1331, found 352.1334; [α]$_D$=−39.3 (c 1.08, CHCl$_3$).

(S,E)-2-(Trimethylsilyl)ethyl 3-(((S)-2-((R)-2-(6-(((tert-butoxycarbonyl)amino)methyl)pyridin-2-yl)-4-methyl-4,5-dihydrothiazole-4-carboxamido)-3-methylbutanoyl)oxy)-7-(tritylthio)hept-4-enoate (P37): To a solution of Fmoc protected amine P23 (2.39 g, 2.85 mmol) in acetonitrile (195 mL) at ambient temperature was added diethylamine (15.0 mL). After 2 h, the reaction mixture was concentrated under reduced vacuum, taken back up in ethyl acetate (50 mL), and concentrated again. In a separate flask, acid P32 (1.00 g, 2.85 mmol). PyBOP (2.97 g. 5.70 mmol), and DIPEA (1.49 mL. 8.55 mmol) was combined in CH$_2$Cl$_2$ (195 mL). The freshly deprotected amine was added via CH$_2$Cl$_2$ (10 mL) to the flask containing the activated acid at ambient temperature. After 3 h. the resulting mixture was concentrated under reduced pressure. The crude residue was purified using flash chromatography (5% to 40% ethyl acetate in hexanes) to obtain the desired amide (2.13 g, 79%): $^1$H-NMR (CDCl$_3$, 400 MHz) δ 8.04 (d, J=8.0 Hz, 1H), 7.69 (t. J=7.6 Hz, 1H), 7.15-7.38 (m, 16H), 5.67 (dt, J=15.2, 6.8 Hz, 1H), 5.59-5.65 (m, 1H), 5.45-5.47 (m, 1H), 5.36 (dd, J=15.6, 7.6 Hz, 1H), 4.45-4.48 (m, 3H), 4.14 (dd, J=9.6, 7.6 Hz, 2H), 3.74 (d, J=11.6 Hz, 1H), 3.28 (d, J=12.0 Hz, 1H), 2.68 (dd, J=15.6, 7.6 Hz, 1H), 2.54 (dd, J=15.6, 5.6 Hz, 1H), 2.00-2.18 (m, 5H), 1.60 (s, 3H), 1.46 (s, 9H), 0.93-0.97 (m. 2H), 0.81 (d, J=6.8 Hz, 3H), 0.74 (d, J=6.8 Hz, 3H), 0.01 (s, 9H); $^{13}$C-NMR (CDCl$_3$, 100 MHz) δ 174.4, 170.9, 170.4, 169.6, 157.6, 156.0, 149.9, 144.8, 137.3, 133.9, 129.5, 127.8, 127.7, 126.6, 123.8, 120.0, 85.6, 79.6, 71.8, 66.6, 63.1, 56.6, 45.4, 40.5, 39.7, 31.3, 31.2, 31.0, 28.4, 24.8, 19.0, 17.4, 17.3, −1.5; IR (neat) 3393, 2960, 1736, 1684, 1508, 1446, 1390, 1249, 1171, 859; HRMS (ESI) m/z calcd for C$_{52}$H$_{66}$N$_4$NaO$_7$S$_2$Si [M+Na]$^+$ 973.4040, found 973.4042: [α]$_D$=−19.0 (c 1.11, CHCl$_3$).

(S,E)-2-(Trimethylsilyl)ethyl 3-(((S)-2-((R)-2-(2-(((tert-butoxycarbonyl)amino)methyl)pyridin-4-yl)-4-methyl-4,5-dihydrothiazole-4-carboxamido)-3-methylbutanoyl)oxy)-7-(tritylthio)hept-4-enoate (P38): To a solution of Fmoc protected amine P23 (1.55 g, 1.84 mmol) in acetonitrile (125 mL) at ambient temperature was added diethylamine (10.0 mL). After 2 h, the reaction mixture was concentrated under reduced vacuum, taken back up in ethyl acetate (50 mL), and concentrated again. In a separate flask, acid P36 (0.650 g, 1.84 mmol), PyBOP (1.92 g, 3.68 mmol), and DIPEA (0.96 mL, 5.52 mmol) was combined in CH$_2$Cl$_2$ (125 mL). The freshly deprotected amine was added via CH$_2$Cl$_2$ (10 mL) to the flask containing the activated acid at ambient temperature. After 3 h, the resulting mixture was concentrated under reduced pressure. The crude residue was purified using flash chromatography (5% to 40% ethyl acetate in hexanes) to obtain the desired amide (1.42 g. 81%): $^1$H-NMR (CDCl$_3$, 400 MHz) δ 8.51-8.52 (m, 1H), 7.72-7.73 (m. 1H), 7.15-7.38 (m, 15H), 7.11 (d, J=8.8 Hz, 1H), 5.69 (dt, J=15.2, 6.8 Hz, 1H), 5.60-5.65 (m, 1H), 5.36 (dd, J=15.2, 7.6 Hz, 1H), 4.54-4.56 (m, 2H), 4.48 (dd, J=8.8, 4.4 Hz, 1H), 4.14 (dd, J=10.0, 8.0 Hz, 2H), 3.84 (d, J=11.6 Hz, 1H), 3.41 (d, J=11.6 Hz, 1H), 2.67 (dd, J=15.6, 8.0 Hz, 1H), 2.54 (dd, J=16.0, 5.6 Hz, 1H), 2.03-2.18 (m, 5H), 1.56 (s, 3H), 1.44 (s, 9H), 0.92-0.97 (m, 2H), 0.81 (d, J=6.8 Hz, 3H), 0.74 (d, J=6.8 Hz, 3H), 0.01 (s, 9H); $^{13}$C-NMR (CDCl$_3$, 100 MHz) δ 173.8, 170.3, 169.6, 167.0, 158.7, 155.9, 149.7, 144.8, 140.3, 133.9, 129.5, 127.8, 127.7, 126.6, 120.3, 119.9, 85.4, 79.6, 71.8, 66.6, 63.1, 56.8, 45.7, 41.7, 39.7, 31.3, 31.1, 31.0, 28.4, 24.5, 19.0, 17.4, 17.2, −1.5; IR (neat) 3390, 2960, 1737, 1681, 1593, 1504, 1444, 1248, 1170, 836, 744; HRMS (ESI) m/z calcd for C$_{52}$H$_{66}$N$_4$NaO$_7$S$_2$Si [M+Na]$^+$ 973.4040, found 973.4058: [α]$_D$=−32.5 (c 1.03, CHCl$_3$).

Trityl Protected Depsipeptide Pyridyl "IN" Macrocycle (P39)

To a solution of depsipeptide P37 (2.10 g, 2.21 mmol) in CH$_2$Cl$_2$ (100 mL) at 0° C. was treated with TFA (20.0 mL) dropwise. The reaction mixture was allowed to stir for 18 h. The mixture was concentrated under reduced pressure, taken back up in toluene (50 mL), and concentrated again. The remaining residue was taken up in acetonitrile (2300 mL) and was treated with HATU (1.68 g. 4.42 mmol), HOBt (0.597 g, 4.42 mmol), and DIPEA (2.32 mL, 13.3 mmol) at room temperature. After 18 h, the reaction mixture was concentrated under reduced pressure. The crude residue was passed through a silica plug using an eluent of 10% MeOH in CH$_2$Cl$_2$. The filtrate was concentrated and taken up in ethyl acetate (150 mL). The solution was washed with a saturated solution of NaHCO$_3$ (100 mL). The aqueous layer was extracted ethyl acetate (3×50 mL) and then the combined organic layers were washed with a saturated solution of NaCl (100 mL). After drying over Na$_2$SO$_4$ and concentrating under reduced vacuum, the crude mixture was purified using flash chromatography (1% to 6% MeOH in DCM) to obtain the macrocycle (0.334 g. 20%): $^1$H-NMR (CDCl$_3$, 400 MHz) δ 7.78 (t, J=7.6 Hz, 1H), 7.62 (d, J=7.6 Hz, 1H), 7.15-7.37 (m, 16H), 7.06 (d, J=4.8 Hz, 1H), 5.74 (dtd, J=15.6, 6.8, 1.2 Hz, 1H), 5.62 (q, J=6.0 Hz, 1H), 5.38 (dd, J=15.6, 6.4 Hz, 1H), 4.97 (dd, J=18.0, 6.8 Hz, 1H), 4.66 (dd, J=10.0, 4.0 Hz, 1H), 4.29 (dd, J=18.0, 2.0 Hz, 1H), 4.07 (d, J=11.2 Hz, 1H), 3.36 (d, J=11.6 Hz, 1H), 2.68-2.70 (m, 2H), 2.08-2.17 (m, 3H), 2.02 (q, J=7.2 Hz, 2H), 1.82 (s, 3H), 0.73 (d, J=7.2 Hz, 3H), 0.52 (d, J=6.8 Hz, 3H; $^{13}$C-NMR (CDCl$_3$, 100 MHz) δ 173.4, 170.8, 168.9, 168.7, 156.5, 149.4, 144.8, 137.7, 133.0, 129.4, 127.8, 127.3, 126.5, 124.1, 123.1, 84.9, 72.9, 66.5, 57.4, 43.8, 43.5, 41.4, 33.5, 31.5, 31.1, 24.7, 18.9, 16.7; IR (neat) 3368, 2960, 1735, 1675, 1575, 1512, 1444, 1242, 1037, 974, 744; HRMS (ESI) m/z calcd for C$_{42}$H$_{44}$N$_4$NaO$_4$S$_2$ [M+Na]$^+$ 755.2702, found 755.2696; [α]$_D$=+27.4 (c 0.57, CHCl$_3$).

Trityl Protected Depsipeptide Pyridyl "OUT" Macrocycle (P40)

To a solution of depsipeptide P38 (2.00 g. 2.10 mmol) in CH$_2$Cl$_2$ (100 mL) at 0° C. was treated with TFA (20.0 mL)

dropwise. The reaction mixture was allowed to stir for 18 h. The mixture was concentrated under reduced pressure, taken back up in toluene (50 mL), and concentrated again. The remaining residue was taken up in acetonitrile (2100 mL) and was treated with HATU (1.60 g. 4.20 mmol), HOBt (0.570 g. 4.20 mmol), and DIPEA (2.19 mL, 12.6 mmol) at room temperature. After 18 h, the reaction mixture was concentrated under reduced pressure. The crude residue was passed through a silica plug using an eluent of 10% MeOH in $CH_2Cl_2$. The filtrate was concentrated and taken up in ethyl acetate (150 mL). The solution was washed with a saturated solution of $NaHCO_3$ (100 mL). The aqueous layer was extracted ethyl acetate (3×50 mL) and then the combined organic layers were washed with a saturated solution of NaCl (100 mL). After drying over $Na_2SO_4$ and concentrating under reduced vacuum, the crude mixture was purified using flash chromatography (1% to 6% MeOH in DCM) to obtain the macrocycle (0.350 g, 23%): $^1$H-NMR ($CDCl_3$, 400 MHz) δ 8.65 (d, J=5.2 Hz, 1H), 7.77 (s, 1H), 7.15-7.40 (m, 16H), 6.97 (d, J=9.2 Hz, 1H), 6.33 (dd, J=8.0, 5.2 Hz, 1H), 5.78 (dtd, J=15.6, 6.4, 0.8 Hz, 1H), 5.71 (q, J=6.0 Hz, 1H), 5.50 (dd, J=15.6, 6.0 Hz, 1H), 4.97 (dd, J=17.6, 8.0 Hz, 1H), 4.52 (dd, J=8.8, 4.0 Hz, 1H), 4.02 (dd, J=18.0, 5.2 Hz, 1H), 3.99 (d, J=11.6 Hz, 1H), 3.38 (d, J=11.6 Hz, 1H), 2.74-2.78 (m, 2H), 2.01-2.29 (m, 5H), 1.74 (s, 3H), 0.76 (d, J=6.8 Hz, 3H), 0.66 (d, J=6.8 Hz, 3H); $^{13}$C-NMR ($CDCl_3$, 100 MHz) δ 173.1, 169.9, 168.4, 168.2, 159.3, 150.5, 144.6, 140.0, 132.6, 129.4, 128.1, 127.9, 126.7, 120.8, 116.9, 84.5, 71.5, 66.7, 58.0, 44.5, 43.5, 40.8, 33.4, 31.2, 31.0, 24.9, 18.9, 17.2; IR (neat) 3405, 2962, 1739, 1683, 1552, 1508, 1404, 1255, 1183, 1029, 748; HRMS (ESI) m/z calcd for $C_{42}H_{44}N_4NaO_4S_2$ [M+Na]$^+$ 755.2702, found 755.2694: $[α]_D$=+27.6 (c 0.58, $CHCl_3$).

Depsipeptide Pyridyl "IN" Thiol (P6)

To a solution of trityl protected thiol P39 (300 mg, 0.409 mmol) in $CH_2Cl_2$ (55 mL) at 0° C. was treated with TFA (2.25 mL) and triisopropylsilane (0.17 mL, 0.818 mmol). The reaction mixture was warmed to ambient temperature and stirred for 2 h. The mixture was concentrated and purified using flash chromatography (1% to 6% MeOH in $CH_2Cl_2$) to obtain the desired thiol (164 mg, 82%): $^1$H-NMR ($CDCl_3$, 400 MHz) δ 7.86 (t, J=7.6 Hz. H), 7.68 (d, J=7.6 Hz, 1H), 7.42 (d, J=8.0 Hz, 1H), 7.35 (bs, 1H), 7.25 (d, J=9.6 Hz, 1H), 5.85 (dtd, J=15.2, 7.2, 1.2 Hz, 1H), 5.64-5.69 (m, 1H), 5.54 (ddt J=15.6, 6.8, 1.2 Hz, 1H), 5.11 (dd, J=18.0, 7.6 Hz, 1H), 4.69 (dd, J=10.0, 4.0 Hz, 1H), 4.34 (dd, J=18.0, 1.6 Hz, 1H), 4.14 (d, J=11.2 Hz, 1H), 3.46 (d, J=11.6 Hz, 1H), 2.87 (dd, J=15.2, 10.0 Hz, 1H), 2.71 (dd, J=15.2, 2.4 Hz, 1H), 2.53 (qd, J 7.6, 0.8 Hz, 1H), 2.31-2.37 (m, 2H), 2.09-2.17 (m, 1H), 1.91 (s, 3H), 1.40 (t, J=8.0 Hz, 1H), 0.71 (d, J=6.8 Hz, 3H), 0.49 (d, J=6.8 Hz, 3H); $^{13}$C-NMR ($CDCl_3$, 100 MHz) δ 174.8, 172.6, 169.7, 168.5, 156.9, 148.0, 138.3, 132.8, 128.4, 125.1, 123.7, 83.5, 72.6, 57.5, 43.7, 43.5, 41.2, 36.4, 33.3, 23.8, 23.8, 18.6, 16.5; IR (neat) 3369, 2962, 1735, 1670, 1572, 1515, 1426, 1295, 1174, 989, 799; HRMS (ESI) m/z calcd for $C_{23}H_{31}N_4O_4S_2$ [M+H]$^+$ 491.1787, found 491.1791. [α]i=+58.5 (c 0.53, $CHCl_3$).

Depsipeptide Pyridyl "OUT" Thiol (P8)

To a solution of trityl protected thiol P40 (320 mg, 0.437 mmol) in $CH_2Cl_2$ (60 mL) at 0° C. was treated with TFA (2.30 mL) and triisopropylsilane (0.18 mL. 0.873 mmol). The reaction mixture was warmed to ambient temperature and stirred for 2 h. The mixture was concentrated and purified using flash chromatography (1% to 6% MeOH in $CH_2Cl_2$) to obtain the desired thiol (188 mg, 89%): $^1$H-NMR ($CDCl_3$, 400 MHz) δ 8.70 (d, J=5.2 Hz, 1H), 7.89 (s, 1H), 7.45 (dd, J=5.2, 1.6 Hz, 1H), 6.92 (d, J=9.2 Hz, 1H), 6.36-6.39 (m, 1H), 5.87 (dt, J=15.6, 6.4 Hz, 1H), 5.73-5.78 (m, 1H), 5.67 (ddt, J=15.6, 6.4, 1.2 Hz, 1H), 5.09 (dd, J=17.6, 8.0 Hz, 1H), 4.57 (dd, J=9.2, 4.0 Hz, 1H), 4.37 (dd, J=17.6, 4.8 Hz, 1H), 4.05 (d, J=11.6 Hz, 1H), 3.40 (d, J=11.6 Hz, 1H), 2.76-2.89 (m, 2H), 2.50-2.64 (m, 2H). 2.30-2.44 (m, 2H), 2.11-2.20 (m, 1H), 1.78 (s, 3H), 1.38 (t, J=7.6 Hz, 1H), 0.75 (d, J=6.8 Hz, 3H), 0.66 (d, J=6.8 Hz, 3H): $^{13}$C-NMR ($CDCl_3$, 100 MHz) 173.1, 169.3, 168.7, 168.4, 158.7, 149.4, 141.1, 132.4, 128.8, 121.3, 117.8, 84.5, 72.2, 57.8, 43.6, 43.6, 40.3, 36.1, 33.6, 24.9, 23.7, 18.9, 17.0; IR (neat) 3319, 2962, 1736, 1670, 1551, 1508, 1242, 1184, 1027, 971, 730; HRMS (ESI) m/z calcd for $C_{23}H_{31}N_4O_4S_2$ [M+H]$^+$ 491.1787, found 491.1795: $[α]_D$=+68.3 (c 0.74, $CHCl_3$).

Depsipeptide Pyridyl "IN" (P5)

To a solution of depsipeptide pyridine "IN" thiol 6 (20.0 mg, 0.041 mmol) in THF (0.8 mL) at ambient temperature was treated with N-octanoyl-imidazole (15.8 mg, 0.082 mmol), imidazole (5.6 mg, 0.082 mmol), and DMAP (0.5 mg, 0.004 mmol). The reaction mixture was warmed to 50° C. and stirred for 6 h. The mixture was cooled and concentrated and purified using flash chromatography (0.5% to 4% MeOH in $CH_2Cl_2$) to obtain the desired octanoyl masked thiol (17.4 mg, 69%): $^1$H-NMR ($CDCl_3$, 400 MHz) δ 7.82 (t, J=7.6 Hz, 1H), 7.65 (d, J=7.6 Hz, 1H), 7.39 (d, J=8.0 Hz. 1H), 7.30 (d, J=9.6 Hz, 1H), 5.85 (dt, J=15.6, 6.8 Hz, 1H), 5.63 (td, J=16.0, 2.0 Hz, 1H), 5.52 (dd, J=15.2, 6.8 Hz, 1H), 5.06-5.12 (min, 1H), 4.67 (dd, J=9.6, 3.6 Hz, 1H), 4.32 (d, J=18.0 Hz, 1H), 4.15 (d, J=11.6 Hz, 1H), 3.42 (d, J=11.6 Hz, 1H), 2.81-2.90 (m, 2H), 2.63 (dd, J=14.0, 1.2 Hz, 1H), 2.47 (t, J=7.6 Hz, 2H), 2.27 (q. J=7.6 Hz, 2H), 2.06-2.13 (m, 1H), 1.92 (s, 3H), 1.56-1.61 (m, 2H), 1.23-1.27 (m, 1H), 0.84 (t, J=6.8 Hz, 3H), 0.69 (d, J=6.8 Hz, 3H), 0.49 (d, J=6.8 Hz, 3H); $^{13}$C-NMR ($CD_3OD$. 100 MHz) δ 199.4, 174.2, 173.7, 170.7, 168.7, 157.5, 147.7, 138.7, 132.3, 128.7, 125.0, 123.2, 83.4, 72.9, 54.1, 43.4, 42.8, 42.7, 40.2, 33.1, 31.9, 31.4, 28.6, 28.5, 27.4, 25.3, 23.0, 22.2, 18.1, 15.3, 13.0; IR (neat) 2959, 2928, 2856, 1737, 1682, 1571, 1419, 1239, 990; HRMS (ESI) m/z calcd for $C_{31}H_{45}N_4O_5S_2$ [M+H]$^+$ 617.2826, found 617.2832; $[α]_D$=+125 (c 0.80, $CHCl_3$).

Depsipeptide Pyridyl "OUT" (7)

To a solution of depsipeptide pyridine "OUT" thiol P8 (85.0 mg, 0.179 mmol) in $CH_2Cl_2$ (15.0 mL) at ambient temperature was treated with octanoyl chloride (0.153 mL, 0.894 mmol) and triethylamine (0.050 mL, 0.357 mmol). The reaction mixture was stirred for 2 h before cooling to 0° C. and quenching with methanol (5.0 mL). The mixture was cooled and concentrated and purified using flash chromatography (0.5% to 4% MeOH in $CH_2Cl_2$) to obtain the desired octanoyl masked thiol (54.0 mg, 49%): $^1$H-NMR ($CDCl_3$, 400 MHz) δ 8.67 (d, J=5.2 Hz, 1H), 7.91 (s, 1H), 7.45 (d, J=4.8 Hz, 1H), 6.89 (d, J=8.8 Hz, 1H), 6.57-6.60 (m, 1H), 5.85 (dt, J=14.8, 7.2 Hz, 1H), 5.62-5.73 (m, 2H), 5.10 (dd, J=18.0, 8.0 Hz, 1H), 4.56 (dd, J=8.8, 3.6 Hz, 1H), 4.42 (dd, J=17.6, 3.6 Hz, 1H), 4.05 (d, J=11.6 Hz, 1H), 3.40 (d, J=11.6 Hz, 1H) 2.74-2.90 (m. 3H), 2.49 (t, J=7.2 Hz, 2H), 2.28-2.34 (m, 1H), 2.12-2.19 (m, 1H), 1.78 (s, 3H), 1.58-1.63 (m, 2H), 1.24-1.26 (m, 10H), 0.84 (t, J=6.8 Hz, 3H), 0.74 (d, J=6.8 Hz, 3H), 0.65 (d, J=6.8 Hz, 3H); $^{13}$C-NMR (CD₃OD, 100 MHz) 199.4, 173.9, 170.2, 169.6, 168.2, 158.6, 149.0, 141.7, 132.0, 128.5, 121.5, 117.9, 84.3, 72.4, 57.7, 43.4, 42.7, 42.7, 39.1, 33.4, 32.0, 31.4, 28.6, 28.5, 27.4, 25.3, 23.6, 22.2, 18.1, 16.1, 13.0; IR (neat) 2959, 2929, 2856, 1740, 1684, 1553, 1420, 1234, 987; HRMS (ESI) m/z calcd for $C_{31}H_{45}N_4O_5S_2$ [M+H]⁺ 617.2826, found 617.2827; $[\alpha]_D$=+94.3 (c 0.62, CHCl₃).

(S,E)-Methyl 3-((S)-2-((R)-2-(6-(((tert-butoxycarbonyl)amino)methyl)pyridin-2-yl)-4-methyl-4,5-dihydrothiazole-4-carboxamido)-3-methylbutanamido)-7-(tritylthio)hept-4-enoate (P41): To a solution of Boc protected amine P28 (500 mg, 0.793 mmol) in CH₂Cl₂ (30 mL) at 0° C. was treated with TFA (3.0 mL). After 2 h, the reaction mixture was concentrated under vacuum, taken back up in toluene 15 mL), and concentrated again. In another flask, acid P32 (278 mg, 0.793 mmol), PyBOP (822 mg, 1.58 mmol), and DIPEA (0.41 mL, 2.37 mmol) were combined in CH₂Cl₂ (35 mL). The freshly deprotected amine was added via CH₂Cl₂ (10 mL) to the flask containing the activated acid at ambient temperature. After 3 h, the resulting mixture was concentrated under reduced pressure. The crude residue was purified using flash chromatography (20% to 90% ethyl acetate in hexanes) to obtain the desired amide (570 mg, 84%): ¹H-NMR (CDCl₃, 400 MHz) δ 8.00 (d, J=7.6 Hz, 1H), 7.73 (t, J=7.6 Hz, 1H), 7.34-7.37 (m, 7H), 7.30 (d, J=8.8 Hz, 1H), 7.15-7.26 (m, 9H), 6.59 (d, J=10.0 Hz, 1H), 5.47 (dtd, J=15.6, 6.4, 0.8 Hz, 1H), 5.36 (dd, J=15.2, 6.0 Hz, 1H), 4.70-4.74 (m, 1H), 4.46 (d, J=5.2 Hz, 2H), 4.17 (dd, J=8.8, 6.0 Hz, 1H), 3.67 (d, J=11.6 Hz, 1H), 3.61 (s, 3H), 3.28 (d, J=11.6 Hz, 1H), 2.57 (d, J=5.6 Hz, 2H), 2.08-2.16 (m, 3H) 2.01 (q, J=6.8 Hz, 2H), 1.56 (s, 3H), 1.45 (s, 9H), 0.82 (d, J=6.8 Hz, 3H), 0.79 (d, J=6.8 Hz, 3H); ¹³C-NMR (CDCl₃. 100 MHz) δ 174.7, 171.5, 171.1, 169.7, 157.7, 156.0, 149.8, 144.8, 137.3, 130.6, 129.5, 127.8, 126.5, 123.8, 120.1, 85.6, 79.6, 66.5, 58.2, 51.7, 47.4, 45.4, 40.6, 38.7, 31.4, 31.3, 31.1, 28.4, 24.7, 19.3, 17.9; IR (neat) 2969, 1654, 1508, 1444, 1365, 1169, 1031, 751; HRMS (ESI) m/z calcd for $C_{48}H_{57}N_5NaO_6S_2$ [M+Na]⁺ 886.3648, found 886.3639: $[\alpha]_D$=−30.8 (c 0.67, CHCl₃).

(S,E)-Methyl 3-((S)-2-((R)-2-(2-(((tert-butoxycarbonyl)amino)methyl)pyridin-4-yl)-4-methyl-4,5-dihydrothiazole-4-carboxamido)-3-methylbutanamido)-7-(tritylthio)hept-4-enoate (P42): To a solution of Boc protected amine P28 (500 mg, 0.793 mmol) in CH₂Cl₂ (30 mL) at 0° C. was treated with TFA (3.0 mL). After 2 h, the reaction mixture was concentrated under vacuum, taken back up in toluene (15 mL), and concentrated again. In another flask, acid P36 (278 mg, 0.793 mmol), PyBOP (822 mg, 1.58 mmol), and DIPEA (0.41 mL, 2.37 mmol) were combined in CH₂Cl₂ (35 mL). The freshly deprotected amine was added via CH₂Cl₂ (10 mL) to the flask containing the activated acid at ambient temperature. After 3 h, the resulting mixture was concentrated under reduced pressure. The crude residue was purified using flash chromatography (20% to 100% ethyl acetate in hexanes) to obtain the desired amide (630 mg, 92%): ¹H-NMR (CDCl₃, 400 MHz) δ 8.61 (dd, J=4.8, 0.8 Hz, 1H), 7.59-7.61 (m, 2H), 7.15-7.38 (m, 16H), 6.59 (d, J=8.8 Hz, 1H), 5.47 (dtd, J=15.6, 6.4, 0.8 Hz, 1H), 5.35 (dd, J=15.2, 6.0 Hz, 1H), 4.69-4.75 (m, 1H), 4.48 (d, J=5.2 Hz, 2H), 4.15 (dd, J=8.8, 6.4 Hz, 1H), 3.79 (d, J=11.6 Hz, 1H), 3.61 (s, 3H), 3.37 (d, J=11.2 Hz, 1H), 2.57 (d, J=5.2 Hz, 2H), 2.08-2.17 (m, 3H), 2.01 (q, J=6.8 Hz, 2H), 1.55 (s, 3H), 1.45 (s, 9H), 0.82 (d, J=6.4 Hz, 3H), 0.79 (d, J=6.8 Hz, 3H); ¹³C-NMR (CDCl₃, 100 MHz) δ 174.1, 171.6, 169.5, 167.2, 158.8, 155.9, 149.7, 144.8, 140.2, 130.6, 129.5, 129.5, 127.8, 126.5, 120.0, 85.3, 79.6, 66.5, 58.4, 51.7, 47.3, 45.7, 41.7, 38.6, 31.4, 31.1, 31.0, 28.4, 24.4, 19.3, 17.9; IR (neat) 2969, 1654, 1511, 1443, 1390, 1366, 1168, 846, 750; HRMS (ESI) m/z calcd for $C_{48}H_{57}N_5NaO_6S_2$ [M+Na]⁺ 886.3648, found 886.3661; $[\alpha]_D$=−29.9 (c 0.64, CHCl₃).

Trityl Protected Peptide Isostere Pyridyl "IN" Macrocycle (P43)

To a solution of methyl ester P41 (530 mg, 0.613 mmol) in THF/H₂O (15 mL, 2:1, v/v) at ambient temperature was added lithium hydroxide monohydrate (77.2 mg, 1.84 mmol). After 2 h, the reaction was cooled to 0° C. and acidified to a pH of ~3 using 1.0 M HCl. The mixture was extracted with CH₂Cl₂ (3×15 mL), dried over Na₂SO₄, and concentrated under vacuum. The freshly furnished acid was taken up in CH₂Cl₂ (20 mL) and cooled to 0° C. The flask was treated with TFA (2.0 mL) and warmed to ambient temperature. After 2 h, the mixture was concentrated under reduced pressure, taken back up in toluene (25 mL), and concentrated again. The crude TFA salt was taken up in acetonitrile (20 mL) and was treated with DIPEA (0.68 mL, 3.90 mmol). The mixture was allowed to stir for 30 min. In another flask containing acetonitrile (610 mL) was added HATU (488 mg, 1.28 mmol), HOBt (173 mg, 1.28 mmol), and DIPEA (0.68 mL, 3.90 mmol) at room temperature. The flask containing the peptide was added to the flask containing the coupling reagents dropwise over 12 h using a syringe pump. After another 12 h, the reaction mixture was concentrated under reduced pressure. The crude residue was taken up in CH₂Cl₂ (15 mL) and the resulting solid was removed using filtration. The filtrate was concentrated and purified using flash chromatography (1% to 6% MeOH in DCM) to obtain the macrocycle (146 mg, 33%): ¹H-NMR (CDCl₃. 400 MHz) δ 7.81 (t, J=7.6 Hz, 1H), 7.62 (d, J=8.0 Hz, 1H), 7.16-7.37 (m, 16H), 6.92 (d, J=6.4 Hz, 1H), 6.73 (d, J=10.8 Hz, 1H), 6.42 (d, J=8.4 Hz, 1H), 5.47 (dt, J=15.6, 6.4 Hz, 1H), 5.34 (dd, J=15.6, 5.6 Hz, 1H), 5.03 (dd, J=18.0, 7.2 Hz, 1H), 4.83-4.90 (m, 1H), 4.60 (dd, J=10.8, 3.2 Hz, 1H), 4.24 (dd, J=17.6, 2.0 Hz, 1H), 3.95 (d, J=12.0 Hz, 1H), 3.45 (d, J=12.0 Hz, 1H), 2.67 (dd, J=14.0, 3.6 Hz, 1H), 2.48-2.52 (m, 1H), 2.44 (dd, J=14.4, 10.8 Hz, 1H), 2.16 (t, J=8.0 Hz, 2H), 1.99-2.06 (m, 2H), 1.87 (s, 3H), 0.74 (d, J=6.8 Hz, 3H), 0.32 (d, J=6.8 Hz, 3H); ¹³C-NMR (CDCl₃. 100 MHz) δ 173.8, 172.8, 169.8, 169.8, 157.5, 149.2, 144.8, 138.0, 130.3, 129.6, 129.5, 127.8, 126.6, 124.6, 122.9, 84.8, 66.5, 57.8, 48.3, 44.3, 43.7, 41.4, 31.4, 31.3, 31.1, 24.4, 19.3, 15.3; IR (neat) 2930, 1681, 1644, 1561, 1489, 1274, 1185, 1030, 842; HRMS (ESI) m/z calcd for $C_{42}H_{45}N_5NaO_3S_2$ [M+Na]⁺ 754.2862, found 754.2872: $[\alpha]_D$=+58.0 (c 0.10, CHCl₃).

Trityl Protected Peptide Isostere Pyridyl "OUT" Macrocycle (P44)

To a solution of methyl ester P42 (480 mg, 0.555 mmol) in THF/H₂O (15 mL, 2:1, v/v) at ambient temperature was added lithium hydroxide monohydrate (69.9 mg, 1.67 mmol). After 2 h, the reaction was cooled to 0° C. and acidified to a pH of ~3 using 1.0 M HCl. The mixture was extracted with CH₂Cl₂ (3×15 mL), dried over Na₂SO₄, and concentrated under vacuum. The freshly furnished acid was taken up in CH₂Cl₂ (20 mL) and cooled to 0° C. The flask was treated with TFA (2.0 mL) and warmed to ambient temperature. After 2 h, the mixture was concentrated under reduced pressure, taken back up in toluene (25 mL), and concentrated again. The crude TFA salt was taken up in acetonitrile (20 mL) and was treated with DIPEA (0.61 mL, 3.52 mmol). The mixture was allowed to stir for 30 min. In another flask containing acetonitrile (550 mL) was added HATU (439 mg, 1.16 mmol), HOBt (157 mg, 1.16 mmol), and DIPEA (0.61 mL, 3.52 mmol) at room temperature. The flask containing the peptide was added to the flask containing the coupling reagents dropwise over 12 h using a syringe pump. After another 12 h, the reaction mixture w as concentrated under reduced pressure. The crude residue was taken up in $CH_2Cl_2$ (15 mL) and the resulting solid was removed using filtration. The filtrate was concentrated and purified using flash chromatography (1% to 6% MeOH in DCM) to obtain the macrocycle (128 mg, 32%): $^1$H-NMR ($CDCl_3$. 400 MHz) δ 8.64 (dd, J=4.8, 0.8 Hz, 1H), 7.79 (d, J=0.8 Hz, 1H), 7.16-7.32 (m, 16H), 6.29-6.35 (m, 2H), 6.12 (d, J=10.0 Hz, 1H), 5.54-5.57 (m, 2H) 4.81-4.86 (m, 1H), 4.67 (dd, J=17.2, 6.4 Hz, 1H), 4.40 (dd, J=10.0, 4.4 Hz, 1H), 4.15 (dd, J=17.2, 5.6 Hz, 1H), 3.80 (d, J=11.6 Hz, 1H), 3.49 (d, J=11.6 Hz, 1H), 2.72 (dd, J=14.8, 4.8 Hz, 1H), 2.51 (dd, J=14.8, 5.6 Hz, 1H), 2.34-2.41 (m, 1H), 2.23 (t, J=7.2 Hz, 2H), 1.92-2.12 (m, 2H), 1.70 (s, 3H), 0.84 (d, J=6.8 Hz, 3H), 0.60 (d, J=6.8 Hz, 3H); $^{13}$C-NMR ($CDCl_3$, 100 MHz) δ 173.1, 170.4, 170.1, 170.1, 159.1, 150.4, 144.6, 139.7, 130.3, 130.1, 129.4, 127.9, 126.7, 120.7, 117.9, 84.5, 66.7, 59.0, 47.9, 45.1, 44.1, 41.3, 31.3, 31.2, 23.8, 23.8, 19.4, 16.5; IR (neat) 2969, 2925, 1708, 1644, 1561, 1409, 1274, 1185, 1030, 842; HRMS (ESI) m/z calcd for $C_{42}H_{45}N_5NaO_3S_2$ [M+Na]$^+$ 754.2862, found 754.2867; $[α]_j$=+32.3 (c 0.13, $CHCl_3$).

Peptide Isostere Pyridyl "IN" Thiol (P10)

To a solution of trityl protected thiol P43 (150 mg, 0.205 mmol) in $CH_2Cl_2$ (27.5 mL) at 0° C. was treated with TFA (1.12 mL) and triisopropylsilane (0.089 mL, 0.410 mmol). The reaction mixture was warmed to ambient temperature and stirred for 2 h. The mixture was concentrated and purified using flash chromatography (1% to 6% MeOH in $CH_2Cl_2$) to obtain the desired thiol (94.6 mg, 94%): $^1$H-NMR ($CDCl_3$, 400 MHz) δ 7.85 (t, J=7.6 Hz, 1H), 7.65 (d, J=7.6 Hz, 1H), 7.40 (d, J 8.0 Hz, 1H), 7.02 (d, J=5.6 Hz, 1H), 6.74 (d, J=10.8 Hz, 1H), 6.56 (d, J=8.0 Hz, 1H), 5.60 dtd, J=15.2, 6.8, 1.2 Hz, 1H), 5.49 (dd, J=15.6, 6.0 Hz, 1H), 5.08 (dd, J=17.6, 7.2 Hz, 1H), 4.89-4.96 (m, 1H), 4.63 (dd, J=10.8, 2.8 Hz, 1H), 4.32 (dd, J=17.6, 1.6 Hz, 1H), 3.98 (d, J=11.6 Hz, 1H), 3.49 (d, J=11.6 Hz, 1H), 2.69 (dd, J=14.0, 3.2 Hz, 1H), 2.49-2.55 (m, 4H), 2.31 (q. J=6.8 Hz, 2H), 1.91 (s, 3H), 1.38 (t, J=8.0 Hz, 1H), 0.74 (d, J=6.8 Hz, 3H), 0.31 (d, J=6.8 Hz, 3H); $^{13}$C-NMR ($CDCl_3$, 100 MHz) δ 174.5, 173.4, 170.1, 169.9, 157.7, 148.6, 138.2, 131.2, 129.1, 125.1, 123.2, 84.1, 57.8, 48.6, 44.3, 43.7, 41.2, 36.3, 31.2, 24.0, 24.0, 19.3, 15.2; IR (neat) 2926, 2864, 1667, 1577, 1500, 1293, 1181, 1049; HRMS (ESI) m/z calcd for $C_{23}H_{32}N_5O_3S_2$ [M+H]$^+$ 490.1947, found 490.1946: $[α]_D$=+105 (c 0.08, $CHCl_3$).

Peptide Isostere Pyridyl "OUT" Thiol (P12)

To a solution of trityl protected thiol P44 (115 mg, 0.157 mmol) in $CH_2Cl_2$ (22.0 mL) at 0° C. was treated with TFA (0.90 mL) and triisopropylsilane (0.065 mL, 0.314 mmol). The reaction mixture was warmed to ambient temperature and stirred for 2 h. The mixture was concentrated and purified using flash chromatography (1% to 6% MeOH in $CH_2Cl_2$) to obtain the desired thiol (68.4 mg, 89%): $^1$H-NMR ($CDCl_3$, 400 MHz) δ 8.66 (d, J=3.6 Hz, 1H), 7.76 (s, 1H), 7.35 (d, J=4.4 Hz, 1H), 7.01 (d, J=8.4 Hz, 1H), 6.86-6.88 (m, 1H), 6.19 (d, J=10.4 Hz, 1H), 5.52-5.53 (m, 2H), 4.89-4.91 (m, 1H), 4.85 (d, J=17.6 Hz, 1H), 4.46 (dd, J=10.4, 4.0 Hz, 1H), 4.36 (d, J=17.2 Hz, 1H), 3.84 (d, J=12.0 Hz, 1H), 3.48 (d, J=12.0 Hz, 1H), 2.44-2.72 (m, 5H), 2.30 (q, J=6.4 Hz, 2H), 1.78 (s, 3H), 1.31 (t, J=7.2 Hz, 1H), 0.80 (d, J=6.8 Hz, 3H), 0.49 (d, J=6.8 Hz, 31H); $^{13}$C-NMR ($CDCl_3$, 100 MHz) δ 173.3, 171.2, 159.6, 150.1, 140.3, 130.8, 128.9, 121.0, 117.8, 84.8, 58.6, 47.9, 44.0, 40.0, 36.2, 31.2, 24.0, 23.9, 23.7, 19.5, 16.1; IR (neat) 2965, 2930, 1655, 1534, 1410, 1201, 1142, 1026; HRMS (ESI) m/z calcd for $C_{23}H_{32}N_5O_3S_2$ [M+H]$^+$ 490.1947, found 490.1952; $[α]_D$=+129 (c 0.08, $CHCl_3$).

Peptide Isostere Pyridyl "IN" (P9)

To a solution of peptide pyridine "IN" thiol P10 (25.0 mg, 0.051 mmol) in THF (1.0 mL) at ambient temperature was treated with N-octanoyl-imidazole (19.8 mg, 0.102 mmol), imidazole (6.9 mg, 0.102 mmol), and DMAP (0.6 mg, 0.005 mmol). The reaction mixture was warmed to 50° C. and stirred for 6 h. The mixture was cooled and concentrated and purified using flash chromatography (0.5% to 6% MeOH in $CH_2Cl_2$) to obtain the desired octanoyl masked thiol (20.6 mg, 66%): $^1$H-NMR ($CD_3OD$. 400 MHz) δ 8.08 (t, J=7.6 Hz, 1H), 7.84 (d, J=7.6 Hz, 1H), 7.66 (d, J=7.6 Hz. 1H), 7.00 (d, J=10.8 Hz, 1H), 5.52-5.64 (m, 2H), 4.92 (d, J=17.6 Hz, 1H), 4.77-4.83 (m, 1H), 4.53-4.57 (m, 1H), 4.38 (d, J=17.2 Hz, 1H), 3.93 (d, J=11.6 Hz, 1H), 3.67 (d, J=12.0 Hz, 1H), 2.89 (t, J=7.2 Hz, 2H), 2.68 (dd, J=14.0, 11.2 Hz, 1H), 2.53 (dd, J=14.0, 4.0 Hz, 1H), 2.52 (t, J=7.2 Hz, 2H), 2.34-2.42 (m, 1H), 2.23-2.30 (m, 2H), 1.89 (s, 3H), 1.59-1.63 (m, 2H), 1.26-1.29 (m, 10H), 0.87 (t, J=6.8 Hz, 3H), 0.75 (d, J=7.2 Hz, 3H), 0.35 (d, J=6.8 Hz, 3H); $^{13}$C-NMR ($CD_3OD$, 100 MHz) δ 203.4, 178.9, 177.9, 175.9, 174.4, 161.2, 151.4, 143.9, 143.8 135.0, 132.5, 129.7, 127.3, 87.3, 61.6, 47.5, 47.3, 47.1, 43.8, 35.8, 35.3, 34.9, 32.5, 32.4, 31.6, 29.3, 26.5, 26.1, 22.4, 18.5, 16.9; IR (neat) 2957, 2928, 2855, 1678, 1530, 1403, 965; HRMS (ESI) m/z calcd for $C_{31}H_{46}N_5NO_4S_2$ [M+H]$^+$ 616.2986, found 616.2988; $[α]_D$=+107 (c 0.23, $CHCl_3$).

Peptide Isostere Pyridyl "OUT" (P11)

To a solution of peptide pyridine "OUT" thiol 12 (8.0 mg, 0.016 mmol) in $CH_2Cl_2$ (0.2 mL) at ambient temperature was treated with octanoyl chloride (0.005 mL. 0.032 mmol). DIPEA (0.011 mL, 0.064 mmol), and DMAP (0.1 mg, 0.008 mmol). The reaction mixture was stirred for 2 h before cooling to 0° C. and quenching with methanol (5.0 mL). The mixture was cooled and concentrated and purified using flash chromatography (0.5% to 6% MeOH in $CH_2Cl_2$) to obtain the desired octanoyl masked thiol (5.4 mg, 55%): $^1$H-NMR ($CDCl_3$, 400 MHz) δ 8.65 (dd, J=4.8, 0.8 Hz, 1H), 7.88 (d, J=0.8 Hz, 1H), 7.33 (dd, J=4.8, 1.6 Hz, 1H), 6.27-6.33 (m, 2H), 6.12 (d. J=10.0 Hz, 1H), 5.61-5.72 (m, 2H), 4.90-4.95 (m, 1H), 4.75 (dd, J=16.8, 6.8 Hz, 1H), 4.53 (dd, J=17.2, 6.0 Hz, 1H), 4.46 (dd, J=10.4, 4.0 Hz, 1H), 3.83 (d, J=12.0, 1H), 3.48 (d, J=11.6 Hz, 1H), 2.86 (t, J=7.2 Hz, 2H), 2.71 (dd, J=15.6, 4.4 Hz, 1H), 2.56 (dd, J=15.6, 7.6 Hz, 1H), 2.43-2.51 (m, 2H), 2.26-2.33 (m, 1H), 1.77 (s, 3H), 1.56-1.64 (m, 2H), 1.24-1.29 (m, 10H), 0.85 (t, J=6.8 Hz, 3H), 0.82 (d, J=6.8 Hz, 3H), 0.52 (d, J=6.8 Hz, 3H): $^{13}$C-NMR ($CD_3OD$, 100 MHz) δ 199.5, 173.4, 171.7, 170.9, 170.4, 158.3, 148.5, 142.1, 130.9, 128.5, 121.3, 118.9, 84.5, 58.1, 43.7, 43.4, 42.9, 39.2, 32.0, 31.4, 31.1, 28.6, 28.5, 27.7, 25.4, 22.3, 22.2, 18.9, 15.8, 12.9; IR (neat) 2956, 2927, 2855, 1679, 1649, 1519, 1403, 1031, 965; HRMS (ESI) m/z calcd for $C_{31}H_{46}N_5O_4S_2$ [M+H]$^+$ 616.2981, found 616.2981; $[α]_D$=+40.6 (c 0.35, $CHCl_3$).

HDAC Biochemical Assay

Compounds P5-P12 were tested against HDAC1-9 and the activity was determined with an optimized homogenous assay performed in a 384-well plate. Reactions were performed in assay buffer (50 mM HEPES. 100 mM KCl, 0.001% Tween-20, 0.05% BSA and pH 7.4. Additional 200 µM TCEP was added for HDAC6) and followed by fluorogenic release of 7-amino-4-methylcoumarin from substrate upon deacetylase and trypsin enzymatic activity. Fluorescence measurements were obtained every five minutes using a multilabel plate reader and plate-stacker (Envision; Perkin-Elmer). Each plate was analyzed by plate repeat, and the first derivative within the linear range was imported into analytical software (Spotfire DecisionSite). Replicate experimental data from incubations with inhibitor were normalized to DMSO controls ([DMSO]<0.5%). $IC_{50}$ is determined by logistic regression with unconstrained maximum and minimum values. The recombinant, full-length HDAC protein (BPS Biosciences) was incubated with fluorophore conjugates substrate. MAZ1600 and MAZ1675 at Km=[substrate].

797 and 10326 Cell Viability

For dose-response cellular viability assays, 797 and 10326 cells were seeded onto separate 384-well tissue culture-treated plates at a density of $2.0 \times 10^4$ cells/well in a volume of 50 µL/well. Addition of compound was performed with a JANUS Workstation (PerkinElmer Life and Analytical Sciences) using a 384-well pinhead tool that is calibrated to deliver 100 nL drug/well. After 48 hours of incubation with compound, cells were analyzed for cell viability using the ATPLite (Perkin Elmer) luminescent assay kit per the manufacturer's instructions. Luminescence was read on an EnVision 2104 Multilabel Plate Reader (PerkinElmer Life and Analytical Sciences). Replicate measurements were analyzed with respect to dose and estimates of $IC_{50}$ were calculated by logistic regression (GraphPad Prism).

Example 18. Anticancer Screening of Compounds

A) Eight compounds were submitted to the National Cancer Institute (NCI) 60 tumor cell line drug discovery program (DTP) for anticancer screening. Compounds included largazole (free thiol form),

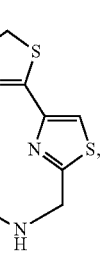

compound of formula A,

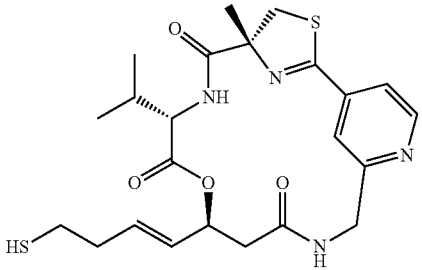 [SMILES: CC(C)[C@@H]1NC(=O)[C@]2(C)CSC(=N2)c2ccnc(c2)CNC(=O)C[C@@H](/C=C/CCS)OC1=O]

(free thiol),

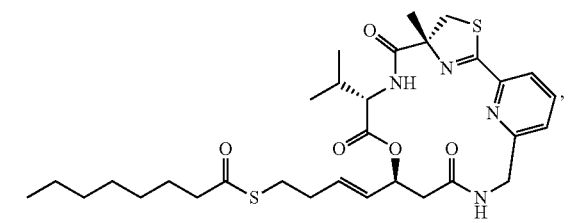 [SMILES: CCCCCCCC(=O)SCC/C=C/[C@@H]1CC(=O)NCc2cccc(n2)C2=N[C@@](C)(CS2)C(=O)N[C@@H](C(C)C)C(=O)O1]

compound of formula C, compound of formula D, and compound of formula E. Cell lines tested as part of the NCI 60 program are grouped into 9 categories, including leukemia, non-small cell lung (NSCL), colon, central nervous system (CNS) melanoma, ovarian, renal, prostate, and breast cancers.

All compounds submitted for screening were initially tested at a single high dose (10-5 M) against the fill NCI 60 cell panel. Only compounds which satisfied pre-determined threshold inhibition criteria in a minimum number of cell lines progressed to a second round of testing utilizing a more comprehensive 5-dose inhibition assay. The threshold inhibition criteria for progression to the 5-dose assays were selected to efficiently capture compounds with anti-proliferative activity based on historical DTP screening data. Single dose studies were initially performed and all compounds except the compound of formula E were advanced to the 5-dose studies.

Interpretation of Cell Data

A value of 100 means there was no growth inhibition over the course of the experiment. A value of 50 would mean 50% growth inhibition (G150) was observed, while a value of 0 represents no net cell growth (total growth inhibition, TGI). Negative values represent levels of lethality from −1 (1% lethality) to −100 (100% lethality), where all cells died in an individual assay. Information from the one-dose and 5-dose studies is migrated into the COMPARE database and can be accessed for comparative analysis.

Tissue source and histology information for the NCI cell lines is shown in Table P3 (FIG. 6A-C).

Figure 7A:
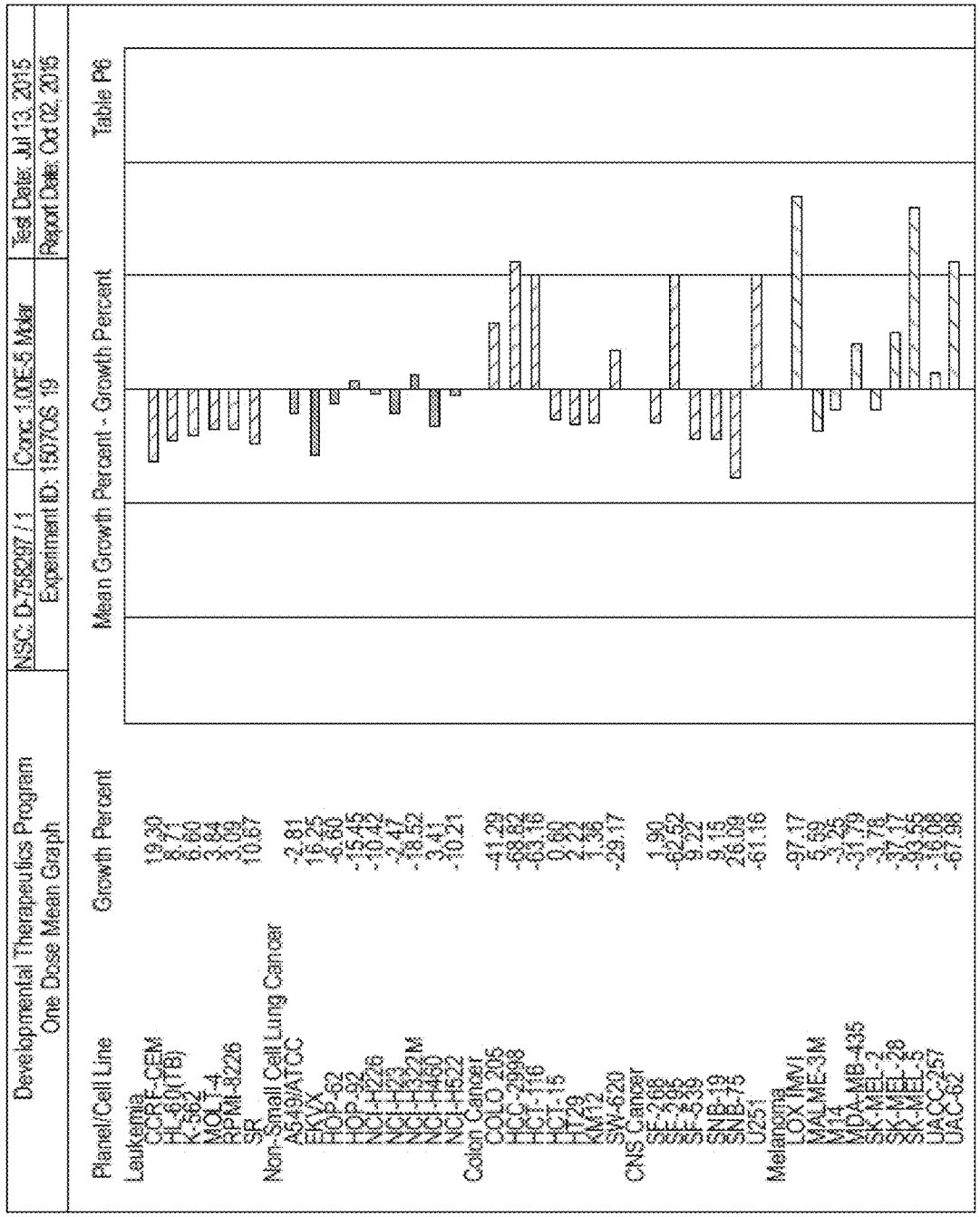
FIG. 7A-B shows a single dose tornado plot for the compound of formula D.
Figure 7B:
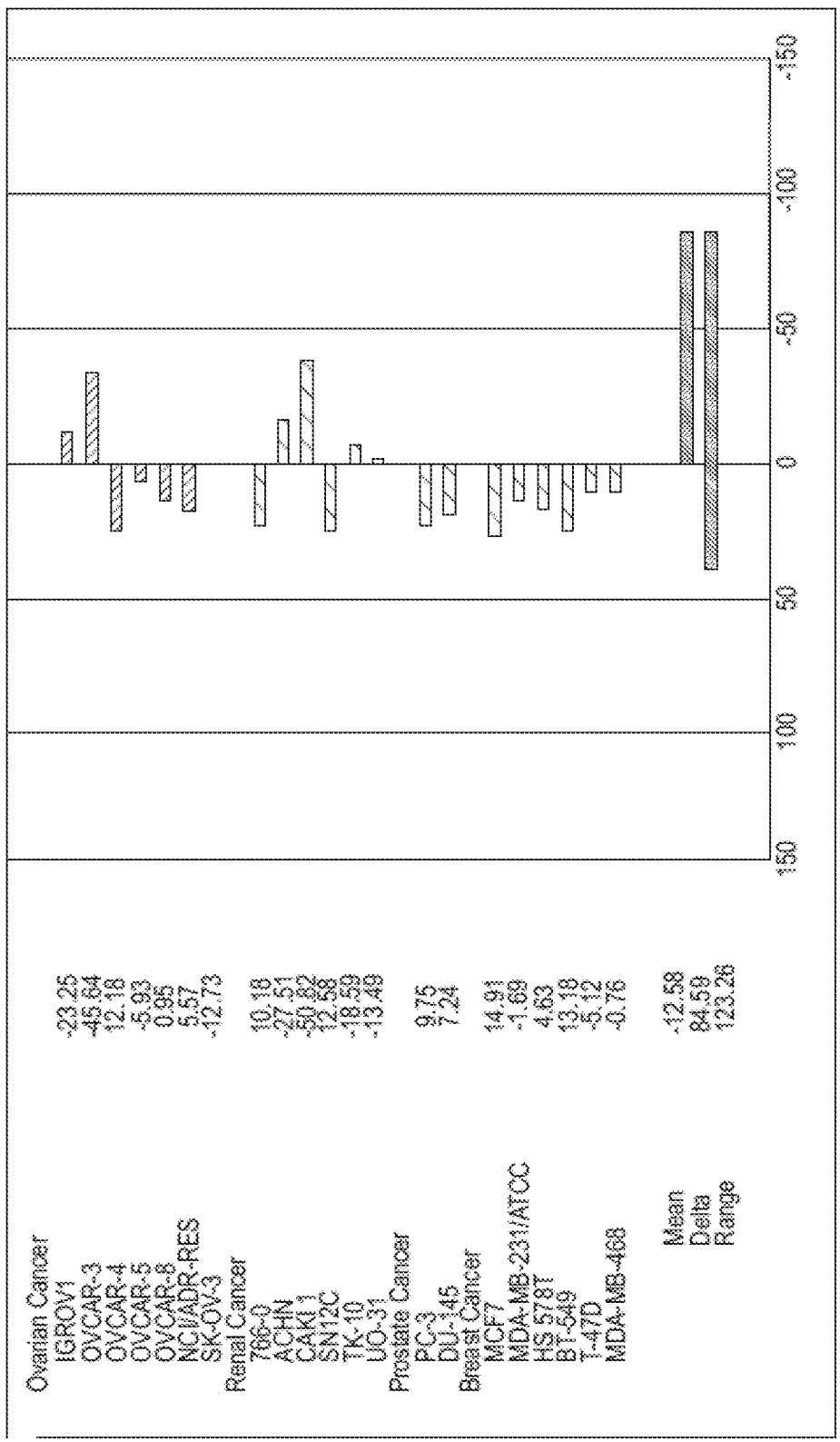
Figure 9:
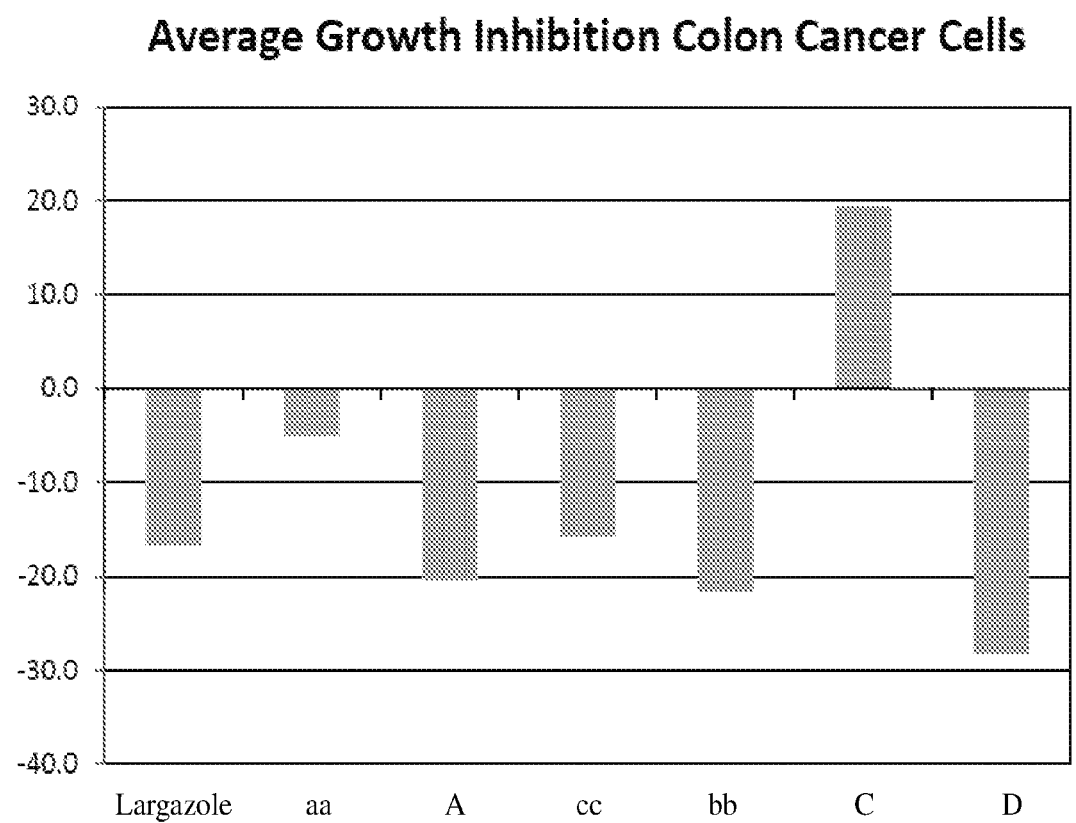
FIG. 9 shows a plot of the average growth inhibition of colon cancer cells for compounds according to the invention.
Figure 10:
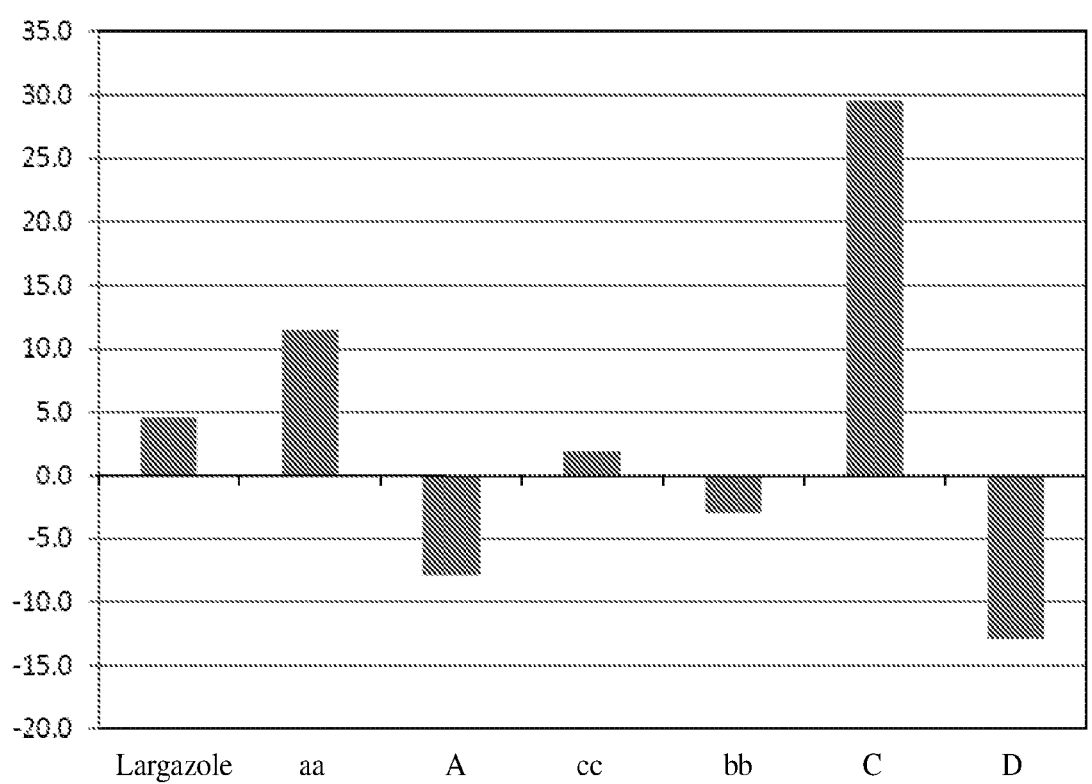
FIG. 10 shows a plot of the average growth inhibition of CNS cancer cells for compounds according to the invention.
Figure 11:
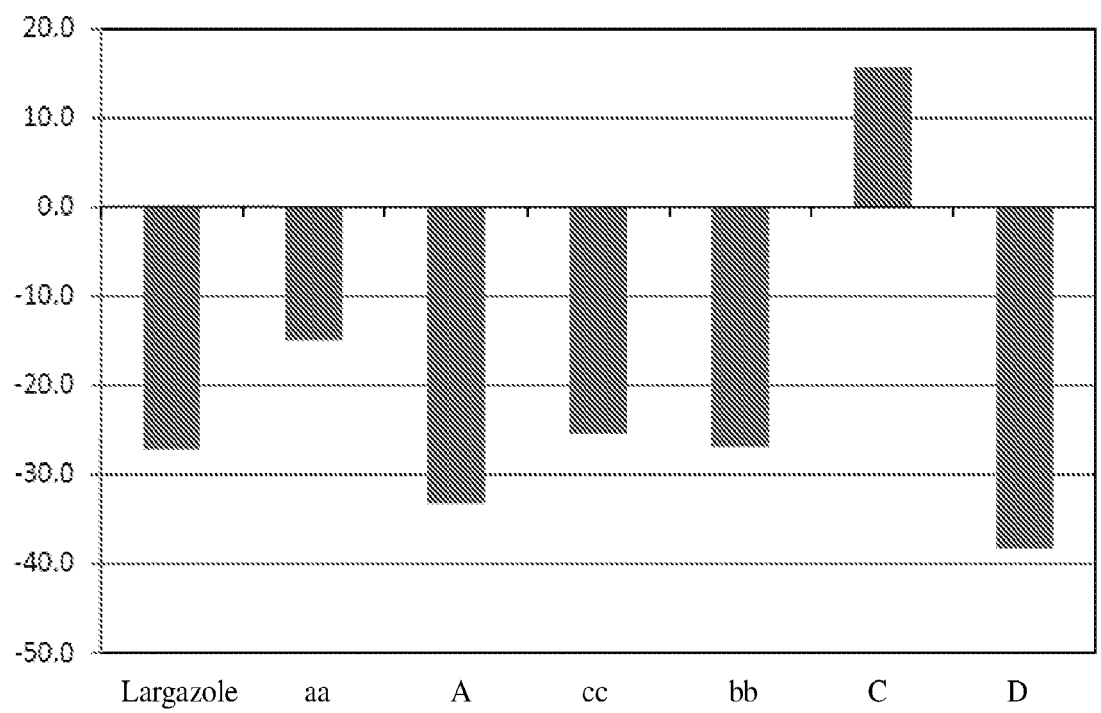
FIG. 11 shows a plot of the average growth inhibition of melanoma cancer cells for compounds according to the invention.
Figure 12:
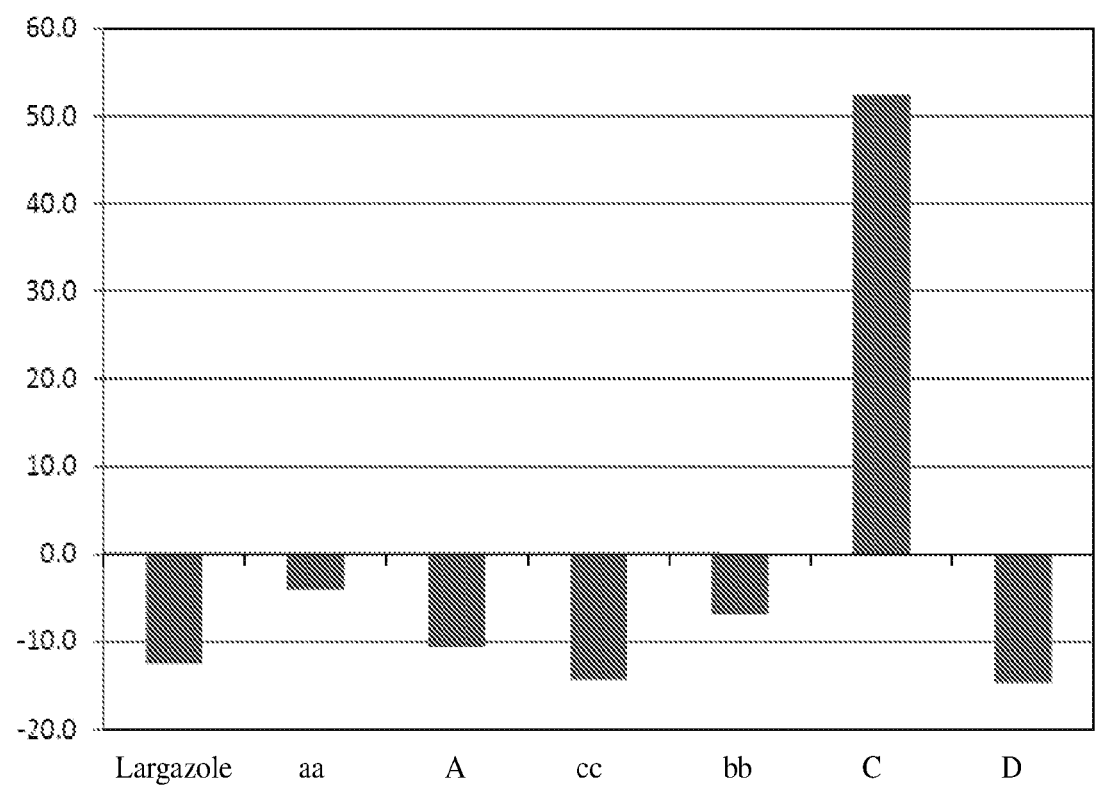
FIG. 12 shows a plot of the average growth inhibition of renal cancer cells for compounds according to the invention.
Figure 15:
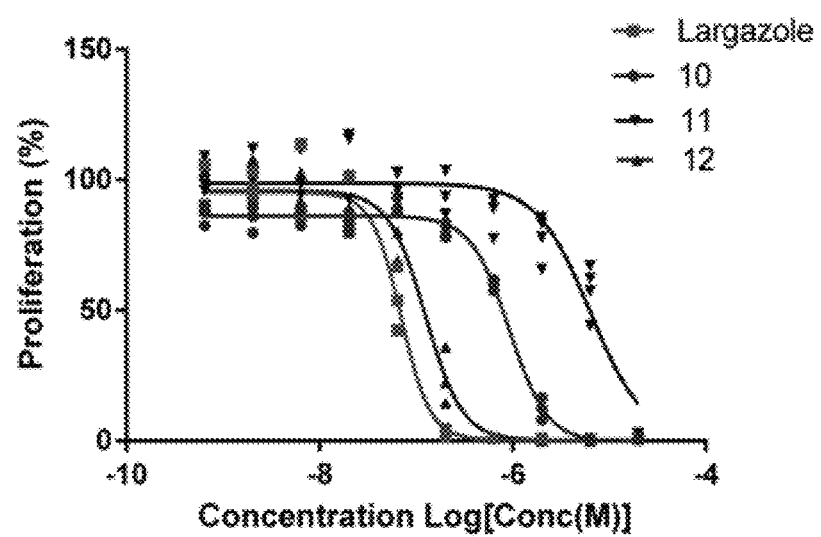
FIG. 15 shows the results of dose response in cellular viability assays.

B) Results of the single dose and 5-dose studies:

One-dose studies were performed using the inventive compounds, and "tornado" plots were generated to represent level of compound lethality for all cancer cell lines tested. An example tornado plot for the compound of formula D is shown in FIGS. 7A and 7B. In general, the inventive compounds were most lethal in cell lines of colon, CNS, melanoma, and renal cancer categories.

Data from one-dose studies was analyzed, and average inhibition for cancer cell lines in the cancer categories calculated (Table P4, FIG. 8). Included in the analysis is an average inhibition/lethality for all cell lines in the NCI panel (bottom Table P4). Data for the four most impacted cancer categories was plotted and is shown in FIGS. 9 to 12.

Of the 8 compounds tested, the compound of formula D was found to have the most lethality against cell lines in the four most impacted cancer categories (Table P4). Additionally, it was found to be the most lethal against all cells in the NCI panel with an average score of −12.6%. The compound of formula D had some level of lethality in 7 of the 9 cell lines for non-small cell lung cancer, 4 of the 7 colon, 2 of the 6 CNS, 8 of the 9 melanoma, 4 of the 7 ovarian, 4 of the 6 renal, and 3 of the 6 breast cancer cells lines. Melanoma cell lines appear to be most impacted by the compound of formula D, with select cell lines showing greater that 90% lethality in the one-dose studies.

A heat plot was generated for the compound of formula D from one-dose data, and lethality against all impacted cell lines was summarized (Table P5, FIG. 13). The compound of formula D had some level of lethality in 32 of 58 (55%) NCI cell lines tested (one cell line not tested).

C) Based on single dose data. 7 of the 8 submitted compounds were advanced by NCI to more extensive 5-dose studies. Compounds included largazole (free thiol form),

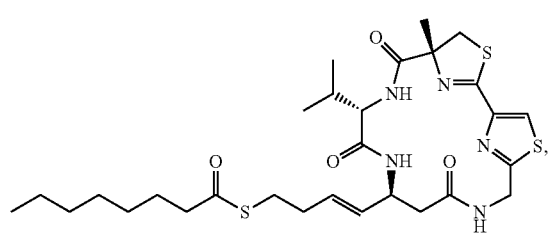 [SMILES: CCCCCCCC(=O)SCC/C=C/[C@@H]1CC(=O)NCc2nc(cs2)C2=N[C@@](C)(CS2)C(=O)N[C@@H](C(C)C)C(=O)N1]

compound of formula A,

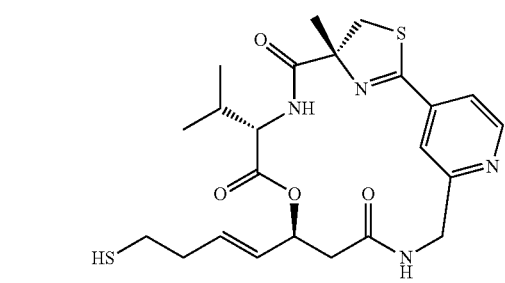 [SMILES: CC(C)[C@@H]1NC(=O)[C@]2(C)CSC(=N2)c2ccnc(c2)CNC(=O)C[C@@H](/C=C/CCS)OC1=O]

(free thiol),

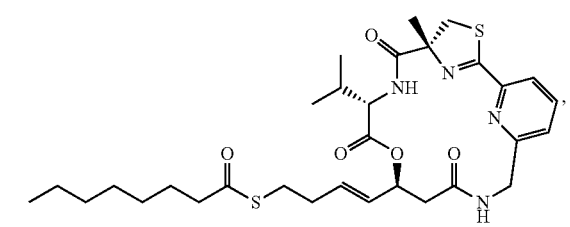 [SMILES: CCCCCCCC(=O)SCC/C=C/[C@@H]1CC(=O)NCc2cccc(n2)C2=N[C@@](C)(CS2)C(=O)N[C@@H](C(C)C)C(=O)O1]

compound of formula C, and compound of formula D. Output of the studies was used by NCI to calculate G150, IC50 (50% inhibitory concentration), TGI, and LC50 (50% lethal concentration) for all cell lines. The four most active compounds based on number of cell lines where 50% lethality was observed include

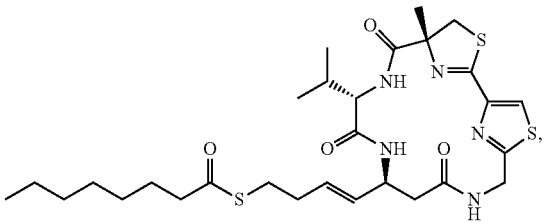 [SMILES: CCCCCCCC(=O)SCC/C=C/[C@@H]1CC(=O)NCc2nc(cs2)C2=N[C@@](C)(CS2)C(=O)N[C@@H](C(C)C)C(=O)N1]

compound of formula A,

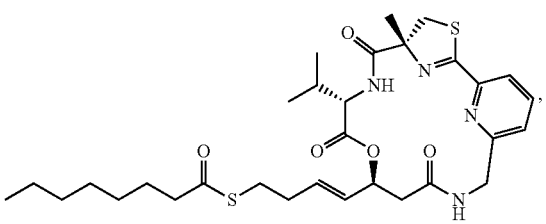 [SMILES: CCCCCCCC(=O)SCC/C=C/[C@@H]1CC(=O)NCc2cccc(n2)C2=N[C@@](C)(CS2)C(=O)N[C@@H](C(C)C)C(=O)O1]

and compound of formula D (data not shown). Data was consistent with results of one-dose studies, with the exception of

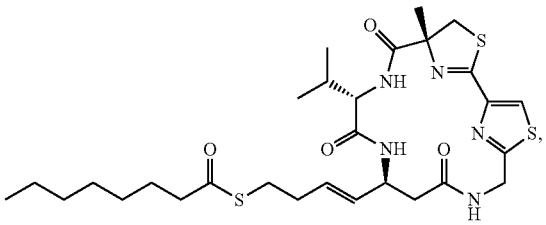 [SMILES: CCCCCCCC(=O)SCC/C=C/[C@@H]1CC(=O)NCc2nc(cs2)C2=N[C@@](C)(CS2)C(=O)N[C@@H](C(C)C)C(=O)N1]

which showed a greater level of lethality in the 5-dose studies.

The NCI data was further evaluated for the 4 most active compounds and included analysis of the parent largazole compound for comparative purposes. Concentrations for G150, IC50, TGI, and LC50 were calculated for all cell lines tested, and heat plots were prepared. An example of the data workup and analysis for the compound of formula D is shown in the Table P6 (FIG. 14A-C). For the compound of formula D, there were a total of 9 cell lines in 5 cancer categories where 50% lethality was observed.

Data for the 4 most active compounds and largazole was summarized and is shown in Table P7, further below. All compounds including largazole resulted in 50% cell growth inhibition of all cell lines tested. G150 concentrations (M) ranged from $10^{-6}$ (largazole) to $10^{-7}$

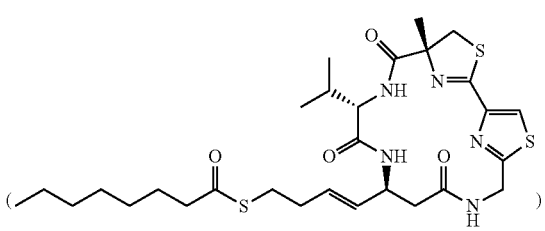 [SMILES: CCCCCCCC(=O)SCC/C=C/[C@@H]1CC(=O)NCc2nc(cs2)C2=N[C@@](C)(CS2)C(=O)N[C@@H](C(C)C)C(=O)N1]

to $10^{-8}$ (compound of formula A,

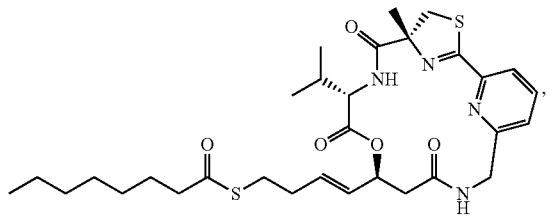 [SMILES: CCCCCCCC(=O)SCC/C=C/[C@@H]1CC(=O)NCc2cccc(n2)C2=N[C@@](C)(CS2)C(=O)N[C@@H](C(C)C)C(=O)O1]

compound of formula D). Total growth inhibition was observed in 47 to 67% of cell lines tested, with the compound of formula D showing the greatest level of inhibition. TGI concentrations for the compounds ranged from $10^{-5}$ to $10^{-7}$. LC50 levels of lethality were observed in 7 to 17% of all cell lines tested, with

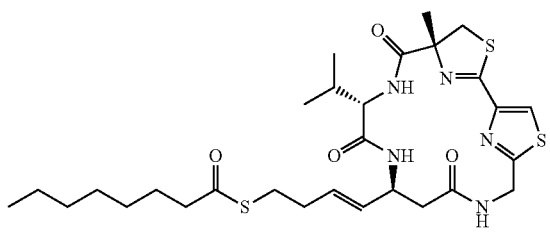 [SMILES: CCCCCCCC(=O)SCC/C=C/[C@@H]1CC(=O)NCc2nc(cs2)C2=N[C@@](C)(CS2)C(=O)N[C@@H](C(C)C)C(=O)N1]

inhibiting 10 cell lines, the compound of formula D and the compound of formula A inhibiting 9 cell lines, followed by

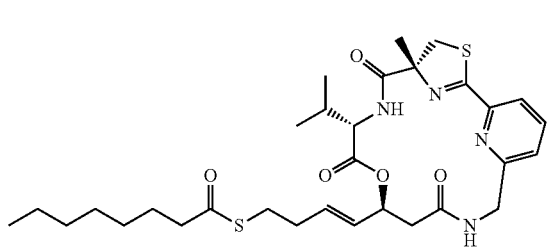 [SMILES: CCCCCCCC(=O)SCC/C=C/[C@@H]1CC(=O)NCc2cccc(n2)C2=N[C@@](C)(CS2)C(=O)N[C@@H](C(C)C)C(=O)O1]

with 7, and largazole inhibiting 4 cell lines. LC50 concentrations for the compounds ranged from $10^{-5}$

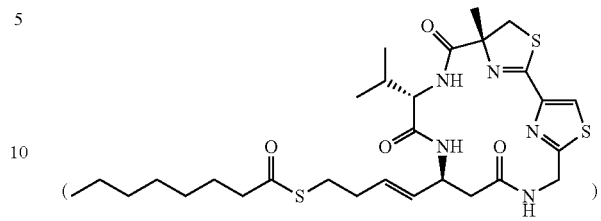

to $10^{-6}$ (largazole, compound of formula A,

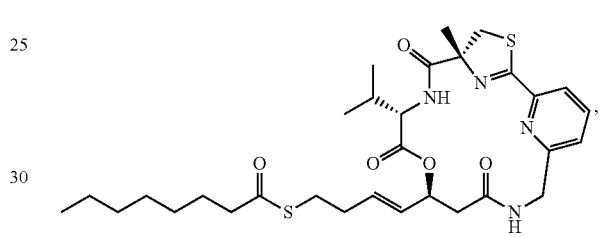

and compound of formula D). LC50 data was further analyzed by cancer category and results shown in Table P8, further below.

TABLE P7

Summary of NCI-60 Cancer Cell Line Screening

| Compound | Inhibition Type | Total Cell Lines Tested (n) | Total Impacted Cell Lines (n) | Percent of Cell Lines Impacted (%) | Average Concentration (M) |
|---|---|---|---|---|---|
| Largazole | GI50 | 59 | 59 | 100% | 2.10E−06 |
| | TGI | 59 | 34 | 58% | 7.37E−06 |
| | LC50 | 58 | 4 | 7% | 4.69E−06 |
| aa | GI50 | 58 | 58 | 100% | 6.56E−07 |
| | TGI | 58 | 37 | 64% | 1.31E−05 |
| | LC50 | 59 | 10 | 17% | 1.32E−05 |
| A | GI50 | 59 | 59 | 100% | 3.29E−08 |
| | TGI | 57 | 32 | 56% | 8.49E−07 |
| | LC50 | 58 | 9 | 16% | 2.50E−06 |
| bb | GI50 | 59 | 59 | 100% | 7.62E−08 |
| | TGI | 57 | 27 | 47% | 2.48E−06 |
| | LC50 | 58 | 7 | 12% | 6.50E−06 |
| D | GI50 | 59 | 59 | 100% | 3.83E−08 |
| | TGI | 57 | 38 | 67% | 4.57E−06 |
| | LC50 | 58 | 9 | 16% | 5.48E−06 |

| Abbreviation | Inhibition Type |
|---|---|
| GI50 | 50% Growth Inhibition |
| TGI | Total Growth Inhibition |
| LC50 | 50% Lethal Concentration |

The compound of formula aa is

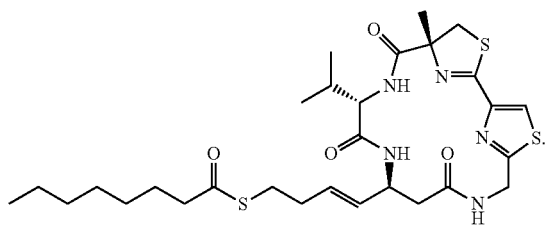 [SMILES: CCCCCCCC(=O)SCC/C=C/[C@@H]1CC(=O)NCc2nc(cs2)C2=N[C@@](C)(CS2)C(=O)N[C@@H](C(C)C)C(=O)N1]

The compound of formula bb is

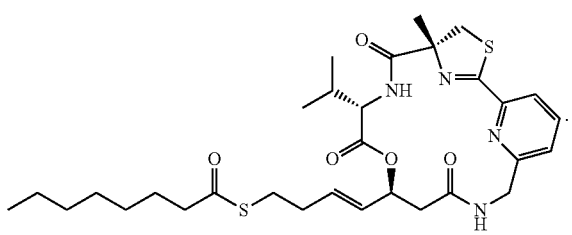 [SMILES: CCCCCCCC(=O)SCC/C=C/[C@@H]1CC(=O)NCc2cccc(n2)C2=N[C@@](C)(CS2)C(=O)N[C@@H](C(C)C)C(=O)O1]

The compound of formula cc is

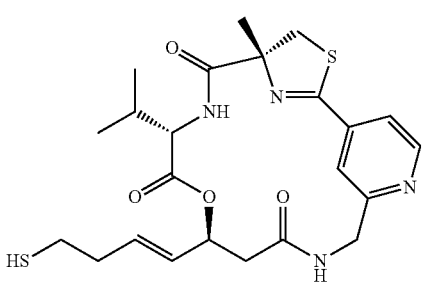 [SMILES: CC(C)[C@@H]1NC(=O)[C@]2(C)CSC(=N2)c2ccnc(c2)CNC(=O)C[C@@H](/C=C/CCS)OC1=O]

(free thiol).

TABLE P8

NCI-60 Cancer Categories where Compounds Achieved 50% Lethality (LC50)

| Compound | Cancer Category | Total Cell Lines Tested (n) | Total Impacted Cell Lines (n) | Percent of Cell Lines Impacted (%) | Average Concentration (M) |
|---|---|---|---|---|---|
| Largazole | Melanoma | 9 | 3 | 33% | 3.55E−06 |
|  | Renal | 7 | 1 | 14% | 8.13E−06 |
| aa | Colon | 7 | 3 | 43% | 9.45E−06 |
|  | CNS | 6 | 2 | 33% | 7.17E−06 |
|  | Melanoma | 8 | 2 | 25% | 6.52E−06 |
|  | Ovarian | 7 | 1 | 14% | 2.00E−06 |
|  | Renal | 8 | 2 | 25% | 3.69E−05 |
| A | Colon | 7 | 3 | 43% | 1.48E−06 |
|  | CNS | 5 | 1 | 20% | 1.38E−05 |
|  | Melanoma | 8 | 3 | 38% | 2.02E−07 |
|  | Renal | 8 | 2 | 25% | 1.81E−06 |
| bb | Colon | 7 | 2 | 29% | 1.29E−05 |
|  | Melanoma | 8 | 3 | 38% | 7.01E−07 |
|  | Renal | 8 | 2 | 25% | 8.77E−06 |
| D | Colon | 7 | 2 | 29% | 1.47E−06 |
|  | CNS | 5 | 1 | 20% | 1.95E−05 |
|  | Melanoma | 8 | 3 | 38% | 3.72E−07 |
|  | Ovarian | 7 | 1 | 14% | 2.34E−06 |
|  | Renal | 8 | 2 | 25% | 1.17E−06 |

There were 5 cancer categories where LC50 levels of inhibition were observed

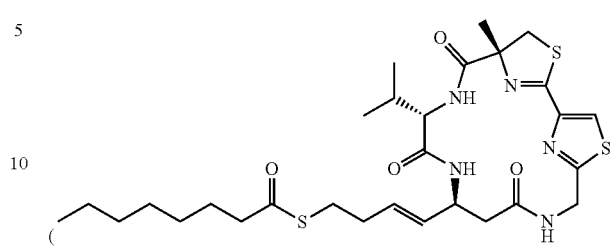

and compound of formula D). These included colon, CNS, melanoma, ovarian, and renal cancer cell lines.

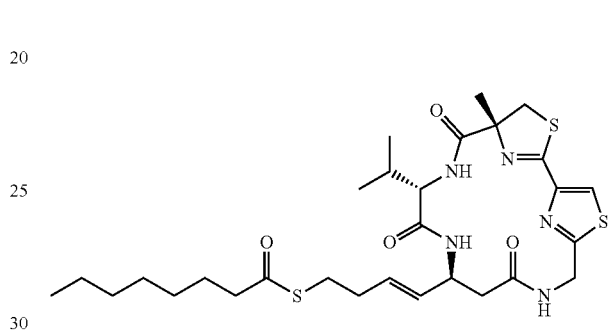

inhibited the greatest number of cell lines (10), followed by compound of formula A and compound of formula D (9),

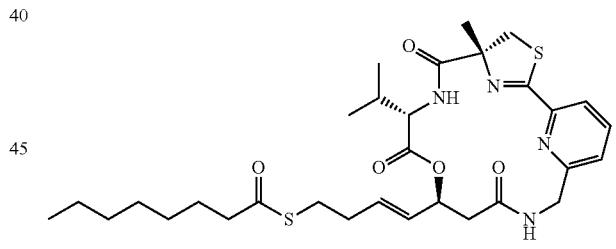

(7), with the parent compound largazole achieving LC50 in 4 cell lines (Table P7, above). Cell lines in the colon, CNS, and melanoma categories appeared to be the most impacted (Table P8, above), with up to 43% of cell lines inhibited in individual cancer categories.

D) The single cell line in the leukemia category of AML origin (HL-60 TB) showed a 93% growth inhibition however, no lethality (6.6%). Results of the 5-dose studies clearly demonstrated the potential of compounds according to the invention to treat solid tumors in the 5 most impacted cancer categories. Additionally, testing in AML-derived cell lines will confirm if the compounds are, indeed, lethal against these cell lines.

E) The creation of an isostere can have a highly variable effect on cytotoxicity against the NCI 60 panel, depending on the context. To examine this relationship, mean cell growth of the entire NCI 60 panel was compared for base compounds and isosteres from the one-dose studies (Table P9, below).

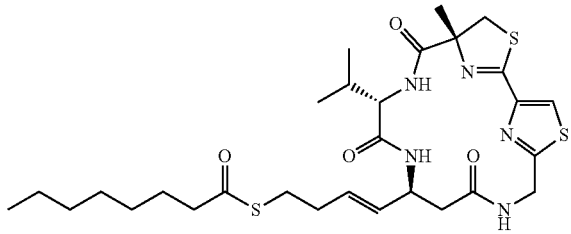 [SMILES: CCCCCCCC(=O)SCC/C=C/[C@@H]1CC(=O)NCc2nc(cs2)C2=N[C@@](C)(CS2)C(=O)N[C@@H](C(C)C)C(=O)N1]

is the isostere of largazole, and mean cell growth changed marginally from −3.4% to +3.7%. The compound of formula C is the isostere of

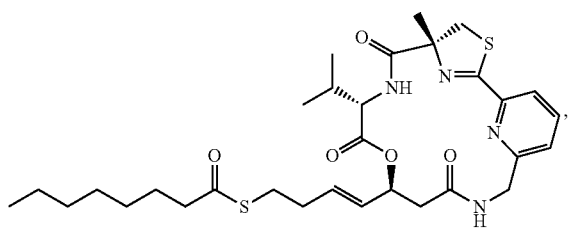 [SMILES: CCCCCCCC(=O)SCC/C=C/[C@@H]1CC(=O)NCc2cccc(n2)C2=N[C@@](C)(CS2)C(=O)N[C@@H](C(C)C)C(=O)O1]

and mean cell growth changed substantially from −5.1% to +26.9%. The compound of formula E is the isostere of the compound of formula D, and mean cell growth changed dramatically from −12.6% to +88.6%.

TABLE P9

Average Inhibition/Lethality for Compounds

| | Compound | Growth (%) | Compound | Growth (%) | Compound | Growth (%) |
|---|---|---|---|---|---|---|
| Base Compound | Largazole | −3.4 | bb | −5.1 | D | −12.6 |
| Isostere | aa | 3.7 | C | 26.9 | E | 88.6 |

The invention claimed is:

1. A compound of Formula (A)

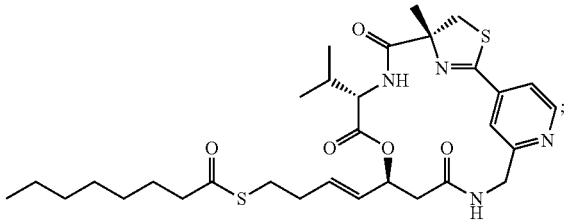 [SMILES: CCCCCCCC(=O)SCC/C=C/[C@@H]1CC(=O)NCc2cc(ccn2)C2=N[C@@](C)(CS2)C(=O)N[C@@H](C(C)C)C(=O)O1]

or a pharmaceutically acceptable salt, solvate, clathrate, prodrug, or stereoisomer thereof.

2. A method for treating histone deacetylase (HDAC) responsive cancer in a subject, comprising inhibiting HDAC by administering to the subject a therapeutically effective amount of the compound of claim 1.

3. The method of claim 2, further comprising administering to said subject an additional form of therapy for cancer.

4. A method for treating a histone deacetylase (HDAC) responsive blood disorder in a subject, comprising inhibiting HDAC by administering to the subject a therapeutically effective amount of the compound of claim 1.

5. The method of claim 4, wherein the blood disorder is at least one of a hemoglobinopathy or a thalassemia.

6. The method of claim 4, further comprising administering to said subject an additional form of therapy for said blood disorder.

7. The method of claim 2, wherein the subject is human.

8. A pharmaceutical composition comprising a therapeutically effective amount of the compound of claim 1 and at least one pharmaceutically acceptable excipient wherein the pharmaceutical composition is useful for treating cancer in a subject.

9. A pharmaceutical composition comprising a therapeutically effective amount of the compound of claim 1 and at least one pharmaceutically acceptable excipient wherein the pharmaceutical composition is useful for treating a blood disorder in a subject.

10. The pharmaceutical composition of claim 9, wherein the blood disorder is at least one of a hemoglobinopathy or a thalassemia.

11. The pharmaceutical composition of claim 8, wherein the subject is human.

12. The compound of claim 1, further comprising a radiolabel.

* * * * *

UNITED STATES PATENT AND TRADEMARK OFFICE
CERTIFICATE OF CORRECTION

PATENT NO. : 10,676,504 B2
APPLICATION NO. : 15/555755
DATED : June 9, 2020
INVENTOR(S) : Robert M. Williams et al.

It is certified that error appears in the above-identified patent and that said Letters Patent is hereby corrected as shown below:

In the Specification

Column 1, Line 21, reading:
This invention was made with government support under grant numbers CA152314, CA136283, GM049631, K08 CA128972, and N01 CO02400 awarded by The National Institutes of Health. The government has certain rights in the invention.
Should read:
This invention was made with government support under grant numbers CA152314, CA136283, GM049631, K08 CA128972, and N01 CO002400 awarded by the National Institutes of Health. The government has certain rights in the invention.

Signed and Sealed this
Seventeenth Day of May, 2022

Katherine Kelly Vidal
*Director of the United States Patent and Trademark Office*